United States Patent
Cotta-Ramusino et al.

(10) Patent No.: US 12,359,223 B2
(45) Date of Patent: Jul. 15, 2025

(54) SYSTEMS AND METHODS FOR MODULATING CHROMOSOMAL REARRANGEMENTS

(71) Applicant: Editas Medicine, Inc., Cambridge, MA (US)

(72) Inventors: Cecilia Cotta-Ramusino, Cambridge, MA (US); Anne Helen Bothmer, Cambridge, MA (US)

(73) Assignee: Editas Medicine, Inc., Cambridge, MA (US)

( * ) Notice: Subject to any disclaimer, the term of this patent is extended or adjusted under 35 U.S.C. 154(b) by 1297 days.

(21) Appl. No.: 16/965,331

(22) PCT Filed: Jan. 30, 2019

(86) PCT No.: PCT/US2019/015847
§ 371 (c)(1),
(2) Date: Jul. 28, 2020

(87) PCT Pub. No.: WO2019/152519
PCT Pub. Date: Aug. 8, 2019

(65) Prior Publication Data
US 2021/0115475 A1   Apr. 22, 2021

Related U.S. Application Data

(60) Provisional application No. 62/623,755, filed on Jan. 30, 2018, provisional application No. 62/664,829, filed on Apr. 30, 2018.

(51) Int. Cl.
| | | |
|---|---|---|
| *C12N 15/11* | (2006.01) | |
| *A61K 48/00* | (2006.01) | |
| *C12N 9/22* | (2006.01) | |
| *C12N 15/90* | (2006.01) | |

(52) U.S. Cl.
CPC .......... *C12N 15/907* (2013.01); *A61K 48/005* (2013.01); *C12N 9/22* (2013.01); *C12N 15/11* (2013.01); *C12N 2310/20* (2017.05); *C12N 2800/80* (2013.01); *C12N 2830/36* (2013.01)

(58) Field of Classification Search
CPC ...... C12N 9/22; C12N 15/85; C12N 2310/16; C12Y 207/07049; C12Y 301/21001; C12Y 301/03005
USPC ........................................................ 435/199
See application file for complete search history.

(56) References Cited

FOREIGN PATENT DOCUMENTS

WO   2017/075475 A1   5/2017

OTHER PUBLICATIONS

Devos et al., (Proteins: Structure, Function and Genetics, 2000, vol. 41: 98-107.*
Whisstock et al., (Quarterly Reviews of Biophysics 2003, vol. 36 (3): 307-340.*
Witkowski et al., (Biochemistry 38:11643-11650, 1999.*
Kisselev L., (Structure, 2002, vol. 10: 8-9.*
Guha et al., Applications of Alternative Nucleases in the Age of CRISPR/Cas9. Int J Mol Sci. Nov. 29, 2017;18(12):2565, 13 pages.
Kweon et al., Fusion guide RNAs for orthogonal gene manipulation with Cas9 and Cpf1. Nat Commun. Nov. 23, 2017;8(1):1723, 6 pages.
International Search Report and Written Opinion for Application No. PCT/US2019/015847, dated Jul. 8, 2019, 17 pages.
Invitation to Pay Additional Fees for Application No. PCT/US2019/015847, dated May 13, 2019, 11 pages.

* cited by examiner

*Primary Examiner* — Robert B Mondesi
*Assistant Examiner* — Mohammad Y Meah
(74) *Attorney, Agent, or Firm* — McCarter & English, LLP; Maria Laccotripe Zacharakis; Marcie B. Clarke

(57) ABSTRACT

The present disclosure provides systems and methods for modulating the occurrence of chromosomal rearrangements, e.g., translocations, in a cell during genome editing. Embodiments are provided for reducing the occurrence of unwanted chromosomal rearrangements, and for increasing the occurrence of desired chromosomal rearrangements.

18 Claims, 28 Drawing Sheets

Specification includes a Sequence Listing.

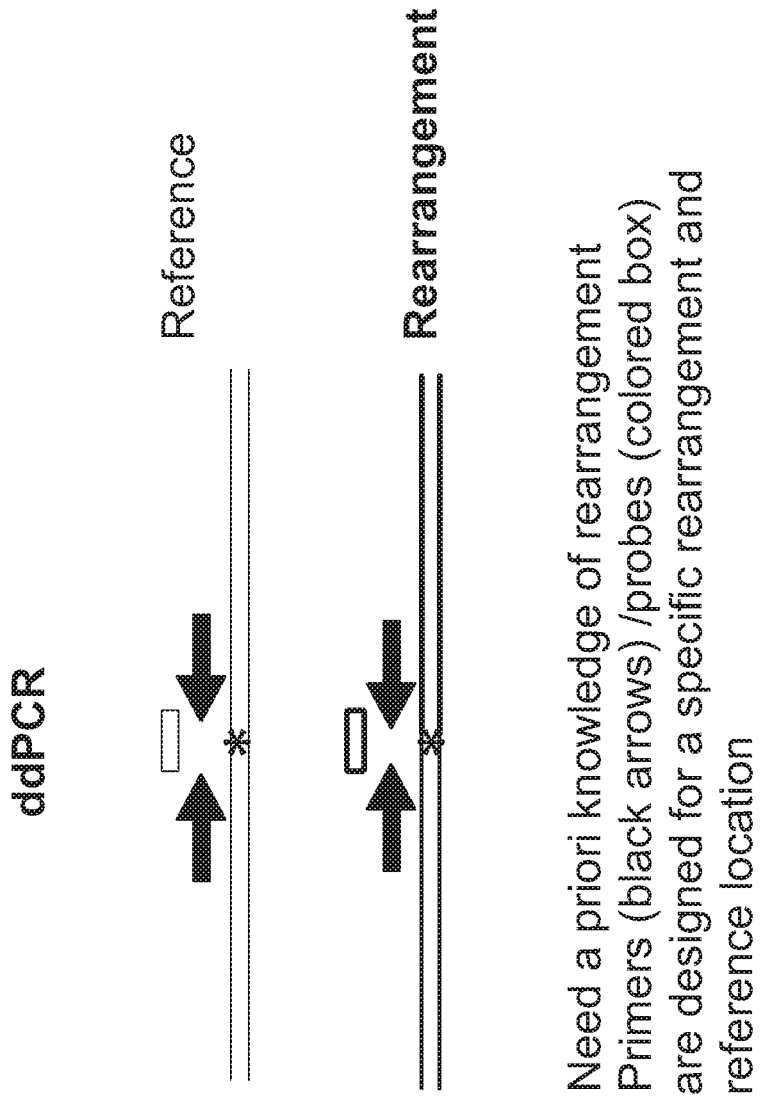

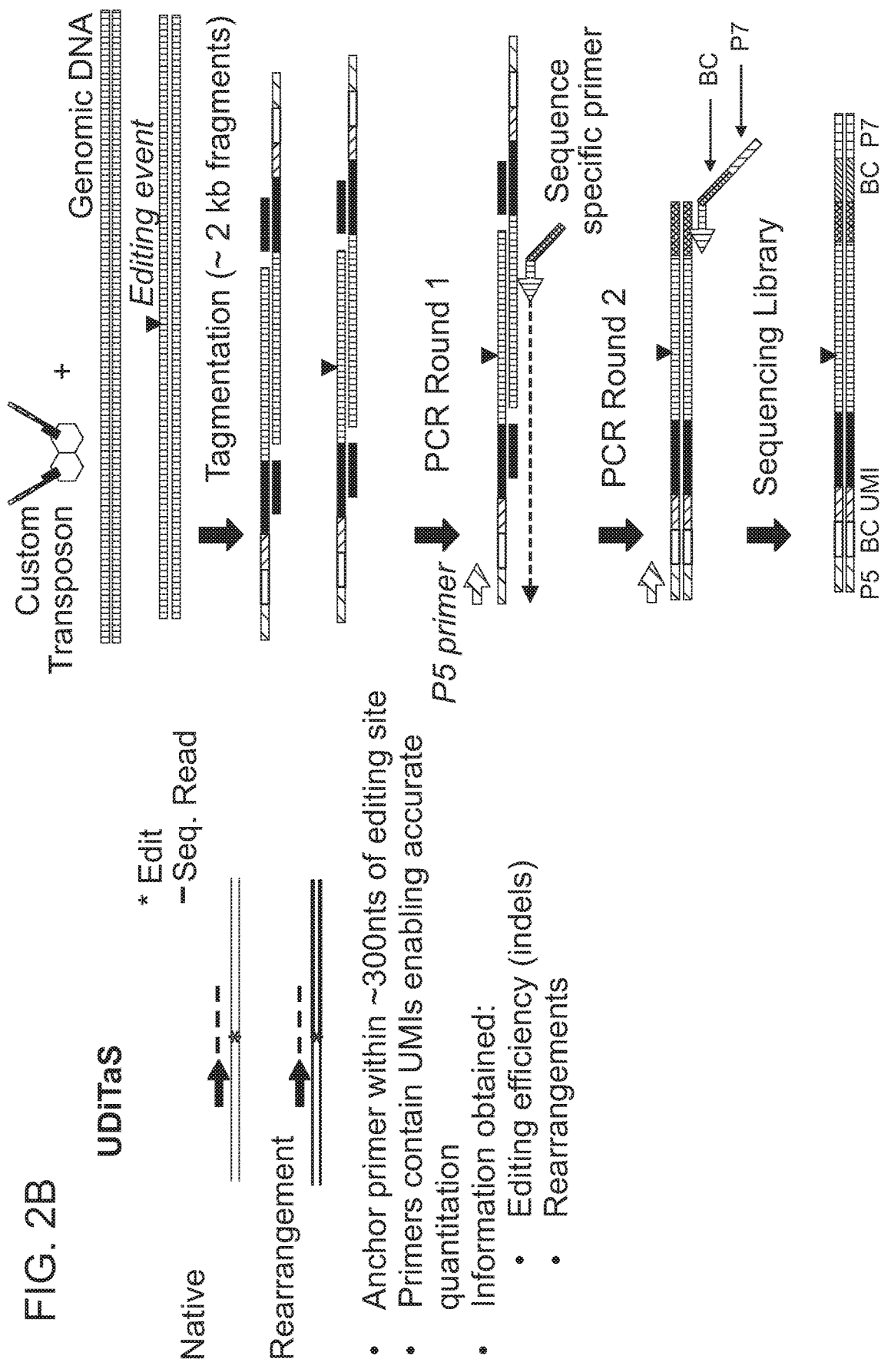

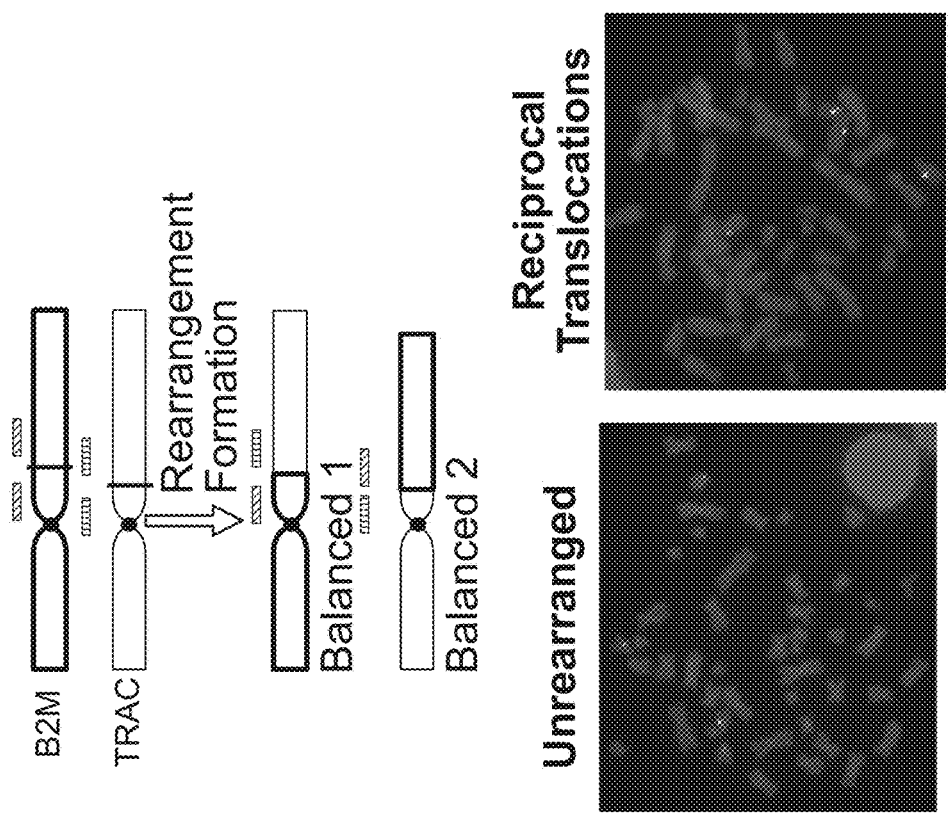
FIG. 3B  FISH
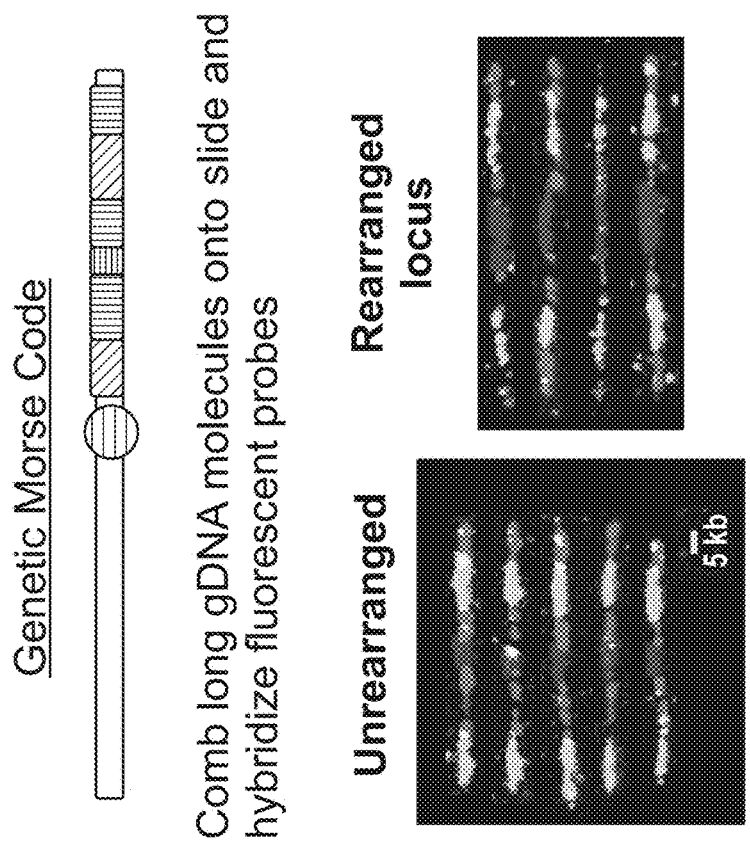
FIG. 3A  Molecular Combing

HA-oligo (STOP): TRAC5_STOP and B2M12_STOP

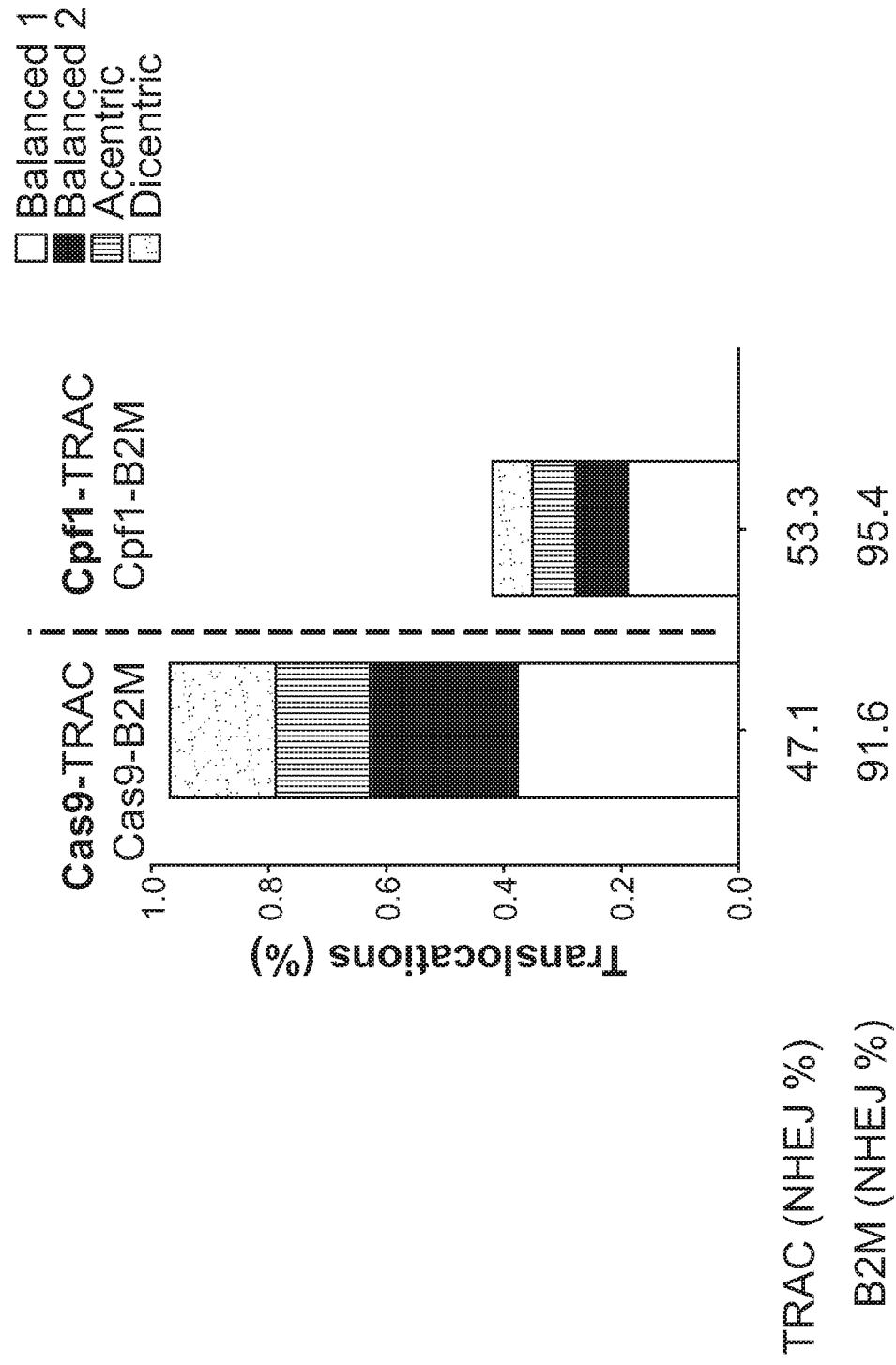

FIG. 9C
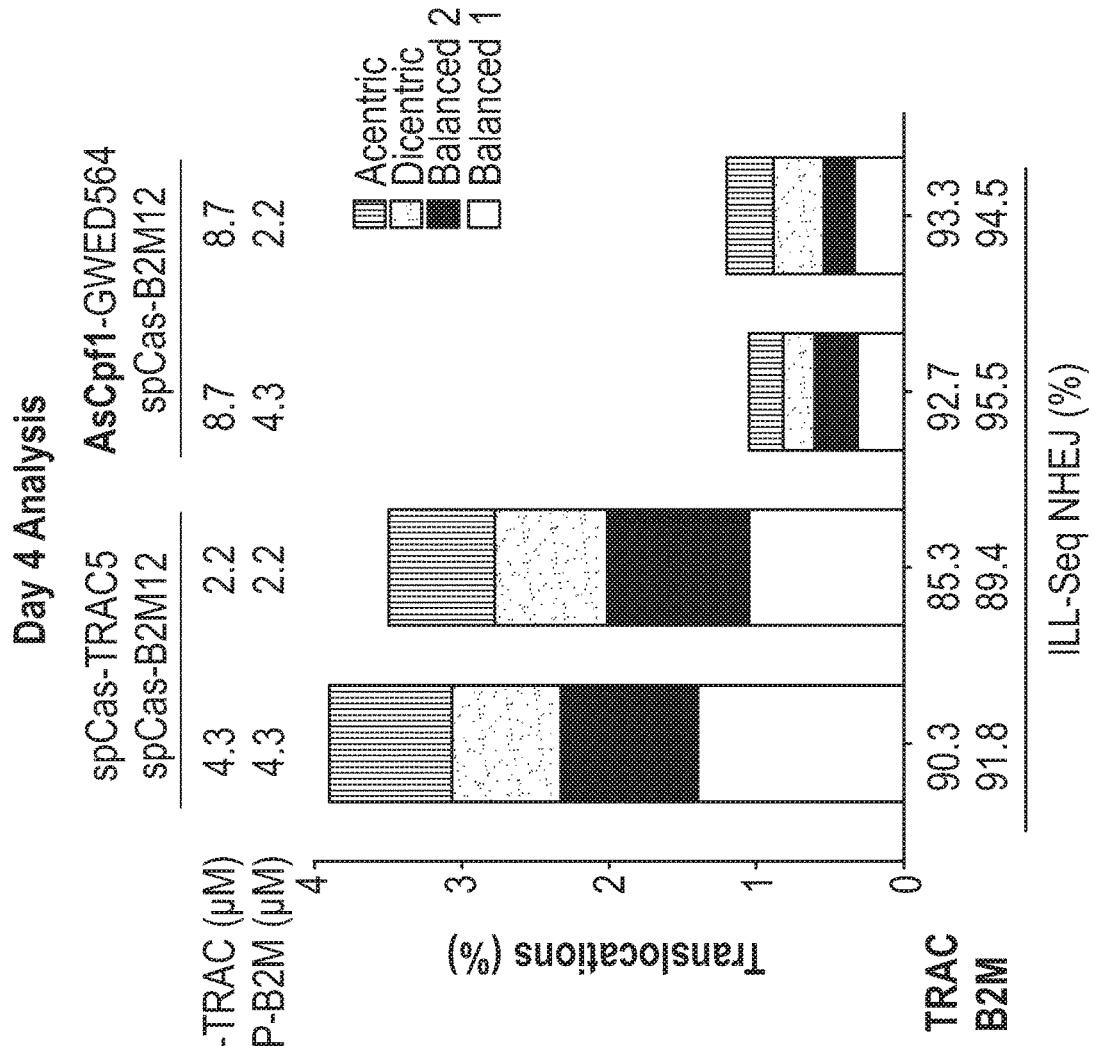
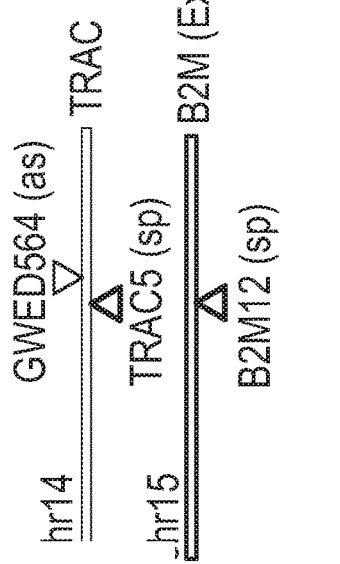

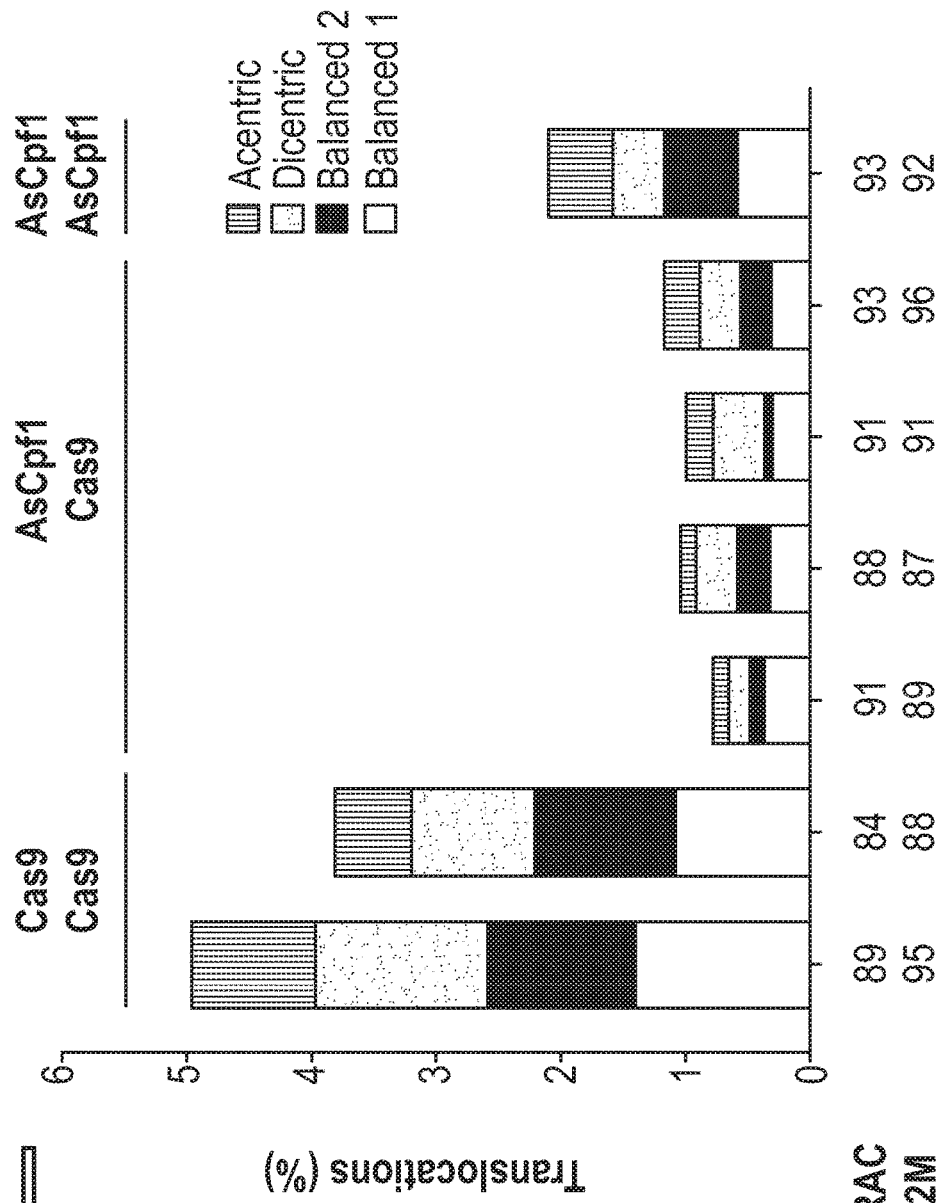
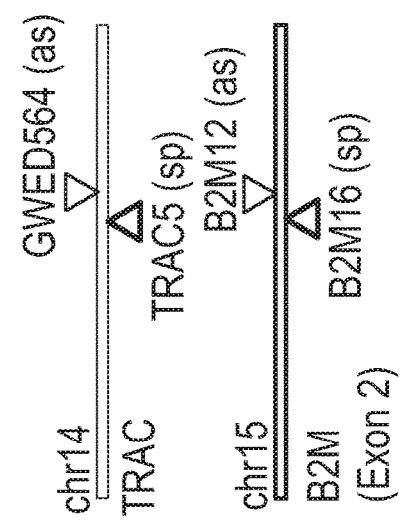
FIG. 9H

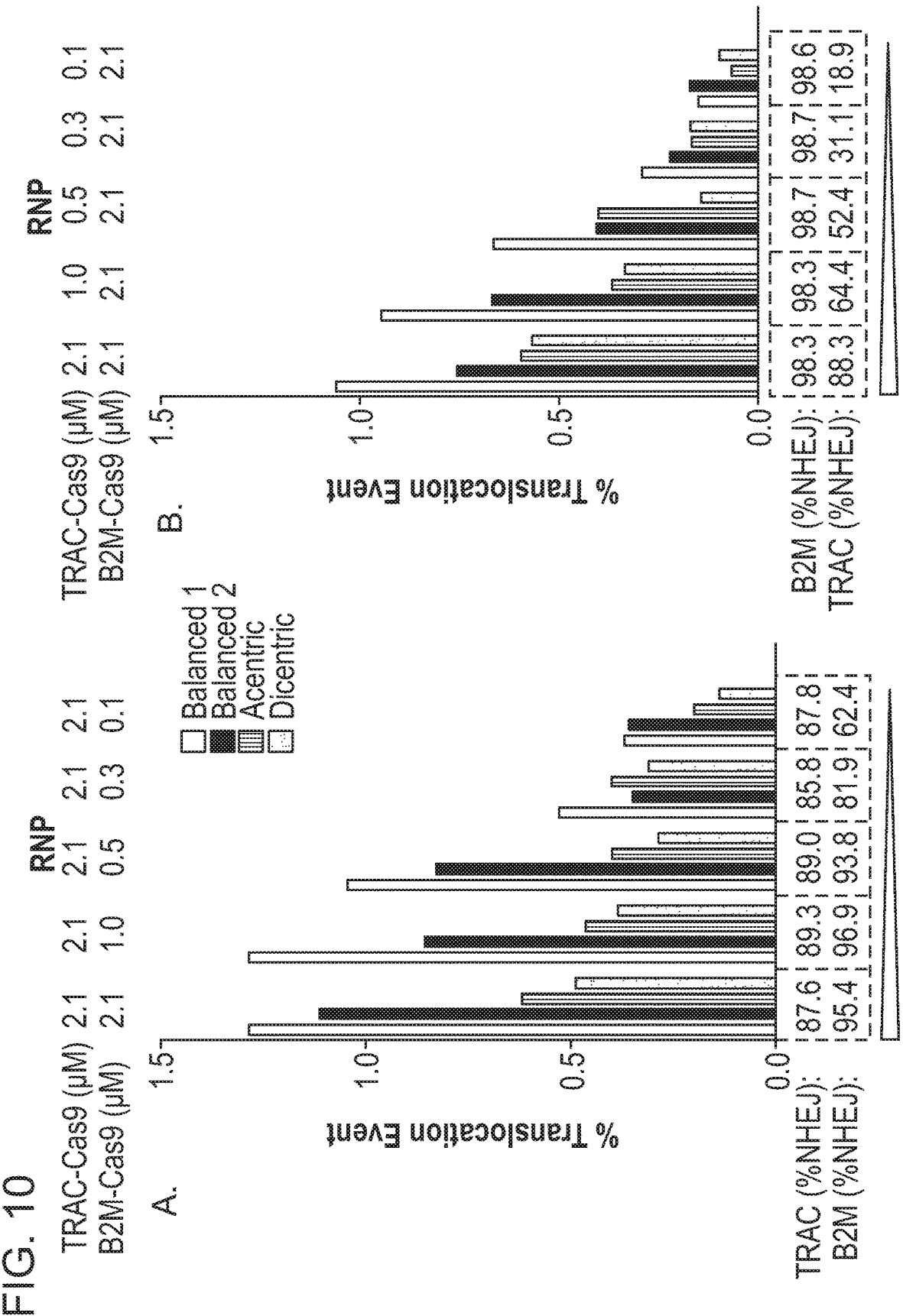

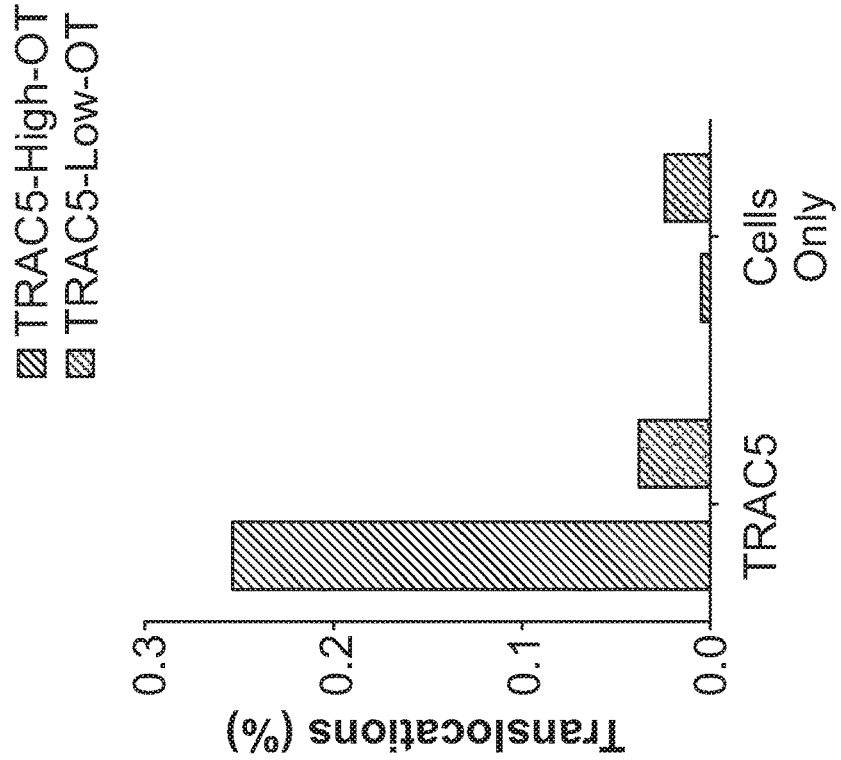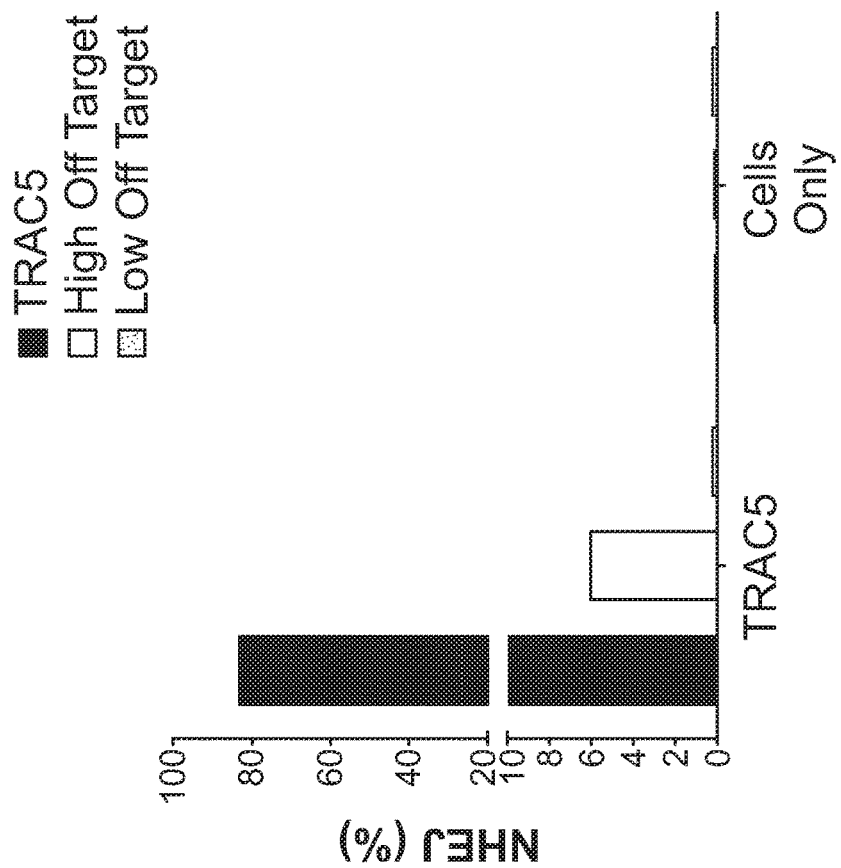

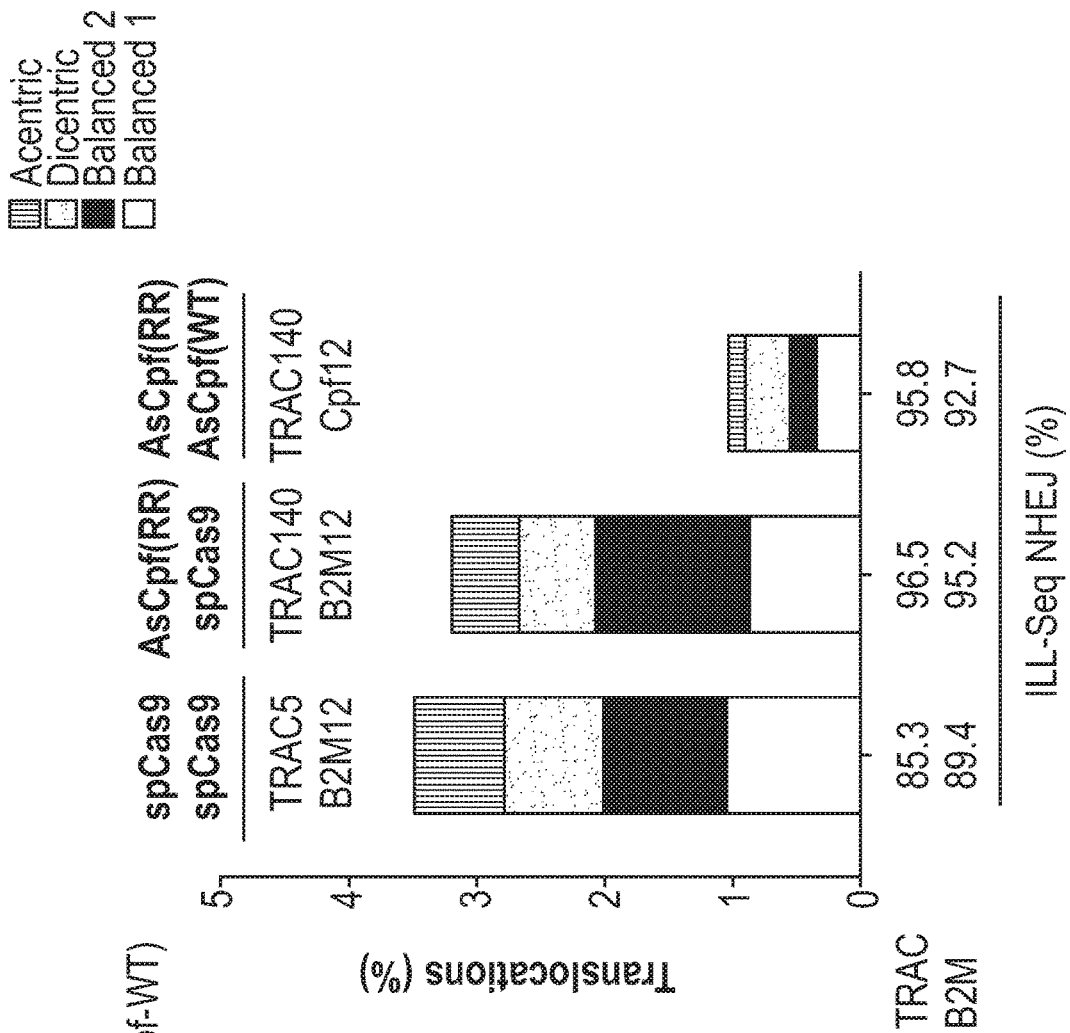
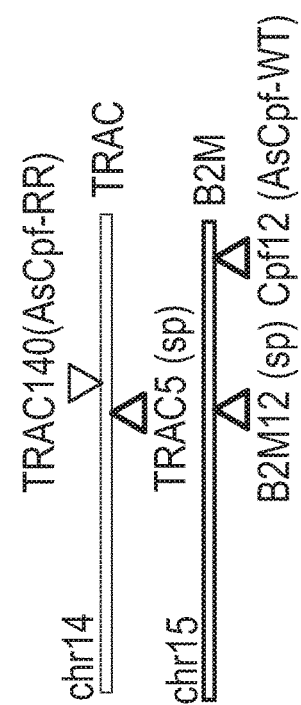
FIG. 16A

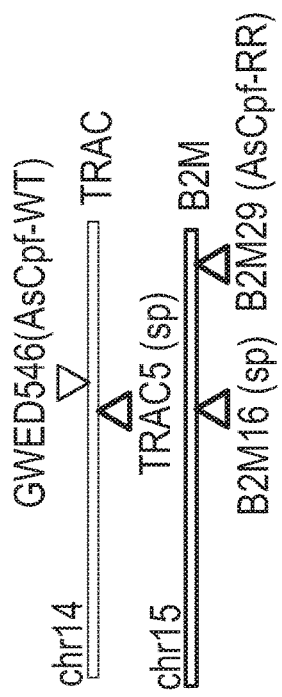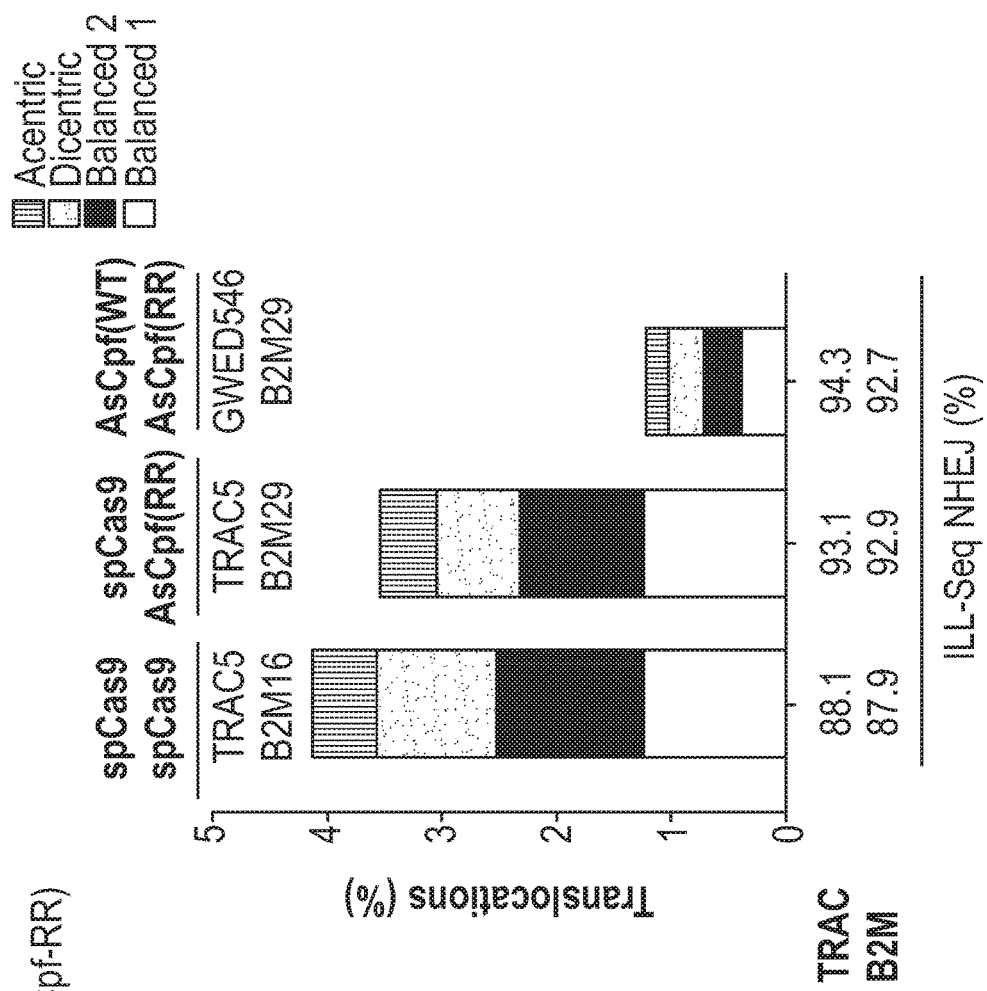
FIG. 16C

SEQUENCE LISTING

<160> NUMBER OF SEQ ID NOS: 25

<210> SEQ ID NO 1
<211> LENGTH: 20
<212> TYPE: DNA
<213> ORGANISM: Unknown
<220> FEATURE:
<221> NAME/KEY: source
<223> OTHER INFORMATION: /note="Description of Unknown: Protospacer
      sequence"

<400> SEQUENCE: 1
tctctcagct ggtacacggc                                               20

<210> SEQ ID NO 2
<211> LENGTH: 20
<212> TYPE: DNA
<213> ORGANISM: Unknown
<220> FEATURE:
<221> NAME/KEY: source
<223> OTHER INFORMATION: /note="Description of Unknown: Protospacer
      sequence"

<400> SEQUENCE: 2
cttcaagagc aacagtgctg                                               20

<210> SEQ ID NO 3
<211> LENGTH: 19
<212> TYPE: DNA
<213> ORGANISM: Unknown
<220> FEATURE:
<221> NAME/KEY: source
<223> OTHER INFORMATION: /note="Description of Unknown: Protospacer
      sequence"

<400> SEQUENCE: 3
cagggttctg gatatctgt                                                19

<210> SEQ ID NO 4
<211> LENGTH: 20
<212> TYPE: DNA
<213> ORGANISM: Unknown
<220> FEATURE:
<221> NAME/KEY: source
<223> OTHER INFORMATION: /note="Description of Unknown: Protospacer
      sequence"

<400> SEQUENCE: 4
ggccacggag cgagacatct                                               20

<210> SEQ ID NO 5
<211> LENGTH: 20
<212> TYPE: DNA
<213> ORGANISM: Unknown
<220> FEATURE:
<221> NAME/KEY: source
<223> OTHER INFORMATION: /note="Description of Unknown: Protospacer
      sequence"

<400> SEQUENCE: 5
gctggtacac ggcagggtca                                               20

<210> SEQ ID NO 6
<211> LENGTH: 20
<212> TYPE: DNA
<213> ORGANISM: Unknown
<220> FEATURE:
<221> NAME/KEY: source

```
<223> OTHER INFORMATION: /note="Description of Unknown: Protospacer
      sequence"

<400> SEQUENCE: 6
cagtaagtca acttcaatgt                                                  20

<210> SEQ ID NO 7
<211> LENGTH: 23
<212> TYPE: DNA
<213> ORGANISM: Unknown
<220> FEATURE:
<221> NAME/KEY: source
<223> OTHER INFORMATION: /note="Description of Unknown: Protospacer
      sequence"

<400> SEQUENCE: 7
gagtctctca gctggtacac ggc                                              23

<210> SEQ ID NO 8
<211> LENGTH: 20
<212> TYPE: DNA
<213> ORGANISM: Unknown
<220> FEATURE:
<221> NAME/KEY: source
<223> OTHER INFORMATION: /note="Description of Unknown: Protospacer
      sequence"

<400> SEQUENCE: 8
agtgggggtg aattcagtgt                                                  20

<210> SEQ ID NO 9
<211> LENGTH: 151
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 9
atcaaaatcg gtgaataggc agacagactt gtcactggat ttagagtctc tcagctggta      60
cacggcaggg ctaattattc atcagggttc tggatatctg tgggacaaga ggatcaggt     120 taggacatga tctcatttcc ctctttgccc c                                    151

<210> SEQ ID NO 10
<211> LENGTH: 151
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 10
tcacgctgga tagcctccag gccagaaaga gagagtagcg cgagcacagc taaggccacg      60
gagcgagaca ctaattattc atctcggccc gaatgctgtc agcttcagga atgcccgcca     120
gcgcgacgcc tccacttata ttaaacgcgt g                                    151

<210> SEQ ID NO 11
<211> LENGTH: 150
<212> TYPE: DNA
<213> ORGANISM: Unknown
<220> FEATURE:
<221> NAME/KEY: source
<223> OTHER INFORMATION: /note="Description of Unknown: Donor template
``` sequence"

<400> SEQUENCE: 11
agagggaaat gagatcatgt cctaaccctg atcctcttgt cccacagata tccagaaccc      60
tgaccctgcc aaagcttctt gtgtaccagc tgagagactc taaatccagt gacaagtctg     120
tctgcctatt caccgatttt gattctcaaa                                      150

<210> SEQ ID NO 12
<211> LENGTH: 150
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 12
attctgatgt gtatatcaca gacaaaactg tgctagacat gaggtctatg gacttcaaga      60
gcaacagtga aagcttcttc tgtggcctgg agcaacaaat ctgactttgc atgtgcaaac     120
gccttcaaca acagcattat tccagaagac                                      150

<210> SEQ ID NO 13
<211> LENGTH: 150
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 13
ggactccagc ctgggttggg gcaaagaggg aaatgagatc atgtcctaac cctgatcctc      60
ttgtcccaca aaagcttctt gatatccaga accctgaccc tgccgtgtac cagctgagag     120
actctaaatc cagtgacaag tctgtctgcc                                      150

<210> SEQ ID NO 14
<211> LENGTH: 150
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 14
cctgttagaa aaatctcatg acattaattc taggtccaga tcctaagaga ggacactcaa      60
gtatccctga aagaagcttt taaagtgcaa tcatccagat gctttctagc cacagttcct     120
gcatccagaa ttttaggaac agccagaaaa                                      150

<210> SEQ ID NO 15
<211> LENGTH: 145
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 15
ttacatattg tgcggtcgaa ttcagggagc cgataatgcg gttacaataa ttcctatact      60
taaatataca aagatttaaa atttcaaaaa atggttacca gcatcgttag tgcgtataca     120
tcaagaggca cgtgccccgg agaca                                                           145

<210> SEQ ID NO 16
<211> LENGTH: 143
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 16
cacgcgttta atataagtgg aggcgtcgcg ctggcgggca ttcctgaagc tgacagcatt         60
cgggccgaga tgatcagggt tctggatatc tgtgggacaa gaggatcagg gttaggacat        120
gatctcattt ccctctttgc ccc                                                143

<210> SEQ ID NO 17
<211> LENGTH: 143
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 17
ggggcaaaga gggaaatgag atcatgtcct aaccctgatc ctcttgtccc acagatatcc         60
agaaccctga tcatctcggc ccgaatgctg tcagcttcag gaatgcccgc cagcgcgacg        120
cctccactta tattaaacgc gtg                                                143

<210> SEQ ID NO 18
<211> LENGTH: 143
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 18
cacgcgttta atataagtgg aggcgtcgcg ctggcgggca ttcctgaagc tgacagcatt         60
cgggccgaga tgaccctgcc gtgtaccagc tgagagactc taaatccagt gacaagtctg        120
tctgcctatt caccgatttt gat                                                143

<210> SEQ ID NO 19
<211> LENGTH: 143
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 19
atcaaaatcg gtgaataggc agacagactt gtcactggat ttagagtctc tcagctggta         60
cacggcaggg tcatctcggc ccgaatgctg tcagcttcag gaatgcccgc cagcgcgacg        120
cctccactta tattaaacgc gtg                                                143

<210> SEQ ID NO 20
<211> LENGTH: 143
<212> TYPE: DNA

```
<213> ORGANISM: Unknown
<220> FEATURE:
<221> NAME/KEY: source
<223> OTHER INFORMATION: /note="Description of Unknown: Donor template
      sequence"

<400> SEQUENCE: 20
ggggcaaaga gggaaatgag atcatgtcct aaccctgatc ctcttgtccc acagatatcc    60
agaaccctga tgatgtctcg ctccgtggcc ttagctgtgc tcgcgctact ctctctttct   120
ggcctggagg ctatccagcg tga                                           143

<210> SEQ ID NO 21
<211> LENGTH: 143
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 21
tcacgctgga tagcctccag gccagaaaga gagagtagcg cgagcacagc taaggccacg    60
gagcgagaca tcatcagggt tctggatatc tgtgggacaa gaggatcagg gttaggacat   120
gatctcattt ccctctttgc ccc                                           143

<210> SEQ ID NO 22
<211> LENGTH: 143
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 22
atcaaaatcg gtgaataggc agacagactt gtcactggat ttagagtctc tcagctggta    60
cacggcaggg tgatgtctcg ctccgtggcc ttagctgtgc tcgcgctact ctctctttct   120
ggcctggagg ctatccagcg tga                                           143

<210> SEQ ID NO 23
<211> LENGTH: 143
<212> TYPE: DNA
<213> ORGANISM: Unknown
<220> FEATURE:
<221> NAME/KEY: source
<223> OTHER INFORMATION: /note="Description of Unknown: Donor template
      sequence"

<400> SEQUENCE: 23
tcacgctgga tagcctccag gccagaaaga gagagtagcg cgagcacagc taaggccacg    60
gagcgagaca tcaccctgcc gtgtaccagc tgagagactc taaatccagt gacaagtctg   120
tctgcctatt caccgatttt gat                                           143

<210> SEQ ID NO 24
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 24
```

```
gtggggggtga attcagtgta                                              20

<210> SEQ ID NO 25
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
gtgacaagtc tgtctgccta                                               20
```

SYSTEMS AND METHODS FOR MODULATING CHROMOSOMAL REARRANGEMENTS

RELATED APPLICATIONS

The instant application is a 35 U.S.C. § 371 national stage filing of International Application No. PCT/US2019/015847, filed on Jan. 30, 2019, which in turn claims priority to U.S. Provisional Application No. 62/623,755, filed on Jan. 30, 2018 and U.S. Provisional Application No. 62/664,829, filed on Apr. 30, 2018. The entire contents of each of the aforementioned applications are expressly incorporated herein by reference.

SEQUENCE LISTING

The instant application contains a Sequence Listing which has been submitted electronically in ASCII format and is hereby incorporated by reference in its entirety. Said ASCII copy, created on Apr. 5, 2019, is named 126454-02020_SL.txt and is 8,483 bytes in size.

FIELD

The present disclosure relates to systems, methods, and compositions for modulating chromosomal rearrangements, and applications thereof in connection with genome editing.

BACKGROUND

CRISPRs (Clustered Regularly Interspaced Short Palindromic Repeats) evolved in bacteria and archea as an adaptive immune system to defend against viral attack. Upon exposure to a virus, short segments of viral DNA are integrated into the CRISPR locus. RNA is transcribed from a portion of the CRISPR locus that includes the viral sequence. That RNA, which contains sequence complementary to the viral genome, mediates targeting of a Cas9 protein to a target sequence in the viral genome. The Cas9 protein, in turn, cleaves and thereby silences the viral target.

Recently, the CRISPR/Cas system has been adapted for genome editing in eukaryotic cells. The introduction of site-specific double strand breaks (DSBs) allows for target sequence alteration through endogenous DNA repair mechanisms, for example non-homologous end-joining (NHEJ) or homology-directed repair (HDR). In addition, targeted integration of a nucleic acid (e.g., a transgene) may be achieved using the CRISPR/Cas system.

Chromosomal rearrangements are side products of DSBs, including Cas9-induced DSBs. In the context of genome editing, chromosomal rearrangements derive from the joining of free DNA ends created by desired DSBs, e.g., Cas9-induced on-target DSBs, to other DSBs in the genome, e.g., spontaneous DSBs due to metabolic activity of a cell, Cas9-induced off-target DSBs, etc. Factors contributing to the frequency of chromosomal rearrangements during genome editing are not well understood. Thus, there remains a need in the art for strategies to modulate the occurrence of chromosomal rearrangements, in order to predictably decrease or increase their formation.

SUMMARY

The present disclosure provides genome editing systems and related methods which allow for the modulation of chromosomal translocation formation. Multiple strategies are provided for decreasing the frequency of chromosomal translocations, by, for example, modulating the DNA repair pathway used by the cell to repair nuclease-induced cleavage events, and/or modulating the kinetics of DNA cleavage and repair. Strategies which allow for increasing the frequency of targeted chromosomal rearrangements are also provided.

In one aspect, the disclosure provides a method for altering a cell at two or more target nucleic acid sites in the cell, the method comprising the step of delivering to the cell two or more ribonucleoprotein (RNP) complexes, wherein each RNP complex comprises a different type of RNA-guided nuclease, thereby altering the cell at two or more target nucleic acid sites.

In one embodiment, the two or more RNP complexes are delivered to the cell sequentially in any order, or simultaneously.

In another aspect, the disclosure provides a population of cells having alterations at two or more target nucleic acids made using any method disclosed herein, wherein the population of cells has a translocation frequency of less than 5%. In one embodiment, the translocation frequency is less than 4%. In one embodiment, the translocation frequency is less than 3%. In one embodiment, the translocation frequency is less than 2%. In one embodiment, the translocation frequency is less than 1%. In one embodiment, the translocation frequency is less than 0.5%. In one embodiment, the translocation frequency is less than 0.25%. In one embodiment, the translocation frequency is less than 0.1%. In one embodiment, the population of cells comprises a translocation frequency that is lower than a translocation frequency of a reference cell population, wherein the reference cell population is altered using RNP complexes comprising the same type of RNA-guided nuclease.

In another aspect, the disclosure provides a method of reducing the risk of translocations in a cell when the cell is altered at two or more target nucleic acid sites, the method comprising delivering to the cell two or more RNP complexes, such that each RNP complex comprises an RNA-guided nuclease different from RNA-guided nuclease in any other RNP complex delivered to the cell.

In one embodiment, the two or more RNP complexes are delivered to the cell sequentially in any order, or simultaneously.

In some embodiments, the methods and genome editing systems of the present disclosure can be used for a method of altering a cell at two or more target nucleic acids in the cell, the method comprising the step of delivering to the cell two or more genome editing systems, wherein each genome editing system comprises a different type of RNA-guided nuclease, thereby altering the cell at the two or more target nucleic acids.

In some embodiments, the methods and genome editing systems of the present disclosure can be used for a method of reducing the risk of translocations in a cell when the cell is altered at two or more target nucleic acids, the method comprising delivering to the cell two or more genome editing systems, wherein each genome editing system comprises a different type of RNA-guided nuclease, thereby reducing the risk of translocations in the cell.

In one embodiment, the two or more RNP complexes are delivered to the cell sequentially in any order, or simultaneously.

In one embodiment, the translocation may occur between an on-target site and an off-target site.

In another aspect, the disclosure provides a method of altering a cell at a first target nucleic acid and a second target nucleic acid, comprising the steps of: forming at least one single- or double-stranded break at a first cleavage site in the first target nucleic acid by delivering to the cell a ribonucleoprotein (RNP) complex comprising a first RNA-guided nuclease and a first guide RNA (gRNA) capable of directing the first RNA-guided nuclease to the first target nucleic acid, wherein the first cleavage site is repaired by at least one DNA repair pathway to produce an altered first target nucleic acid; and forming at least one single- or double-stranded break at a second cleavage site in the second target nucleic acid by delivering to the cell a second RNA-guided nuclease expressed in the cell from an exogenous nucleic acid encoding the second RNA-guided nuclease, wherein the second cleavage site is repaired by at least one DNA repair pathway to produce an altered second target nucleic acid, wherein the first RNA-guided nuclease is a different type from the second RNA-guided nuclease and wherein the first and the second RNA complexes may be delivered simultaneously or sequentially in any order.

In one embodiment, the first RNA-guided nuclease is a nuclease selected from Table 2 and the second RNA-guided nuclease is any other nuclease in Table 2.

In one embodiment, the first RNA-guided nuclease is a Cas9 nuclease and the second RNA-guided nuclease is a Cpf1 nuclease.

In another aspect, the disclosure provides a method of altering a cell at a first target nucleic acid and a second target nucleic acid, comprising the steps of: forming at least one single- or double-stranded break at a first cleavage site in the first target nucleic acid by delivering to the cell a first ribonucleoprotein (RNP) complex comprising a first RNA-guided nuclease and a first guide RNA (gRNA) capable of directing the first RNA-guided nuclease to the first cleavage site in the first target nucleic acid, wherein the first cleavage site is repaired by at least one DNA repair pathway to produce an altered first target nucleic acid; and after a period of time sufficient for repair of the first cleavage site, forming at least one single- or double-stranded break at a second cleavage site by delivering to the cell a second ribonucleoprotein (RNP) complex comprising a second RNA-guided nuclease and a second guide RNA (gRNA) capable of directing the second RNA-guided nuclease to the second cleavage site in the second target nucleic acid, wherein the second cleavage site is repaired by at least one DNA repair pathway to produce an altered second target nucleic acid, thereby altering the cell.

In one embodiment, the first RNP complex and the second RNP complex are delivered in different concentrations. In one embodiment, the concentration of the second RNP complex is at least 2-fold, 3-fold, 4-fold, 5-fold, 10-fold, 20-fold, 30-fold or 50-fold lower than the concentration of the first RNP complex.

In one embodiment, the time sufficient for repair of the first cleavage site is at least 12 hours, at least 24 hours, at least 36 hours, at least 48 hours, at least 72 hours, at least 96 hours, or at least 120 hours.

In one embodiment, the nuclease in the first RNP complex is same or different type than the nuclease in the second RNP complex.

In one aspect, the disclosure provides an isolated oligonucleotide donor template which comprises, from 5' to 3', A1--C--A2, wherein A1 is a homology arm that is substantially identical to a first homology arm of a target nucleic acid; C is a nucleic acid cargo; and A2 is a homology arm that is substantially identical to a second homology arm of the target nucleic acid.

In one embodiment, the nucleic acid cargo comprises the formula $N_x$, where N is a nucleotide, and X represents the number of nucleotides in the cargo. In one embodiment, X is an integer that is not evenly divisible by 3. Such a cargo nucleic acid can, in some embodiments, alter the reading frame of the target nucleic acid. In one embodiment, X is an integer selected from 1, 2, 4, 5, 7, 8, 10, 11, 13, 14, 16, 17, 19, 20, 22, 23, 25, 26, 28, 29, 31, 32, 34, 35, 37, 38, 40, 41, 43, 44, 46, 47, 49 or 50.

In one embodiment, the nucleic acid cargo is a coding sequence. In other embodiments, the nucleic acid cargo is a non-coding sequence.

In one aspect, the present disclosure provides an isolated oligonucleotide donor template which comprises, from 5' to 3', A1-$S_N$--A2, wherein A1 is a homology arm that is substantially identical to a first homology arm of a target nucleic acid; S is a stop codon; N is equal to or greater than 1; and A2 is a homology arm that is substantially identical to a second homology arm of the target nucleic acid.

In one embodiment of this aspect, N is equal to 1. In one embodiment, the stop codon comprises a sequence, from 5' to 3', selected from the group consisting of TAG, TAA, and TGA. In another embodiment, N is an integer greater than 1. For example, in some embodiments, N is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50. In some embodiments, N is an integer between 2-5. In other embodiments, N is an integer between 5-10. In other embodiments, N is an integer between 10-20. In other embodiments, N is an integer between 20-50. In one embodiment, each stop codon comprises a sequence, from 5' to 3', selected from the group consisting of TAG, TAA, and TGA.

In one embodiment, the isolated oligonucleotide donor template contains A1 and A2 sequences that are of equal or approximately equal length. In another embodiment, A1 has a sequence that is at least 40 nucleotides in length, and A2 has a sequence that is at least 40 nucleotides in length. In another embodiment, A1 has a sequence that is at least 65% identical to the first homology arm of the target nucleic acid, and/or A2 has a sequence that is at least 65% identical to the second homology arm of the target nucleic acid. In another embodiment, A1 has a sequence that is at least 90% identical to the first homology arm of the target nucleic acid, and/or A2 has a sequence that is at least 90% identical to the second homology arm of the target nucleic acid. In another embodiment, A1 has a sequence that is identical to the first homology arm of the target nucleic acid, and/or A2 has a sequence that is identical to the second homology arm of the target nucleic acid.

In one embodiment, the isolated oligonucleotide donor template contains A1 and A2 sequences wherein A1 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from the first homology arm of the target nucleic acid. In another embodiment, A2 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from the second homology arm of the target nucleic acid.

In one aspect, the present disclosure provides a genome editing system which comprises: (a) an RNA-guided nuclease; (b) at least one gRNA molecule; and (c) an isolated oligonucleotide donor template comprising a stop codon, as described herein.

In another aspect, the present disclosure provides a method of altering a cell, comprising forming, in a target nucleic acid of the cell, at least one single- or double-stranded break at a cleavage site, wherein the target nucleic acid comprises a first homology arm 5' to the cleavage site, and a second homology arm 3' to the cleavage site; and recombining an exogenous oligonucleotide donor template with the target nucleic acid by homologous recombination to produce an altered nucleic acid, wherein a first strand of the exogenous oligonucleotide donor template comprises, from 5' to 3', A1--$S_N$--A2, wherein A1 is a first homology arm that is substantially identical to the first homology arm of the target nucleic acid; S is a stop codon; N is equal to or greater than 1; and A2 is a second homology arm that is substantially identical to the second homology arm of the target nucleic acid; thereby altering the cell.

In one embodiment, the altered cell comprises an altered target nucleic acid, wherein the altered target nucleic acid comprises, from 5' to 3', the first donor homology arm, one or more stop codons, and the second donor homology arm. In another embodiment, the step of forming the at least one single- or double-strand break comprises contacting the cell with an RNA-guided nuclease. In one embodiment, the step of contacting the cell with an RNA-guided nuclease comprises introducing into the cell a ribonucleoprotein (RNP) complex comprising the RNA-guided nuclease and a guide RNA (gRNA). In another embodiment, the step of recombining the exogenous oligonucleotide donor template into the nucleic acid by homologous recombination comprises introducing the exogenous oligonucleotide donor template into the cell. In another embodiment, the step of introducing comprises electroporation of the cell in the presence of the RNP complex and/or the exogenous oligonucleotide donor template.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, the method comprising: contacting the cell with (i) a RNA-guided nuclease molecule; (ii) at least one gRNA molecule; and (iii) an exogenous oligonucleotide donor template, wherein a first strand of the exogenous oligonucleotide donor template comprises, from 5' to 3', A1-$S_N$--A2, wherein A1 is a first homology arm that is substantially identical to the first homology arm of the target nucleic acid; S is a stop codon; N is equal to or greater than 1; and A2 is a second homology arm that is substantially identical to the second homology arm of the target nucleic acid; wherein the gRNA molecule and the RNA-guided nuclease molecule interact with the target nucleic acid, resulting in a cleavage event at or near the cleavage site, and wherein the cleavage event is repaired by at least one DNA repair pathway to produce an altered nucleic acid, thereby altering the target nucleic acid in the cell.

In one embodiment the method can further comprise contacting the cell with (iv) a second gRNA molecule, wherein the second gRNA molecule and the RNA-guided nuclease molecule interact with the target nucleic acid, resulting in a second cleavage event at or near the cleavage site, and wherein the second cleavage event is repaired by the at least one DNA repair pathway. In another embodiment, the altered nucleic acid comprises, from 5' to 3', the first donor homology arm, one or more stop codons, and the second donor homology arm. In another embodiment, the cell is contacted first with the at least one gRNA molecule and the RNA-guided nuclease molecule, followed by contacting the cell with the exogenous oligonucleotide donor template. In another embodiment, the cell is contacted with the at least one gRNA molecule, the RNA-guided nuclease molecule, and the exogenous oligonucleotide donor template at the same time. In another embodiment, the DNA repair pathway repairs the target nucleic acid to result in targeted integration of the exogenous oligonucleotide donor template.

In one embodiment, the cleavage event, or both the cleavage event and the second cleavage event, is/are repaired by gene correction. In another embodiment, the gRNA molecule is a gRNA nucleic acid, and wherein the RNA-guided nuclease molecule is a RNA-guided nuclease protein. In another embodiment, the gRNA molecule is a gRNA nucleic acid, and the RNA-guided nuclease molecule is encoded by a RNA-guided nuclease nucleic acid. In another embodiment, the cell is contacted with the gRNA molecule and the RNA-guided nuclease molecule as a pre-formed complex. In another embodiment, the target nucleic acid encodes a protein. In another embodiment, the cleavage site is located within an exon.

In one aspect, the foregoing methods can employ any implementation of the exogenous oligonucleotide donor templates described herein. In another embodiment, the exogenous oligonucleotide donor template is a ssODN. In another embodiment, the exogenous oligonucleotide donor template is present in a dsODN. In another embodiment, the exogenous oligonucleotide donor template is present in a vector. In another embodiment, the vector is a viral vector. In another embodiment, the viral vector is an AAV vector or a lentiviral vector.

In one embodiment, the RNA-guided nuclease is a Class 2 Clustered Regularly Interspersed Repeat (CRISPR)-associated nuclease. In another embodiment, the RNA-guided nuclease is selected from the group consisting of wild-type Cas9, a Cas9 nickase, a wild-type Cpf1, and a Cpf1 nickase.

In one aspect, the present disclosure provides a method of altering a first target nucleic acid and a second target nucleic acid in a population of cells, comprising: contacting the population of cells with (i) at least one RNA-guided nuclease, (ii) at least one first gRNA molecule capable of directing the RNA-guided nuclease to a first target nucleic acid; (iii) at least one second gRNA molecule capable of directing the RNA-guided nuclease to a second target nucleic acid; and (iv) an exogenous oligonucleotide donor template comprising one or more stop codons; wherein the RNA-guided nuclease and the first gRNA molecule interact with the first target nucleic acid, resulting in a first cleavage event in the first target nucleic acid, wherein the first cleavage event is repaired by at least one DNA repair pathway to produce an altered first target nucleic acid; and wherein the RNA-guided nuclease and the second gRNA molecule interact with the second target nucleic acid, resulting in a second cleavage event in the second target nucleic acid, wherein the second cleavage event is repaired by at least one DNA repair pathway to produce an altered second target nucleic acid; thereby altering the first target nucleic acid and the second target nucleic acid in the population of cells.

In one embodiment, the percentage of cells in the population of cells that undergo a translocation event during alteration of the first target nucleic acid and the second target nucleic acid is reduced relative to the percentage of cells in a population of cells that undergo a translocation event in the absence of the exogenous oligonucleotide donor template comprising one or more stop codons.

In one embodiment, the exogenous oligonucleotide donor template is a first exogenous oligonucleotide donor template which comprises, from 5' to 3', A1-S$_N$--A2, wherein A1 is a first homology arm that is substantially identical to a first homology arm of the first target nucleic acid; S is a stop codon; N is equal to or greater than 1; and A2 is a second homology arm that is substantially identical to a second homology arm of the first target nucleic acid.

In another embodiment, the population of cells is contacted with a second exogenous oligonucleotide donor template comprising one or more stop codons. In one embodiment, the second exogenous oligonucleotide donor template comprises, from 5' to 3', A1-S$_N$--A2, wherein A1 is a first homology arm that is substantially identical to a first homology arm of the second target nucleic acid; S is a stop codon; N is equal to or greater than 1; and A2 is a second homology arm that is substantially identical to the second homology arm of the second target nucleic acid. The population of cells can be contacted, in some embodiments, with the first oligonucleotide donor template and the second oligonucleotide donor template simultaneously, or sequentially.

In one embodiment, the foregoing method comprises the steps of (a) contacting the population of cells with (i) at least one first RNA-guided nuclease, (ii) at least one first gRNA molecule capable of directing the RNA-guided nuclease to a first target nucleic acid; and (iii) a first exogenous oligonucleotide donor template comprising one or more stop codons; and (b) contacting the population of cells with (i) at least one second RNA-guided nuclease, (ii) at least one second gRNA molecule capable of directing the RNA-guided nuclease to a second target nucleic acid; and (iii) a second exogenous oligonucleotide donor template comprising one or more stop codons. In another embodiment, step (a) and step (b) are performed simultaneously. In another embodiment, step (a) and step (b) are performed sequentially.

In one embodiment, the first target nucleic acid and/or the second target nucleic acid encodes a protein. In another embodiment, the first cleavage event occurs in an exon of the first target nucleic acid, and/or wherein the second cleavage event occurs in an exon of the second target nucleic acid. In another embodiment, the exogenous oligonucleotide donor template comprises an isolated oligonucleotide donor template, as set forth herein. In another embodiment, the first cleavage event and/or the second cleavage event are repaired by gene correction.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, comprising: contacting the cell with (i) a RNA-guided nuclease; (ii) at least one gRNA molecule; and (iii) an exogenous oligonucleotide donor template comprising one or more stop codons; wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid; and wherein the cell is contacted with a concentration of the RNA-guided nuclease that is at least 5-fold lower than a reference concentration, wherein the reference concentration is the concentration of the RNA-guided nuclease capable of altering the target nucleic acid in at least 80% of cells in a cell population in the absence of the exogenous oligonucleotide donor template comprising one or more stop codons; thereby altering the target nucleic acid in the cell. In one embodiment, the cell is contacted with a concentration of the RNA-guided nuclease that is at least 10-fold lower than the reference concentration.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, comprising: contacting the cell with (i) a RNA-guided nuclease; (ii) at least one gRNA molecule; and (iii) an exogenous oligonucleotide; wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid; and wherein the cell is contacted with a concentration of the RNA-guided nuclease and/or the gRNA molecule that is at least 2-fold lower than a reference concentration, wherein the reference concentration is the concentration of the RNA-guided nuclease and/or the gRNA molecule capable of altering the target nucleic acid in at least 80% of cells in a cell population in the absence of the exogenous oligonucleotide; thereby altering the target nucleic acid in the cell.

In one embodiment, the exogenous oligonucleotide is an exogenous oligonucleotide donor template. In another embodiment, the cell is contacted with a concentration of the RNA-guided nuclease and/or the gRNA molecule that is at least 3-fold, 4-fold or 5-fold lower than the reference concentration.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, comprising: contacting the cell with (i) a RNA-guided nuclease; (ii) at least one gRNA molecule; and (iii) an exogenous oligonucleotide donor template comprising one or more stop codons; wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid; and wherein the cell is contacted with a concentration of the RNA-guided nuclease that is 0.6 µM or less, 0.5 µM or less, 0.4 µM or less, 0.3 µM or less, or 0.2 µM or less, thereby altering the target nucleic acid in the cell. In another embodiment, the cell is contacted with a concentration of the RNA-guided nuclease that is about 0.28 µM.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, comprising: contacting the cell with (i) a RNA-guided nuclease; (ii) at least one gRNA molecule; and (iii) an exogenous oligonucleotide donor template comprising one or more stop codons; wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid; and wherein the cell is contacted with a concentration of the gRNA molecule that is at least 5-fold lower than a reference concentration, wherein the reference concentration is the concentration of the gRNA molecule capable of altering the target nucleic acid in at least 80% of cells in a cell population in the absence of the exogenous oligonucleotide donor template comprising one or more stop codons; thereby altering the target nucleic acid in the cell. In one embodiment, the cell is contacted with a concentration of the gRNA molecule that is at least 10-fold lower than the reference concentration.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, comprising: contacting the cell with (i) a RNA-guided nuclease; (ii) at least one gRNA molecule; and (iii) an exogenous oligonucleotide donor template comprising one or more stop codons; wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid; and wherein the cell is contacted with a concentration of the gRNA molecule that is 0.6 µM or less, 0.5 µM or less, 0.4 µM or less, 0.3 µM or less, or 0.2 µM or less, thereby altering the target nucleic acid in the cell. In one embodiment, the cell is contacted with a concentration of the gRNA molecule that is about 0.28 µM.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, comprising: contacting the cell with (i) at least one RNP complex comprising a RNA-guided nuclease and a gRNA; and (ii) an exogenous oligonucleotide donor template comprising one or more stop codons; wherein the RNP complex interacts with the target nucleic acid, resulting in a cleavage event at or near the cleavage site, wherein the cleavage event is repaired by at least one DNA repair pathway to produce an altered nucleic acid; and wherein the cell is contacted with a concentration of the RNP complex that is at least 5-fold lower than a reference concentration, wherein the reference concentration is the concentration of the RNP complex capable of altering the target nucleic acid in at least 80% of cells in a cell population in the absence of the exogenous oligonucleotide donor template comprising one or more stop codons; thereby altering the target nucleic acid in the cell. In one embodiment, the cell is contacted with a concentration of the RNP complex that is at least 10-fold lower than the reference concentration.

In one aspect, the present disclosure provides a method of altering a target nucleic acid in a cell, wherein the target nucleic acid comprises a first strand comprising a cleavage site, a first homology arm 5' to the cleavage site, and a second homology arm 3' to the cleavage site, comprising: contacting the cell with (i) at least one RNP complex comprising a RNA-guided nuclease and a gRNA; and (ii) an exogenous oligonucleotide donor template comprising one or more stop codons; wherein the RNP complex interacts with the target nucleic acid, resulting in a cleavage event at or near the cleavage site, wherein the cleavage event is repaired by at least one DNA repair pathway to produce an altered nucleic acid; and wherein the cell is contacted with a concentration of the RNP complex that is 0.6 µM or less, 0.5 µM or less, 0.4 µM or less, 0.3 µM or less, or 0.2 µM or less, thereby altering the target nucleic acid in the cell. In one embodiment, the cell is contacted with a concentration of the RNP complex that is about 0.28 µM.

In one embodiment, the exogenous oligonucleotide donor template comprises, from 5' to 3', A1-$S_N$--A2, wherein A1 is a first homology arm that is substantially identical to the first homology arm of the target nucleic acid; S is a stop codon; N is equal to or greater than 1; and A2 is a second homology arm that is substantially identical to the second homology arm of the target nucleic acid. In another embodiment, the target nucleic acid encodes a protein. In another embodiment, the cleavage site is located within an exon. The exogenous oligonucleotide donor template can comprise any implementation of the isolated oligonucleotide donor template described herein. In another embodiment, the method further comprises altering a second target nucleic acid in the cell. In one embodiment, the disclosure provides a cell, or population of cells, altered by any of the methods described herein.

In one aspect, the present disclosure provides a method of altering a cell at a first target nucleic acid and a second target nucleic acid, comprising the steps of: forming at least one single- or double-stranded break at a first cleavage site in the first target nucleic acid, wherein the first cleavage site is repaired by at least one DNA repair pathway to produce an altered first target nucleic acid; and after a period of time sufficient for repair of the first cleavage site, forming at least one single- or double-stranded break at a second cleavage site in the second target nucleic acid, wherein the second cleavage site is repaired by at least one DNA repair pathway to produce an altered second target nucleic acid, thereby altering the cell.

In one embodiment, the time sufficient for repair of the first cleavage site is at least 12 hours, at least 24 hours, at least 36 hours, at least 48 hours, at least 72 hours, at least 96 hours, or at least 120 hours. In another embodiment, the time sufficient for repair of the first cleavage site is about 24-120 hours, e.g., about 24-36 hours, about 24-48 hours, about 24-72 hours, about 24-96 hours, or about 24-120 hours.

In one embodiment, the method comprises recombining a first exogenous oligonucleotide donor template with the first target nucleic acid by homologous recombination. In another embodiment, the first target nucleic acid comprises a first homology arm 5' to the cleavage site, and a second homology arm 3' to the cleavage site, wherein the first exogenous oligonucleotide donor template comprises a first homology arm substantially identical to the first homology arm of the first target nucleic acid and a second homology arm substantially identical to the second homology arm of the first target nucleic acid. In another embodiment, the method further comprises recombining a second exogenous oligonucleotide donor template with the second target nucleic acid by homologous recombination.

In one embodiment, the second target nucleic acid comprises a first homology arm 5' to the cleavage site, and a second homology arm 3' to the cleavage site, wherein the second exogenous oligonucleotide donor template comprises a first homology arm substantially identical to the first homology arm of the second target nucleic acid and a second homology arm substantially identical to the second homology arm of the second target nucleic acid. In another embodiment, the first exogenous oligonucleotide donor template and/or the second exogenous oligonucleotide donor template comprises one or more stop codons. In another embodiment, the first exogenous oligonucleotide donor template and/or the second exogenous oligonucleotide donor template comprises an isolated oligonucleotide donor template.

In one embodiment, the step of forming the at least one single- or double-stranded break comprises contacting the cell with an RNA-guided nuclease. In another embodiment, the step of contacting the cell with an RNA-guided nuclease comprises introducing into the cell a ribonucleoprotein (RNP) complex comprising the RNA-guided nuclease and a guide RNA (gRNA). In another embodiment, the step of recombining the first exogenous oligonucleotide donor template with the first target nucleic acid by homologous recombination comprises introducing the first exogenous oligonucleotide donor template into the cell. In another embodiment, the step of recombining the second exogenous oligonucleotide donor template with the second target nucleic acid by homologous recombination comprises introducing the second exogenous oligonucleotide donor template into the cell. In another embodiment, the step of introducing comprises electroporation of the cell in the presence of the RNP complex and/or the first exogenous oligonucleotide donor template and/or the second exogenous oligonucleotide donor template.

In one aspect, the present disclosure provides a method of altering a first target nucleic acid and a second target nucleic acid in a cell, comprising: (a) contacting the cell with (i) a first RNA-guided nuclease molecule, and (ii) at least one first gRNA molecule capable of directing the first RNA-guided nuclease molecule to the first target nucleic acid, and, optionally (iii) a first exogenous oligonucleotide donor template, wherein a first RNP complex comprising the first RNA-guided nuclease molecule and the first gRNA molecule interacts with the first target nucleic acid resulting in a first cleavage event in the first target nucleic acid, wherein the first cleavage event is repaired by at least one DNA repair pathway to produce an altered first target nucleic acid; and (b) after a period of time sufficient for degradation of the first RNP complex, contacting the cell with (i) a second RNA-guided nuclease molecule, (ii) at least one second gRNA molecule capable of directing the second RNA-guided nuclease molecule to the second target nucleic acid, and, optionally (iii) a second exogenous oligonucleotide donor template, wherein a second RNP complex comprising the second RNA-guided nuclease molecule and the second gRNA molecule interacts with the second target nucleic acid, resulting in a second cleavage event in the second target nucleic acid, wherein the second cleavage event is repaired by at least one DNA repair pathway to produce an altered second target nucleic acid.

In one aspect, the present disclosure provides a method of reducing the percentage of cells in a population of cells that undergo a translocation event during alteration of a first target nucleic acid and a second target nucleic acid, comprising: (a) contacting the population of cells with (i) a first RNA-guided nuclease molecule, (ii) at least one first gRNA molecule capable of directing the first RNA-guided nuclease molecule to the first target nucleic acid, and, optionally (iii) a first exogenous oligonucleotide donor template, wherein a first RNP complex comprising the first RNA-guided nuclease molecule and the first gRNA molecule interacts with the first target nucleic acid, resulting in a first cleavage event in the first target nucleic acid, wherein the first cleavage event is repaired by at least one DNA repair pathway to produce an altered first target nucleic acid; and (b) after a period of time sufficient for degradation of the first RNP complex, contacting the population of cells with (i) a second RNA-guided nuclease molecule, (ii) at least one second gRNA molecule capable of directing the second RNA-guided nuclease molecule to the second target nucleic acid, and, optionally (iii) a second exogenous oligonucleotide donor template, wherein a second RNP complex comprising the second RNA-guided nuclease molecule and the second gRNA molecule interacts with the second target nucleic acid, resulting in a second cleavage event in the second target nucleic acid, wherein the second cleavage event is repaired by at least one DNA repair pathway to produce an altered second target nucleic acid, thereby reducing the percentage of cells in the population of cells that undergo a translocation event during alteration of the first target nucleic acid and the second target nucleic acid, relative to the percentage of cells in a population of cells that undergo a translocation event when first target nucleic acid and the second target nucleic acid are altered simultaneously.

In one embodiment, the period of time sufficient for degradation of the first RNP complex is at least 12 hours, at least 24 hours, at least 36 hours, at least 48 hours, at least 72 hours, at least 96 hours, or at least 120 hours. In another embodiment, the period of time sufficient for degradation of the first RNP complex is about 24-120 hours, e.g., about 24-36 hours, about 24-48 hours, about 24-72 hours, about 24-96 hours, or about 24-120 hours.

In one embodiment, the first RNA-guided nuclease molecule and/or the second RNA-guided nuclease molecule is a RNA-guided nuclease protein. In another embodiment, the first RNA-guided nuclease molecule and/or the second RNA-guided nuclease molecule is a RNA-guided nuclease nucleic acid. In another embodiment, the cell is contacted with a pre-formed complex comprising the first RNA-guided nuclease and the first gRNA molecule, and/or wherein the cell is contacted with a pre-formed complex comprising the second RNA-guided nuclease and the second gRNA molecule.

In one embodiment, the first target nucleic acid comprises a first homology arm 5' to the cleavage site, and a second homology arm 3' to the cleavage site, and wherein the first exogenous oligonucleotide donor template comprises a first homology arm substantially identical to the first homology arm of the first target nucleic acid and a second homology arm substantially identical to the second homology arm of the first target nucleic acid. In another embodiment, the second target nucleic acid comprises a first homology arm 5' to the cleavage site, and a second homology arm 3' to the cleavage site, and wherein the second exogenous oligonucleotide donor template comprises a first homology arm substantially identical to the first homology arm of the second target nucleic acid and a second homology arm substantially identical to the second homology arm of the second target nucleic acid.

In one embodiment, the first exogenous oligonucleotide donor template and/or the second exogenous oligonucleotide donor template is a ssODN. In another embodiment, the first exogenous oligonucleotide donor template and/or the second exogenous oligonucleotide donor template is present in a dsODN. In another embodiment, the first exogenous oligonucleotide donor template and/or the second exogenous oligonucleotide donor template is present in a vector. In another embodiment, the vector is a viral vector. In another embodiment, the viral vector is an AAV vector or a lentiviral vector. In another embodiment, the first exogenous oligonucleotide donor template and/or the second exogenous oligonucleotide donor template comprises one or more stop codons.

In one embodiment, the first exogenous oligonucleotide donor template and/or the second exogenous oligonucleotide donor template comprises an isolated oligonucleotide donor template. In another embodiment, the DNA repair pathway repairs the first target nucleic acid to result in targeted integration of the first exogenous oligonucleotide donor template, and/or wherein the DNA repair pathway repairs the second target nucleic acid to result in targeted integration of the second exogenous oligonucleotide donor template.

In one embodiment, the first RNA-guided nuclease and the second RNA-guided nuclease are Class 2 Clustered Regularly Interspersed Repeat (CRISPR)-associated nucleases. In another embodiment, the first RNA-guided nuclease and the second RNA-guided nuclease are selected from the group consisting of wild-type Cas9, a Cas9 nickase, a wild-type Cpf1, and a Cpf1 nickase. In another embodiment, the first RNA-guided nuclease molecule and the second RNA-guided nuclease molecule are the same type of RNA-guided nuclease molecule. In another embodiment, the first RNA-guided nuclease molecule is different from the second RNA-guided nuclease molecule.

In one embodiment, (a) the first RNA-guided nuclease is Cas9, or a nuclease derived therefrom, and the second RNA-guided nuclease is Cpf1, or a nuclease derived therefrom, or (b) the first RNA-guided nuclease is Cpf1, or a nuclease derived therefrom and the second RNA-guided nuclease is Cas9, or a nuclease derived therefrom. In another embodiment, the first RNA-guided nuclease and the second RNA-guided nuclease are derived from different species. In another embodiment, (a) the first RNA-guided nuclease is derived from *S. pyogenes* and the second RNA-guided nuclease is derived from *S. aureus*, or (b) the first RNA-guided nuclease is derived from *S. aureus* and the second RNA-guided nuclease is derived from *S. pyogenes*.

In one embodiment, (a) the first RNA-guided nuclease has an inactivated RuvC domain, and the second RNA-guided nuclease has an inactivated HNH domain, or (b) the first RNA-guided nuclease has an inactivated HNH domain, and the second RNA-guided nuclease has an inactivated RuvC domain. In one embodiment, a cell, or population of cells, is altered.

In one aspect, the present disclosure provides a method of altering a cell at a first target nucleic acid and a second target nucleic acid, comprising the steps of: forming at least one single- or double-stranded break at a first cleavage site in the first target nucleic acid using a first RNA-guided nuclease, wherein the first cleavage site is repaired by at least one DNA repair pathway to produce an altered first target nucleic acid; and forming at least one single- or double-stranded break at a second cleavage site in the second target nucleic acid using a second RNA-guided nuclease, wherein the second RNA-guided nuclease is a different type of RNA-guided nuclease molecule from the first RNA-guided nuclease, and wherein the second cleavage site is repaired by at least one DNA repair pathway to produce an altered second target nucleic acid, thereby altering the cell.

In one embodiment, the method further comprises recombining a first exogenous oligonucleotide donor template with the first target nucleic acid by homologous recombination. In another embodiment, the first target nucleic acid comprises a first homology arm 5' to the cleavage site, and a second homology arm 3' to the cleavage site, wherein the first exogenous oligonucleotide donor template comprises a first homology arm substantially identical to the first homology arm of the first target nucleic acid and a second homology arm substantially identical to the second homology arm of the first target nucleic acid. In another embodiment, the method comprises recombining a second exogenous oligonucleotide donor template with the second target nucleic acid by homologous recombination.

In one embodiment, the second target nucleic acid comprises a first homology arm 5' to the cleavage site, and a second homology arm 3' to the cleavage site, and wherein the second exogenous oligonucleotide donor template comprises a first homology arm substantially identical to the first homology arm of the second target nucleic acid and a second homology arm substantially identical to the second homology arm of the second target nucleic acid.

In one embodiment, the first exogenous oligonucleotide donor template and/or the second exogenous oligonucleotide donor template comprises one or more stop codons. In another embodiment, the first exogenous oligonucleotide donor template and/or the second exogenous oligonucleotide donor template comprises any implementation of the isolated oligonucleotide donor template described herein.

In another embodiment, the step of forming the at least one single- or double-stranded break comprises contacting the cell with an RNA-guided nuclease. In one embodiment the step of contacting the cell with an RNA-guided nuclease comprises introducing into the cell a ribonucleoprotein (RNP) complex comprising the RNA-guided nuclease and a guide RNA (gRNA). In another embodiment, the step of recombining the first exogenous oligonucleotide donor template with the first target nucleic acid by homologous recombination comprises introducing the first exogenous oligonucleotide donor template into the cell. In another embodiment, the step of recombining the second exogenous oligonucleotide donor template with the second target nucleic acid by homologous recombination comprises introducing the second exogenous oligonucleotide donor template into the cell. In another embodiment, the step of introducing comprises electroporation of the cell in the presence of the RNP complex and/or the first exogenous oligonucleotide donor template and/or the second exogenous oligonucleotide donor template.

In one aspect, the present disclosure provides a method of altering a first target nucleic acid and a second target nucleic acid in a cell, comprising: (a) contacting the cell with at least one first RNP complex comprising a first RNA-guided nuclease and a first gRNA molecule capable of directing the first RNA-guided nuclease to the first target nucleic acid; (b) contacting the cell with at least one second RNP complex comprising a second RNA-guided nuclease and a second gRNA molecule capable of directing the second RNA-guided nuclease to the second target nucleic acid; and optionally (c) contacting the cell with a first exogenous oligonucleotide donor template and/or a second exogenous oligonucleotide donor template; wherein the first RNP complex interacts with the first target nucleic acid, resulting in a first cleavage event, wherein the first cleavage event is repaired by at least one DNA repair pathway to produce an altered first target nucleic acid; wherein the second RNP complex interacts with the second target nucleic acid, resulting in a second cleavage event, wherein the second cleavage event is repaired by at least one DNA repair pathway to produce an altered second target nucleic acid; and wherein the first RNA-guided nuclease is a different type of RNA-guided nuclease molecule than the second RNA-guided nuclease.

In one aspect, the present disclosure provides a method of reducing the percentage of cells in a population of cells that undergo a translocation event during alteration of a first target nucleic acid and a second target nucleic acid, comprising: (a) contacting the population of cells with at least one first RNP complex comprising a first RNA-guided nuclease and a first gRNA molecule capable of directing the first RNA-guided nuclease to the first target nucleic acid; (b) contacting the population of cells with at least one second RNP complex comprising a second RNA-guided nuclease and a second gRNA molecule capable of directing the second RNA-guided nuclease to the second target nucleic acid; wherein the second RNA-guided nuclease is a different type of RNA-guided nuclease molecule than the first RNA-guided nuclease; and optionally (c) contacting the population of cells with a first exogenous oligonucleotide donor template and/or a second exogenous oligonucleotide donor template; wherein the first RNP complex interacts with the first target nucleic acid, resulting in a first cleavage event in the first target nucleic acid, wherein the first cleavage event is repaired by at least one DNA repair pathway to produce an altered first target nucleic acid; wherein the second RNP complex interacts with the second target nucleic acid, resulting in a second cleavage event in the second target nucleic acid, wherein the second cleavage event is repaired by at least one DNA repair pathway to produce an altered second target nucleic acid; thereby reducing the percentage of cells in the population of cells that undergo a translocation event during alteration of the first target nucleic acid and the second target nucleic acid, relative to the percentage of cells in a population of cells that undergo a translocation event when the first RNA-guided nuclease is the same type of RNA-guided nuclease molecule as the second RNA-guided nuclease. In one embodiment of this method, step (a) and step (b) are performed simultaneously.

In one embodiment the first RNA-guided nuclease and the second RNA-guided nuclease are Class 2 Clustered Regularly Interspersed Repeat (CRISPR)-associated nucleases. In another embodiment, the first RNA-guided nuclease and the second RNA-guided nuclease are selected from the group consisting of wild-type Cas9, a Cas9 nickase, a wild-type Cpf1, and a Cpf1 nickase.

In one embodiment, (a) the first RNA-guided nuclease is Cas9, or a nuclease derived therefrom, and the second RNA-guided nuclease is Cpf1, or a nuclease derived therefrom, or (b) the first RNA-guided nuclease is Cpf1, or a nuclease derived therefrom and the second RNA-guided nuclease is Cas9, or a nuclease derived therefrom.

In another embodiment, the first RNA-guided nuclease and the second RNA-guided nuclease are derived from different species. In one embodiment, (a) the first RNA-guided nuclease is derived from *S. pyogenes* and the second RNA-guided nuclease is derived from *S. aureus*, or (b) the first RNA-guided nuclease is derived from *S. aureus* and the second RNA-guided nuclease is derived from *S. pyogenes*.

In one embodiment, (a) the first RNA-guided nuclease has an inactivated RuvC domain, and the second RNA-guided nuclease has an inactivated HNH domain, or (b) the first RNA-guided nuclease has an inactivated HNH domain, and the second RNA-guided nuclease has an inactivated RuvC domain.

In one embodiment, the first target nucleic acid comprises a first homology arm 5' to the cleavage site, and a second homology arm 3' to the cleavage site, wherein the first exogenous oligonucleotide donor template comprises a first homology arm substantially identical to the first homology arm of the first target nucleic acid and a second homology arm substantially identical to the second homology arm of the first target nucleic acid. In another embodiment, the second target nucleic acid comprises a first homology arm 5' to the cleavage site, and a second homology arm 3' to the cleavage site, wherein the second exogenous oligonucleotide donor template comprises a first homology arm substantially identical to the first homology arm of the second target nucleic acid and a second homology arm substantially identical to the second homology arm of the second target nucleic acid.

In one embodiment, the first exogenous oligonucleotide donor template and/or the second exogenous oligonucleotide donor template is a ssODN. In another embodiment, the first exogenous oligonucleotide donor template and/or the second exogenous oligonucleotide donor template is present in a dsODN. In another embodiment, the first exogenous oligonucleotide donor template and/or the second exogenous oligonucleotide donor template is present in a vector. In one embodiment, the vector is a viral vector. In another embodiment, the viral vector is an AAV vector or a lentiviral vector.

In one embodiment, the first exogenous oligonucleotide donor template and/or the second exogenous oligonucleotide donor template comprises one or more stop codons. In another embodiment, the first exogenous oligonucleotide donor template and/or the second exogenous oligonucleotide donor template comprises any implementation of the isolated oligonucleotide donor template described herein. In another embodiment, the DNA repair pathway repairs the first target nucleic acid to result in targeted integration of the first exogenous oligonucleotide donor template, and/or wherein the DNA repair pathway repairs the second target nucleic acid to result in targeted integration of the second exogenous oligonucleotide donor template. In another embodiment, the disclosure provides a cell, or population of cells, altered in accordance with the methods described herein.

In one aspect, the present disclosure provides a method of altering a cell at a first target nucleic acid and a second target nucleic acid, comprising the steps of: forming at least one single- or double-stranded break at a first cleavage site in the first target nucleic acid using a ribonucleoprotein (RNP) complex comprising a first RNA-guided nuclease and a first guide RNA (gRNA) capable of directing the first RNA-guided nuclease to the first target nucleic acid, wherein the first cleavage site is repaired by at least one DNA repair pathway to produce an altered first target nucleic acid; and forming at least one single- or double-stranded break at a second cleavage site in the second target nucleic acid using a second RNA-guided nuclease expressed in the cell from an exogenous nucleic acid encoding the second RNA-guided nuclease, wherein the second cleavage site is repaired by at least one DNA repair pathway to produce an altered second target nucleic acid, thereby altering the cell.

In one embodiment, the step of forming the at least one single- or double-stranded break in the first target nucleic acid comprises introducing into the cell the RNP complex comprising the first RNA-guided nuclease and the first gRNA. In another embodiment, the step of forming the at least one single- or double-stranded break in the second target nucleic acid comprises introducing into the cell: (a) the exogenous nucleic acid encoding the second RNA-guided nuclease, and (b) a second gRNA capable of directing the second RNA-guided nuclease to the second target nucleic acid.

In one embodiment, the step of forming the at least one single- or double-stranded break in the second target nucleic acid comprises introducing into the cell: (a) the exogenous nucleic acid encoding the second RNA-guided nuclease, and (b) an exogenous nucleic acid encoding a second gRNA capable of directing the second RNA-guided nuclease to the second target nucleic acid. In another embodiment, the exogenous nucleic acid encoding the second RNA-guided nuclease is a mRNA molecule. In another embodiment, the exogenous nucleic acid encoding the second RNA-guided nuclease is a DNA molecule. In another embodiment, the exogenous nucleic acid encoding the second gRNA is a DNA molecule. In another embodiment, the exogenous nucleic acid encoding the second RNA-guided nuclease and/or the second gRNA is contained in a vector. In another embodiment, the vector is a plasmid vector or a viral vector.

In another embodiment, the viral vector is an AAV vector or a lentiviral vector. In another embodiment, the method further comprises recombining a first exogenous oligonucleotide donor template with the first target nucleic acid by homologous recombination.

In one embodiment, the first target nucleic acid comprises a first homology arm 5' to the cleavage site, and a second homology arm 3' to the cleavage site, and wherein the first exogenous oligonucleotide donor template comprises a first homology arm substantially identical to the first homology arm of the first target nucleic acid and a second homology arm substantially identical to the second homology arm of the first target nucleic acid. In another embodiment, the method further comprises recombining a second exogenous oligonucleotide donor template with the second target nucleic acid by homologous recombination.

In one embodiment, the second target nucleic acid comprises a first homology arm 5' to the cleavage site, and a second homology arm 3' to the cleavage site, wherein the second exogenous oligonucleotide donor template comprises a first homology arm substantially identical to the first homology arm of the second target nucleic acid and a second homology arm substantially identical to the second homology arm of the second target nucleic acid. In another embodiment, the first exogenous oligonucleotide donor template and/or the second exogenous oligonucleotide donor template comprises one or more stop codons. In another embodiment, the first exogenous oligonucleotide donor template and/or the second exogenous oligonucleotide donor template comprises any implementation of the isolated oligonucleotide donor template described herein.

In one embodiment, the step of recombining the first exogenous oligonucleotide donor template with the first target nucleic acid by homologous recombination comprises introducing the first exogenous oligonucleotide donor template into the cell. In another embodiment, the step of recombining the second exogenous oligonucleotide donor template with the second target nucleic acid by homologous recombination comprises introducing the second exogenous oligonucleotide donor template into the cell. In another embodiment, the step of introducing comprises electroporation of the cell in the presence of the first exogenous oligonucleotide donor template and/or the second exogenous oligonucleotide donor template.

In one aspect, the present disclosure provides a method of altering a first target nucleic acid and a second target nucleic acid in a cell, comprising: (a) contacting the cell with at least one RNP complex comprising a first RNA-guided nuclease and a first gRNA molecule capable of directing the first RNA-guided nuclease to the first target nucleic acid; (b) contacting the cell with an exogenous nucleic acid molecule encoding a second RNA-guided nuclease; and (c) contacting the cell with at least one second gRNA molecule, or an exogenous nucleic acid molecule encoding the second gRNA molecule, wherein the second gRNA molecule is capable of directing the second RNA-guided nuclease to the second target nucleic acid; wherein the at least one RNP complex interacts with the first target nucleic acid, resulting in a first cleavage event, wherein the first cleavage event is repaired by at least one DNA repair pathway to produce an altered first target nucleic acid; and wherein the second RNA-guided nuclease and the second gRNA molecule interact with the second target nucleic acid, resulting in a second cleavage event, wherein the second cleavage event is repaired by at least one DNA repair pathway to produce an altered second target nucleic acid.

In one aspect, the present disclosure provides a method of reducing the percentage of cells in a population of cells that undergo a translocation event during alteration of a first target nucleic acid and a second target nucleic acid, comprising: (a) contacting the population of cells with at least one RNP complex comprising a first RNA-guided nuclease and a first gRNA molecule capable of directing the first RNA-guided nuclease to the first target nucleic acid; (b) contacting the population of cells with an exogenous nucleic acid molecule encoding a second RNA-guided nuclease; and (c) contacting the population of cells with at least one second gRNA molecule, or an exogenous nucleic acid molecule encoding the second gRNA molecule, wherein the second gRNA molecule is capable of directing the second RNA-guided nuclease to the second target nucleic acid; wherein the at least one RNP complex interacts with the first target nucleic acid, resulting in a first cleavage event, wherein the first cleavage event is repaired by at least one DNA repair pathway to produce an altered first target nucleic acid; and wherein the second RNA-guided nuclease and the second gRNA molecule interact with the second target nucleic acid, resulting in a second cleavage event, wherein the second cleavage event is repaired by at least one DNA repair pathway to produce an altered second target nucleic acid; thereby reducing the percentage of cells in the population of cells that undergo a translocation event during alteration of the first target nucleic acid and the second target nucleic acid, relative to the percentage of cells in a population of cells that undergo a translocation event when the cells are contacted with the RNP complex comprising the first RNA-guided nuclease and the first gRNA molecule and a second RNP complex comprising the second RNA-guided nuclease and the second gRNA molecule.

In one embodiment, the exogenous nucleic acid molecule encoding the second RNA-guided nuclease is a mRNA molecule. In another embodiment, the exogenous nucleic acid molecule encoding the second RNA-guided nuclease is a DNA molecule. In another embodiment, the exogenous nucleic acid molecule encoding the second gRNA is a DNA molecule. In another embodiment, the exogenous nucleic acid encoding the second RNA-guided nuclease and/or the second gRNA is contained in a vector. In another embodiment, the vector is a plasmid vector or a viral vector. In another embodiment, the viral vector is an AAV vector or a lentiviral vector. In another embodiment, steps (a), (b), and (c) are performed simultaneously. In another embodiment, the method comprises contacting the cell with a first exogenous oligonucleotide donor template and/or a second exogenous oligonucleotide donor template.

In one embodiment, the first target nucleic acid comprises a first homology arm 5' to the cleavage site, and a second homology arm 3' to the cleavage site, wherein the first exogenous oligonucleotide donor template comprises a first homology arm substantially identical to the first homology arm of the first target nucleic acid and a second homology arm substantially identical to the second homology arm of the first target nucleic acid.

In another embodiment, the second target nucleic acid comprises a first homology arm 5' to the cleavage site, and a second homology arm 3' to the cleavage site, wherein the second exogenous oligonucleotide donor template comprises a first homology arm substantially identical to the first homology arm of the second target nucleic acid and a second homology arm substantially identical to the second homology arm of the second target nucleic acid.

In one embodiment, the first exogenous oligonucleotide donor template and/or the second exogenous oligonucleotide donor template is a ssODN. In another embodiment, the first exogenous oligonucleotide donor template and/or the second exogenous oligonucleotide donor template is present in a dsODN. In another embodiment, the first exogenous oligonucleotide donor template and/or the second exogenous oligonucleotide donor template is present in a vector. In another embodiment, the vector is a viral vector. In another embodiment, the viral vector is an AAV vector or a lentiviral vector. In another embodiment, the first exogenous oligonucleotide donor template and/or the second exogenous oligonucleotide donor template comprises one or more stop codons. In another embodiment, the first exogenous oligonucleotide donor template and/or the second exogenous oligonucleotide donor template comprises any implementation of the isolated oligonucleotide donor template described herein. In another embodiment, the DNA repair pathway repairs the first target nucleic acid to result in targeted integration of the first exogenous oligonucleotide donor template, and/or wherein the DNA repair pathway repairs the second target nucleic acid to result in targeted integration of the second exogenous oligonucleotide donor template.

In one embodiment, the first RNA-guided nuclease and the second RNA-guided nuclease are Class 2 Clustered Regularly Interspersed Repeat (CRISPR)-associated nucleases. In another embodiment, the first RNA-guided nuclease and the second RNA-guided nuclease are selected from the group consisting of wild-type Cas9, a Cas9 nickase, a wild-type Cpf1, and a Cpf1 nickase. In another embodiment, the first RNA-guided nuclease molecule and the second RNA-guided nuclease molecule are the same type of RNA-guided nuclease molecule. In another embodiment, the first RNA-guided nuclease molecule is different from the second RNA-guided nuclease molecule. In another embodiment, (a) the first RNA-guided nuclease is Cas9, or a nuclease derived therefrom, and the second RNA-guided nuclease is Cpf1, or a nuclease derived therefrom, or (b) the first RNA-guided nuclease is Cpf1, or a nuclease derived therefrom and the second RNA-guided nuclease is Cas9, or a nuclease derived therefrom.

In one embodiment, the first RNA-guided nuclease and the second RNA-guided nuclease are derived from different species. In another embodiment, (a) the first RNA-guided nuclease is derived from *S. pyogenes* and the second RNA-guided nuclease is derived from *S. aureus*, or (b) the first RNA-guided nuclease is derived from *S. aureus* and the second RNA-guided nuclease is derived from *S. pyogenes*.

In one embodiment, (a) the first RNA-guided nuclease has an inactivated RuvC domain, and the second RNA-guided nuclease has an inactivated HNH domain, or (b) the first RNA-guided nuclease has an inactivated HNH domain, and the second RNA-guided nuclease has an inactivated RuvC domain.

In one aspect, the disclosure provides a cell, or population of cells, altered by one or more methods set forth herein.

In one aspect, the disclosure provides a method of altering a cell at a first target nucleic acid and a second target nucleic acid, comprising forming two single-stranded breaks at a first cleavage site in the first target nucleic acid, wherein the two single-stranded breaks produce 5' overhangs at the first cleavage site; and forming two single-stranded breaks at a second cleavage site in the second target nucleic acid, wherein the two single-stranded breaks produce 3' overhangs at the second cleavage site; wherein the first cleavage site is repaired by at least one DNA repair pathway to produce an altered first target nucleic acid, and wherein the second cleavage site is repaired by at least one DNA repair pathway to produce an altered second target nucleic acid, thereby altering the cell.

In one embodiment, the steps of forming two single-stranded breaks at the first cleavage site, and forming two single-stranded breaks at the second cleavage site, are performed simultaneously. In one embodiment, the steps of forming two single-stranded breaks at the first cleavage site, and forming two single-stranded breaks at the second cleavage site, are performed sequentially. In one embodiment, the step of forming two single-stranded breaks at the first cleavage site is performed using a first RNA-guided nuclease having an inactivated RuvC domain, for example, a Cas9 nuclease or a Cpf1 nuclease having an inactivated RuvC domain. In one embodiment, the step of forming two single-stranded breaks at the second cleavage site is performed using a second RNA-guided nuclease having an inactivated HNH domain, for example, a Cas9 nuclease or a Cpf1 nuclease having an inactivated HNH domain.

In one aspect, the present disclosure provides an isolated oligonucleotide donor template which comprises, from 5' to 3', A1--$L_N$--B1, wherein A1 is a homology arm that is substantially identical to a homology arm of a first target nucleic acid; L is a nucleotide sequence comprising N nucleotides which links A1 and B1; N is an integer equal to or greater than 0; and B1 is a homology arm that is substantially identical to a homology arm of a second target nucleic acid, wherein the first target nucleic acid comprises a first cleavage site, a centromeric homology arm centromeric to the first cleavage site, and an acentromeric homology arm acentromeric to the first cleavage site, and wherein the second target nucleic acid comprises a second cleavage site, a centromeric homology arm centromeric to the second cleavage site, and an acentromeric homology arm acentromeric to the second cleavage site. In one embodiment, the first target nucleic acid and the second target nucleic acid are on different chromosomes. In another embodiment, the first target nucleic acid and the second target nucleic acid are on the same chromosome.

In one embodiment, in the isolated oligonucleotide donor template, A1 is substantially identical to the centromeric homology arm of the first target nucleic acid, and B1 is substantially identical to the acentromeric homology arm of the second target nucleic acid. In another embodiment, A1 is substantially identical to the acentromeric homology arm of the first target nucleic acid, and B1 is substantially identical to the centromeric homology arm of the second target nucleic acid. In another embodiment, A1 is substantially identical to the centromeric homology arm of the first target nucleic acid, and B1 is substantially identical to the centromeric homology arm of the second target nucleic acid. In another embodiment, A1 is substantially identical to the acentromeric homology arm of the first target nucleic acid, and B1 is substantially identical to the acentromeric homology arm of the second target nucleic acid.

In one embodiment, in the isolated oligonucleotide donor template N is equal to zero. In another embodiment, N is an integer between 1 and 5 (i.e., 1, 2, 3, 4, or 5). In another embodiment, N is an integer between 5 and 10 (i.e., 5, 6, 7, 8, 9, or 10). In another embodiment, N is an integer between 10 and 20 (i.e., 10, 11, 12, 13, 14, 15, 16, 17, 18, 19, or 20). In another embodiment, N is 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

In one embodiment, N in the isolated oligonucleotide donor template is less than 5, less than 10, less than 20, less than 30, less than 40, less than 50, less than 60, less than 70, less than 80, less than 90, or less than 100. In another embodiment, N is at least 2, at least 5, at least 10, at least 20, at least 30, at least 40, at least 50, at least 60, at least 70, at least 80, at least 90, or at least 100. In another embodiment, N is 2. In another embodiment, L comprises the sequence GA.

In one embodiment, A1 and B1 in the isolated oligonucleotide donor template have sequences that are of approximately equal length. In another embodiment, A1 and B1 have sequences that are of equal length. In another embodiment, A1 has a sequence that is at least 40 nucleotides in length, and B1 has a sequence that is at least 40 nucleotides in length. In another embodiment, A1 has a sequence that is at least 40 nucleotides in length, and B1 has a sequence that is at least 70 nucleotides in length. In another embodiment, A1 has a sequence that is about 50-100 nucleotides in length, and B1 has a sequence that is about 50-100 nucleotides in length. In another embodiment, A1 has a sequence that is about 70 nucleotides in length, and B1 has a sequence that is about 70 nucleotides in length.

In one embodiment, in the isolated oligonucleotide donor template, A1 has a sequence that is at least 65% identical to the homology arm of the first target nucleic acid, and/or B1 has a sequence that is at least 65% identical to the homology arm of the second target nucleic acid. In another embodiment, A1 has a sequence that is at least 90% identical to the homology arm of the first target nucleic acid, and/or B1 has a sequence that is at least 90% identical to the homology arm of the second target nucleic acid.

In one embodiment, in the isolated oligonucleotide donor template, A1 has a sequence that is at identical to the homology arm of the first target nucleic acid, and/or B1 has a sequence that is identical to the homology arm of the second target nucleic acid. In another embodiment, A1 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from the homology arm of the first target nucleic acid. In another embodiment, B1 has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from the homology arm of the second target nucleic acid.

In one aspect, the present disclosure provides a genome editing system comprising: (a) at least one RNA-guided nuclease; (b) at least one first gRNA molecule capable of directing the RNA-guided nuclease to a first target nucleic acid; (c) at least one second gRNA molecule capable of directing the RNA-guided nuclease to a second target nucleic acid; and (d) the isolated oligonucleotide donor template described above.

In one aspect, the present disclosure provides a method of introducing a chromosomal rearrangement in a cell, comprising the steps of: forming, in a first target nucleic acid located on a first chromosome of the cell, at least one single- or double-stranded break at a first cleavage site, wherein the first target nucleic acid comprises a centromeric homology arm centromeric to the first cleavage site, and an acentromeric homology arm acentromeric to the first cleavage site; forming, in a second target nucleic acid located on a second chromosome of the cell, at least one single- or double-stranded break at a second cleavage site, wherein the second target nucleic acid comprises a centromeric homology arm centromeric to the second cleavage site, and an centromeric homology arm acentromeric to the second cleavage site; and recombining the first target nucleic acid and the second target nucleic acid with an exogenous oligonucleotide donor template by homologous recombination to produce a chromosomal rearrangement between the first chromosome and the second chromosome, wherein a first strand of the exogenous oligonucleotide donor template comprises, from 5' to 3', A1--$L_N$--B1, wherein A1 is a homology arm that is substantially identical to a homology arm of the first target nucleic acid; L is a nucleotide sequence comprising N nucleotides which links A1 and B1; N is an integer equal to or greater than 0; and B1 is a homology arm that is substantially identical to a homology arm of the second target nucleic acid.

In one embodiment, A1 is substantially identical to the centromeric homology arm of the first target nucleic acid. In another embodiment, A1 is substantially identical to the acentromeric homology arm of the first target nucleic acid. In another embodiment, B1 is substantially identical to the centromeric homology arm of the second target nucleic acid. In another embodiment, B1 is substantially identical to the acentromeric homology arm of the second target nucleic acid.

In another aspect, the disclosure provides a method of introducing an intrachromosomal rearrangement in a cell, comprising forming, in a first target nucleic acid, at least one single- or double-stranded break at a first cleavage site; forming, in a second target nucleic acid, at least one single- or double-stranded break at a second cleavage site, wherein the first target nucleic acid and the second target nucleic acid are located on the same chromosome; and recombining the first target nucleic acid and the second target nucleic acid with an exogenous oligonucleotide donor template by homologous recombination to produce a chromosomal rearrangement between the first target nucleic acid and the second target nucleic acid.

In one embodiment of the foregoing aspects, the exogenous oligonucleotide donor template comprises any implementation of the isolated oligonucleotide donor template described herein as a "translocation ODN".

In one embodiment, the step of forming the at least one single- or double-strand break at the first cleavage site comprises contacting the cell with an RNA-guided nuclease and at least one gRNA molecule capable of directing the RNA-guided nuclease to the first target nucleic acid. In another embodiment, the step of contacting the cell comprises introducing into the cell a ribonucleoprotein (RNP) complex comprising the RNA-guided nuclease and the at least one gRNA molecule capable of directing the RNA-guided nuclease to the first target nucleic acid. In another embodiment, the step of forming the at least one single- or double-strand break at the second cleavage site comprises contacting the cell with an RNA-guided nuclease and at least one gRNA molecule capable of directing the RNA-guided nuclease to the second target nucleic acid. In another embodiment, the step of contacting the cell comprises introducing into the cell a ribonucleoprotein (RNP) complex comprising the RNA-guided nuclease and the at least one gRNA molecule capable of directing the RNA-guided nuclease to the second target nucleic acid. In another embodiment, the step of recombining the first target nucleic acid and the second target nucleic acid with an exogenous oligonucleotide donor template comprises introducing the exogenous oligonucleotide donor template into the cell. In another embodiment, the step of introducing is performed using electroporation.

In one aspect, the present disclosure provides a method of introducing a chromosomal rearrangement in a cell, comprising: contacting the cell with (i) at least one RNA-guided nuclease, (ii) at least one first gRNA molecule capable of directing the RNA-guided nuclease to a first target nucleic acid located on a first chromosome, (iii) at least one second gRNA molecule capable of directing the RNA-guided nuclease to a second target nucleic acid located on a second chromosome, and (iv) an exogenous oligonucleotide donor template, wherein the RNA-guided nuclease and the at least one first gRNA molecule interact with the first target nucleic acid, resulting in a cleavage event at a first cleavage site in the first target nucleic acid, wherein the first target nucleic acid comprises a centromeric homology arm centromeric to the first cleavage site, and an acentromeric homology arm acentromeric to the first cleavage site; wherein the RNA-guided nuclease and the at least one second gRNA molecule interact with the second target nucleic acid, resulting in a cleavage event at a second cleavage site in the second target nucleic acid, wherein the second target nucleic acid comprises a centromeric homology arm centromeric to the second cleavage site, and an acentromeric homology arm acentromeric to the second cleavage site, wherein the exogenous oligonucleotide donor template comprises, from 5' to 3', A1--$L_N$--B1, wherein A1 is a homology arm that is substantially identical to a homology arm of the first target nucleic acid; L is a nucleotide sequence comprising N nucleotides which links A1 and B1; N is an integer equal to or greater than 0; and B1 is a homology arm that is substantially identical to a homology arm of the second target nucleic acid; and wherein the first target nucleic acid and the second target nucleic acid recombine with the exogenous oligonucleotide donor template by homologous recombination, thereby introducing a chromosomal rearrangement in the cell.

In one embodiment, A1 is substantially identical to the centromeric homology arm of the first target nucleic acid. In another embodiment, A1 is substantially identical to the acentromeric homology arm of the first target nucleic acid. In another embodiment, B1 is substantially identical to the centromeric homology arm of the second target nucleic acid. In another embodiment, B1 is substantially identical to the acentromeric homology arm of the second target nucleic acid.

In another aspect, the disclosure provides a method of introducing an intrachromosomal rearrangement in a cell, comprising contacting the cell with (i) at least one RNA-guided nuclease, (ii) at least one first gRNA molecule capable of directing the RNA-guided nuclease to a first target nucleic acid, (iii) at least one second gRNA molecule capable of directing the RNA-guided nuclease to a second target nucleic acid, wherein the first target nucleic acid and the second target nucleic acid are located on the same chromosome, and (iv) an exogenous oligonucleotide donor template, wherein the RNA-guided nuclease and the at least one first gRNA molecule can interact with the first target nucleic acid, resulting in a cleavage event at a first cleavage site in the first target nucleic acid, and wherein the RNA-guided nuclease and the at least one second gRNA molecule can interact with the second target nucleic acid, resulting in a cleavage event at a second cleavage site in the second target nucleic acid, wherein the exogenous oligonucleotide donor template comprises, from 5' to 3', A1--$L_N$--B1, wherein A1 is a homology arm that is substantially identical to a homology arm of the first target nucleic acid; L is a nucleotide sequence comprising N nucleotides which links A1 and B1; N is an integer equal to or greater than 0; and B1 is a homology arm that is substantially identical to a homology arm of the second target nucleic acid; and wherein the first target nucleic acid and the second target nucleic acid recombine with the exogenous oligonucleotide donor template by homologous recombination, thereby introducing an intrachromosomal rearrangement in the cell.

In one embodiment, the exogenous oligonucleotide donor template comprises any implementation of the isolated oligonucleotide donor template described herein as a "translocation ODN". In another embodiment, the RNA-guided nuclease is a RNA-guided nuclease protein. In another embodiment, the RNA-guided nuclease is a RNA-guided nuclease nucleic acid. In another embodiment, the cell is contacted with the gRNA molecule and the RNA-guided nuclease molecule as a pre-formed complex.

In one embodiment, the RNA-guided nuclease is a Class 2 Clustered Regularly Interspersed Repeat (CRISPR)-associated nuclease. In another embodiment, the RNA-guided nuclease is selected from the group consisting of wild-type Cas9, a Cas9 nickase, a wild-type Cpf1, and a Cpf1 nickase.

In one embodiment, the exogenous oligonucleotide donor template is a ssODN. In another embodiment, the exogenous oligonucleotide donor template is present in a dsODN. In another embodiment, the exogenous oligonucleotide donor template is present in a vector. In another embodiment, the vector is a viral vector. In another embodiment, the viral vector is an AAV vector or a lentiviral vector.

In another aspect, the disclosure provides a cell, or population of cells, comprising a chromosomal rearrangement introduced by any one or more of the methods described herein.

In another aspect, the disclosure provides a cell population comprising cells having engineered modifications at two or more target nucleic acids, wherein the cell population has a translocation frequency of less than 5%. In another embodiment, the translocation frequency is less than 4%. In another embodiment, the translocation frequency is less than 3%. In another embodiment, the translocation frequency is less than 2%. In another embodiment, the translocation frequency is less than 1%. In another embodiment, the translocation frequency is less than 0.5%. In another embodiment, the translocation frequency is less than 0.1%. In one embodiment, the population of cells comprises a translocation frequency that is lower than a translocation frequency of a reference cell population, wherein the reference cell population is altered using RNP complexes comprising the same type of RNA-guided nuclease. The cell population can be produced, in various embodiments, according to any of the methods described herein.

In one embodiment, the disclosure provides methods of using genome editing systems for altering a target nucleic acid in a cell which is isolated from a subject. In some embodiments, the cell is isolated from a subject suffering from a disease or disorder. In one embodiment, the disease or disorder is an eye disease or a liver disease. In another embodiment, the disease or disorder is Duchenne muscular dystrophy. In another embodiment, the disease or disorder is a blood disease, an immune disease, a neurological disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or a pain disorder.

In some embodiments, the methods of the disclosure may be used to alter a cell or population of cells where it is desirable to modify the genome of a cell at more than one target nucleic acid site.

In one embodiment, the method of altering a target nucleic acid in a cell is performed in vitro. In another embodiment, the method of altering a target nucleic acid in a cell is performed ex vivo. In another embodiment, the method of altering a target nucleic acid in a cell is performed in vivo, where the genome editing systems described herein are delivered to a cell or cells or an organ in a subject in need thereof.

In one embodiment, the disclosure provides genome editing systems for altering a target nucleic acid, wherein the first target nucleic acid is the TRAC locus. In another embodiment, the second target nucleic acid is B2M. In another embodiment, the second target nucleic acid is TRBC. In another embodiment, the second target nucleic acid is CIITA.

In one embodiment, the disclosure provides genome editing systems for altering a target nucleic acid, wherein the first target nucleic acid is the B2M locus. In another embodiment, the second target nucleic acid is TRAC. In another embodiment, the second target nucleic acid is TRBC. In another embodiment, the second target nucleic acid is CIITA.

In one embodiment, the disclosure provides genome editing systems for altering a target nucleic acid, wherein the first target nucleic acid is the TRBC locus. In another embodiment, the second target nucleic acid is B2M. In another embodiment, the second target nucleic acid is TRAC. In another embodiment, the second target nucleic acid is CIITA.

In one embodiment, the disclosure provides genome editing systems for altering a target nucleic acid, wherein the first target nucleic acid is the CIITA locus. In another embodiment, the second target nucleic acid is B2M. In another embodiment, the second target nucleic acid is TRBC. In another embodiment, the second target nucleic acid is TRAC.

In one embodiment, the disclosure provides genome editing systems for altering a target nucleic acid, wherein the first target nucleic acid and the second target nucleic acid are different.

In one embodiment, the disclosure provides genome editing systems for altering a cell, wherein the cell is a T cell, an NK cell, an embryonic stem cell, an induced pluripotent stem cell (iPSC), a CD34+ cell, or a hematopoietic stem/progenitor cell (HSPC).

In one embodiment, the method disclosed herein is an in vivo method. In another embodiment, the method disclosed herein is an ex vivo method.

In some embodiments, the methods and genome editing systems of the present disclosure can be used for multiplexing in a cell or a population of cells, e.g., an immune cell or population of cells. In some embodiments, the cell is a T cell, a CD8+ T cell, a CD8+ naïve T cell, a CD4+ central memory T cell, a CD8+ central memory T cell, a CD4+ effector memory T cell, a CD4+ effector memory T cell, a CD4+ T cell, a CD4+ stem cell memory T cell, a CD8+ stem cell memory T cell, a CD4+ helper T cell, a regulatory T cell, a cytotoxic T cell, a natural killer T cell, a CD4+ naïve T cell, a TH17 CD4+ T cell, a TH1 CD4+ T cell, a TH2 CD4+ T cell, a TH9 CD4+ T cell, a CD4+ Foxp3+ T cell, a CD4+ CD25+ CD127− T cell, a CD4+ CD25+ CD127− Foxp3+ T cell, or a population of cells thereof. In some embodiments, the cell is an NK cell, or population of NK cells.

BRIEF DESCRIPTION OF THE DRAWINGS

The accompanying drawings are intended to provide illustrative, and schematic rather than comprehensive, examples of certain aspects and embodiments of the present disclosure. The drawings are not intended to be limiting or binding to any particular theory or model, and are not necessarily to scale. Without limiting the foregoing, nucleic acids and polypeptides may be depicted as linear sequences, or as schematic two- or three-dimensional structures; these depictions are intended to be illustrative rather than limiting or binding to any particular model or theory regarding their structure.

FIG. 2A and FIG. 2B depict exemplary PCR-based methods for detecting chromosomal rearrangements. FIG. 2A depicts the ddPCR method. FIG. 2B depicts the UDITAS method.

FIG. 3A and FIG. 3B depict exemplary optical-based methods for detecting chromosomal rearrangements. FIG. 3A depicts the molecular combing technique. FIG. 3B depicts the Fluorescence In Situ Hybridization (FISH) technique.

FIG. 5A depicts the percentage of cells containing a functional knockout (TCR(−)) following gene editing. FIG. 5B depicts the type of gene editing event that occurred in treated cells.

FIG. 7A depicts the percentage of cells containing a modification at the first target locus (B2M). FIG. 7B depicts the percentage of cells containing a modification at the second target locus (TRAC). FIG. 7C depicts the percentage of cells containing a chromosomal translocation.

FIG. 8A provides the protocol used to generate the cell groups depicted in FIG. 8B. FIG. 8B depicts the percentage of cells undergoing a translocation event when two target loci are edited sequentially or simultaneously.

FIG. 9A-FIG. 9H depict the percentage of cells undergoing a translocation event when two target loci are edited simultaneously using the same type of nuclease (Cas9), or using distinct nucleases (Cas9 and Cpf1). FIG. 9A depicts a first experiment in which primary human T cells were simultaneously nucleofected with (i) an RNP complex containing Cas9 and gRNA targeting TRAC (TRAC5), and an RNP complex containing Cas9 and gRNA targeting B2M (B2M16) (left); or (ii) an RNP complex containing Cpf1 and gRNA targeting TRAC (TRAC5), and an RNP complex containing Cas9 and a gRNA targeting B2M (B2M16) (right). FIG. 9B depicts a second experiment in which primary human T cells were simultaneously nucleofected with (i) an RNP complex containing Cas9 and gRNA targeting TRAC (TRAC5), and an RNP complex containing Cas9 and gRNA targeting B2M (B2M16) (left); or (ii) an RNP complex containing Cpf1 and gRNA targeting TRAC (GWED546), and an RNP complex containing Cpf1 and a gRNA targeting B2M (B2M-Cpf-12) (right). FIG. 9C-H depict the results of additional experiments in which primary human T cells were simultaneously nucleofected with RNP complexes containing Cas9 or Cpf1, as indicated therein.

FIG. 10A and FIG. 10B depict the percentage of cells undergoing a translocation event when two target loci are edited at different concentrations of RNP complex. FIG. 10A depicts the percentage of cells undergoing a translocation event when cells are treated simultaneously with an RNP complex targeting the TRAC locus, and an RNP complex targeting the B2M locus. Cells were contacted with a single concentration of RNP complex targeting TRAC, and with varying concentrations of RNP complex targeting B2M. FIG. 10B depicts the percentage of cells undergoing a translocation event when cells are treated simultaneously with an RNP complex targeting the B2M locus, and an RNP complex targeting the TRAC locus. Cells were contacted with a single concentration of RNP complex targeting B2M, and with varying concentrations of RNP complex targeting TRAC.

FIG. 11A schematically depicts the design of oligonucleotide donor templates which promote formation of balanced, acentric, and dicentric translocation events between chromosome 14 and chromosome 15. FIG. 11B depicts the translocation frequency in cells treated with each of the (+)-strand or a (−)-strand oligonucleotide donor templates depicted in FIG. 11A.

FIG. 13A depicts the percentage of NHEJ at the B2M and TRAC loci, which is measured by UDiTAS™. FIG. 13B depicts translocation frequency that was determined by ddPCR, UDiTAS™ and FISH analysis.

FIGS. 15A and 15B depict the percentages of cells undergoing a translocation event between on and off-target sites. Primary human T cells treated with a RNP complex of Cas9 and a gRNA targeting TRAC (TRAC5) or in cells left untreated (cells only). FIG. 15A depicts NHEJ efficiency that was measured by Illumina sequencing at the TRAC5 on-target site, as well as on two off-target sites: high off target and low off target. FIG. 15B depicts translocation rates which were measured between the on target TRAC5 site and the TRAC5 high off-target site or the TRAC5 low off target site.

FIGS. 16A, 16B and 16C depict the reduction of the percentages of cells undergoing a translocation event with different nuclease combinations. Primary human T cells were simultaneously nucleofected with two RNP complexes each targeting distinct genetic loci. Editing was assessed using Illumina sequencing, and translocation frequency was measured using ddPCR (in samples that had comparable editing efficiencies). FIG. 16A depicts the percentages of the cells undergoing a translocation event in three subsets of cells. In one subset of cells, the first RNP complex at 2.2 µM contains Cas9 and a gRNA targeting TRAC (TRAC5), and the second RNP complex at 2.2 µM contains Cas9 and a gRNA targeting B2M (B2M12). In a second subset of cells, the first RNP complex at 8.7 µM contains the AsCpf1-RR variant and a gRNA targeting TRAC (TRAC140; GTGACAAGTCTGTCTGCCTA; SEQ ID NO:25), and the second RNP complex at 2.2 µM contains Cas9 and a gRNA targeting B2M (B2M12). In a third subset of cells, the first RNP complex at 8.7 µM contains the AsCpf1-RR variant and a gRNA targeting TRAC (TRAC140), and the second RNP complex at 2.2 µM contains AsCpf1-WT and a gRNA targeting B2M-Cpf1-12. FIG. 16B also depicts the percentages of cells undergoing a translocation event in three subsets of cells. In one subset of cells, the first RNP complex at 4.3 µM contains Cas9 and a gRNA targeting TRAC (TRAC5), and the second RNP complex at 4.3 µM contains Cas9 and a gRNA targeting B2M (B2M16). In a second subset of cells, the first RNP complex at 8.7 µM contains the AsCpf1-RR variant and a gRNA targeting TRAC (TRAC140), and the second RNP complex at 4.3 µM contains Cas9 and a gRNA targeting B2M (B2M16). In a third subset of cells, the first RNP complex at 8.7 µM contains the AsCpf1-RR variant and a gRNA targeting TRAC (TRAC140), and the second RNP complex at 2.2 µM contains AsCpf1-WT and a gRNA targeting B2M-Cpf1-12. FIG. 16C again depicts the percentages of the cells undergoing a translocation event in three subsets of cells. In one subset of cells, the first RNP complex at 4.3 µM contains Cas9 and a gRNA targeting TRAC (TRAC5), and the second RNP complex at 4.3 µM contains Cas9 and a gRNA targeting B2M (B2M16). In a second subset of cells, the first RNP complex at 4.3 µM contains the AsCpf1-RR variant and a gRNA targeting B2M (B2M29; GTGGGGGTGAATTCAGTGTA; SEQ ID NO:24), and the second RNP complex at 8.7 µM contains Cas9 and a gRNA targeting TRAC (TRAC5). In a third subset of cells, the first RNP complex at 8.7 µM contains the AsCpf1-RR variant and a gRNA targeting B2M (B2M29), and the second RNP complex at 8.7 µM contains AsCpf1-WT and a gRNA targeting TRAC (GWED546).

DETAILED DESCRIPTION

Definitions and Abbreviations

Figure 1:
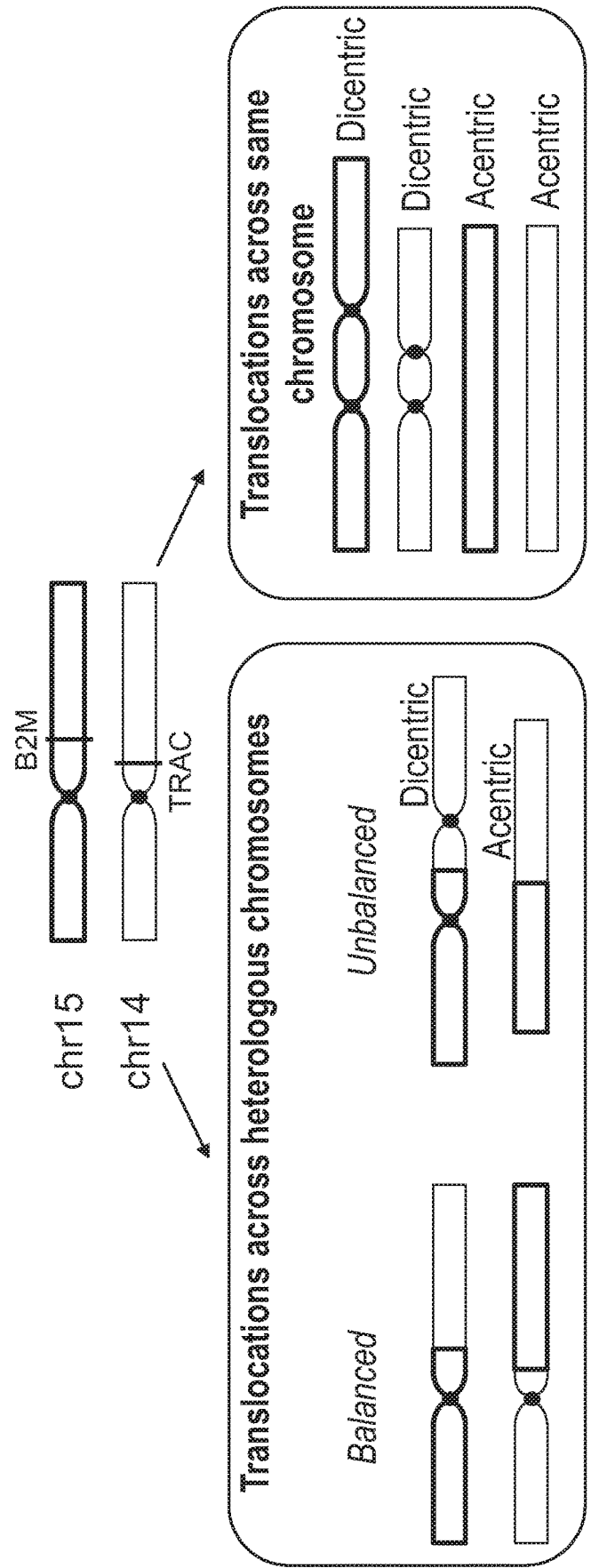
FIG. 1 depicts exemplary outcomes following two simultaneous DSBs on different chromosomes. For illustrative purposes, this figure depicts the simultaneous introduction of Cas9-induced DSBs on two heterologous chromosomes using WT Cas9+TRAC5 gRNA targeting chromosome 14, and WT Cas9+B2M12 gRNA targeting chromosome 15. The resulting heterologous chromosomal translocations can either be balanced or unbalanced. Each Cas9-induced DSB will also give rise to same chromosome translocations, which are obligate unbalanced (dicentric or acentric) rearrangements.

Unless otherwise specified, each of the following terms has the meaning associated with it in this section.

The indefinite articles "a" and "an" refer to at least one of the associated noun, and are used interchangeably with the terms "at least one" and "one or more." For example, "a module" means at least one module, or one or more modules.

The conjunctions "or" and "and/or" are used interchangeably as non-exclusive disjunctions.

The phrase "consisting essentially of" means that the species recited are the predominant species, but that other species may be present in trace amounts or amounts that do not affect structure, function or behavior of the subject composition. For instance, a composition that consists essentially of a particular species will generally comprise 90%, 95%, 96%, or more of that species.

"Domain" is used to describe a segment of a protein or nucleic acid. Unless otherwise indicated, a domain is not required to have any specific functional property.

An "indel" is an insertion and/or deletion in a nucleic acid sequence. An indel may be the product of the repair of a DNA double strand break, such as a double strand break formed by a genome editing system of the present disclosure. An indel is most commonly formed when a break is repaired by an "error prone" repair pathway such as the NHEJ pathway described below.

"Gene conversion" refers to the alteration of a DNA sequence by incorporation of an endogenous homologous sequence (e.g. a homologous sequence within a gene array). "Gene correction" refers to the alteration of a DNA sequence by incorporation of an exogenous homologous sequence, such as an exogenous single- or double stranded donor template DNA. Gene conversion and gene correction are products of the repair of DNA double-strand breaks by HDR pathways such as those described below.

Indels, gene conversion, gene correction, and other genome editing outcomes are typically assessed by sequencing (most commonly by "next-gen" or "sequencing-by-synthesis" methods, though Sanger sequencing may still be used) and are quantified by the relative frequency of numerical changes (e.g., ±1, ±2 or more bases) at a site of interest among all sequencing reads. DNA samples for sequencing may be prepared by a variety of methods known in the art, and may involve the amplification of sites of interest by polymerase chain reaction (PCR), the capture of DNA ends generated by double strand breaks, as in the GUIDEseq process described in Tsai et al. (Nat. Biotechnol. 34(5): 483 (2016), incorporated by reference herein) or by other means well known in the art. Genome editing outcomes may also be assessed by in situ hybridization methods such as the FiberComb™ system commercialized by Genomic Vision (Bagneux, France), and by any other suitable methods known in the art.

"Alt-HDR," "alternative homology-directed repair," or "alternative HDR" are used interchangeably to refer to the process of repairing DNA damage using a homologous nucleic acid (e.g., an endogenous homologous sequence, e.g., a sister chromatid, or an exogenous nucleic acid, e.g., a template nucleic acid). Alt-HDR is distinct from canonical HDR in that the process utilizes different pathways from canonical HDR, and can be inhibited by the canonical HDR mediators, RAD51 and BRCA2. Alt-HDR is also distinguished by the involvement of a single-stranded or nicked homologous nucleic acid template, whereas canonical HDR generally involves a double-stranded homologous template.

"Canonical HDR," "canonical homology-directed repair" or "cHDR" refer to the process of repairing DNA damage using a homologous nucleic acid (e.g., an endogenous homologous sequence, e.g., a sister chromatid, or an exogenous nucleic acid, e.g., a template nucleic acid). Canonical HDR typically acts when there has been significant resection at the double strand break, forming at least one single stranded portion of DNA. In a normal cell, cHDR typically involves a series of steps such as recognition of the break, stabilization of the break, resection, stabilization of single stranded DNA, formation of a DNA crossover intermediate, resolution of the crossover intermediate, and ligation. The process requires RAD51 and BRCA2, and the homologous nucleic acid is typically double-stranded.

Unless indicated otherwise, the term "HDR" as used herein encompasses both canonical HDR and alt-HDR.

"Non-homologous end joining" or "NHEJ" refers to ligation mediated repair and/or non-template mediated repair including canonical NHEJ (cNHEJ) and alternative NHEJ (altNHEJ), which in turn includes microhomology-mediated end joining (MMEJ), single-strand annealing (SSA), and synthesis-dependent microhomology-mediated end joining (SD-MMEJ).

"Replacement" or "replaced," when used with reference to a modification of a molecule (e.g. a nucleic acid or protein), does not require a process limitation but merely indicates that the replacement entity is present.

"Subject" means a human or non-human animal. A human subject can be any age (e.g., an infant, child, young adult, or adult), and may suffer from a disease, or may be in need of alteration of a gene or a combination of specific genes. Alternatively, the subject may be an animal, which term includes, but is not limited to, mammals, birds, fish, reptiles, amphibians, and more particularly non-human primates, rodents (such as mice, rats, hamsters, etc.), rabbits, guinea pigs, dogs, cats, and so on. In certain embodiments of this disclosure, the subject is livestock, e.g., a cow, a horse, a sheep, or a goat. In certain embodiments, the subject is poultry.

"Treat," "treating," and "treatment" mean the treatment of a disease in a subject (e.g., a human subject), including one or more of inhibiting the disease, i.e., arresting or preventing its development or progression; relieving the disease, i.e., causing regression of the disease state; relieving one or more symptoms of the disease; and curing the disease.

"Prevent," "preventing," and "prevention" refer to the prevention of a disease in a mammal, e.g., in a human, including (a) avoiding or precluding the disease; (b) affecting the predisposition toward the disease; or (c) preventing or delaying the onset of at least one symptom of the disease.

A "Kit" refers to any collection of two or more components that together constitute a functional unit that can be employed for a specific purpose. By way of illustration (and not limitation), one kit according to this disclosure can include a guide RNA complexed or able to complex with an RNA-guided nuclease, and accompanied by (e.g. suspended in, or suspendable in) a pharmaceutically acceptable carrier. The kit can be used to introduce the complex into, for example, a cell or a subject, for the purpose of causing a desired genomic alteration in such cell or subject. The components of a kit can be packaged together, or they may be separately packaged. Kits according to this disclosure also optionally include directions for use (DFU) that describe the use of the kit e.g., according to a method of this disclosure. The DFU can be physically packaged with the kit, or it can be made available to a user of the kit, for instance by electronic means.

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides, nucleotide sequences, nucleic acids etc. can be chimeric mixtures or derivatives or modified versions thereof, single-stranded or double-stranded. They can be modified at the base moiety, sugar moiety, or phosphate backbone, for example, to improve stability of the molecule, its hybridization parameters, etc. A nucleotide sequence typically carries genetic information, including, but not limited to, the information used by cellular machinery to make proteins and enzymes. These terms include double- or single-stranded genomic DNA, RNA, any synthetic and genetically manipulated polynucleotide, and both sense and antisense polynucleotides. These terms also include nucleic acids containing modified bases.

Conventional IUPAC notation is used in nucleotide sequences presented herein, as shown in Table 1, below (see also Cornish-Bowden A, Nucleic Acids Res. 1985 May 10; 13(9):3021-30, incorporated by reference herein). It should be noted, however, that "T" denotes "Thymine or Uracil" in those instances where a sequence may be encoded by either DNA or RNA, for example in gRNA targeting domains.

TABLE 1

IUPAC nucleic acid notation

| Character | Base |
|---|---|
| A | Adenine |
| T | Thymine or Uracil |
| G | Guanine |
| C | Cytosine |
| U | Uracil |
| K | G or T/U |
| M | A or C |
| R | A or G |
| Y | C or T/U |
| S | C or G |
| W | A or T/U |
| B | C, G or T/U |
| V | A, C or G |
| H | A, C or T/U |
| D | A, G or T/U |
| N | A, C, G or T/U |

The terms "protein," "peptide" and "polypeptide" are used interchangeably to refer to a sequential chain of amino acids linked together via peptide bonds. The terms include individual proteins, groups or complexes of proteins that associate together, as well as fragments or portions, variants, derivatives and analogs of such proteins. Peptide sequences are presented herein using conventional notation, beginning with the amino or N-terminus on the left, and proceeding to the carboxyl or C-terminus on the right. Standard one-letter or three-letter abbreviations can be used.

The term "variant" refers to an entity such as a polypeptide, polynucleotide or small molecule that shows significant structural identity with a reference entity but differs structurally from the reference entity in the presence or level of one or more chemical moieties as compared with the reference entity. In many embodiments, a variant also differs functionally from its reference entity. In general, whether a particular entity is properly considered to be a "variant" of a reference entity is based on its degree of structural identity with the reference entity.

The terms "RNA-guided nuclease" and "RNA-guided nuclease molecule" are used interexchangably herein. In some embodiments, the RNA-guided nuclease is a RNA-guided DNA endonuclease enzyme. In some embodiments, the RNA-guided nuclease is a CRISPR nuclease. Examples of RNA-guided nucleases are listed in Table 2 below, and the methods and compositions disclosed herein can use any combination of RNA-guided nucleases disclosed herein, or known to those of ordinary skill in the art.

TABLE 2

RNA-Guided Nucleases

| Nuclease | Length (a.a.) | PAM | Reference |
|---|---|---|---|
| SpCas9 | 1368 | NGG | Cong et al., Science. 2013; 339(6121): 819-23 |
| SaCas9 | 1053 | NNGRRT | Ran et al., Nature. 2015; 520(7546): 186-91. |
| (KKH) SaCas9 | 1067 | NNNRRT | Kleinstiver et al., Nat Biotechnol. 2015; 33(12): 1293-1298 |
| AsCpf1 (AsCas12a) | 1353 | TTTV | Zetsche et al., Nat Biotechnol. 2017; 35(1): 31-34. |
| LbCpf1 (LbCas12a) | 1274 | TTTV | Zetsche et al., Cell. 2015; 163(3): 759-71. |
| CasX | 980 | TTC | Burstein et al., Nature. 2017; 542(7640): 237-241. |
| CasY | 1200 | TA | Burstein et al., Nature. 2017; 542(7640): 237-241. |
| Cas12h1 | 870 | RTR | Yan et al., Science. 2019; 363(6422): 88-91. |
| Cas12i1 | 1093 | TTN | Yan et al., Science. 2019; 363(6422): 88-91. |
| Cas12c1 | unknown | TG | Yan et al., Science. 2019; 363(6422): 88-91. |
| Cas12c2 | unknown | TN | Yan et al., Science. 2019; 363(6422): 88-91. |
| eSpCas9 | 1423 | NGG | Chen et al., Nature. 2017; 550(7676): 407-410. |
| Cas9-HF1 | 1367 | NGG | Chen et al., Nature. 2017; 550(7676): 407-410. |
| HypaCas9 | 1404 | NGG | Chen et al., Nature. 2017; 550(7676): 407-410. |
| dCas9-Fok1 | 1623 | NGG | U.S. Pat. No. 9,322,037 |
| Sniper-Cas9 | 1389 | NGG | Lee et al., Nat Commun. 2018; 9(1): 3048. |
| xCas9 | 1786 | NGG, NG, GAA, GAT | Wang et al., Plant Biotechnol J. 2018; pbi.13053. |
| AaCas12b | 1129 | TTN | Teng et al. Cell Discov. 2018; 4: 63. |
| evoCas9 | 1423 | NGG | Casini et al., Nat Biotechnol. 2018; 36(3): 265-271. |
| SpCas9-NG | 1423 | NG | Nishimasu et al., Science. 2018; 361(6408): 1259-1262. |
| VRQR | 1368 | NGA | Li et al., The CRISPR Journal, 2018; 01:01 |
| VRER | 1372 | NGCG | Kleinstiver et al., Nature. 2016; 529(7587): 490-5. |
| NmeCas9 | 1082 | NNNNGATT | Amrani et al., Genome Biol. 2018; 19(1): 214. |
| CjCas9 | 984 | NNNNRYAC | Kim et al., Nat Commun. 2017; 8: 14500. |
| BhCas12b | 1108 | ATTN | Strecker et al., Nat Commun. 2019 Jan. 22; 10(1): 212. |
| BhCas12b V4 | 1108 | ATTN | Strecker et al., Nat Commun. 2019 Jan. 22; 10(1): 212. |

In one embodiment, the RNA-guided nuclease is a *Acidaminococcus* sp. Cpf1 RR variant (AsCpf1-RR). In another embodiment, the RNA-guided nuclease is a Cpf1 RVR variant.

In some embodiments, the first enzyme, or variant thereof, cleaves a DNA target, and the second enzyme, or variant thereof, cleaves a DNA target. In other embodiments, the first enzyme, or variant thereof, cleaves an RNA target, and the second enzyme, or variant thereof, cleaves an RNA target. In some embodiments, the first enzyme, or variant thereof, cleaves a DNA target, or is a variant thereof and the second enzyme, or variant thereof, cleaves an RNA target or is a variant thereof. In other embodiments, the first enzyme cleaves an RNA target, or is a variant thereof, and the second enzyme cleaves a DNA target, or is a variant thereof.

In yet other embodiments, the first enzyme mediates a single strand cleavage, or is a variant thereof or mediates a double strand cleavage or is a variant thereof. In still other embodiments, the second enzyme mediates a single strand cleavage, or is a variant thereof or mediates a double strand cleavage, or is a variant thereof. In still other embodiments, the first enzyme mediates a double strand cleavage, or is a variant thereof and the second enzyme mediates a single strand cleavage, or is a variant thereof. In another embodiment, the first enzyme mediates a double strand cleavage or is a variant thereof, and the second enzyme mediates a single strand cleavage, or is a variant thereof. In various embodiments, the first and/or second enzymes may be delivered in the form of an RNP complex to a cell, simultaneously or sequentially, using suitable means in the form of an RNP complex.

In one embodiment, the first enzyme is SpCas9. In another embodiment, the first enzyme is SaCas9. In another embodiment, the first enzyme is (KKH) SaCas9. In another embodiment, the first enzyme is AsCpf1 (AsCas12a). In another embodiment, the first enzyme is LbCpf1 (LbCas12a). In another embodiment, the first enzyme is CasX. In another embodiment, the first enzyme is CasY. In another embodiment, the first enzyme is Cas12h1. In another embodiment, the first enzyme is Cas12i1. In another embodiment, the first enzyme is Cas12c1. In another embodiment, the first enzyme is Cas12c2. In another embodiment, the first enzyme is eSpCas9. In another embodiment, the first enzyme is Cas9-HF1. In another embodiment, the first enzyme is HypaCas9. In another embodiment, the first enzyme is dCas9-Fok1. In another embodiment, the first enzyme is Sniper-Cas9. In another embodiment, the first enzyme is xCas9. In another embodiment, the first enzyme is AaCas12b. In another embodiment, the first enzyme is evoCas9. In another embodiment, the first enzyme is SpCas9-NG. In another embodiment, the first enzyme is VRQR. In another embodiment, the first enzyme is VRER. In another embodiment, the first enzyme is NmeCas9. In another embodiment, the first enzyme is CjCas9. In another embodiment, the first enzyme is BhCas12b. In another embodiment, the first enzyme is BhCas12b V4.

In one embodiment, the second enzyme is SpCas9. In another embodiment, the second enzyme is SaCas9. In another embodiment, the second enzyme is (KKH) SaCas9. In another embodiment, the second enzyme is AsCpf1 (AsCas12a). In another embodiment, the second enzyme is LbCpf1 (LbCas12a). In another embodiment, the second enzyme is CasX. In another embodiment, the second enzyme is CasY. In another embodiment, the second enzyme is Cas12h1. In another embodiment, the second enzyme is Cas12i1. In another embodiment, the second enzyme is Cas12c1. In another embodiment, the second enzyme is Cas12c2. In another embodiment, the second enzyme is eSpCas9. In another embodiment, the second enzyme is Cas9-HF1. In another embodiment, the second enzyme is HypaCas9. In another embodiment, the second enzyme is dCas9-Fok1. In another embodiment, the second enzyme is Sniper-Cas9. In another embodiment, the second enzyme is xCas9. In another embodiment, the second enzyme is AaCas12b. In another embodiment, the second enzyme is evoCas9. In another embodiment, the second enzyme is SpCas9-NG. In another embodiment, the second enzyme is VRQR. In another embodiment, the second enzyme is VRER. In another embodiment, the second enzyme is NmeCas9. In another embodiment, the second enzyme is CjCas9. In another embodiment, the second enzyme is BhCas12b. In another embodiment, the second enzyme is BhCas12b V4.

Overview

Provided herein are systems and methods for modulating the formation of chromosomal rearrangements, e.g., translocations, in the context of genome editing.

Chromosomal Rearrangements

Chromosomal rearrangements are side products of DSBs, including Cas9-induced DSBs. In the context of genome editing, chromosomal rearrangements derive from the joining of free DNA ends created by desired DSBs, e.g., Cas9-induced on-target DSBs, to other DSBs in the genome, e.g., spontaneous DSBs due to metabolic activity of a cell, Cas9-induced off-target DSBs, etc. Chromosomal rearrangements can also occur when multiplexing, by the joining of a first Cas9-induced DSB to a second Cas9-induced DSB at a second location in the genome. FIG. 1 illustrates the rearrangement products that can occur when two DSBs occur on heterologous chromosomes. Rearrangement products that can occur across heterologous chromosomes include balanced translocations, in which the chromosomal arms are swapped, and unbalanced translocations, which lead to the formation of dicentric and acentric chromosomes. In addition to the foregoing heterologous chromosomal translocations, each individual Cas9-induced DSB also leads to the formation of "same chromosome" translocations, which are obligate unbalanced rearrangements. Such "same chromosome" translocations can result from fusion between homologous chromosomes, or between sister chromatids during replication.

Strategies are provided herein for modulating the formation of chromosomal rearrangements, including same chromosome translocations and heterologous chromosomal translocations. In general, a chromosomal rearrangement frequency of about 5-10% is seen under standard conditions when editing two or more nucleic acid sequences in parallel. It is generally desirable to reduce the frequency of occurrence of chromosomal rearrangements during genome editing, particularly when multiplexing, to mitigate disruptions to genomic integrity in edited cells. In other embodiments, it can be desirable enhance the formation of chromosomal rearrangements during genome editing, in order to better study the functional consequences resulting from the rearrangements. Thus, strategies for increasing or decreasing the frequency of chromosomal rearrangements are provided herein. In particular embodiments, the strategies provided herein can modulate the formation of chromosomal rearrangements by modulating the DNA repair pathway implicated during DSB repair, and/or modulating the kinetics of the DSB cut/repair reaction.

Strategies for Modulating Chromosomal Rearrangements

As demonstrated herein, translocation frequency is increased when DSBs are repaired through NHEJ, and is decreased when DSBs are repaired through HDR. Without wishing to be bound by theory, the mechanism of HDR-mediated gene correction may capture and sequester free DNA ends created by DSBs. Thus, free DNA ends engaged in a HDR-mediated repair process are unavailable to participate in chromosomal rearrangements. Accordingly, strategies to shift the predominance of the repair pathway toward HDR and away from NHEJ can reduce the translocation frequency in edited cells.

In addition, as demonstrated herein, translocation frequency is increased by the simultaneous co-occurrence of DSBs in different chromosomes in the same cell. Thus, strategies that minimize the co-occurrence of DSBs in different target genes can reduce the translocation frequency in edited cells.

Strategies described herein for reducing the frequency of chromosomal rearrangements include, for example, (i) editing one or more target nucleic acids in the presence of an oligonucleotide donor template containing a stop codon; (ii) reducing the concentration of nuclease, gRNA and/or RNP complex used to target one or multiple target nucleic acids, (iii) varying the type of DNA ends created by cleavage events introduced in multiple target nucleic acids, such that each target nucleic acid has free DNA ends that are not compatible for NHEJ, (iv) varying the timing of the cleavage events occurring in multiple target nucleic acids, such that the cleavage events do not occur simultaneously, (v) varying the type of nuclease used to generate a cleavage event in multiple target nucleic acids, and/or (vi) varying the nuclease implementation (e.g., RNP complex and exogenous nucleic acid encoding a nuclease) used to generate a cleavage event in multiple target nucleic acids, as described herein. In some embodiments, any one or more of the foregoing strategies may be used in combination to reduce the translocation frequency during genome editing.

The disclosure provides, in some embodiments, a cell, or population of cells, comprising engineered modifications introduced using one or more of the foregoing strategies. In one embodiment, the disclosure provides a cell, or population of cells, having engineered modifications at two or more target nucleic acids, wherein the cell population has a reduced translocation frequency. In one embodiment, the translocation frequency of the cell population is reduced relative to the translocation frequency in a population of cells that was engineered without use of the foregoing strategies. In one embodiment, the disclosure provides a cell population having engineered modifications at two or more (e.g., 2, 3, 4, 5, 6, 7, 8, 9, 10 or more) target nucleic acids, wherein fewer than 10% (e.g., fewer than 10%, fewer than 9%, fewer than 8%, fewer than 7%, fewer than 6%, fewer than 5%, fewer than 4%, fewer than 3%, fewer than 2%, fewer than 1%, fewer than 0.75%, fewer than 0.5%, fewer than 0.25%, fewer than 0.1%, or less) of cells in the cell population contain a translocation. In one embodiment, the disclosure provides a cell population having engineered modifications at two or more target nucleic acids, wherein fewer than 1% of cells in the cell population contain a translocation. In one embodiment, the cell population is not a clonal cell population. Thus, in one embodiment, the cell population is not derived from a single cell clone isolated following introduction of the engineered modifications. In another embodiment, the cell population having engineered modifications at two or more target nucleic acids is not sorted or otherwise purified on the basis of a translocation phenotype and/or genotype.

Strategies for modulating the formation of chromosomal rearrangements are described in detail below.

(A) Oligonucleotide Donor Templates for Gene Disruption (i) STOP Oligonucleotide Donor Template Altering a target nucleic acid in the presence of a donor template containing one or more stop codons is one strategy for modulating repair pathway selection toward HDR, thereby preventing NHEJ-mediated translocation formation. Such a strategy can be particularly useful in situations where, for example, the desired outcome of gene editing is functional knockout of the target nucleic acid. The presence of a stop codon in the donor template can result in functional knockout of the target nucleic acid when HDR-mediated gene correction uses the donor template to incorporate the stop codon into the coding region of the target nucleic acid. A DNA oligodeoxynucleotide (ODN) donor template comprising one or more stop codons is referred to herein as a "STOP ODN". The STOP ODN can be single-stranded (ssODN) or double stranded (dsODN), and can be used to facilitate HDR-based repair of a double-stranded break.

In addition to reducing translocation frequency, the STOP ODN allows functional editing to be achieved at lower concentrations of gRNA and/or RNA-guided nuclease, relative to cells edited in the absence of a donor template containing one or more stop codon(s). For example, functional editing can be achieved at lower concentrations of RNP complex in cells contacted with the STOP ODN, relative to the concentration of RNP complex required to achieve functional editing in the absence of the STOP ODN.

Accordingly, in one aspect, the disclosure provides an isolated oligonucleotide donor template that comprises one or more stop codons. The isolated oligonucleotide donor template can comprise, from 5' to 3', the elements A1--$S_N$--A2, wherein A1 is a homology arm that is substantially identical to a first homology arm of a target nucleic acid, S is a stop codon, N is equal to or greater than 1, and A2 is a homology arm that is substantially identical to a second homology arm of the target nucleic acid. The stop codon can be any sequence of three nucleotides that signals termination of translation during protein synthesis. For example, the stop codon can comprise the sequence TAG, TAA, or TGA. In one embodiment, the oligonucleotide donor template contains one stop codon (e.g., TAG, TAA, or TGA). In another embodiment, the oligonucleotide donor template contains more than one stop codon. In embodiments where the oligonucleotide donor template contains more than one stop codon (i.e., where N is greater than 1), the same stop codon, or a combination of different stop codons, can be used. In one embodiment, the stop codon is TAG. In another embodiment, the stop codon is TAA. In another embodiment, the stop codon is TGA. In another embodiment, the oligonucleotide donor template comprises TAG, TAA, TGA, or a combination or subcombination thereof, e.g., TAG and TAA, TAG and TGA, TAA and TGA, or TAG, TAA, and TGA. In one embodiment, the stop codon is the reverse complement of TAG, TAA, or TGA, i.e., CTA, TTA, or TCA. In exemplary embodiments, the oligonucleotide donor template can contain 1-50 stop codons, i.e., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 stop codons, or ranges encompassed therein, for example, 2-5 stop codons, 5-10 stop codons, 10-20 stop codons, 20-50 stop codons, etc. In one embodiment, the donor template contains 1 stop codon. In another embodiment, the donor template contains 2 stop codons. In another embodiment, the donor template contains 3 stop codons. In another embodiment, the donor template contains 4 stop codons. In another embodiment, the donor template contains 5 stop codons. In another embodiment, the donor template contains 6 stop codons. In another embodiment, the donor template contains 7 stop codons. In another embodiment, the donor template contains 8 stop codons. In another embodiment, the donor template contains 9 stop codons. In another embodiment, the donor template contains 10 stop codons.

The isolated oligonucleotide donor template can be implemented in any form suitable for genome editing, including without limitation single stranded or double stranded DNA, linear or circular, naked or comprised within a vector, and/or associated, covalently or non-covalently (e.g., by direct hybridization or splint hybridization) with a guide RNA. In some embodiments, the donor template is a ssODN. Where a linear ssODN is used, it can be configured to (i) anneal to a nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, or no more than 150-200 nucleotides (e.g., 150, 160, 170, 180, 190, or 200 nucleotides). In other embodiments, the donor template is a dsODN. In one embodiment, the donor template comprises a first strand. In another embodiment, a donor template comprises a first strand and a second strand. In some embodiments, a donor template is an exogenous oligonucleotide, e.g., an oligonucleotide that is not naturally present in a cell. In embodiments, the donor template is present in a vector, for example, a plasmid vector or a viral vector. In one embodiment, the donor template is present in an adenoviral vector, an adeno-associated virus (AAV) vector, or a lentiviral vector.

The isolated oligonucleotide donor template can contain one or more regions that are homologous to regions of DNA, e.g., a target nucleic acid, within or near (e.g., flanking or adjoining) a target sequence to be cleaved, e.g., the cleavage site. These homologous regions are referred to herein as "homology arms," and are illustrated schematically below:

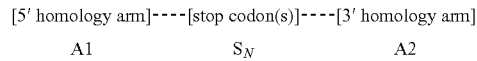

The homology arms of the oligonucleotide donor templates described herein may be of any suitable length, provided such length is sufficient to allow efficient resolution of a cleavage site on a targeted nucleic acid by a DNA repair process requiring a donor template. In some embodiments, where amplification by, e.g., PCR, of the homology arm is desired, the homology arm is of a length such that the amplification may be performed. In some embodiments, where sequencing of the homology arm is desired, the homology arm is of a length such that the sequencing may be performed.

In some embodiments, the 5' homology arm is between 50 to 250 nucleotides in length. In some embodiments, the 5' homology arm is 700 nucleotides or less in length. In some embodiments, the 5' homology arm is 650 nucleotides or less in length. In some embodiments, the 5' homology arm is 600 nucleotides or less in length. In some embodiments, the 5' homology arm is 550 nucleotides or less in length. In some embodiments, the 5' homology arm is 500 nucleotides or less in length. In some embodiments, the 5' homology arm is 400 nucleotides or less in length. In some embodiments, the 5' homology arm is 300 nucleotides or less in length. In some embodiments, the 5' homology arm is 250 nucleotides or less in length. In some embodiments, the 5' homology arm is 200 nucleotides or less in length. In some embodiments, the 5' homology arm is 150 nucleotides or less in length. In some embodiments, the 5' homology arm is 100 nucleotides or less in length. In some embodiments, the 5' homology arm is 50 nucleotides in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 5' homology arm is at least 20 nucleotides in length. In some embodiments, the 5' homology arm is at least 40 nucleotides in length. In some embodiments, the 5' homology arm is at least 50 nucleotides in length. In some embodiments, the 5' homology arm is at least 70 nucleotides in length. In some embodiments, the 5' homology arm is 20 nucleotides in length. In some embodiments, the 5' homology arm is 40 nucleotides in length. In some embodiments, the 5' homology arm is 50 nucleotides in length. In some embodiments, the 5' homology arm is 70 nucleotides in length.

In some embodiments, the 3' homology arm is between 50 to 250 nucleotides in length. In some embodiments, the 3' homology arm is 700 nucleotides or less in length. In some embodiments, the 3' homology arm is 650 nucleotides or less in length. In some embodiments, the 3' homology arm is 600 nucleotides or less in length. In some embodiments, the 3' homology arm is 550 nucleotides or less in length. In some embodiments, the 3' homology arm is 500 nucleotides or less in length. In some embodiments, the 3' homology arm is 400 nucleotides or less in length. In some embodiments, the 3' homology arm is 300 nucleotides or less in length. In some embodiments, the 3' homology arm is 250 nucleotides or less in length. In some embodiments, the 3' homology arm is 200 nucleotides in length or less. In some embodiments, the 3' homology arm is 150 nucleotides in length or less. In some embodiments, the 3' homology arm is 100 nucleotides in length or less. In some embodiments, the 3' homology arm is 50 nucleotides in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 3' homology arm is at least 20 nucleotides in length. In some embodiments, the 3' homology arm is at least 40 nucleotides in length. In some embodiments, the 3' homology arm is at least 50 nucleotides in length. In some embodiments, the 3' homology arm is at least 70 nucleotides in length. In some embodiments, the 3' homology arm is 20 nucleotides in length. In some embodiments, the 3' homology arm is 40 nucleotides in length. In some embodiments, the 3' homology arm is 50 nucleotides in length. In some embodiments, the 3' homology arm is 70 nucleotides in length.

In some embodiments, the 5' homology arm is between 50 to 250 base pairs in length. In some embodiments, the 5' homology arm is 700 base pairs or less in length. In some embodiments, the 5' homology arm is 650 base pairs or less in length. In some embodiments, the 5' homology arm is 600 base pairs or less in length. In some embodiments, the 5' homology arm is 550 base pairs or less in length. In some embodiments, the 5' homology arm is 500 base pairs or less in length. In some embodiments, the 5' homology arm is 400 base pairs or less in length. In some embodiments, the 5' homology arm is 300 base pairs or less in length. In some embodiments, the 5' homology arm is 250 base pairs or less in length. In some embodiments, the 5' homology arm is 200 base pairs or less in length. In some embodiments, the 5' homology arm is 150 base pairs or less in length. In some embodiments, the 5' homology arm is 100 base pairs or less in length. In some embodiments, the 5' homology arm is 50 base pairs in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs in length. In some embodiments, the 5' homology arm is at least 20 base pairs in length. In some embodiments, the 5' homology arm is at least 40 base pairs in length. In some embodiments, the 5' homology arm is at least 50 base pairs in length. In some embodiments, the 5' homology arm is at least 70 base pairs in length. In some embodiments, the 5' homology arm is 20 base pairs in length. In some embodiments, the 5' homology arm is 40 base pairs in length. In some embodiments, the 5' homology arm is 50 base pairs in length. In some embodiments, the 5' homology arm is 70 base pairs in length.

In some embodiments, the 3' homology arm is between 50 to 250 base pairs in length. In some embodiments, the 3' homology arm is 700 base pairs or less in length. In some embodiments, the 3' homology arm is 650 base pairs or less in length. In some embodiments, the 3' homology arm is 600 base pairs or less in length. In some embodiments, the 3' homology arm is 550 base pairs or less in length. In some embodiments, the 3' homology arm is 500 base pairs or less in length. In some embodiments, the 3' homology arm is 400 base pairs or less in length. In some embodiments, the 3' homology arm is 300 base pairs or less in length. In some embodiments, the 3' homology arm is 250 base pairs or less in length. In some embodiments, the 3' homology arm is 200 base pairs in length or less. In some embodiments, the 3' homology arm is 150 base pairs in length or less. In some embodiments, the 3' homology arm is 100 base pairs in length or less. In some embodiments, the 3' homology arm is 50 base pairs in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs in length. In some embodiments, the 3' homology arm is at least 20 base pairs in length. In some embodiments, the 3' homology arm is at least 40 base pairs in length. In some embodiments, the 3' homology arm is at least 50 base pairs in length. In some embodiments, the 3' homology arm is at least 70 base pairs in length. In some embodiments, the 3' homology arm is 20 base pairs in length. In some embodiments, the 3' homology arm is 40 base pairs in length. In some embodiments, the 3' homology arm is 50 base pairs in length. In some embodiments, the 3' homology arm is 70 base pairs in length.

The 5' and 3' homology arms can be of the same length or can differ in length. In some embodiments, the 5' and 3' homology arms are amplified to allow for the quantitative assessment of gene editing events, such as targeted integration, at a target nucleic acid. In some embodiments, the quantitative assessment of the gene editing events may rely on the amplification of both the 5' junction and 3' junction at the site of targeted integration by amplifying the whole or a part of the homology arm using a single pair of PCR primers in a single amplification reaction. Accordingly, although the length of the 5' and 3' homology arms may differ, the length of each homology arm can be capable of amplification (e.g., using PCR), if desired. Moreover, when amplification of both the 5' and 3' homology arms in a single PCR reaction is desired, the length between the 5' and 3' homology arms can be selected to allow for PCR amplification using a single pair of PCR primers.

In some embodiments, the length of the 5' and 3' homology arms does not differ by more than 75 nucleotides. Thus, in some embodiments, when the 5' and 3' homology arms differ in length, the length difference between the homology arms is less than 70, 60, 50, 40, 30, 20, 10, 9, 8, 7, 6, 5, 4, 3, 2, or 1 nucleotides or base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides. In some embodiments, the length difference between the 5' and 3' homology arms is less than 70, 60, 50, 40, 30, 20, 10, 9, 8, 7, 6, 5, 4, 3, 2, or 1 base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 base pairs.

In one embodiment, the homology arms of the oligonucleotide donor template are of approximately equal length. For example, the length of the 5' homology arm can be 80%, 85%, 90%, 95%, 97%, 99%, or 100% as long as the 3' homology arm, or the length of the 3' homology arm can be 80%, 85%, 90%, 95%, 97%, 99%, or 100% as long as the 5' homology arm. In one embodiment, the homology arms of the oligonucleotide donor template are of equal length.

In one embodiment, the homology arms of the oligonucleotide donor template are substantially identical to the homology arms of the target nucleic acid. For example, where the oligonucleotide donor template contains two homology arms flanking the stop codon, one homology arm can be substantially identical to a first homology arm of the target nucleic acid, and the second homology arm can be substantially identical to a second homology arm of the target nucleic acid.

In one embodiment, a homology arm of the oligonucleotide donor template can contain sufficient identity to the target nucleic acid to allow the homology arm of the oligonucleotide donor template to hybridize to the complementary strand of the homology arm in the target nucleic acid in the target cell. In one embodiment, the sequence of the first homology arm of the oligonucleotide donor template is at least about 65% identical to the first homology arm of the target nucleic acid. For example, in one embodiment, the first homology arm of the oligonucleotide donor template is at least about 65%, 70%, 75%, 80%, 85%, 90%, 95%, 97%, 98%, 99%, or 100% identical to the first homology arm of the target nucleic acid. In one embodiment, the first homology arm of the oligonucleotide donor template is at least about 90% identical to the first homology arm of the target nucleic acid. In another embodiment, the first homology arm of the oligonucleotide donor template is at least about 95% identical to the first homology arm of the target nucleic acid. In another embodiment, the first homology arm of the oligonucleotide donor template is at least about 99% identical to the first homology arm of the target nucleic acid. In another embodiment, the first homology arm of the oligonucleotide donor template is 100% identical to the first homology arm of the target nucleic acid. In some embodiments, the first homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides from the first homology arm of the target nucleic acid. In some embodiments the first homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from the first homology arm of the target nucleic acid.

In another embodiment, the sequence of the second homology arm of the oligonucleotide donor template is at least about 65% identical to the second homology arm of the target nucleic acid. For example, in one embodiment, the second homology arm of the oligonucleotide donor template is at least about 65%, 70%, 75%, 80%, 85%, 90%, 95%, 97%, 98%, 99%, or 100% identical to the second homology arm of the target nucleic acid. In one embodiment, the second homology arm of the oligonucleotide donor template is at least about 90% identical to the second homology arm of the target nucleic acid. In another embodiment, the second homology arm of the oligonucleotide donor template is at least about 95% identical to the second homology arm of the target nucleic acid. In another embodiment, the second homology arm of the oligonucleotide donor template is at least about 99% identical to the second homology arm of the target nucleic acid. In another embodiment, the second homology arm of the oligonucleotide donor template is 100% identical to the second homology arm of the target nucleic acid. In some embodiments, the second homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides from the second homology arm of the target nucleic acid. In some embodiments the second homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from the second homology arm of the target nucleic acid.

An oligonucleotide donor template comprising the foregoing elements can direct insertion of the one or more stop codon(s) at the region of the target nucleic acid between the two homology arms.

The oligonucleotide donor template can optionally contain an intervening or linker sequence between the one or more stop codon(s) and the homology arms. The linker sequence is a sequence that is not part of a stop codon, and which does not have substantial identity to the homology arms of the target nucleic acid. In one embodiment, the oligonucleotide donor template contains a linker sequence between the 5' homology arm and the one or more stop codons. In one embodiment, the oligonucleotide donor template contains a linker sequence between the one or more stop codons and the 3' homology arm. In one embodiment, the oligonucleotide donor template contains a linker sequence between multiple stop codons. In some embodiments, an intervening or linker sequence can be present in an isolated oligonucleotide donor template in the following configuration, from 5' to 3': A1--$L_{x1}$--$S_N$-$L_{x2}$--A2, wherein A1 is a homology arm that is substantially identical to a first homology arm of a target nucleic acid, S is a stop codon, N is equal to or greater than 1, A2 is a homology arm that is substantially identical to a second homology arm of the target nucleic acid, L is a linker sequence, $X_1$ is the number of nucleotides in the linker sequence positioned between A1 and S, and $X_2$ is the number of nucleotides in the linker sequence positioned between S and A2. In some embodiments, $X_1$ and/or $X_2$ are equal to zero, indicating that the donor template does not contain a linker sequence. In embodiments where a linker sequence is present, the linker sequence can be of any suitable length that does not interfere with the function of the oligonucleotide donor template. In one embodiment, the linker sequence is 1-3 nucleotides. In one embodiment, the linker sequence is 3-5 nucleotides. In one embodiment, the linker sequence is 5-10 nucleotides. In one embodiment, the linker sequence is 10-20 nucleotides. In one embodiment, the linker sequence is 20-50 nucleotides. In exemplary embodiments, the linker sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides. In one embodiment, the linker sequence is less than 5 nucleotides. In one embodiment, the linker sequence is less than 10 nucleotides. In one embodiment, the linker sequence is less than 20 nucleotides. In one embodiment, the linker sequence is less than 30 nucleotides. In one embodiment, the linker sequence is less than 40 nucleotides. In one embodiment, the linker sequence is less than 50 nucleotides. In one embodiment, the linker sequence is less than 100 nucleotides. In one embodiment, the linker sequence is less than 150 nucleotides. In one embodiment, the linker sequence is less than 200 nucleotides. In one embodiment, the linker sequence is at least 5 nucleotides. In one embodiment, the linker sequence is at least 10 nucleotides. In one embodiment, the linker sequence is at least 20 nucleotides. In one embodiment, the linker sequence is at least 20 nucleotides. In one embodiment, the linker sequence is at least 30 nucleotides. In one embodiment, the linker sequence is at least 50 nucleotides. In one embodiment, the linker sequence is at least 100 nucleotides. In one embodiment, the linker sequence is at least 150 nucleotides. In one embodiment, the linker sequence is at least 200 nucleotides.

In one aspect, the disclosure provides a genome editing system comprising an RNA-guided nuclease, at least one gRNA molecule, and an isolated oligonucleotide donor template containing one or more stop codons, as described above. Additional features of the genome editing systems of the disclosure are described below. Such genome editing systems can be used to selectively introduce one or more stop codons in a target nucleic acid sequence. Where the target nucleic acid sequence contains the coding region of a gene, the genome editing systems can be used to induce a functional knockout of the gene in a cell that contains the target nucleic acid sequence. In some embodiments, the genome editing systems can be used to reduce the translocation frequency in edited cells, relative to the translocation frequency that occurs in cells that are edited without the donor template containing one or more stop codons. In other embodiments, the genome editing systems can be used to alter the target nucleic acid sequence at lower concentrations of nuclease, gRNA, and/or RNP complex, relative to the concentrations required to achieve functional editing in the absence of the donor template containing one or more stop codons.

(ii) Oligonucleotide Donor Templates for Targeted Integration

In another aspect, the disclosure provides oligonucleotide donor templates that can be used to insert a nucleic acid cargo at a specific chromosomal location by HDR-mediated targeted integration. Such oligonucleotide donor templates can be single-stranded (ssODN) or double-stranded (dsODN), and can be used to facilitate HDR-based repair of a double-stranded break.

Use of the oligonucleotide donor templates in genome editing advantageously reduces the translocation frequency in edited cells, particularly when multiplex editing. In addition to reducing translocation frequency, the oligonucleotide donor templates described herein allow functional editing to be achieved at lower concentrations of gRNA and/or RNA-guided nuclease, relative to cells edited in the absence of an oligonucleotide donor template. For example, functional editing can be achieved at lower concentrations of RNP complex in cells contacted with the oligonucleotide donor template, relative to the concentration of RNP complex required to achieve functional editing in the absence of the oligonucleotide donor template.

Accordingly, in one aspect, the disclosure provides an isolated oligonucleotide donor template that comprises a nucleic acid cargo. The isolated oligonucleotide donor template can comprise, from 5' to 3', the elements A1--C--A2, wherein A1 is a homology arm that is substantially identical to a first homology arm of a target nucleic acid, C is a nucleic acid cargo, and A2 is a homology arm that is substantially identical to a second homology arm of the target nucleic acid.

In one embodiment, the nucleic acid cargo is designed to disrupt the reading frame of the target nucleic acid. In one embodiment, the nucleic acid cargo comprises the formula $N_x$, where N is a nucleotide, and X represents the number of nucleotides in the cargo. For purposes of disrupting the reading frame of the target nucleic acid, X can be an integer that is not evenly divisible by 3. Accordingly, in some embodiments, X can be an integer selected from 1, 2, 4, 5, 7, 8, 10, 11, 13, 14, 16, 17, 19, 20, 22, 23, 25, 26, 28, 29, 31, 32, 34, 35, 37, 38, 40, 41, 43, 44, 46, 47, 49 or 50.

In another embodiment, the nucleic acid cargo is designed to correct a mutation that is present in the target nucleic acid. If the mutation in the target nucleic acid is a frameshift mutation, the nucleic acid cargo can be designed to insert an appropriate number of nucleic acids to restore the correct reading frame of the target nucleic acid. In some embodiments, the nucleic acid cargo contains 1, 2, 4, 5, 7, 8, 10, 11, 13, 14, 16, 17, 19, 20, 22, 23, 25, 26, 28, 29, 31, 32, 34, 35, 37, 38, 40, 41, 43, 44, 46, 47, 49 or 50 nucleotides. In some embodiments, the nucleic acid cargo is designed to restore the correct (wild-type) sequence to the target nucleic acid.

If the mutation is a substitution, the nucleic acid cargo can be designed to correct the substitution. Accordingly, the nucleic acid cargo can contain regions flanking the substitution that are identical to the target nucleic acid, and can contain the correct (wild-type) nucleotide at the site of the substitution. In some embodiments, the nucleic acid cargo is designed to restore the correct (wild-type) sequence to the target nucleic acid.

In one embodiment, the nucleic acid cargo comprises one or more stop codon(s). In another embodiment, the nucleic acid cargo does not comprise a stop codon.

In some embodiments, the nucleic acid cargo is designed to insert a desired nucleic acid sequence at a particular genomic location. In some embodiments, the nucleic acid cargo is a coding sequence that encodes a protein. In other embodiments, the nucleic acid cargo is a non-coding sequence. By way of example, the nucleic acid cargo can be designed to deliver a coding sequence to a location where it will be expressed from a promoter sequence of the target nucleic acid.

The foregoing isolated oligonucleotide donor template can be implemented in any form suitable for genome editing, including without limitation single stranded or double stranded DNA, linear or circular, naked or comprised within a vector, and/or associated, covalently or non-covalently (e.g., by direct hybridization or splint hybridization) with a guide RNA. In some embodiments, the donor template is a ssODN. Where a linear ssODN is used, it can be configured to (i) anneal to a nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, or no more than 150-200 nucleotides (e.g., 150, 160, 170, 180, 190, or 200 nucleotides). In other embodiments, the donor template is a dsODN. In one embodiment, the donor template comprises a first strand. In another embodiment, a donor template comprises a first strand and a second strand. In some embodiments, a donor template is an exogenous oligonucleotide, e.g., an oligonucleotide that is not naturally present in a cell. In embodiments, the donor template is present in a vector, for example, a plasmid vector or a viral vector. In one embodiment, the donor template is present in an adenoviral vector, an adeno-associated virus (AAV) vector, or a lentiviral vector.

The isolated oligonucleotide donor template can contain one or more regions that are homologous to regions of DNA, e.g., a target nucleic acid, within or near (e.g., flanking or adjoining) a target sequence to be cleaved, e.g., the cleavage site. These homologous regions are referred to herein as "homology arms," and are illustrated schematically below:

[5' homology arm]----[nucleic acid cargo]----[3' homology arm]
      A1                      C                    A2

The homology arms of the oligonucleotide donor templates described herein may be of any suitable length, provided such length is sufficient to allow efficient resolution of a cleavage site on a targeted nucleic acid by a DNA repair process requiring a donor template. In some embodiments, where amplification by, e.g., PCR, of the homology arm is desired, the homology arm is of a length such that the amplification may be performed. In some embodiments, where sequencing of the homology arm is desired, the homology arm is of a length such that the sequencing may be performed. Optional features of the homology arms are described above, with respect to oligonucleotide donor templates that comprise a stop codon. Homology arms having these features are suitable for inclusion in the oligonucleotide donor templates for targeted integration described herein.

In one aspect, the disclosure provides a genome editing system comprising an RNA-guided nuclease, at least one gRNA molecule, and an isolated oligonucleotide donor template containing a nucleic acid cargo, as described herein. Additional features of the genome editing systems of the disclosure are described below. Such genome editing systems can be used to selectively introduce the nucleic acid cargo in a target nucleic acid sequence. Where the target nucleic acid sequence contains the coding region of a gene, genome editing systems containing cargo that disrupts the reading frame of the gene can be used to induce a functional knockout of the gene in a cell that contains the target nucleic acid sequence. In some embodiments, the genome editing systems can be used to reduce the translocation frequency in edited cells, relative to the translocation frequency that occurs in cells that are edited without the oligonucleotide donor template. In other embodiments, the genome editing systems can be used to alter the target nucleic acid sequence at lower concentrations of nuclease, gRNA, and/or RNP complex, relative to the concentrations required to achieve functional editing in the absence of the donor template.

(B) Genome Editing using a STOP Oligonucleotide Donor Template and/or an Oligonucleotide Donor Template for Targeted Integration In some embodiments, the disclosure provides methods of genome editing using the STOP ODN described above. An exogenous oligonucleotide donor template comprising a stop codon and homology arms substantially identical to the homology arms of a target nucleic acid can be used to incorporate the stop codon into the target nucleic acid at a specified location. The exogenous oligonucleotide donor template promotes repair through HDR-mediated gene correction. Following incorporation of the exogenous oligonucleotide donor template, the target nucleic acid will contain the stop codon flanked by the donor homology arms. The target nucleic acid can comprise any suitable sequence in the genome. For example, the target nucleic acid can comprise an exon of a gene, an intron of a gene, a cDNA sequence, a transcriptional regulatory element, a portion of any of the foregoing, or the reverse complement of any of the foregoing.

In other embodiments, the disclosure provides methods of genome editing using the oligonucleotide donor templates for targeted integration described above. Following incorporation of the oligonucleotide donor template, the target nucleic acid will contain the nucleic acid cargo flanked by the donor homology arms. The target nucleic acid can comprise any suitable sequence in the genome. For example, the target nucleic acid can comprise an exon of a gene, an intron of a gene, a cDNA sequence, a transcriptional regulatory element, a portion of any of the foregoing, or the reverse complement of any of the foregoing.

By engaging the HDR repair pathway, the donor templates described herein can advantageously reduce the frequency of chromosomal rearrangements that occur when genome editing is performed without the donor template, where repair is mediated primarily by NHEJ. Accordingly, the foregoing donor templates, e.g., the STOP ODN, can be used, in some embodiments, to reduce the percentage of cells in a cell population that undergo a translocation event during alteration of one or more target nucleic acid(s). In embodiments in which one target nucleic acid is altered, the oligonucleotide donor templates, e.g., the STOP ODN, can be used to reduce the occurrence of same-chromosome translocations. In multiplex embodiments in which more than one target nucleic acid is altered, the oligonucleotide donor templates, e.g., the STOP ODN, can be used to reduce the occurrence of both same chromosome translocations and heterologous chromosome translocations.

Generating Protein Truncations

In exemplary embodiments, the STOP ODN is used to insert one or more stop codons in the coding region of a gene of interest, e.g., in an exon of a gene of interest. During translation of the edited gene into a protein, the translation machinery will encounter the stop codon(s), and prematurely terminate translation. Consequently, the encoded protein will be truncated at the amino acid preceding the inserted stop codon(s). Accordingly, in one embodiment, the STOP ODN can be used to generate an altered nucleic acid, wherein the altered nucleic acid encodes a truncated protein. The length of the truncated protein can be modulated by varying the position of the inserted stop codon(s) within the gene of interest, through selection of the appropriate homology arm sequences.

In one embodiment, the altered nucleic acid encodes a truncated protein that is nonfunctional. In this embodiment, the STOP ODN is used to generate functional knockouts of a gene of interest, by inserting a premature stop codon in the coding region of the target gene. In contrast to commonly used methods of gene disruption by inducing NHEJ-mediated insertions and deletions (indels), the STOP oligonucleotide donor templates described herein can be used to insert one or more stop codons at a precise location in the target gene via HDR-mediated gene correction.

In another embodiment, the altered nucleic acid encodes a truncated protein that is functional. For example, the truncation may occur at a position that does not alter the function of the encoded protein. In one embodiment, the altered nucleic acid encodes a truncated protein that is a gain-of-function mutant relative to the unaltered protein. For example, the truncation may occur at a position that eliminates negative regulatory domains within the protein.

Reducing the Concentration of gRNA and/or Nuclease During Genome Editing

Surprisingly, an oligonucleotide donor template, including those described herein, allows functional genome editing to take place in the presence of a reduced concentration of gRNA, nuclease, and/or RNP complex. In many genome editing applications, it is desirable to minimize the amount of gRNA, nuclease, and/or RNP complex used to perform genome editing. For example, increased numbers of DSBs occur in the genome in the presence of increased concentrations of nuclease and/or RNP complex. Additional DSBs create opportunities for chromosomal rearrangements to occur as a by-product of gene editing. Minimizing the concentration of these reagents reduces the number of DSBs, and thereby reduces the translocation frequency in edited cells.

In one aspect, the disclosure provides methods of altering a target nucleic acid in a cell using reduced concentrations of a gRNA molecule, an RNA-guided nuclease, or a RNP complex by contacting the cell during the editing process with an exogenous oligonucleotide donor template described herein. In one embodiment, the oligonucleotide donor template comprises one or more stop codons. Such methods advantageously reduce the translocation frequency in edited cells without sacrificing the editing efficiency achievable at higher concentrations of gRNA, RNA-guided nuclease, or RNP complex in the absence of the exogenous oligonucleotide comprising the stop codon(s).

As shown herein, gene editing in the presence of an exogenous oligonucleotide comprising one or more stop codons can be performed using a reduced concentration of gRNA, nuclease, and/or RNP complex, irrespective of whether the oligonucleotide contains homology arms having substantial identity to the corresponding regions of the target gene. Accordingly, in some embodiments, the methods of gene editing using reduced concentrations of gRNA, nuclease, and/or RNP complex described herein can be performed using a nonspecific oligonucleotide comprising one or more stop codons. The nonspecific oligonucleotide lacks sufficient identity to the target gene to serve as a donor template for HDR-mediated gene correction. In other embodiments, the methods described herein can be performed using an exogenous oligonucleotide comprising a stop codon which contains sufficient identity to the target gene to serve as a donor template for HDR. If the exogenous oligonucleotide contains homology arms having sufficient identity to the target gene to permit incorporation of the oligonucleotide into the target gene by HDR-mediated gene correction, the translocation frequency in edited cells can be further reduced.

In one aspect, the disclosure provides a method of altering a target nucleic acid in a cell, wherein the target nucleic acid comprises a first strand comprising a cleavage site, a first homology arm 5' to the cleavage site, and a second homology arm 3' to the cleavage site, the method comprising contacting the cell with a RNA-guided nuclease, at least one gRNA molecule, and an exogenous oligonucleotide donor template comprising one or more stop codons, wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid, and wherein the concentration of the RNA-guided nuclease used to contact the cells is reduced relative to a reference concentration, thereby altering the target nucleic acid in the cell.

In another aspect, the disclosure provides a method of altering a target nucleic acid in a cell, wherein the target nucleic acid comprises a first strand comprising a cleavage site, a first homology arm 5' to the cleavage site, and a second homology arm 3' to the cleavage site, the method comprising contacting the cell with a RNA-guided nuclease, at least one gRNA molecule, and an exogenous oligonucleotide donor template comprising a nucleic acid cargo, wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid, and wherein the concentration of the RNA-guided nuclease used to contact the cells is reduced relative to a reference concentration, thereby altering the target nucleic acid in the cell.

In the foregoing aspects, the concentration of RNA-guided nuclease is reduced relative to a reference concentration. The reference concentration is the concentration of RNA-guided nuclease required to achieve editing of the target gene (e.g., by introduction of NHEJ-mediated indels) in a specified percentage of cells in a cell population, in the absence of the exogenous oligonucleotide donor template. For example, the reference concentration can be the concentration of RNA-guided nuclease required to achieve editing of the target gene in at least 50%, at least 55%, at least 60%, at least 65%, at least 70%, at least 75%, at least 80%, at least 85%, at least 90%, at least 95%, etc. of cells in a cell population, in the absence of the exogenous oligonucleotide donor template. In an exemplary embodiment, the reference concentration is the concentration of RNA-guided nuclease required to achieve editing of the target gene in at least 80% of cells in a cell population, in the absence of the exogenous oligonucleotide donor template. Efficient gene editing can be performed at reduced concentrations of RNA-guided nuclease in the presence of an exogenous oligonucleotide donor template, as described herein. For example, in one embodiment, gene editing is performed using a concentration of RNA-guided nuclease at least 2-10 fold lower than the reference concentration. For example, in embodiments, gene editing is performed using a concentration of RNA-guided nuclease at least 2-fold lower, at least 3-fold lower, at least 4-fold lower, at least 5-fold lower, at least 6-fold lower, at least 7-fold lower, at least 8-fold lower, at least 9-fold lower, or at least 10-fold lower than the reference concentration. In an exemplary embodiment, gene editing is performed using a concentration of RNA-guided nuclease at least 5-fold lower than the reference concentration. In another exemplary embodiment, gene editing is performed using a concentration of RNA-guided nuclease at least 10-fold lower than the reference concentration. In one embodiment, gene editing is performed using a concentration of RNA-guided nuclease that is equal to or less than 0.6 µM, for example, 0.6 µM or less, 0.5 µM or less, 0.4 µM or less, 0.3 µM or less, 0.2 µM or less, or 0.1 µM or less. In another embodiment, gene editing is performed using a concentration of RNA-guided nuclease that is about 0.6 µM-0.1 µM, or about 0.5 µM-0.2 µM, or about 0.4 µM-0.2 µM, or about 0.3 µM-0.2 µM. In exemplary embodiments, gene editing is performed using a concentration of RNA-guided nuclease that is about 0.4 µM, or about 0.3 µM, or about 0.28 µM, or about 0.25 µM, or about 0.2 µM. Any RNA-guided nuclease described herein is suitable for performing the methods of the disclosure. In one embodiment, the nuclease is a CRISPR-associated nuclease, for example, wild-type Cas9, Cas9 nickase, wild-type Cpf1, or Cpf1 nickase.

In one aspect, the disclosure provides a method of altering a target nucleic acid in a cell, wherein the target nucleic acid comprises a first strand comprising a cleavage site, a first homology arm 5' to the cleavage site, and a second homology arm 3' to the cleavage site, the method comprising contacting the cell with a RNA guided nuclease, at least one gRNA molecule, and an exogenous oligonucleotide donor template comprising one or more stop codons, wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid, and wherein the concentration of the gRNA molecule used to contact the cell is reduced relative to a reference concentration, thereby altering the target nucleic acid in the cell.

In another aspect, the disclosure provides a method of altering a target nucleic acid in a cell, wherein the target nucleic acid comprises a first strand comprising a cleavage site, a first homology arm 5' to the cleavage site, and a second homology arm 3' to the cleavage site, the method comprising contacting the cell with a RNA guided nuclease, at least one gRNA molecule, and an exogenous oligonucleotide donor template comprising a nucleic acid cargo, wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid, and wherein the concentration of the gRNA molecule used to contact the cell is reduced relative to a reference concentration, thereby altering the target nucleic acid in the cell.

In the foregoing aspects, the concentration of gRNA is reduced relative to a reference concentration. The reference concentration is the concentration of gRNA required to achieve editing of the target gene (e.g., by introduction of NHEJ-mediated indels) in a specified percentage of cells in a cell population, in the absence of the exogenous oligonucleotide donor template. For example, the reference concentration can be the concentration of gRNA required to achieve editing of the target gene in at least 50%, at least 55%, at least 60%, at least 65%, at least 70%, at least 75%, at least 80%, at least 85%, at least 90%, at least 95%, etc. of cells in a cell population, in the absence of the exogenous oligonucleotide donor template. In an exemplary embodiment, the reference concentration is the concentration of gRNA required to achieve editing of the target gene in at least 80% of cells in a cell population, in the absence of the exogenous oligonucleotide donor template. Efficient gene editing can be performed at reduced concentrations of gRNA in the presence of the exogenous oligonucleotide donor template, as described herein. For example, in one embodiment, gene editing is performed using a concentration of gRNA at least 2-10 fold lower than the reference concentration. For example, in embodiments, gene editing is performed using a concentration of gRNA at least 2-fold lower, at least 3-fold lower, at least 4-fold lower, at least 5-fold lower, at least 6-fold lower, at least 7-fold lower, at least 8-fold lower, at least 9-fold lower, or at least 10-fold lower than the reference concentration. In an exemplary embodiment, gene editing is performed using a concentration of gRNA at least 5-fold lower than the reference concentration. In another exemplary embodiment, gene editing is performed using a concentration of gRNA at least 10-fold lower than the reference concentration. In one embodiment, gene editing is performed using a concentration of gRNA that is equal to or less than 0.6 µM, for example, 0.6 µM or less, 0.5 µM or less, 0.4 µM or less, 0.3 µM or less, 0.2 µM or less, or 0.1 µM or less. In another embodiment, gene editing is performed using a concentration of gRNA that is about 0.6 µM-0.1 µM, or about 0.5 µM-0.2 µM, or about 0.4 µM-0.2 µM, or about 0.3 µM-0.2 µM. In exemplary embodiments, gene editing is performed using a concentration of gRNA that is about 0.4 µM, or about 0.3 µM, or about 0.28 µM, or about 0.25 µM, or about 0.2 µM.

In one aspect, the disclosure provides a method of altering a target nucleic acid in a cell, wherein the target nucleic acid comprises a first strand comprising a cleavage site, a first homology arm 5' to the cleavage site, and a second homology arm 3' to the cleavage site, the method comprising contacting the cell with (i) at least one RNP complex comprising a RNA-guided nuclease and a gRNA, and (ii) an exogenous oligonucleotide donor template comprising one or more stop codons, wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid, and wherein the concentration of the RNP complex used to contact the cells is reduced relative to a reference concentration, thereby altering the target nucleic acid in the cell.

In another aspect, the disclosure provides a method of altering a target nucleic acid in a cell, wherein the target nucleic acid comprises a first strand comprising a cleavage site, a first homology arm 5' to the cleavage site, and a second homology arm 3' to the cleavage site, the method comprising contacting the cell with (i) at least one RNP complex comprising a RNA-guided nuclease and a gRNA, and (ii) an exogenous oligonucleotide donor template comprising a nucleic acid cargo, wherein the gRNA molecule and the RNA-guided nuclease interact with the target nucleic acid, resulting in a cleavage event at or near the cleavage site, wherein the cleavage event is repaired by at least one DNA repair pathway to produce an altered nucleic acid, and wherein the concentration of the RNP complex used to contact the cells is reduced relative to a reference concentration, thereby altering the target nucleic acid in the cell.

In the foregoing aspects, as described herein, gene editing is accomplished by contacting cells with a ribonucleoprotein (RNP) complex comprising an RNA-guided nuclease protein complexed with a gRNA molecule. In some embodiments, the concentration of RNP complex is reduced relative to a reference concentration. The reference concentration is the concentration of RNP complex required to achieve editing of the target gene (e.g., by introduction of NHEJ-mediated indels) in a specified percentage of cells in a cell population, in the absence of the exogenous oligonucleotide donor template. For example, the reference concentration can be the concentration of RNP complex required to achieve editing of the target gene in at least 50%, at least 55%, at least 60%, at least 65%, at least 70%, at least 75%, at least 80%, at least 85%, at least 90%, at least 95%, etc. of cells in a cell population, in the absence of the exogenous oligonucleotide donor template. In an exemplary embodiment, the reference concentration is the concentration of RNP complex required to achieve editing of the target gene in at least 80% of cells in a cell population, in the absence of the exogenous oligonucleotide donor template. Efficient gene editing can be performed at reduced concentrations of RNP complex in the presence of the exogenous oligonucleotide donor template, as described herein. For example, in one embodiment, gene editing is performed using a concentration of RNP complex at least 2-10 fold lower than the reference concentration. For example, in embodiments, gene editing is performed using a concentration of RNP complex at least 2-fold lower, at least 3-fold lower, at least 4-fold lower, at least 5-fold lower, at least 6-fold lower, at least 7-fold lower, at least 8-fold lower, at least 9-fold lower, or at least 10-fold lower than the reference concentration. In an exemplary embodiment, gene editing is performed using a concentration of RNP complex at least 5-fold lower than the reference concentration. In another exemplary embodiment, gene editing is performed using a concentration of RNP complex at least 10-fold lower than the reference concentration. In one embodiment, gene editing is performed using a concentration of RNP complex that is equal to or less than 0.6 μM, for example, 0.6 μM or less, 0.5 μM or less, 0.4 μM or less, 0.3 μM or less, 0.2 μM or less, or 0.1 μM or less. In another embodiment, gene editing is performed using a concentration of RNP complex that is about 0.6 μM-0.1 μM, or about 0.5 μM-0.2 μM, or about 0.4 μM-0.2 μM, or about 0.3 μM-0.2 μM. In exemplary embodiments, gene editing is performed using a concentration of RNP complex that is about 0.4 μM, or about 0.3 μM, or about 0.28 μM, or about 0.25 μM, about 0.2 μM, or about 0.1 μM.

The foregoing methods of genome editing using reduced concentrations of RNA-guided nuclease, gRNA and/or RNP complex can be readily adapted to the various embodiments of genome editing described herein. For example, in embodiments in which a first gRNA is used to direct a nickase to produce a first cleavage event at or near the cleavage site of a target gene, and a second gRNA is used to direct a nickase to produce a second cleavage event at or near the cleavage site on the opposite strand of the target gene, the concentration of an RNP complex comprising the first gRNA, and/or an RNP complex comprising the second gRNA, can be reduced when editing is performed in the presence of an oligonucleotide donor template, e.g., an oligonucleotide donor template comprising one or more stop codons, or an oligonucleotide donor template comprising a nucleic acid cargo. Alternatively, the concentration of the first gRNA and/or the second gRNA can be reduced when editing is performed in the presence of the oligonucleotide donor template. In addition, the concentration of the RNA-guided nuclease (e.g., the nickase) can be reduced when editing is performed in the presence of the oligonucleotide donor template.

In multiplex strategies of genome editing, which involve introducing alterations into two or more target genes, the concentration of RNA-guided nuclease, gRNA, and/or RNP complex directing the alteration of each target gene can be reduced in the presence of an oligonucleotide donor template, e.g., a donor template comprising one or more stop codons. For example, in one embodiment, when alterations are introduced into two target genes, the concentration of reagents (RNA-guided nuclease, gRNA, and/or RNP complex) directing the alteration of the first target gene can be reduced in the presence of the oligonucleotide donor template, while reagents (RNA-guided nuclease, gRNA, and/or RNP complex) directing the alteration of the second target gene are used at a higher concentration. Alternatively, the concentration of reagents directing the alteration of the first target gene and reagents directing the alteration of the second target gene can both be reduced in the presence of the oligonucleotide donor template. A similar approach can be taken when altering more than two (e.g., 3, 4, 5, 6, 7, 8, 9, 10, etc.) target genes, i.e., reagents directing the alteration of some or all of the target genes can be reduced in the presence of the oligonucleotide donor template. Additional multiplexing strategies are described below.

Altering Multiple Target Nucleic Acids Using Oligonucleotide Donor Templates

As noted above, by engaging the HDR repair pathway, donor templates comprising one or more stop codons, or a nucleic acid cargo, as described herein can advantageously reduce the frequency of chromosomal rearrangements that occur when genome editing is performed in the absence the donor template, where repair is mediated primarily by NHEJ. Accordingly, the STOP ODN and/or oligonucleotide donor template containing a nucleic acid cargo can be used, in some embodiments, to reduce the percentage of cells in a cell population that undergo a translocation event during alteration of one or more target nucleic acid(s). This strategy is particularly useful when altering multiple target nucleic acids, as cutting the DNA at more than one location can give rise to chromosomal rearrangements between heterologous and homologous chromosomes. In multiplex embodiments in which more than one target nucleic acid is altered, one or more oligonucleotide donor templates described herein can be used to reduce the occurrence of both same chromosome translocations and heterologous chromosome translocations.

In multiplex embodiments, one or more oligonucleotide donor templates (e.g., STOP ODNs, oligonucleotide donor templates containing a nucleic acid cargo, or a combination thereof) can be used, wherein each donor template has homology arms substantially identical to the homology arms of one of the target nucleic acids. For example, in embodiments where two target nucleic acids are altered, a cell can be contacted with a first STOP ODN, which comprises (i) a first homology arm substantially identical to the first homology arm of the first target nucleic acid, (ii) one or more stop codons, and (iii) a second homology arm substantially identical to the second homology arm of the first target nucleic acid. In addition, the cell can optionally be contacted with a second STOP ODN, which comprises (i) a first homology arm substantially identical to the first homology arm of the second target nucleic acid, (ii) one or more stop codons, and (iii) a second homology arm substantially identical to the second homology arm of the second target nucleic acid. In another embodiment, a cell can be contacted with a first oligonucleotide donor template, which comprises (i) a first homology arm substantially identical to the first homology arm of the first target nucleic acid, (ii) a nucleic acid cargo, and (iii) a second homology arm substantially identical to the second homology arm of the first target nucleic acid. In addition, the cell can optionally be contacted with a second oligonucleotide donor template, which comprises (i) a first homology arm substantially identical to the first homology arm of the second target nucleic acid, (ii) a nucleic acid cargo, and (iii) a second homology arm substantially identical to the second homology arm of the second target nucleic acid.

In embodiments where three target nucleic acids are altered, a cell can be contacted with a first oligonucleotide donor template and/or a second oligonucleotide donor template, as described above, and optionally with a third oligonucleotide donor template, wherein the third oligonucleotide donor template comprises (i) a first homology arm substantially identical to the first homology arm of the third target nucleic acid, (ii) a nucleic acid cargo and/or one or more stop codons, and (iii) a second homology arm substantially identical to the second homology arm of the third target nucleic acid.

In embodiments where four target nucleic acids are altered, the cell can be contacted with a first oligonucleotide donor template and/or a second oligonucleotide donor template and/or a third oligonucleotide donor template, as described above, and optionally with a fourth oligonucleotide donor template, wherein the fourth oligonucleotide donor template comprises (i) a first homology arm substantially identical to the first homology arm of the fourth target nucleic acid, (ii) a nucleic acid cargo and/or one or more stop codons, and (iii) a second homology arm substantially identical to the second homology arm of the fourth target nucleic acid.

In embodiments where five target nucleic acids are altered, the cell can be contacted with a first oligonucleotide donor template and/or a second oligonucleotide donor template and/or a third oligonucleotide donor template and/or a fourth oligonucleotide donor template, as described above, and optionally with a fifth oligonucleotide donor template, wherein the fifth oligonucleotide donor template comprises (i) a first homology arm substantially identical to the first homology arm of the fifth target nucleic acid, (ii) a nucleic acid cargo and/or one or more stop codons, and (iii) a second homology arm substantially identical to the second homology arm of the fifth target nucleic acid. The foregoing principles can be applied when altering six, seven, eight, nine, ten, or more target nucleic acids in a cell.

The use of an oligonucleotide donor template as described herein can reduce the percentage of cells in a cell population that undergo a translocation event during alteration of two or more target genes, relative to the percentage of cells in a cell population that undergo a translocation event in the absence of the oligonucleotide donor template. In one embodiment, the percentage of cells that undergo a translocation event is reduced by 10% or more, e.g., 20% or more, 30% or more, 40% or more, 50% or more, 60% or more, 70% or more, 80% or more, 90% or more, 95% or more 99% or more, or by 100%. In an exemplary embodiment, the percentage of cells that undergo a translocation event is reduced by 50% or more.

Multiple strategies for reducing chromosomal rearrangements can be used in combination. For example, one or more target nucleic acids can be altered by simultaneously (i) reducing the concentration of nuclease, gRNA and/or RNP complex used to target one or multiple target nucleic acids, (ii) varying the type of DNA ends created by the cleavage event occurring in each target nucleic acid, such that each target nucleic acid has free DNA ends that are not compatible for NHEJ, (iii) varying the timing of the cleavage events occurring in each target nucleic acid, such that the cleavage events do not occur simultaneously, (iv) varying the type of nuclease used to generate a cleavage event in each target nucleic acid, and/or (v) varying the nuclease implementation (e.g., RNP complex and exogenous nucleic acid encoding a nuclease) used to generate a cleavage event in each target nucleic acid, as described herein. Any one or more of the foregoing strategies can be implemented, in some embodiments, using a STOP ODN, and/or an oligonucleotide donor template comprising a nucleic acid cargo, as described herein.

(C) Modulating Chromosomal Rearrangements by Selection of Non-Compatible DNA Ends In another aspect, the disclosure provides methods of reducing the frequency of chromosomal rearrangements during multiplex editing, by introducing multiple cuts having non-compatible DNA ends. As described herein, various end structures (e.g., 5' overhangs, 3' overhangs, or blunt ends) can be created through selection of a nuclease/gRNA combination configured to produce the desired ends at the cut site. Strategies for generating cuts having 5' overhangs, 3' overhangs, and blunt ends are described herein. For example, one cut could be introduced using a Cas9 nickase (N863A variant) and two gRNAs with PAMs facing outwards, resulting in a cut having 3' overhangs. A second cut at a different locus could be introduced using a Cas9 nickase (D10A variant) and two gRNAs with PAMs facing outwards, resulting in a cut having 5' overhangs. Without wishing to be bound by theory, the different DNA ends may engage different DNA repair pathways that may not be compatible with direct NHEJ-mediated end ligation, through which translocations are normally formed.

Accordingly, in one aspect, provided herein is a method of altering a cell at a first target nucleic acid and a second target nucleic acid, comprising forming two single-stranded breaks at a first cleavage site in the first target nucleic acid, wherein the two single-stranded breaks produce 5' overhangs at the first cleavage site; and forming two single-stranded breaks at a second cleavage site in the second target nucleic acid, wherein the two single-stranded breaks produce 3' overhangs at the second cleavage site; wherein the first cleavage site is repaired by at least one DNA repair pathway to produce an altered first target nucleic acid, and wherein the second cleavage site is repaired by at least one DNA repair pathway to produce an altered second target nucleic acid, thereby altering the cell.

The steps of forming two single-stranded breaks at the first cleavage site, and forming two single-stranded breaks at the second cleavage site, can be performed simultaneously or sequentially, in any order. In one embodiment, the steps are performed simultaneously.

In one embodiment, the step of forming two single-stranded breaks at the first cleavage site is performed using a first RNA-guided nuclease having an inactivated RuvC domain. In some embodiments, the first RNA-guided nuclease is a Cas9 nuclease or a Cpf1 nuclease. In some embodiments, the RNA-guided nuclease contains a substitution at position D10, e.g., a D10A substitution. The first RNA-guided nuclease can be used in conjunction with two gRNAs that direct the nuclease to the first cleavage site. In one embodiment, the two gRNAs have outward-facing PAMs.

In one embodiment, the step of forming two single-stranded breaks at the first cleavage site is performed by contacting the cell with the first RNA-guided nuclease, and two gRNAs capable of directing the first RNA-guided nuclease to opposite strands of the first target nucleic acid at the first cleavage site. In this manner, the first target nucleic acid is cleaved at the first cleavage site, leaving ends having 5' overhangs.

In one embodiment, the step of forming two single-stranded breaks at the second cleavage site is performed using a second RNA-guided nuclease having an inactivated HNH domain. In some embodiments, the second RNA-guided nuclease is a Cas9 nuclease or a Cpf1 nuclease. In some embodiments, the RNA guided nuclease contains a substitution at position H840, e.g., a H840A substitution, or a substitution at position N863, e.g., a N863A substitution.

In one embodiment, the step of forming two single-stranded breaks at the second cleavage site is performed by contacting the cell with the second RNA-guided nuclease, and two gRNAs capable of directing the second RNA-guided nuclease to opposite strands of the second target nucleic acid at the second cleavage site. In this manner, the second target nucleic acid is cleaved at the second cleavage site, leaving ends having 3' overhangs.

Alternatively, a cleavage site having 5' overhangs can be generated using an RNA-guided nuclease having an inactivated HNH domain, paired with two gRNAs having PAMs facing inward. Likewise, a cleavage site having 3' overhangs can be generated using an RNA-guided nuclease having an inactivated RuvC domain, paired with two gRNAs having PAMs facing inward.

Additional methods of generating cleavage events having 5' overhangs or 3' overhangs are described herein, and are known in the art.

In one aspect, provided herein is a method of reducing the translocation frequency during alteration of a first target nucleic acid and a second target nucleic acid, comprising forming a first cleavage site in the first target nucleic acid, and forming a second cleavage site in the second target nucleic acid, wherein the first cleavage site and the second cleavage site have incompatible ends, and wherein the first cleavage site is repaired by at least one DNA repair pathway to produce an altered first target nucleic acid, and wherein the second cleavage site is repaired by at least one DNA repair pathway to produce an altered second target nucleic acid. In one embodiment, the first cleavage site has 5' overhangs, and the second cleavage site has 3' overhangs. In one embodiment, the first cleavage site has 3' overhangs, and the second cleavage site has 5' overhangs. In one embodiment, the first cleavage site has 5' overhangs, and the second cleavage site has blunt ends. In another embodiment, the first cleavage site has 3' overhangs, and the second cleavage site has blunt ends. The first and second cleavage sites can be formed simultaneously or sequentially, in any order. In one embodiment, the cleavage sites are formed simultaneously.

The methods described herein can reduce the percentage of cells in a cell population that undergo a translocation event during alteration of the first target nucleic acid and the second target nucleic acid, relative to the percentage of cells in a cell population that undergo a translocation event when the first cleavage site and the second cleavage site have compatible ends (e.g., 3' overhangs and 3' overhangs, or 5' overhangs and 5' overhangs). In one embodiment, the percentage of cells that undergo a translocation event is reduced by 10% or more, e.g., 20% or more, 30% or more, 40% or more, 50% or more, 60% or more, 70% or more, 80% or more, 90% or more, 95% or more 99% or more, or by 100%. In an exemplary embodiment, the percentage of cells that undergo a translocation event is reduced by 50% or more.

(D) Modulating Chromosomal Rearrangements by Staggering DNA Cleavage Events

Chromosomal translocations form between two double-stranded breaks in the genomic DNA. The frequency of translocation formation is increased during multiplex genome editing, where more than one target nucleic acid is edited simultaneously, because each editing event requires cleavage of the corresponding target nucleic acid. Translocations can form between any of the cleavage sites introduced in the target nucleic acids.

Provided herein are strategies for reducing the formation of translocations during multiplex genome editing, by staggering multiple DNA cleavage events to minimize the co-occurrence of multiple double-stranded breaks in a cell. As shown herein, preventing the simultaneous introduction of multiple double-stranded breaks reduces the frequency of translocation formation during multiplex genome editing.

Differential Timing of Nuclease Exposure

One strategy for reducing the frequency of translocation formation during multiplex genome editing is to introduce a first cleavage event into a first target nucleic acid, and, after a period of time sufficient for repair of the first cleavage site, introducing a second cleavage site into a second target nucleic acid.

In the event that more than two target nucleic acids are to be edited, subsequent cleavage events can be introduced after a period of time sufficient for the prior cleavage events to be repaired. Thus, where three target nucleic acids are to be edited, a third cleavage site can be introduced into a third target nucleic acid after a period of time sufficient for repair of the second cleavage site. Where four target nucleic acids are to be edited, a fourth cleavage site can be introduced into a fourth target nucleic acid after a period of time sufficient for repair of the third cleavage site. Where five target nucleic acids are to be edited, a fifth cleavage site can be introduced into a fifth target nucleic acid after a period of time sufficient for repair of the fourth cleavage site. Where six target nucleic acids are to be edited, a sixth cleavage site can be introduced into a sixth target nucleic acid after a period of time sufficient for repair of the fifth cleavage site. Similar principles can be followed for editing additional target nucleic acids, e.g., 7, 8, 9, 10 or more target nucleic acids, in a cell.

In one aspect, the disclosure provides a method of altering a cell at a first target nucleic acid and a second target nucleic acid. The method can comprise forming at least one single- or double-stranded break at a first cleavage site in the first target nucleic acid, wherein the first cleavage site is repaired by at least one DNA repair pathway to produce an altered first target nucleic acid; and after a period of time sufficient for repair of the first cleavage site, forming at least one single- or double-stranded break at a second cleavage site in the second target nucleic acid, wherein the second cleavage site is repaired by at least one DNA repair pathway to produce an altered second target nucleic acid, thereby altering the cell.

In another aspect, the disclosure provides a method of altering a first target nucleic acid and a second target nucleic acid in a cell, comprising contacting the cell with a first RNA-guided nuclease molecule, at least one first gRNA molecule capable of directing the first RNA-guided nuclease molecule to the first target nucleic acid, and, optionally a first exogenous oligonucleotide donor template, wherein a first RNP complex comprising the first RNA-guided nuclease molecule and the first gRNA molecule interacts with the first target nucleic acid resulting in a first cleavage event in the first target nucleic acid, wherein the first cleavage event is repaired by at least one DNA repair pathway to produce an altered first target nucleic acid. After a period of time sufficient for degradation of the first RNP complex, the cell is then contacted with a second RNA-guided nuclease molecule, at least one second gRNA molecule capable of directing the second RNA-guided nuclease molecule to the second target nucleic acid, and, optionally a second exogenous oligonucleotide donor template, wherein a second RNP complex comprising the second RNA-guided nuclease molecule and the second gRNA molecule interacts with the second target nucleic acid, resulting in a second cleavage event in the second target nucleic acid, wherein the second cleavage event is repaired by at least one DNA repair pathway to produce an altered second target nucleic acid.

The foregoing methods can reduce the translocation frequency in the edited cells, relative to cells in which the first target nucleic acid and the second nucleic acid are altered simultaneously. In one embodiment, the percentage of cells that undergo a translocation event is reduced by 10% or more, e.g., 20% or more, 30% or more, 40% or more, 50% or more, 60% or more, 70% or more, 80% or more, 90% or more, 95% or more 99% or more, or by 100%. In an exemplary embodiment, the percentage of cells that undergo a translocation event is reduced by 50% or more.

The time sufficient for repair of a cleavage event can be determined empirically, by detecting the presence of the altered nucleic acid in the cell. In exemplary embodiments, the time sufficient for repair of a cleavage event is at least 6 hours, at least 12 hours, at least 24 hours, at least 36 hours, at least 48 hours, at least 72 hours, at least 96 hours, or at least 120 hours. In other embodiments, the period of time sufficient for degradation of an RNP complex is at least 6 hours, at least 12 hours, at least 24 hours, at least 36 hours, at least 48 hours, at least 72 hours, at least 96 hours, or at least 120 hours.

In some embodiments, such as when edited cells are being prepared for administration to a subject, it may be desirable to perform multiple editing events as close in time as possible, to minimize the time the cells are maintained in culture, while also reducing the occurrence of chromosomal translocations. Accordingly, in some embodiments, the time between cleavage events is about 6-120 hours, e.g., about 6-12 hours, 6-24 hours, 6-36 hours, 6-48 hours, 6-72 hours, 6-96 hours, or 6-120 hours. In other embodiments, the time between cleavage events is about 12-120 hours, e.g., about 12-24 hours, 12-36 hours, 12-48 hours, 12-72 hours, 12-96 hours, or 12-120 hours. In other embodiments, the time between cleavage events is about 24-120 hours, e.g., about 24-36 hours, 24-48 hours, 24-72 hours, 24-96 hours, or 24-120 hours. In other embodiments, the time between cleavage events is about 36-120 hours, e.g., about 36-48 hours, 36-72 hours, 36-96 hours, or 36-120 hours. In other embodiments, the time between cleavage events is about 48-120 hours, e.g., about 48-72 hours, 48-96 hours, or 48-120 hours. In other embodiments, the time between cleavage events is about 72-120 hours, e.g., about 72-96 hours, or 72-120 hours. In other embodiments, the time between cleavage events is about 96-120 hours In an exemplary embodiment, the time between cleavage events is 24-48 hours. In another exemplary embodiment, the time between cleavage events is 24-72 hours. In some embodiments, the time between cleavage events is about 6 hours, about 12 hours, about 24 hours, about 36 hours, about 48 hours, about 72 hours, about 96 hours, or about 120 hours.

In some embodiments, the foregoing methods are performed in the absence of an exogenous oligonucleotide donor template. In such embodiments, the cleavage events introduced by the RNA-guided nuclease are repaired primarily through the NHEJ repair pathway. In other embodiments, the foregoing methods are performed in the presence of an exogenous oligonucleotide donor template. In such embodiments, the cleavage events introduced by the RNA-guided nuclease are repaired primarily through the HDR repair pathway. The donor template can contain a first homology arm substantially identical to a first homology arm in the target nucleic acid positioned 5' of the cleavage site, and/or a second homology arm substantially identical to a second homology arm in the target nucleic acid positioned 3' of the cleavage site. An exogenous oligonucleotide donor template can be used for recombination with any one or more of the target nucleic acids undergoing gene editing. Thus, in embodiments where two genes are being edited in a cell, the method can comprise (i) contacting the cell with a first exogenous oligonucleotide donor template that contains a first homology arm substantially identical to a first homology arm in the first target nucleic acid 5' to the cleavage site, and a second homology arm substantially identical to a second homology arm in the first target nucleic acid 3' to the cleavage site, and/or (ii) contacting the cell with a second exogenous oligonucleotide donor template that contains a first homology arm substantially identical to a first homology arm in the second target nucleic acid 5' to the cleavage site, and a second homology arm substantially identical to a second homology arm in the second target nucleic acid 3' to the cleavage site. In embodiments where three genes are being edited in a cell, the method can further comprise contacting the cell with a third exogenous oligonucleotide donor template that contains a first homology arm substantially identical to a first homology arm in the third target nucleic acid 5' to the cleavage site, and a second homology arm substantially identical to a second homology arm in the third target nucleic acid 3' to the cleavage site. Exogenous oligonucleotide donor templates can similarly be introduced for recombination with additional target genes, where 4, 5, 6 or more target nucleic acids are edited in a cell. Additional features of the exogenous oligonucleotide donor templates are described herein. In one embodiment, one or more exogenous oligonucleotide donor templates comprises a stop codon, as described above.

Generating Multiple Cleavage Events Using Different Nucleases

As noted above, the translocation frequency is increased during multiplex genome editing when DSBs occur simultaneously in multiple target nucleic acids in a cell. In some applications, it may not be possible or desirable to introduce reagents for genome editing (e.g., a RNA-guided nuclease and at least one gRNA) at multiple, different times. For example, multiple rounds of electroporation may affect the viability of the edited cells. Different RNA-guided nucleases have different on/off kinetics and/or different kinetics for induction of double-stranded breaks, which can affect the timing at which nuclease-induced DSBs are formed and processed. Accordingly, multiplex editing using a different nuclease to introduce a cleavage site into each target nucleic acid can reduce the simultaneous occurrence of DSBs in more than one target nucleic acid, thereby reducing the formation of chromosomal translocations. The use of different nucleases can allow for the sequential formation of DSBs, even in embodiments where the reagents for editing multiple target nucleic acids are introduced into the cell simultaneously.

In one aspect, the disclosure provides a method of altering a cell at a first target nucleic acid and a second target nucleic acid using different nucleases. The method comprises forming at least one single- or double-stranded break at a first cleavage site in the first target nucleic acid using a first RNA-guided nuclease, wherein the first cleavage site is repaired by at least one DNA repair pathway to produce an altered first target nucleic acid, and forming at least one single- or double-stranded break at a second cleavage site in the second target nucleic acid using a second RNA-guided nuclease, wherein the second cleavage site is repaired by at least one DNA repair pathway to produce an altered second target nucleic acid, and wherein the second RNA-guided nuclease is a different type of RNA-guided nuclease molecule from the first RNA-guided nuclease. In one embodiment, the step of forming at least one single- or double-stranded break at the first cleavage site and the step of forming at least one single- or double-stranded break at the second cleavage site are performed simultaneously. In another embodiment, the step of forming at least one single- or double-stranded break at the first cleavage site and the step of forming at least one single- or double-stranded break at the second cleavage site are performed sequentially.

In another aspect, the disclosure provides a method of altering a first target nucleic acid and a second target nucleic acid in a cell, comprising (a) contacting the cell with at least one first RNP complex that contains a first RNA-guided nuclease and a first gRNA molecule capable of directing the first RNA-guided nuclease to the first target nucleic acid; (b) contacting the cell with at least one second RNP complex that contains a second RNA-guided nuclease and a second gRNA molecule capable of directing the second RNA-guided nuclease to the second target nucleic acid; and optionally (c) contacting the cell with a first exogenous oligonucleotide donor template and/or a second exogenous oligonucleotide donor template; wherein the first RNP complex interacts with the first target nucleic acid, resulting in a first cleavage event, wherein the first cleavage event is repaired by at least one DNA repair pathway to produce an altered first target nucleic acid; wherein the second RNP complex interacts with the second target nucleic acid, resulting in a second cleavage event, wherein the second cleavage event is repaired by at least one DNA repair pathway to produce an altered second target nucleic acid; and wherein the first RNA-guided nuclease is a different type of RNA-guided nuclease molecule than the second RNA-guided nuclease. In one embodiment, the cell is contacted with the first RNP complex and the second RNP complex simultaneously. In another embodiment, the cell is contacted with the first RNP complex and the second RNP complex sequentially.

The foregoing methods can be performed using any RNA-guided nuclease described herein. In one embodiment, the first RNA-guided nuclease and the second RNA-guided nuclease are CRISPR-associated nucleases. In one embodiment, the first RNA-guided nuclease and the second RNA-guided nuclease are different nuclease orthologs. In one embodiment, the first RNA-guided nuclease and the second RNA-guided nuclease are selected from a wild-type Cas9, a Cas9 nickase, a wild-type Cpf1, and a Cpf1 nickase. For example, the first RNA-guided nuclease can be Cas9, or a nuclease derived therefrom, e.g., a Cas9 nickase, and the second RNA-guided nuclease can be Cpf1, or a nuclease derived therefrom, e.g., a Cpf1 nickase. Alternatively, the first RNA-guided nuclease can be Cpf1, or a nuclease derived therefrom, e.g., a Cpf1 nickase, and the second RNA-guided nuclease can be Cas9, or a nuclease derived therefrom, e.g., a Cas9 nickase. In one embodiment, one RNA-guided nuclease can be S. pyogenes Cas9, or a nuclease derived therefrom, e.g., a Cas9 nickase, and the other RNA-guided nuclease can be Acidaminococcus sp. Cpf1, or a nuclease derived therefrom, e.g., a Cpf1 nickase.

In one embodiment, the first RNA-guided nuclease and the second RNA-guided nuclease can be derived from different species. For example, the first nuclease can be derived from S. pyogenes, while the second nuclease can be derived from S. aureus. Alternatively, the first nuclease can be derived from S. aureus, while the second nuclease can be derived from S. pyogenes. In another example, the first nuclease can be derived from S. pyogenes, while the second nuclease can be derived from Acidaminococcus. Alternatively, the first nuclease can be derived from Acidaminococcus, while the second nuclease can be derived from S. pyogenes. Nuclease molecules of, derived from, or based on the RNA-guided nuclease proteins of other species listed herein can be used as well. These include, for example, RNA-guided nuclease molecules (e.g., Cas9 molecules) from Acidaminococcus sp., Acidovorax avenae, Actinobacillus pleuropneumoniae, Actinobacillus succinogenes, Actinobacillus suis, Actinomyces sp., cycliphilus denitrificans, Aminomonas paucivorans, Bacillus cereus, Bacillus smithii, Bacillus thuringiensis, Bacteroides sp., Blastopirellula marina, Bradyrhizobium sp., Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis sp., Methylosinus trichosporium, Mobiluncus mulieris, Neisseria bacilliformis, Neisseria cinerea, Neisseria flavescens, Neisseria lactamica, Neisseria sp., Neisseria wadsworthii, Nitrosomonas sp., Parvibaculum lavamentivorans, Pasteurella multocida, Phascolarctobacterium succinatutens, Ralstonia syzygii, Rhodopseudomonas palustris, Rhodovulum sp., Simonsiella muelleri, Sphingomonas sp., Sporolactobacillus vineae, Staphylococcus lugdunensis, Streptococcus sp., Subdoligranulum sp., Tistrella mobilis, Treponema sp., or Verminephrobacter eiseniae.

In one embodiment, the first RNA-guided nuclease is derived from S. pyogenes, while the second nuclease is derived from one of the following species: Acidaminococcus sp., Acidovorax avenae, Actinobacillus pleuropneumoniae, Actinobacillus succinogenes, Actinobacillus suis, Actinomyces sp., cycliphilus denitrificans, Aminomonas paucivorans, Bacillus cereus, Bacillus smithii, Bacillus thuringiensis, Bacteroides sp., Blastopirellula marina, Bradyrhizobium sp., Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis sp., Methylosinus trichosporium, Mobiluncus mulieris, Neisseria bacilliformis, Neisseria cinerea, Neisseria flavescens, Neisseria lactamica, Neisseria sp., Neisseria wadsworthii, Nitrosomonas sp., Parvibaculum

*lavamentivorans, Pasteurella multocida, Phascolarctobacterium succinatutens, Ralstonia syzygii, Rhodopseudomonas palustris, Rhodovulum* sp., *S. aureus, Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

In another embodiment, the first nuclease is derived from *S. aureus*, while the second nuclease is derived from one of the following species: *Acidaminococcus* sp., *Acidovorax avenae, Actinobacillus pleuropneumoniae, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *S. pyogenes, Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

In another embodiment, the first nuclease is derived from *Acidaminococcus* sp., while the second nuclease is derived from one of the following species: *Acidovorax avenae, Actinobacillus pleuropneumoniae, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *S. aureus, S. pyogenes, Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

In one embodiment, the first RNA-guided nuclease and the second RNA-guided nuclease are different nickases. For example, the first RNA-guided nuclease can have an inactivated RuvC domain, and the second RNA-guided nuclease can have an inactivated HNH domain. Alternatively, the first RNA-guided nuclease can have an inactivated HNH domain, and the second RNA-guided nuclease can have an inactivated RuvC domain.

The foregoing methods can reduce the translocation frequency in the edited cells, relative to cells in which the first target nucleic acid and the second nucleic acid are altered using the same nuclease. In one embodiment, the percentage of cells that undergo a translocation event is reduced by 10% or more, e.g., 20% or more, 30% or more, 40% or more, 50% or more, 60% or more, 70% or more, 80% or more, 90% or more, 95% or more 99% or more, or by 100%. In an exemplary embodiment, the percentage of cells that undergo a translocation event is reduced by 50% or more.

In one embodiment of the foregoing methods, the target nucleic acids are performed in the absence of an exogenous oligonucleotide donor template. In such embodiments, the cleavage events introduced by the RNA-guided nuclease are repaired primarily through the NHEJ repair pathway. In other embodiments, the foregoing methods are performed in the presence of an exogenous oligonucleotide donor template. In such embodiments, the cleavage events introduced by the RNA-guided nuclease are repaired primarily through the HDR repair pathway. The donor template can contain a first homology arm substantially identical to a first homology arm in the target nucleic acid positioned 5' of the cleavage site, and/or a second homology arm substantially identical to a second homology arm in the target nucleic acid positioned 3' of the cleavage site. An exogenous oligonucleotide donor template can be used for recombination with any one or more of the target nucleic acids undergoing gene editing. Thus, in embodiments where two genes are being edited in a cell, the method can comprise (i) contacting the cell with a first exogenous oligonucleotide donor template that contains a first homology arm substantially identical to a first homology arm in the first target nucleic acid 5' to the cleavage site, and a second homology arm substantially identical to a second homology arm in the first target nucleic acid 3' to the cleavage site, and/or (ii) contacting the cell with a second exogenous oligonucleotide donor template that contains a first homology arm substantially identical to a first homology arm in the second target nucleic acid 5' to the cleavage site, and a second homology arm substantially identical to a second homology arm in the second target nucleic acid 3' to the cleavage site. In embodiments where three genes are being edited in a cell, the method can further comprise contacting the cell with a third exogenous oligonucleotide donor template that contains a first homology arm substantially identical to a first homology arm in the third target nucleic acid 5' to the cleavage site, and a second homology arm substantially identical to a second homology arm in the third target nucleic acid 3' to the cleavage site. Exogenous oligonucleotide donor templates can similarly be introduced for recombination with additional target genes, where 4, 5, 6 or more target nucleic acids are edited in a cell. Additional features of the exogenous oligonucleotide donor templates are described herein. The design and implementation of oligonucleotide donor templates is described herein. For example, the oligonucleotide donor template can be a ssODN or a dsODN. The donor template can also be present in a vector, e.g., a plasmid vector, or a viral vector, for example, an AAV vector or a lentiviral vector. In one embodiment, the donor template contains one or more stop codons, as described herein.

Generating Multiple Cleavage Events Using Different Nuclease Implementations

Another strategy for minimizing the formation of translocations during multiplex genome editing is to modulate the timing of nuclease availability, such that reagents for altering each target nucleic acid (e.g., RNA-guided nuclease and gRNA) are active in a cell at different times. For example, a cell can be provided with a pre-formed RNP complex for editing a first target nucleic acid, and an exogenous nucleic acid encoding a nuclease for editing a second target nucleic acid. The RNP complex can initiate alteration of the first target nucleic acid immediately following introduction of the RNP complex into the cell, while the nuclease encoded by the exogenous nucleic acid must be translated into protein and complexed with a gRNA prior to initiating alteration of the second target nucleic acid. Consequently, DSBs are introduced into the first target nucleic acid and the second target nucleic acid at different times, even in embodiments where the cell is simultaneously provided with the RNP complex and the exogenous nucleic acid encoding the nuclease. The additional translation step offsets the activity of the encoded nuclease relative to the immediately active RNP complex, thereby reducing the time during which DSBs could simultaneously occur in the first target nucleic acid and the second target nucleic acid. Consequently, the translocation frequency is reduced, relative to embodiments in which cells are contacted simultaneously with the same nuclease implementation (i.e., two RNP complexes, or two exogenous nucleic acids) for altering each target nucleic acid.

In one aspect, the disclosure provides a method of altering a cell at a first target nucleic acid and a second target nucleic acid. The method comprises (i) forming at least one single- or double-stranded break at a first cleavage site in the first target nucleic acid using a ribonucleoprotein (RNP) complex comprising a first RNA-guided nuclease and a first guide RNA (gRNA) capable of directing the first RNA-guided nuclease to the first target nucleic acid, wherein the first cleavage site is repaired by at least one DNA repair pathway to produce an altered first target nucleic acid; and (ii) forming at least one single- or double-stranded break at a second cleavage site in the second target nucleic acid using a second RNA-guided nuclease expressed in the cell from an exogenous nucleic acid encoding the second RNA-guided nuclease, wherein the second cleavage site is repaired by at least one DNA repair pathway to produce an altered second target nucleic acid.

In one embodiment, the step of forming the at least one single- or double-stranded break in the first target nucleic acid can comprise introducing the RNP complex into the cell.

In one embodiment, the step of forming the at least one single- or double-stranded break in the second target nucleic acid can comprise introducing into the cell (i) the exogenous nucleic acid encoding the second RNA-guided nuclease, and (ii) a second gRNA capable of directing the second RNA-guided nuclease to the second target nucleic acid. In another embodiment, the step of forming the at least one single- or double-stranded break in the second target nucleic acid can comprise introducing into the cell can comprise introducing into the cell (i) the exogenous nucleic acid encoding the second RNA-guided nuclease, and (ii) an exogenous nucleic acid encoding a second gRNA capable of directing the second RNA-guided nuclease to the second target nucleic acid.

In another aspect, the disclosure provides a method of altering a first target nucleic acid and a second target nucleic acid in a cell, which comprises contacting the cell with at least one RNP complex comprising a first RNA-guided nuclease and a first gRNA molecule capable of directing the first RNA-guided nuclease to the first target nucleic acid; contacting the cell with an exogenous nucleic acid molecule encoding a second RNA-guided nuclease; and contacting the cell with at least one second gRNA molecule, or an exogenous nucleic acid molecule encoding the second gRNA molecule, wherein the second gRNA molecule is capable of directing the second RNA-guided nuclease to the second target nucleic acid. In this aspect, the at least one RNP complex interacts with the first target nucleic acid, resulting in a first cleavage event repaired by at least one DNA repair pathway to produce an altered first target nucleic acid, and the second RNA-guided nuclease and the second gRNA molecule interact with the second target nucleic acid, resulting in a second cleavage event repaired by at least one DNA repair pathway to produce an altered second target nucleic acid.

In one embodiment, cells are contacted simultaneously with the at least one RNP complex, the exogenous nucleic acid molecule encoding the second RNA-guided nuclease, and the second gRNA. In another embodiment, cells are contacted sequentially with the at least one RNP complex, the exogenous nucleic acid molecule encoding the second RNA-guided nuclease, and the second gRNA, in any order.

Suitable exogenous nucleic acids for encoding an RNA-guided nuclease include, but are not limited to, mRNA molecules and DNA molecules. For example, an mRNA encoding the nuclease can be provided to cells receiving the RNP complex. Alternatively, the cell can be provided with a vector expressing the nuclease, e.g., a plasmid vector, or a viral vector, such as an AAV vector or a lentiviral vector. gRNA molecules can be provided to the cells directly, or can be expressed from a vector, e.g., a plasmid vector or viral vector.

The foregoing methods can reduce the translocation frequency in the edited cells, relative to cells in which the first target nucleic acid and the second nucleic acid are altered using the same nuclease. In one embodiment, the percentage of cells that undergo a translocation event is reduced by 10% or more, e.g., 20% or more, 30% or more, 40% or more, 50% or more, 60% or more, 70% or more, 80% or more, 90% or more, 95% or more 99% or more, or by 100%. In an exemplary embodiment, the percentage of cells that undergo a translocation event is reduced by 50% or more.

The cell can optionally be contacted with an oligonucleotide donor template suitable for recombination with the first target nucleic acid, and/or an oligonucleotide donor template suitable for recombination with the second target nucleic acid. The design and implementation of oligonucleotide donor templates is described herein. The donor template can contain a first homology arm substantially identical to a first homology arm in the target nucleic acid positioned 5' of the cleavage site, and/or a second homology arm substantially identical to a second homology arm in the target nucleic acid positioned 3' of the cleavage site. An exogenous oligonucleotide donor template can be used for recombination with any one or more of the target nucleic acids undergoing gene editing. Thus, in embodiments where two genes are being edited in a cell, the method can comprise (i) contacting the cell with a first exogenous oligonucleotide donor template that contains a first homology arm substantially identical to a first homology arm in the first target nucleic acid 5' to the cleavage site, and a second homology arm substantially identical to a second homology arm in the first target nucleic acid 3' to the cleavage site, and/or (ii) contacting the cell with a second exogenous oligonucleotide donor template that contains a first homology arm substantially identical to a first homology arm in the second target nucleic acid 5' to the cleavage site, and a second homology arm substantially identical to a second homology arm in the second target nucleic acid 3' to the cleavage site. In embodiments where three genes are being edited in a cell, the method can further comprise contacting the cell with a third exogenous oligonucleotide donor template that contains a first homology arm substantially identical to a first homology arm in the third target nucleic acid 5' to the cleavage site, and a second homology arm substantially identical to a second homology arm in the third target nucleic acid 3' to the cleavage site. Exogenous oligonucleotide donor templates can similarly be introduced for recombination with additional target genes, where 4, 5, 6 or more target nucleic acids are edited in a cell. Additional features of the exogenous oligonucleotide donor templates are described herein. For example, the oligonucleotide donor template can be a ssODN or a dsODN. The donor template can also be present in a vector, e.g., a plasmid vector, or a viral vector, for example, an AAV vector or a lentiviral vector. In one embodiment, the donor template contains one or more stop codons, as described herein.

(E) Strategies for Increasing the Occurrence of Chromosomal Rearrangements

In some embodiments, it may be desirable to enhance the formation of chromosomal rearrangements. For example, it may be desirable to enhance the formation of chromosomal translocations in order to facilitate analysis of translocation formation, and the functional consequences thereof. Accordingly, the disclosure provides, in one embodiment, an oligonucleotide donor template that enhances the formation of specific chromosomal rearrangements, referred to herein as a "translocation ODN".

Translocation ODN

To enhance the formation of a specific chromosomal rearrangement, an oligonucleotide donor template (translocation ODN) can be designed that contains a first homology arm substantially identical to a homology arm of a first target nucleic acid on a first chromosome, and a second homology arm substantially identical to a homology arm of a second target nucleic acid on a second chromosome. The homology arms of the first target nucleic acid and the second target nucleic acid should flank a cleavage site on each chromosome. The first homology arm and the second homology arm of the translocation ODN link the first chromosome and the second chromosome, thereby facilitating recombination of the chromosomes at the cleavage sites.

A translocation ODN can also be designed to promote the formation of intrachromosomal rearrangements, by joining one segment of a chromosome to a different segment of the same chromosome. If deletion of a region on a chromosome is desired, cleavage sites can be introduced at the boundaries of the region to be excised. For example, a first cleavage site can be introduced at a first target nucleic acid on a first chromosome, and a second cleavage site can be introduced at a second target nucleic acid on the first chromosome. A translocation ODN can be used to bring together the chromosomal regions flanking the portion to be deleted. This is illustrated schematically in FIG. 12. In this embodiment, an oligonucleotide donor template can be designed with homology arms targeting the portions of the chromosome flanking the deletion site. For example, a first homology arm can have substantial identity to a sequence adjacent to the first cleavage site, and a second homology arm can have substantial identity to a sequence adjacent to the second cleavage site. The first homology arm and the second homology arm of the translocation ODN link the portions of the chromosome to be joined, thereby facilitating intrachromosomal recombination at the cleavage sites.

The first homology arm and the second homology arm of the translocation ODN can optionally be connected by a linker. Linkers suitable for joining two nucleic acid sequences are known in the art, and include nucleic acid linkers and non-nucleic acid linkers (e.g., polypeptide linkers, polymer linkers, etc.). In a preferred embodiment, the linker is a nucleic acid linker. Use of a nucleic acid linker allows for the introduction of additional nucleotides at the junction site, which enables rearrangements induced by the donor template to be differentiated from rearrangements that occur spontaneously.

In one aspect, the disclosure provides an isolated oligonucleotide donor template that comprises, from 5' to 3', the elements $A1\text{-}L_N\text{-}B1$, wherein A1 is a homology arm that is substantially identical to a homology arm of a first target nucleic acid, L is a nucleotide sequence comprising N nucleotides which links A1 and B1, N is an integer equal to or greater than 0, and B1 is a homology arm that is substantially identical to a homology arm of a second target nucleic acid. In one embodiment, the first target nucleic acid and the second target nucleic acid are on different chromosomes.

In another embodiment, the first target nucleic acid and the second target nucleic acid are on the same chromosome. Where the first target nucleic acid and the second target nucleic acid are located on the same chromosome, in some embodiments, the first target nucleic acid is separated from the second target nucleic acid by at least 1 kilobase (kb) of intervening sequence. In exemplary embodiments, the first target nucleic acid and the second nucleic acid are separated by at least 2 kb, 3 kb, 4 kb, 5 kb, 6 kb, 7 kb, 8 kb, 9 kb, 10 kb, 20 kb, 25 kb, 30 kb, 40 kb, 50 kb, 100 kb, 200 kb, 250 kb, 500 kb, 100 kb or more. In some embodiments, the intrachromosomal rearrangement is a deletion of 2 kb, 3 kb, 4 kb, 5 kb, 6 kb, 7 kb, 8 kb, 9 kb, 10 kb, 20 kb, 25 kb, 30 kb, 40 kb, 50 kb, 100 kb, 200 kb, 250 kb, 500 kb, 100 kb or more.

The homology arms of the oligonucleotide donor templates described herein may be of any suitable length, provided such length is sufficient to allow efficient resolution of a cleavage site on the first chromosome and a cleavage site on the second chromosome, or to allow efficient resolution of two cleavage sites on the same chromosome. In some embodiments, where amplification by, e.g., PCR, of the homology arm is desired, the homology arm is of a length such that the amplification may be performed. In some embodiments, where sequencing of the homology arm is desired, the homology arm is of a length such that the sequencing may be performed.

In some embodiments, the 5' homology arm is between 50 to 250 nucleotides in length. In some embodiments, the 5' homology arm is 700 nucleotides or less in length. In some embodiments, the 5' homology arm is 650 nucleotides or less in length. In some embodiments, the 5' homology arm is 600 nucleotides or less in length. In some embodiments, the 5' homology arm is 550 nucleotides or less in length. In some embodiments, the 5' homology arm is 500 nucleotides or less in length. In some embodiments, the 5' homology arm is 400 nucleotides or less in length. In some embodiments, the 5' homology arm is 300 nucleotides or less in length. In some embodiments, the 5' homology arm is 250 nucleotides or less in length. In some embodiments, the 5' homology arm is 200 nucleotides or less in length. In some embodiments, the 5' homology arm is 150 nucleotides or less in length. In some embodiments, the 5' homology arm is 100 nucleotides or less in length. In some embodiments, the 5' homology arm is 50 nucleotides in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 5' homology arm is at least 20 nucleotides in length. In some embodiments, the 5' homology arm is at least 40 nucleotides in length. In some embodiments, the 5' homology arm is at least 50 nucleotides in length. In some embodiments, the 5' homology arm is at least 70 nucleotides in length. In some embodiments, the 5' homology arm is 20 nucleotides in length. In some embodiments, the 5' homology arm is 40 nucleotides in length. In some embodiments, the 5' homology arm is 50 nucleotides in length. In some embodiments, the 5' homology arm is 70 nucleotides in length.

In some embodiments, the 3' homology arm is between 50 to 250 nucleotides in length. In some embodiments, the 3' homology arm is 700 nucleotides or less in length. In some embodiments, the 3' homology arm is 650 nucleotides or less in length. In some embodiments, the 3' homology arm is 600 nucleotides or less in length. In some embodiments, the 3' homology arm is 550 nucleotides or less in length. In some embodiments, the 3' homology arm is 500 nucleotides or less in length. In some embodiments, the 3' homology arm is 400 nucleotides or less in length. In some embodiments, the 3' homology arm is 300 nucleotides or less in length. In some embodiments, the 3' homology arm is 250 nucleotides or less in length. In some embodiments, the 3' homology arm is 200 nucleotides in length or less. In some embodiments, the 3' homology arm is 150 nucleotides in length or less. In some embodiments, the 3' homology arm is 100 nucleotides in length or less. In some embodiments, the 3' homology arm is 50 nucleotides in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 nucleotides in length. In some embodiments, the 3' homology arm is at least 20 nucleotides in length. In some embodiments, the 3' homology arm is at least 40 nucleotides in length. In some embodiments, the 3' homology arm is at least 50 nucleotides in length. In some embodiments, the 3' homology arm is at least 70 nucleotides in length. In some embodiments, the 3' homology arm is 20 nucleotides in length. In some embodiments, the 3' homology arm is 40 nucleotides in length. In some embodiments, the 3' homology arm is 50 nucleotides in length. In some embodiments, the 3' homology arm is 70 nucleotides in length.

In some embodiments, the 5' homology arm is between 50 to 250 base pairs in length. In some embodiments, the 5' homology arm is 700 base pairs or less in length. In some embodiments, the 5' homology arm is 650 base pairs or less in length. In some embodiments, the 5' homology arm is 600 base pairs or less in length. In some embodiments, the 5' homology arm is 550 base pairs or less in length. In some embodiments, the 5' homology arm is 500 base pairs or less in length. In some embodiments, the 5' homology arm is 400 base pairs or less in length. In some embodiments, the 5' homology arm is 300 base pairs or less in length. In some embodiments, the 5' homology arm is 250 base pairs or less in length. In some embodiments, the 5' homology arm is 200 base pairs or less in length. In some embodiments, the 5' homology arm is 150 base pairs or less in length. In some embodiments, the 5' homology arm is 100 base pairs or less in length. In some embodiments, the 5' homology arm is 50 base pairs in length or less. In some embodiments, the 5' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs in length. In some embodiments, the 5' homology arm is at least 20 base pairs in length. In some embodiments, the 5' homology arm is at least 40 base pairs in length. In some embodiments, the 5' homology arm is at least 50 base pairs in length. In some embodiments, the 5' homology arm is at least 70 base pairs in length. In some embodiments, the 5' homology arm is 20 base pairs in length. In some embodiments, the 5' homology arm is 40 base pairs in length. In some embodiments, the 5' homology arm is 50 base pairs in length. In some embodiments, the 5' homology arm is 70 base pairs in length.

In some embodiments, the 3' homology arm is between 50 to 250 base pairs in length. In some embodiments, the 3' homology arm is 700 base pairs or less in length. In some embodiments, the 3' homology arm is 650 base pairs or less in length. In some embodiments, the 3' homology arm is 600 base pairs or less in length. In some embodiments, the 3' homology arm is 550 base pairs or less in length. In some embodiments, the 3' homology arm is 500 base pairs or less in length. In some embodiments, the 3' homology arm is 400 base pairs or less in length. In some embodiments, the 3' homology arm is 300 base pairs or less in length. In some embodiments, the 3' homology arm is 250 base pairs or less in length. In some embodiments, the 3' homology arm is 200 base pairs in length or less. In some embodiments, the 3' homology arm is 150 base pairs in length or less. In some embodiments, the 3' homology arm is 100 base pairs in length or less. In some embodiments, the 3' homology arm is 50 base pairs in length or less. In some embodiments, the 3' homology arm is 250, 200, 190, 180, 170, 160, 150, 140, 130, 120, 110, 100, 90, 80, 70, 60, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, or 20 base pairs in length. In some embodiments, the 3' homology arm is at least 20 base pairs in length. In some embodiments, the 3' homology arm is at least 40 base pairs in length. In some embodiments, the 3' homology arm is at least 50 base pairs in length. In some embodiments, the 3' homology arm is at least 70 base pairs in length. In some embodiments, the 3' homology arm is 20 base pairs in length. In some embodiments, the 3' homology arm is 40 base pairs in length. In some embodiments, the 3' homology arm is 50 base pairs in length. In some embodiments, the 3' homology arm is 70 base pairs in length.

The 5' and 3' homology arms can be of the same length or can differ in length. In some embodiments, the 5' and 3' homology arms are amplified to allow for the quantitative assessment of gene editing events, such as targeted integration, at a target nucleic acid. In some embodiments, the quantitative assessment of the gene editing events may rely on the amplification of both the 5' junction and 3' junction at the site of targeted integration by amplifying the whole or a part of the homology arm using a single pair of PCR primers in a single amplification reaction. Accordingly, although the length of the 5' and 3' homology arms may differ, the length of each homology arm can be capable of amplification (e.g., using PCR), if desired. Moreover, when amplification of both the 5' and the difference in lengths of the 5' and 3' homology arms in a single PCR reaction is desired, the length difference between the 5' and 3' homology arms should allow for PCR amplification using a single pair of PCR primers.

In some embodiments, the length of the 5' and 3' homology arms does not differ by more than 75 nucleotides. Thus, in some embodiments, when the 5' and 3' homology arms differ in length, the length difference between the homology arms is less than 70, 60, 50, 40, 30, 20, 10, 9, 8, 7, 6, 5, 4, 3, 2, or 1 nucleotides or base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 nucleotides. In some embodiments, the length difference between the 5' and 3' homology arms is less than 70, 60, 50, 40, 30, 20, 10, 9, 8, 7, 6, 5, 4, 3, 2, or 1 base pairs. In some embodiments, the 5' and 3' homology arms differ in length by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, or 75 base pairs.

In one embodiment, the homology arms of the oligonucleotide donor template are of approximately equal length. For example, the length of the 5' homology arm can be 80%, 85%, 90%, 95%, 97%, 99%, or 100% as long as the 3' homology arm, or the length of the 3' homology arm can be 80%, 85%, 90%, 95%, 97%, 99%, or 100% as long as the 5' homology arm. In one embodiment, the homology arms of the oligonucleotide donor template are of equal length.

Each target nucleic acid contains two homology arms that flank a cleavage site, as described herein. One of the homology arms will be positioned on the chromosome on the side of the cleavage site that contains the centromere ("centromeric" to the cleavage site), while the other homology arm will be positioned on the side of the cleavage site that does not contain the centromere ("acentromeric" to the cleavage site). The translocation ODN described herein can be designed to induce chromosomal rearrangements that are balanced, dicentric, or acentric, based on the selection of donor template homology arms that are substantially identical to the centromeric or acentromeric homology arms of the target nucleic acids. For example, balanced chromosomal rearrangements can be generated using an oligonucleotide donor template that comprises a first homology arm that is substantially identical to a homology arm centromeric to the cleavage site of the first target nucleic acid, and a second homology arm that is substantially identical to a homology arm acentromeric to the cleavage site of the second target nucleic acid. This oligonucleotide donor template will facilitate joining of the centromeric portion of the first chromosome with the acentromeric portion of the second chromosome. Dicentric chromosomal rearrangements can be generated using an oligonucleotide donor template that comprises a first homology arm that is substantially identical to a homology arm centromeric to the cleavage site of the first target nucleic acid, and a second homology arm that is substantially identical to a homology arm centromeric to the cleavage site of the second target nucleic acid. This oligonucleotide donor template will facilitate joining of the centromeric portion of the first chromosome with the centromeric portion of the second chromosome. Acentric chromosomal rearrangements can be generated using an oligonucleotide donor template that comprises a first homology arm that is substantially identical to a homology arm acentromeric to the cleavage site of the first target nucleic acid, and a second homology arm that is substantially identical to a homology arm acentromeric to the cleavage site of the second target nucleic acid. This oligonucleotide donor template will facilitate joining of the acentromeric portion of the first chromosome with the acentromeric portion of the second chromosome.

Accordingly, the first homology arm of the donor template can comprise a sequence that is substantially identical to either the centromeric or the acentromeric homology arm of a first target nucleic acid on a first chromosome, and the second homology arm of the donor template can comprise a sequence that is substantially identical to either the centromeric or the acentromeric homology arm of a second target nucleic acid on a second chromosome.

In embodiments wherein the oligonucleotide donor template comprises, from 5' to 3', the elements A1--$L_N$--B1, as described above, A1 can be substantially identical to the centromeric homology arm of the first target nucleic acid located on the first chromosome, or A1 can be substantially identical to the acentromeric homology arm of the first target nucleic acid located on the first chromosome. Likewise, B1 can be substantially identical to the centromeric homology arm of the second target nucleic acid located on the second chromosome, or B1 can be substantially identical to the acentromeric homology arm of the second target nucleic acid located on the second chromosome.

In one embodiment, A1 is substantially identical to the centromeric homology arm of the first target nucleic acid, and B1 is substantially identical to the acentromeric homology arm of the second target nucleic acid. In this embodiment, the donor template facilitates the formation of balanced translocations between the first chromosome and the second chromosome, which incorporate the centromeric portion of the first chromosome and the acentromeric portion of the second chromosome.

In one embodiment, A1 is substantially identical to the acentromeric homology arm of the first target nucleic acid, and B1 is substantially identical to the centromeric homology arm of the second target nucleic acid. In this embodiment, the donor template facilitates the formation of balanced translocations between the first chromosome and the second chromosome, which incorporate the acentromeric portion of the first chromosome and the centromeric portion of the second chromosome.

In one embodiment, A1 is substantially identical to the centromeric homology arm of the first target nucleic acid, and B1 is substantially identical to the centromeric homology arm of the second target nucleic acid. In this embodiment, the donor template facilitates the formation of dicentric translocations between the first chromosome and the second chromosome.

In one embodiment, A1 is substantially identical to the acentromeric homology arm of the first target nucleic acid, and B1 is substantially identical to the acentromeric homology arm of the second target nucleic acid. In this embodiment, the donor template facilitates the formation of acentric translocations between the first chromosome and the second chromosome.

In one embodiment, a homology arm of the oligonucleotide donor template can contain sufficient identity to the target nucleic acid to allow the homology arm of the oligonucleotide donor template to hybridize to the complementary strand of the homology arm in the target nucleic acid in the target cell. In one embodiment, the sequence of the first homology arm of the oligonucleotide template is at least about 65% identical to a homology arm of the first target nucleic acid. For example, in one embodiment, the first homology arm of the oligonucleotide donor template is at least about 65%, 70%, 75%, 80%, 85%, 90%, 95%, 97%, 98%, 99%, or 100% identical to a homology arm of the first target nucleic acid. In one embodiment, the first homology arm of the oligonucleotide donor template is at least about 90% identical to a homology arm of the first target nucleic acid. In another embodiment, the first homology arm of the oligonucleotide donor template is at least about 95% identical to a homology arm of the first target nucleic acid. In another embodiment, the first homology arm of the oligonucleotide donor template is at least about 99% identical to a homology arm of the first target nucleic acid. In another embodiment, the first homology arm of the oligonucleotide donor template is 100% identical to a homology arm of the first target nucleic acid. In some embodiments, the first homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides from a homology arm of the first target nucleic acid. In some embodiments the first homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from a homology arm of the first target nucleic acid.

In another embodiment, the sequence of the second homology arm of the oligonucleotide donor template is at least about 65% identical to a homology arm of the second target nucleic acid. For example, in one embodiment, the second homology arm of the oligonucleotide donor template is at least about 65%, 70%, 75%, 80%, 85%, 90%, 95%, 97%, 98%, 99%, or 100% identical to a homology arm of the second target nucleic acid. In one embodiment, the second homology arm of the oligonucleotide donor template is at least about 90% identical to a homology arm of the second target nucleic acid. In another embodiment, the second homology arm of the oligonucleotide donor template is at least about 95% identical to a homology arm of the second target nucleic acid. In another embodiment, the second homology arm of the oligonucleotide donor template is at least about 99% identical to a homology arm of the second target nucleic acid. In another embodiment, the second homology arm of the oligonucleotide donor template is 100% identical to a homology arm of the second target nucleic acid. In some embodiments, the second homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 nucleotides from a homology arm of the second target nucleic acid. In some embodiments the second homology arm of the oligonucleotide donor template has a sequence that is identical to, or differs by no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 base pairs from a homology arm of the second target nucleic acid.

In some embodiments, the first target nucleic acid and the second target nucleic acid are on different chromosomes.

In other embodiments, the first target nucleic acid and the second target nucleic acid are on the same chromosome.

The linker joining A1 and B1 is optional. Thus, in some embodiments, the donor template does not contain a linker, and N is equal to zero. In other embodiments, the donor template contains a linker comprising N nucleotides. In embodiments where a linker sequence is present, the linker sequence can be of any suitable length that does not interfere with the function of the donor template. In exemplary embodiments, the linker sequence is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 nucleotides. In one embodiment, the linker sequence is less than 5 nucleotides. In one embodiment, the linker sequence is less than 10 nucleotides. In one embodiment, the linker sequence is less than 20 nucleotides. In one embodiment, the linker sequence is less than 30 nucleotides. In one embodiment, the linker sequence is less than 40 nucleotides. In one embodiment, the linker sequence is less than 50 nucleotides. In one embodiment, the linker sequence is less than 60 nucleotides. In one embodiment, the linker sequence is less than 70 nucleotides. In one embodiment, the linker sequence is less than 80 nucleotides. In one embodiment, the linker sequence is less than 90 nucleotides. In one embodiment, the linker sequence is less than 100 nucleotides. In one embodiment, the linker sequence is less than 150 nucleotides. In one embodiment, the linker sequence is less than 200 nucleotides. In one embodiment, the linker sequence is 1-5 nucleotides. In another embodiment, the linker sequence is 5-10 nucleotides. In another embodiment, the linker sequence is 10-20 nucleotides. In other embodiments, the linker sequence is at least 2, at least 5, at least 10, at least 20, at least 30, at least 40, at least 50, at least 60, at least 70, at least 80, at least 90, or at least 100 nucleotides.

In one embodiment, the disclosure provides a genome editing system comprising a translocation ODN, as described herein. In exemplary embodiments, the genome editing system can further comprise (a) at least one RNA-guided nuclease, and/or (b) at least one first gRNA molecule capable of directing the RNA-guided nuclease to a first target nucleic acid, and/or (c) at least one second gRNA molecule capable of directing the RNA-guided nuclease to a second target nucleic acid.

The genome editing system can include any RNA-guided nuclease described herein. In exemplary embodiments, the RNA-guided nuclease is a CRISPR-associated nuclease, e.g., Cas9, or derivatives thereof, or Cpf1, or derivatives thereof. For example, the at least one RNA-guided nuclease can be a wild-type Cas9, a Cas9 nickase, a wild-type Cpf1, or a Cpf1 nickase. In embodiments where the RNA-guided nuclease is capable of cleaving both strands of a target nucleic acid, for example, wild-type Cas9 or wild-type Cpf1, the genome editing system may contain one first gRNA capable of directing the nuclease to the first target nucleic acid, and/or one second gRNA capable of directing the nuclease to the second target nucleic acid. In embodiments where the RNA-guided nuclease is capable of cleaving only one strand of a target nucleic acid, for example, Cas9 nickase or Cpf1 nickase, the genome editing system can contain two first gRNA molecules each capable of directing the RNA-guided nuclease to opposite strands of the first target nucleic acid, and/or two second gRNA molecules each capable of directing the RNA-guided nuclease to opposite strands of the second target nucleic acid. The two gRNA molecules can be designed to direct the nickase to the same position on each strand of the target nucleic acid, resulting in a blunt-ended cleavage site, or the two gRNA molecules can be designed to direct the nickase to staggered positions on each strand of the target nucleic acid, resulting in a cleavage site with 5' or 3' overhangs, as described below. In some embodiments the genome editing system contains a pre-formed ribonucleoprotein (RNP) complex comprising the RNA-guided nuclease and a gRNA molecule.

Generating Chromosomal Rearrangements Using a Translocation ODN

The translocation ODN described herein can be used to introduce targeted chromosomal rearrangements between specified chromosomes, at specified positions. A cleavage event (e.g., a single- or double-stranded break) can be introduced into the chromosome(s) at the desired point of translocation, followed by recombination with an exogenous oligonucleotide donor template comprising (i) a first homology arm substantially identical to a homology arm of the first target nucleic acid, and (ii) a second homology arm substantially identical to a homology arm of the second target nucleic acid. The homology arms of the first and second target nucleic acids flank the respective cleavage sites. In one embodiment, the first target nucleic acid and the second target nucleic acid are on different chromosomes, e.g., a first chromosome and a second chromosome. In another embodiment, the first target nucleic acid and the second target nucleic acid are on the same chromosome. The cleavage events can be introduced using any method described herein. The exogenous oligonucleotide donor template can include any implementation of the translocation ODN described herein. Recombination with the oligonucleotide donor template introduces a translocation at the respective cleavage sites, for example, between a first chromosome and a second chromosome, or between two regions of the same chromosome.

In one aspect, the disclosure provides a method of introducing a chromosomal rearrangement in a cell. The method can comprise forming, in a first target nucleic acid located on a first chromosome of the cell, at least one single- or double-stranded break at a first cleavage site, wherein the first target nucleic acid comprises a centromeric homology arm centromeric to the first cleavage site, and an acentromeric homology arm acentromeric to the first cleavage site; forming, in a second target nucleic acid located on a second chromosome of the cell, at least one single- or double-stranded break at a second cleavage site, wherein the second target nucleic acid comprises a centromeric homology arm centromeric to the second cleavage site, and an acentromeric homology arm acentromeric to the second cleavage site; and recombining the first target nucleic acid and the second target nucleic acid with an exogenous oligonucleotide donor template by homologous recombination to produce a chromosomal rearrangement between the first chromosome and the second chromosome.

In another aspect, the disclosure provides a method of introducing an intrachromosomal rearrangement in a cell. The method can comprise forming, in a first target nucleic acid, at least one single- or double-stranded break at a first cleavage site; forming, in a second target nucleic acid, at least one single- or double-stranded break at a second cleavage site, wherein the first target nucleic acid and the second target nucleic acid are located on the same chromosome; and recombining the first target nucleic acid and the second target nucleic acid with an exogenous oligonucleotide donor template by homologous recombination to produce a chromosomal rearrangement between the first target nucleic acid and the second target nucleic acid.

In the foregoing aspects, the exogenous oligonucleotide donor template can be any implementation of the translocation ODN described herein. In one embodiment, a first strand of the exogenous oligonucleotide donor template comprises, from 5' to 3', A1--$L_N$--B1, wherein A1 is a homology arm that is substantially identical to a homology arm of the first target nucleic acid; L is a nucleotide sequence comprising N nucleotides which links A1 and B1; N is an integer equal to or greater than 0; and B1 is a homology arm that is substantially identical to a homology arm of the second target nucleic acid.

In the foregoing method, the step of recombining the first target nucleic acid and the second target nucleic acid with an exogenous oligonucleotide donor template can comprise, for example, introducing the exogenous oligonucleotide donor template into the cell.

In another aspect, the disclosure provides a method of introducing a chromosomal rearrangement in a cell, comprising contacting the cell with (i) at least one RNA-guided nuclease, (ii) at least one first gRNA molecule capable of directing the RNA-guided nuclease to a first target nucleic acid located on a first chromosome, (iii) at least one second gRNA molecule capable of directing the RNA-guided nuclease to a second target nucleic acid located on a second chromosome, and (iv) an exogenous oligonucleotide donor template. In this aspect, the RNA-guided nuclease and the at least one first gRNA molecule can interact with the first target nucleic acid, resulting in a cleavage event at a first cleavage site in the first target nucleic acid. The first target nucleic acid comprises a centromeric homology arm centromeric to the first cleavage site, and an acentromeric homology arm acentromeric to the first cleavage site, as described above. Similarly, the RNA-guided nuclease and the at least one second gRNA molecule can interact with the second target nucleic acid, resulting in a cleavage event at a second cleavage site in the second target nucleic acid. The second target nucleic acid likewise comprises a centromeric homology arm centromeric to the second cleavage site, and an acentromeric homology arm acentromeric to the second cleavage site.

In another aspect, the disclosure provides a method of introducing an intrachromosomal rearrangement in a cell, comprising contacting the cell with (i) at least one RNA-guided nuclease, (ii) at least one first gRNA molecule capable of directing the RNA-guided nuclease to a first target nucleic acid, (iii) at least one second gRNA molecule capable of directing the RNA-guided nuclease to a second target nucleic acid, wherein the first target nucleic acid and the second target nucleic acid are located on the same chromosome, and (iv) an exogenous oligonucleotide donor template. In this aspect, the RNA-guided nuclease and the at least one first gRNA molecule can interact with the first target nucleic acid, resulting in a cleavage event at a first cleavage site in the first target nucleic acid. Similarly, the RNA-guided nuclease and the at least one second gRNA molecule can interact with the second target nucleic acid, resulting in a cleavage event at a second cleavage site in the second target nucleic acid.

In the foregoing aspects, the exogenous oligonucleotide donor template can be any implementation of the translocation ODN described herein. In one embodiment, a first strand of the exogenous oligonucleotide donor template comprises, from 5' to 3', A1--$L_N$--B1, wherein A1 is a homology arm that is substantially identical to a homology arm of the first target nucleic acid; L is a nucleotide sequence comprising N nucleotides which links A1 and B1; N is an integer equal to or greater than 0; and B1 is a homology arm that is substantially identical to a homology arm of the second target nucleic acid. The first target nucleic acid and the second target nucleic acid can recombine with the exogenous oligonucleotide donor template by homologous recombination, introducing a chromosomal rearrangement in the cell.

The foregoing methods can be used to introduce chromosomal rearrangements that are balanced, dicentric, or acentric, as described herein. Accordingly, A1 can be substantially identical to either the centromeric or the acentromeric homology arm of the first target nucleic acid, and B1 can be substantially identical to either the centromeric or the acentromeric homology arm of the second target nucleic acid. For example, A1 can be substantially identical to the centromeric homology arm of the first target nucleic acid, and B1 can be substantially identical to the acentromeric homology arm of the second target nucleic acid. Alternatively, A1 can be substantially identical to the acentromeric homology arm of the first target nucleic acid, and B1 can be substantially identical to the centromeric homology arm of the second target nucleic acid. In another embodiment, A1 can be substantially identical to the centromeric homology arm of the first target nucleic acid, and B1 can be substantially identical to the centromeric homology arm of the second target nucleic acid. Alternatively, A1 can be substantially identical to the acentromeric homology arm of the first target nucleic acid, and B1 can be substantially identical to the acentromeric homology arm of the second target nucleic acid.

The foregoing methods can employ any RNA-guided nuclease described herein. In exemplary embodiments, the RNA-guided nuclease is a CRISPR-associated nuclease, e.g., Cas9, or derivatives thereof, or Cpf1, or derivatives thereof. For example, the at least one RNA-guided nuclease can be a wild-type Cas9, a Cas9 nickase, a wild-type Cpf1, or a Cpf1 nickase. In embodiments where the RNA-guided nuclease is capable of cleaving both strands of a target nucleic acid, for example, wild-type Cas9 or wild-type Cpf1, the method may employ one first gRNA capable of directing the nuclease to the first target nucleic acid, and/or one second gRNA capable of directing the nuclease to the second target nucleic acid. In embodiments where the RNA-guided nuclease is capable of cleaving only one strand of a target nucleic acid, for example, Cas9 nickase or Cpf1 nickase, the method may employ two first gRNA molecules each capable of directing the RNA-guided nuclease to opposite strands of the first target nucleic acid, and/or two second gRNA molecules each capable of directing the RNA-guided nuclease to opposite strands of the second target nucleic acid. The two gRNA molecules can be designed to direct the nickase to the same position on each strand of the target nucleic acid, resulting in a blunt-ended cleavage site, or the two gRNA molecules can be designed to direct the nickase to staggered positions on each strand of the target nucleic acid, resulting in a cleavage site with 5' or 3' overhangs, as described below.

The oligonucleotide donor template can be provided in any implementation described herein. For example, the donor template can be a ssODN, or it may be present in a dsODN. In one embodiment, the donor template is present in a vector, e.g., a viral vector, such as an AAV vector or a lentiviral vector, or a plasmid vector.

In one embodiment, the disclosure provides a cell comprising a chromosomal rearrangement, e.g., a translocation, produced by the methods described herein.

Detecting Chromosomal Rearrangements

Several methods are known in the art for detecting chromosomal rearrangements, e.g., chromosomal translocations.

Some such methods are PCR-based. For example, Digital Droplet PCR (ddPCR) can be used to quantitatively detect rearrangements of interest. In this method, droplets are formed in a water/oil emulsion to partition template DNA molecules, and PCR amplification is carried out within each droplet. A fluorescent probe anneals to the amplified product, and is read by a droplet analyzer. ddPCR is capable of providing an absolute count of target DNA molecules in a given sample. To detect chromosomal translocations, PCR primers and a detection probe that anneals to the amplified product are designed to detect a specific rearrangement at a specific location, as shown in FIG. 2A. Consequently, this method requires prior knowledge of the rearrangement to be detected.

Another PCR-based method, Uni-Directional Targeted Sequencing ("UDITAS"), can detect the presence of genomic modifications, e.g., indels and rearrangements, without specific knowledge regarding the nature of the alteration. In the UDITAS method, genomic DNA that has been cleaved, modified, and/or edited as described herein is contacted with a transposon under conditions (e.g., in the presence of a transposase) whereby the transposon is inserted into the nucleic acid template. Such transposition reactions and conditions are known in the art (see, e.g., U.S. Pat. Nos. 6,593,113 and 9,080,211). In some embodiments, transposition conditions are selected with the desired fragment size in mind. The transposition reaction results in fragmentation of the nucleic acid template into a plurality of tagmented double-stranded nucleic acid fragments, where the 3' end of the transferred strand of the transposon is attached to the 5' end of the nucleic acid fragments. The transferred strand of the transposon comprises a first detection sequence at the 5' end of the transferred strand. Following the transposition reaction, the tagmented nucleic acid fragments are amplified, e.g., using PCR, using a set of primers. A first primer can be a fixed primer, comprising a nucleotide sequence complementary to a predetermined location in the genomic DNA. A first primer can also be a fixed primer, comprising a nucleotide sequence complementary to at least a portion of a double-stranded oligonucleotide as described herein. The first primer also includes a second detection sequence at its 5' end. A second primer is a selective primer, comprising a nucleotide sequence complementary to at least a portion of the first detection sequence. The amplification forms amplified nucleic acid fragments, which include (in 5' to 3' orientation): the first detection sequence, the transferred strand of the transposon attached to the 5' end of the nucleic acid fragments, and the second detection sequence. The amplified nucleic acid fragments can then be sequenced. For example, the first and second detection sequences can include sequencing tags described herein to facilitate sequencing. In some embodiments, the method can include a size separation step after tagmentation and before PCR. This method is depicted in FIG. 2B.

Chromosomal rearrangements can also be detected using optical detection methods. Molecular combing is a technique in which long pieces of DNA are stretched onto a slide and probed with fluorescently labeled probes (Genetic Morse Code). The code signature of the locus allows for characterization, as shown in FIG. 3A.

Fluorescence In Situ Hybridization (FISH) is a chromosome-wide technique in which regions of interest can be labelled with fluorescent probes. Regions flanking the site of a potential cleavage event can be labelled with fluorescent probes, using a different probe to label different chromosomes. A rearrangement can be detected by juxtaposition of different probes on the same chromosome. This method is depicted in FIG. 3B, wherein the B2M and TRAC genes are flanked by green and red probes, respectively. A rearrangement between TRAC and B2M can be detected by juxtaposition of red and green on the same chromosome.

Additional methods for detecting chromosomal rearrangements are known to those in the art and are available commercially.

General Considerations

Any of the gene editing strategies described herein can employ any RNA-guided nuclease described herein. In exemplary embodiments, the RNA-guided nuclease is a CRISPR-associated nuclease, e.g., Cas9, or derivatives thereof, or Cpf1, or derivatives thereof. For example, the at least one RNA-guided nuclease can be a wild-type Cas9, a Cas9 nickase, a wild-type Cpf1, or a Cpf1 nickase. In embodiments where the RNA-guided nuclease is capable of cleaving both strands of a target nucleic acid, for example, wild-type Cas9 or wild-type Cpf1, the method may employ one first gRNA capable of directing the nuclease to a first target nucleic acid. In multiplex embodiments, the method may further employ one second gRNA capable of directing the nuclease to the second target nucleic acid. In embodiments where the RNA-guided nuclease is capable of cleaving only one strand of a target nucleic acid, for example, Cas9 nickase or Cpf1 nickase, the method may employ two first gRNA molecules each capable of directing the RNA-guided nuclease to opposite strands of the first target nucleic acid. In multiplex embodiments, the method may further employ two second gRNA molecules each capable of directing the RNA-guided nuclease to opposite strands of the second target nucleic acid. The two gRNA molecules can be designed to direct the nickase to the same position on each strand of the target nucleic acid, resulting in a blunt-ended cleavage site, or the two gRNA molecules can be designed to direct the nickase to staggered positions on each strand of the target nucleic acid, resulting in a cleavage site with 5' or 3' overhangs, as described below.

In addition, in any of the gene editing strategies described herein involving use of an oligonucleotide donor template, the oligonucleotide donor template can be provided in any implementation described herein. For example, the donor template can be a ssODN, or it may be present in a dsODN. In one embodiment, the donor template is present in a vector, e.g., a viral vector, such as an AAV vector or a lentiviral vector, or a plasmid vector.

Other features that may be used to implement various embodiments of any of the methods of the disclosure are described below.

Genome Editing Systems

The term "genome editing system" refers to any system having RNA-guided DNA editing activity. Genome editing systems of the present disclosure include at least two components adapted from naturally occurring CRISPR systems: a guide RNA (gRNA) and an RNA-guided nuclease. These two components form a complex that is capable of associating with a specific nucleic acid sequence and editing the DNA in or around that nucleic acid sequence, for instance by making one or more of a single-strand break (an SSB or nick), a double-strand break (a DSB) and/or a point mutation.

Naturally occurring CRISPR systems are organized evolutionarily into two classes and five types (Makarova et al. Nat Rev Microbiol. 2011 June; 9(6): 467-477 (Makarova), incorporated by reference herein), and while genome editing systems of the present disclosure may adapt components of any type or class of naturally occurring CRISPR system, the embodiments presented herein are generally adapted from Class 2, and type II or V CRISPR systems. Class 2 systems, which encompass types II and V, are characterized by relatively large, multidomain RNA-guided nuclease proteins (e.g., Cas9 or Cpf1) and one or more guide RNAs (e.g., a crRNA and, optionally, a tracrRNA) that form ribonucleoprotein (RNP) complexes that associate with (i.e. target) and cleave specific loci complementary to a targeting (or spacer) sequence of the crRNA. Genome editing systems according to the present disclosure similarly target and edit cellular DNA sequences, but differ significantly from CRISPR systems occurring in nature. For example, the unimolecular guide RNAs described herein do not occur in nature, and both guide RNAs and RNA-guided nucleases according to this disclosure may incorporate any number of non-naturally occurring modifications.

Genome editing systems can be implemented (e.g. administered or delivered to a cell or a subject) in a variety of ways, and different implementations may be suitable for distinct applications. For instance, a genome editing system is implemented, in certain embodiments, as a protein/RNA complex (a ribonucleoprotein, or RNP), which can be included in a pharmaceutical composition that optionally includes a pharmaceutically acceptable carrier and/or an encapsulating agent, such as a lipid or polymer micro- or nano-particle, micelle, liposome, etc. In certain embodiments, a genome editing system is implemented as one or more nucleic acids encoding the RNA-guided nuclease and guide RNA components described above (optionally with one or more additional components); in certain embodiments, the genome editing system is implemented as one or more vectors comprising such nucleic acids, for instance a viral vector such as an adeno-associated virus; and in certain embodiments, the genome editing system is implemented as a combination of any of the foregoing. Additional or modified implementations that operate according to the principles set forth herein will be apparent to the skilled artisan and are within the scope of this disclosure.

It should be noted that the genome editing systems of the present disclosure can be targeted to a single specific nucleotide sequence, or may be targeted to—and capable of editing in parallel—two or more specific nucleotide sequences through the use of two or more guide RNAs. The use of multiple gRNAs is referred to as "multiplexing" throughout this disclosure, and can be employed to target multiple, unrelated target sequences of interest, or to form multiple SSBs or DSBs within a single target domain and, in some cases, to generate specific edits within such target domain. For example, International Patent Publication No. WO 2015/138510 by Maeder et al. (Maeder), which is incorporated by reference herein, describes a genome editing system for correcting a point mutation (C.2991+1655A to G) in the human CEP290 gene that results in the creation of a cryptic splice site, which in turn reduces or eliminates the function of the gene. The genome editing system of Maeder utilizes two guide RNAs targeted to sequences on either side of (i.e., flanking) the point mutation, and forms DSBs that flank the mutation. This, in turn, promotes deletion of the intervening sequence, including the mutation, thereby eliminating the cryptic splice site and restoring normal gene function.

As another example, WO 2016/073990 by Cotta-Ramusino, et al. ("Cotta-Ramusino"), incorporated by reference herein, describes a genome editing system that utilizes two gRNAs in combination with a Cas9 nickase (a Cas9 that makes a single strand nick such as S. pyogenes D10A), an arrangement termed a "dual-nickase system." The dual-nickase system of Cotta-Ramusino is configured to make two nicks on opposite strands of a sequence of interest that are offset by one or more nucleotides, which nicks combine to create a double strand break having an overhang (5' in the case of Cotta-Ramusino, though 3' overhangs are also possible). The overhang, in turn, can facilitate homology directed repair events in some circumstances. And, as another example, WO 2015/070083 by Palestrant et al. ("Palestrant", incorporated by reference herein) describes a gRNA targeted to a nucleotide sequence encoding Cas9 (referred to as a "governing RNA"), which can be included in a genome editing system comprising one or more additional gRNAs to permit transient expression of a Cas9 that might otherwise be constitutively expressed, for example in some virally transduced cells. These multiplexing applications are intended to be exemplary, rather than limiting, and the skilled artisan will appreciate that other applications of multiplexing are generally compatible with the genome editing systems described here.

Genome editing systems can, in some instances, form double strand breaks that are repaired by cellular DNA double-strand break mechanisms such as NHEJ or HDR. These mechanisms are described throughout the literature, for example by Davis & Maizels, PNAS, 111(10):E924-932, Mar. 11, 2014 (Davis) (describing Alt-HDR); Frit et al. DNA Repair 17 (2014) 81-97 (Frit) (describing Alt-NHEJ); and Iyama and Wilson III, DNA Repair (Amst.) 2013-August; 12(8): 620-636 (Iyama) (describing canonical HDR and NHEJ pathways generally).

Where genome editing systems operate by forming DSBs, such systems optionally include one or more components that promote or facilitate a particular mode of double-strand break repair or a particular repair outcome. For instance, Cotta-Ramusino also describes genome editing systems in which a single stranded oligonucleotide "donor template" is added; the donor template is incorporated into a target region of cellular DNA that is cleaved by the genome editing system, and can result in a change in the target sequence.

In some embodiments, genome editing systems operate by forming paired single-stranded breaks, resulting in cleavage events in which the cleaved DNA has unpaired overhangs. Such overhangs can be at the 5' end or at the 3' end.

In certain embodiments, genome editing systems modify a target sequence, or modify expression of a gene in or near the target sequence, without causing single- or double-strand breaks. For example, a genome editing system may include an RNA-guided nuclease fused to a functional domain that acts on DNA, thereby modifying the target sequence or its expression. As one example, an RNA-guided nuclease can be connected to (e.g. fused to) a cytidine deaminase functional domain, and may operate by generating targeted C-to-A substitutions. Exemplary nuclease/deaminase fusions are described in Komor et al. Nature 533, 420-424 (19 May 2016) ("Komor"), which is incorporated by reference. Alternatively, a genome editing system may utilize a cleavage-inactivated (i.e. a "dead") nuclease, such as a dead Cas9 (dCas9), and may operate by forming stable complexes on one or more targeted regions of cellular DNA, thereby interfering with functions involving the targeted region(s) including, without limitation, mRNA transcription, chromatin remodeling, etc.

Reducing the Risk of Translocations

The phrase "reducing the risk of translocations" refers to a method of minimizing the amount of translocations that occur as a result of gene editing, especially when two or more target nucleic acids are being modified or altered, e.g., during multiplexing. In one embodiment, reducing the risk of translocations may comprise altering a first population of cells at two or more nucleic acid sites using two or more RNP complexes, wherein each RNP complex includes the same type of nuclease, and measuring the frequency of translcoations in the first population of cells. The method may further comprise altering a second population of cells at two or more nucleic acid sites using two or more RNP complexes, wherein each RNP complex includes different types of nucleases, and measuring the frequency of translocations in the second population of cells. The method may further comprise comparing the frequency of translocations in the two populations utilizing any of the assays as described in the disclosure, and identifying that the frequency of translocations is lowered in the second population of cells relative to the first population of cells.

In another embodiment, reducing the risk of translocations may comprise: i) contacting at least a first population of cells with a first genome editing system, wherein the first genome editing system comprises a first RNA-guided nuclease, a first at least one gRNA molecule, and an isolated oligonucleotide donor template of the disclosure, contacting at least a second population of cells with a second genome editing system, wherein the second genome editing system comprises a second RNA-guided nuclease, a second at least one gRNA molecule, and a second isolated oligonucleotide donor template of the disclosure; ii) measuring a percentage of cells in the first population of cells which comprise a translocation, and measuring a percentage of cells in the second population of cells which comprise a translocation, by utilizing any of the assays as described in the disclosure; iii) comparing the percentage of cells in the first population of cells which comprise a translocation to the percentage of cells in the second population of cells which comprise a translocation; and iv) selecting the genome editing system which results in a lower percentage of cells comprising a translocation in step iii), thereby minimizing the amount of translocations that occur as a result of gene editing.

Guide RNA (gRNA) Molecules

The terms "guide RNA" and "gRNA" refer to any nucleic acid that promotes the specific association (or "targeting") of an RNA-guided nuclease such as a Cas9 or a Cpf1 to a target sequence such as a genomic or episomal sequence in a cell. gRNAs can be unimolecular (comprising a single RNA molecule, and referred to alternatively as chimeric), or modular (comprising more than one, and typically two, separate RNA molecules, such as a crRNA and a tracrRNA, which are usually associated with one another, for instance by duplexing). gRNAs and their component parts are described throughout the literature, for instance in Briner et al. (Molecular Cell 56(2), 333-339, Oct. 23, 2014 (Briner), which is incorporated by reference), and in Cotta-Ramusino.

In bacteria and archea, type II CRISPR systems generally comprise an RNA-guided nuclease protein such as Cas9, a CRISPR RNA (crRNA) that includes a 5' region that is complementary to a foreign sequence, and a trans-activating crRNA (tracrRNA) that includes a 5' region that is complementary to, and forms a duplex with, a 3' region of the crRNA. While not intending to be bound by any theory, it is thought that this duplex facilitates the formation of—and is necessary for the activity of—the Cas9/gRNA complex. As type II CRISPR systems were adapted for use in gene editing, it was discovered that the crRNA and tracrRNA could be joined into a single unimolecular or chimeric guide RNA, in one non-limiting example, by means of a four nucleotide (e.g. GAAA) "tetraloop" or "linker" sequence bridging complementary regions of the crRNA (at its 3' end) and the tracrRNA (at its 5' end). (Mali et al. Science. 2013 Feb. 15; 339(6121): 823-826 ("Mali"); Jiang et al. Nat Biotechnol. 2013 March; 31(3): 233-239 ("Jiang"); and Jinek et al., 2012 Science August 17; 337(6096): 816-821 ("Jinek"), all of which are incorporated by reference herein.)

Guide RNAs, whether unimolecular or modular, include a "targeting domain" that is fully or partially complementary to a target domain within a target sequence, such as a DNA sequence in the genome of a cell where editing is desired. Targeting domains are referred to by various names in the literature, including without limitation "guide sequences" (Hsu et al., Nat Biotechnol. 2013 September; 31(9): 827-832, ("Hsu"), incorporated by reference herein), "complementarity regions" (Cotta-Ramusino), "spacers" (Briner) and generically as "crRNAs" (Jiang). Irrespective of the names they are given, targeting domains are typically 10-30 nucleotides in length, and in certain embodiments are 16-24 nucleotides in length (for instance, 16, 17, 18, 19, 20, 21, 22, 23 or 24 nucleotides in length), and are at or near the 5' terminus of in the case of a Cas9 gRNA, and at or near the 3' terminus in the case of a Cpf1 gRNA.

In addition to the targeting domains, gRNAs typically (but not necessarily, as discussed below) include a plurality of domains that may influence the formation or activity of gRNA/Cas9 complexes. For instance, as mentioned above, the duplexed structure formed by first and secondary complementarity domains of a gRNA (also referred to as a repeat:anti-repeat duplex) interacts with the recognition (REC) lobe of Cas9 and can mediate the formation of Cas9/gRNA complexes. (Nishimasu et al., Cell 156, 935-949, Feb. 27, 2014 (Nishimasu 2014) and Nishimasu et al., Cell 162, 1113-1126, Aug. 27, 2015 (Nishimasu 2015), both incorporated by reference herein). It should be noted that the first and/or second complementarity domains may contain one or more poly-A tracts, which can be recognized by RNA polymerases as a termination signal. The sequence of the first and second complementarity domains are, therefore, optionally modified to eliminate these tracts and promote the complete in vitro transcription of gRNAs, for instance through the use of A-G swaps as described in Briner, or A-U swaps. These and other similar modifications to the first and second complementarity domains are within the scope of the present disclosure.

Along with the first and second complementarity domains, Cas9 gRNAs typically include two or more additional duplexed regions that are involved in nuclease activity in vivo but not necessarily in vitro. (Nishimasu 2015). A first stem-loop one near the 3' portion of the second complementarity domain is referred to variously as the "proximal domain," (Cotta-Ramusino) "stem loop 1" (Nishimasu 2014 and 2015) and the "nexus" (Briner). One or more additional stem loop structures are generally present near the 3' end of the gRNA, with the number varying by species: S. pyogenes gRNAs typically include two 3' stem loops (for a total of four stem loop structures including the repeat:anti-repeat duplex), while S. aureus and other species have only one (for a total of three stem loop structures). A description of conserved stem loop structures (and gRNA structures more generally) organized by species is provided in Briner.

While the foregoing description has focused on gRNAs for use with Cas9, it should be appreciated that other RNA-guided nucleases have been (or may in the future be) discovered or invented which utilize gRNAs that differ in some ways from those described to this point. For instance, Cpf1 ("CRISPR from Prevotella and Franciscella 1") is a recently discovered RNA-guided nuclease that does not require a tracrRNA to function. (Zetsche et al., 2015, Cell 163, 759-771 Oct. 22, 2015 (Zetsche I), incorporated by reference herein). A gRNA for use in a Cpf1 genome editing system generally includes a targeting domain and a complementarity domain (alternately referred to as a "handle"). It should also be noted that, in gRNAs for use with Cpf1, the targeting domain is usually present at or near the 3' end, rather than the 5' end as described above in connection with Cas9 gRNAs (the handle is at or near the 5' end of a Cpf1 gRNA).

Those of skill in the art will appreciate that, although structural differences may exist between gRNAs from different prokaryotic species, or between Cpf1 and Cas9 gRNAs, the principles by which gRNAs operate are generally consistent. Because of this consistency of operation, gRNAs can be defined, in broad terms, by their targeting domain sequences, and skilled artisans will appreciate that a given targeting domain sequence can be incorporated in any suitable gRNA, including a unimolecular or chimeric gRNA, or a gRNA that includes one or more chemical modifications and/or sequential modifications (substitutions, additional nucleotides, truncations, etc.). Thus, for economy of presentation in this disclosure, gRNAs may be described solely in terms of their targeting domain sequences.

More generally, skilled artisans will appreciate that some aspects of the present disclosure relate to systems, methods and compositions that can be implemented using multiple RNA-guided nucleases. For this reason, unless otherwise specified, the term gRNA should be understood to encompass any suitable gRNA that can be used with any RNA-guided nuclease, and not only those gRNAs that are compatible with a particular species of Cas9 or Cpf1. By way of illustration, the term gRNA can, in certain embodiments, include a gRNA for use with any RNA-guided nuclease occurring in a Class 2 CRISPR system, such as a type II or type V or CRISPR system, or an RNA-guided nuclease derived or adapted therefrom.

gRNA Design

Methods for selection and validation of target sequences as well as off-target analyses have been described previously, e.g., in Mali; Hsu; Fu et al., 2014 Nat Biotechnol 32(3): 279-84, Heigwer et al., 2014 Nat methods 11(2):122-3; Bae et al. (2014) Bioinformatics 30(10): 1473-5; and Xiao A et al. (2014) Bioinformatics 30(8): 1180-1182. Each of these references is incorporated by reference herein. As a non-limiting example, gRNA design may involve the use of a software tool to optimize the choice of potential target sequences corresponding to a user's target sequence, e.g., to minimize total off-target activity across the genome. While off-target activity is not limited to cleavage, the cleavage efficiency at each off-target sequence can be predicted, e.g., using an experimentally-derived weighting scheme. These and other guide selection methods are described in detail in Maeder and Cotta-Ramusino.

gRNA Modifications

The activity, stability, or other characteristics of gRNAs can be altered through the incorporation of certain modifications. As one example, transiently expressed or delivered nucleic acids can be prone to degradation by, e.g., cellular nucleases. Accordingly, the gRNAs described herein can contain one or more modified nucleosides or nucleotides which introduce stability toward nucleases. While not wishing to be bound by theory it is also believed that certain modified gRNAs described herein can exhibit a reduced innate immune response when introduced into cells. Those of skill in the art will be aware of certain cellular responses commonly observed in cells, e.g., mammalian cells, in response to exogenous nucleic acids, particularly those of viral or bacterial origin. Such responses, which can include induction of cytokine expression and release and cell death, may be reduced or eliminated altogether by the modifications presented herein.

Certain exemplary modifications discussed in this section can be included at any position within a gRNA sequence including, without limitation at or near the 5' end (e.g., within 1-10, 1-5, or 1-2 nucleotides of the 5' end) and/or at or near the 3' end (e.g., within 1-10, 1-5, or 1-2 nucleotides of the 3' end). In some cases, modifications are positioned within functional motifs, such as the repeat-anti-repeat duplex of a Cas9 gRNA, a stem loop structure of a Cas9 or Cpf1 gRNA, and/or a targeting domain of a gRNA.

As one example, the 5' end of a gRNA can include a eukaryotic mRNA cap structure or cap analog (e.g., a G(5')ppp(5')G cap analog, a m7G(5')ppp(5')G cap analog, or a 3'-O-Me-m7G(5')ppp(5')G anti reverse cap analog (ARCA)), as shown below:

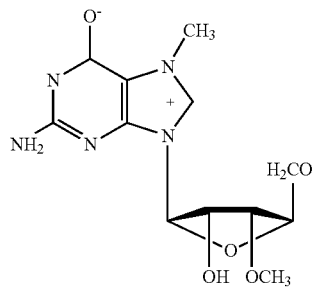

The cap or cap analog can be included during either chemical synthesis or in vitro transcription of the gRNA.

Along similar lines, the 5' end of the gRNA can lack a 5' triphosphate group. For instance, in vitro transcribed gRNAs can be phosphatase-treated (e.g., using calf intestinal alkaline phosphatase) to remove a 5' triphosphate group.

Another common modification involves the addition, at the 3' end of a gRNA, of a plurality (e.g., 1-10, 10-20, or 25-200) of adenine (A) residues referred to as a polyA tract. The polyA tract can be added to a gRNA during chemical synthesis, following in vitro transcription using a polyadenosine polymerase (e.g., *E. coli* Poly(A)Polymerase), or in vivo by means of a polyadenylation sequence, as described in Maeder.

It should be noted that the modifications described herein can be combined in any suitable manner, e.g. a gRNA, whether transcribed in vivo from a DNA vector, or in vitro transcribed gRNA, can include either or both of a 5' cap structure or cap analog and a 3' polyA tract.

Guide RNAs can be modified at a 3' terminal U ribose. For example, the two terminal hydroxyl groups of the U ribose can be oxidized to aldehyde groups and a concomitant opening of the ribose ring to afford a modified nucleoside as shown below:

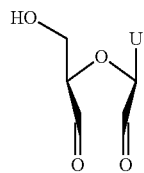

wherein "U" can be an unmodified or modified uridine.

The 3' terminal U ribose can be modified with a 2'3' cyclic phosphate as shown below:

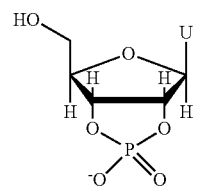

wherein "U" can be an unmodified or modified uridine.

Guide RNAs can contain 3' nucleotides which can be stabilized against degradation, e.g., by incorporating one or more of the modified nucleotides described herein. In certain embodiments, uridines can be replaced with modified uridines, e.g., 5-(2-amino)propyl uridine, and 5-bromo uridine, or with any of the modified uridines described herein; adenosines and guanosines can be replaced with modified adenosines and guanosines, e.g., with modifications at the 8-position, e.g., 8-bromo guanosine, or with any of the modified adenosines or guanosines described herein.

In certain embodiments, sugar-modified ribonucleotides can be incorporated into the gRNA, e.g., wherein the 2' OH-group is replaced by a group selected from H, —OR, —R (wherein R can be, e.g., alkyl, cycloalkyl, aryl, aralkyl, heteroaryl or sugar), halo, —SH, —SR (wherein R can be, e.g., alkyl, cycloalkyl, aryl, aralkyl, heteroaryl or sugar), amino (wherein amino can be, e.g., NH₂; alkylamino, dialkylamino, heterocyclyl, arylamino, diarylamino, heteroarylamino, diheteroarylamino, or amino acid); or cyano (—CN). In certain embodiments, the phosphate backbone can be modified as described herein, e.g., with a phosphothioate (PhTx) group. In certain embodiments, one or more of the nucleotides of the gRNA can each independently be a modified or unmodified nucleotide including, but not limited to 2'-sugar modified, such as, 2'-O-methyl, 2'-O-methoxyethyl, or 2'-Fluoro modified including, e.g., 2'-F or 2'-O-methyl, adenosine (A), 2'-F or 2'-O-methyl, cytidine (C), 2'-F or 2'-O-methyl, uridine (U), 2'-F or 2'-O-methyl, thymidine (T), 2'-F or 2'-O-methyl, guanosine (G), 2'-O-methoxyethyl-5-methyluridine (Teo), 2'-O-methoxyethyladenosine (Aeo), 2'-O-methoxyethyl-5-methylcytidine (m5Ceo), and any combinations thereof.

Guide RNAs can also include "locked" nucleic acids (LNA) in which the 2' OH-group can be connected, e.g., by a C1-6 alkylene or C1-6 heteroalkylene bridge, to the 4' carbon of the same ribose sugar. Any suitable moiety can be used to provide such bridges, include without limitation methylene, propylene, ether, or amino bridges; O-amino (wherein amino can be, e.g., NH₂; alkylamino, dialkylamino, heterocyclyl, arylamino, diarylamino, heteroarylamino, or diheteroarylamino, ethylenediamine, or polyamino) and aminoalkoxy or $O(CH_2)_n$-amino (wherein amino can be, e.g., $NH_2$; alkylamino, dialkylamino, heterocyclyl, arylamino, diarylamino, heteroarylamino, or diheteroarylamino, ethylenediamine, or polyamino).

In certain embodiments, a gRNA can include a modified nucleotide which is multicyclic (e.g., tricyclo; and "unlocked" forms, such as glycol nucleic acid (GNA) (e.g., R-GNA or S-GNA, where ribose is replaced by glycol units attached to phosphodiester bonds), or threose nucleic acid (TNA, where ribose is replaced with α-L-threofuranosyl-(3'→2')).

Generally, gRNAs include the sugar group ribose, which is a 5-membered ring having an oxygen. Exemplary modified gRNAs can include, without limitation, replacement of the oxygen in ribose (e.g., with sulfur (S), selenium (Se), or alkylene, such as, e.g., methylene or ethylene); addition of a double bond (e.g., to replace ribose with cyclopentenyl or cyclohexenyl); ring contraction of ribose (e.g., to form a 4-membered ring of cyclobutane or oxetane); ring expansion of ribose (e.g., to form a 6- or 7-membered ring having an additional carbon or heteroatom, such as for example, anhydrohexitol, altritol, mannitol, cyclohexanyl, cyclohexenyl, and morpholino that also has a phosphoramidate backbone). Although the majority of sugar analog alterations are localized to the 2' position, other sites are amenable to modification, including the 4' position. In certain embodiments, a gRNA comprises a 4'-S, 4'-Se or a 4'-C-aminomethyl-2'-O-Me modification.

In certain embodiments, deaza nucleotides, e.g., 7-deaza-adenosine, can be incorporated into the gRNA. In certain embodiments, O- and N-alkylated nucleotides, e.g., N6-methyl adenosine, can be incorporated into the gRNA. In certain embodiments, one or more or all of the nucleotides in a gRNA are deoxynucleotides.

RNA-Guided Nucleases

RNA-guided nucleases according to the present disclosure include, but are not limited to, naturally-occurring Class 2 CRISPR nucleases such as Cas9, and Cpf1, as well as other nucleases derived or obtained therefrom. In functional terms, RNA-guided nucleases are defined as those nucleases that: (a) interact with (e.g. complex with) a gRNA; and (b) together with the gRNA, associate with, and optionally cleave or modify, a target region of a DNA that includes (i) a sequence complementary to the targeting domain of the gRNA and, optionally, (ii) an additional sequence referred to as a "protospacer adjacent motif," or "PAM," which is described in greater detail below. As the following examples will illustrate, RNA-guided nucleases can be defined, in broad terms, by their PAM specificity and cleavage activity, even though variations may exist between individual RNA-guided nucleases that share the same PAM specificity or cleavage activity. Skilled artisans will appreciate that some aspects of the present disclosure relate to systems, methods and compositions that can be implemented using any suitable RNA-guided nuclease having a certain PAM specificity and/or cleavage activity. For this reason, unless otherwise specified, the term RNA-guided nuclease should be understood as a generic term, and not limited to any particular type (e.g. Cas9 vs. Cpf1), species (e.g. S. pyogenes vs. S. aureus) or variation (e.g. full-length vs. truncated or split; naturally-occurring PAM specificity vs. engineered PAM specificity, etc.) of RNA-guided nuclease.

As used herein, the phrase "same type" of RNA-guided nuclease refers to individual RNA-guided nucleases that are the same molecule and share the same PAM specificity and cleavage activity (e.g., spCas9 and spCas9). The "same type" of RNA-guided nuclease molecule would not be, for example, a wild-type and a variant of a nuclease. In some embodiments, the "same type" of RNA-guided nuclease may refer to two nucleases of identical amino acid sequence.

In contrast, the phrase "different type" of RNA-guided nuclease refers to individual RNA-guided nucleases that may be, for example, derived from a different species (e.g., a SpCas9 molecule and an SaCas9 molecule), a wild-type RNA-guided nuclease molecule and a variant RNA-guided nuclease molecule, e.g., a RNA-guided nuclease molecule comprising a modification resulting in alteration of its PAM specificity or cleavage activity (e.g., mediating a double-strand cleavage and a single-strand cleavage, e.g., a wild-type Cas9 molecule and a N863A Cas9 molecule), or a different RNA-guided nuclease (e.g., a Cas9 molecule and a Cpf1 molecule). In some embodiments, a "different type" of RNA-guided nuclease may refer to a second nuclease which does not have an identical sequence to a first nuclease.

The PAM sequence takes its name from its sequential relationship to the "protospacer" sequence that is complementary to gRNA targeting domains (or "spacers"). Together with protospacer sequences, PAM sequences define target regions or sequences for specific RNA-guided nuclease/gRNA combinations.

Various RNA-guided nucleases may require different sequential relationships between PAMs and protospacers. In general, Cas9s recognize PAM sequences that are 3' of the protospacer as visualized relative to the top or complementary strand:

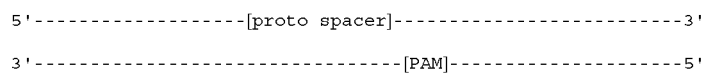

Cpf1, on the other hand, generally recognizes PAM sequences that are 5' of the protospacer:

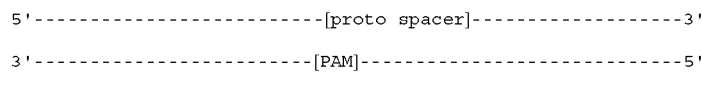

In addition to recognizing specific sequential orientations of PAMs and protospacers, RNA-guided nucleases can also recognize specific PAM sequences. S. aureus Cas9, for instance, recognizes a PAM sequence of NNGRRT or NNGRRV, wherein the N residues are immediately 3' of the region recognized by the gRNA targeting domain. S. pyogenes Cas9 recognizes NGG PAM sequences. And F. novicida Cpf1 recognizes a TTN PAM sequence. PAM sequences have been identified for a variety of RNA-guided nucleases, and a strategy for identifying novel PAM sequences has been described by Shmakov et al., 2015, Molecular Cell 60, 385-397, Nov. 5, 2015. It should also be noted that engineered RNA-guided nucleases can have PAM specificities that differ from the PAM specificities of reference molecules (for instance, in the case of an engineered RNA-guided nuclease, the reference molecule may be the naturally occurring variant from which the RNA-guided nuclease is derived, or the naturally occurring variant having the greatest amino acid sequence homology to the engineered RNA-guided nuclease).

In addition to their PAM specificity, RNA-guided nucleases can be characterized by their DNA cleavage activity: naturally-occurring RNA-guided nucleases typically form DSBs in target nucleic acids, but engineered variants have been produced that generate only SSBs (discussed above) Ran & Hsu, et al., Cell 154(6), 1380-1389, Sep. 12, 2013 (Ran), incorporated by reference herein), or that that do not cut at all.

Cas9

Crystal structures have been determined for *S. pyogenes* Cas9 (Jinek 2014), and for *S. aureus* Cas9 in complex with a unimolecular guide RNA and a target DNA (Nishimasu 2014; Anders 2014; and Nishimasu 2015).

A naturally occurring Cas9 protein comprises two lobes: a recognition (REC) lobe and a nuclease (NUC) lobe; each of which comprise particular structural and/or functional domains. The REC lobe comprises an arginine-rich bridge helix (BH) domain, and at least one REC domain (e.g. a REC1 domain and, optionally, a REC2 domain). The REC lobe does not share structural similarity with other known proteins, indicating that it is a unique functional domain. While not wishing to be bound by any theory, mutational analyses suggest specific functional roles for the BH and REC domains: the BH domain appears to play a role in gRNA:DNA recognition, while the REC domain is thought to interact with the repeat:anti-repeat duplex of the gRNA and to mediate the formation of the Cas9/gRNA complex.

The NUC lobe comprises a RuvC domain, an HNH domain, and a PAM-interacting (PI) domain. The RuvC domain shares structural similarity to retroviral integrase superfamily members and cleaves the non-complementary (i.e. bottom) strand of the target nucleic acid. It may be formed from two or more split RuvC motifs (such as RuvC I, RuvCII, and RuvCIII in *S. pyogenes* and *S. aureus*). The HNH domain, meanwhile, is structurally similar to HNN endonuclease motifs, and cleaves the complementary (i.e. top) strand of the target nucleic acid. The PI domain, as its name suggests, contributes to PAM specificity.

While certain functions of Cas9 are linked to (but not necessarily fully determined by) the specific domains set forth above, these and other functions may be mediated or influenced by other Cas9 domains, or by multiple domains on either lobe. For instance, in *S. pyogenes* Cas9, as described in Nishimasu 2014, the repeat:antirepeat duplex of the gRNA falls into a groove between the REC and NUC lobes, and nucleotides in the duplex interact with amino acids in the BH, PI, and REC domains. Some nucleotides in the first stem loop structure also interact with amino acids in multiple domains (PI, BH and REC1), as do some nucleotides in the second and third stem loops (RuvC and PI domains).

Cas9 molecules of a variety of species can be used in the methods and compositions described herein. While *S. pyogenes* and *S. aureus* Cas9 molecules are the subject of much of the disclosure herein, Cas9 molecules of, derived from, or based on the Cas9 proteins of other species listed herein can be used as well. These include, for example, Cas9 molecules from *Acidovorax avenae, Actinobacillus pleuropneumoniae, Actinobacillus succinogenes, Actinobacillus suis, Actinomyces* sp., *cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum, gamma proteobacterium, Gluconacetobacter diazotrophicus, Haemophilus parainfluenzae, Haemophilus sputorum, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

Cpf1

The crystal structure of *Acidaminococcus* sp. Cpf1 in complex with crRNA and a double-stranded (ds) DNA target including a TTTN PAM sequence has been solved by Yamano et al. (Cell. 2016 May 5; 165(4): 949-962 (Yamano), incorporated by reference herein). Cpf1, like Cas9, has two lobes: a REC (recognition) lobe, and a NUC (nuclease) lobe. The REC lobe includes REC1 and REC2 domains, which lack similarity to any known protein structures. The NUC lobe, meanwhile, includes three RuvC domains (RuvC-I, -II and -III) and a BH domain. However, in contrast to Cas9, the Cpf1 REC lobe lacks an HNH domain, and includes other domains that also lack similarity to known protein structures: a structurally unique PI domain, three Wedge (WED) domains (WED-I, -II and -III), and a nuclease (Nuc) domain.

While Cas9 and Cpf1 share similarities in structure and function, it should be appreciated that certain Cpf1 activities are mediated by structural domains that are not analogous to any Cas9 domains. For instance, cleavage of the complementary strand of the target DNA appears to be mediated by the Nuc domain, which differs sequentially and spatially from the HNH domain of Cas9. Additionally, the non-targeting portion of Cpf1 gRNA (the handle) adopts a pseudoknot structure, rather than a stem loop structure formed by the repeat:antirepeat duplex in Cas9 gRNAs.

Modifications of RNA-Guided Nucleases

The RNA-guided nucleases described above have activities and properties that can be useful in a variety of applications, but the skilled artisan will appreciate that RNA-guided nucleases can also be modified in certain instances, to alter cleavage activity, PAM specificity, or other structural or functional features.

Turning first to modifications that alter cleavage activity, mutations that reduce or eliminate the activity of domains within the NUC lobe have been described above. Exemplary mutations that may be made in the RuvC domains, in the Cas9 HNH domain, or in the Cpf1 Nuc domain are described in Ran and Yamano, as well as in Cotta-Ramusino. In general, mutations that reduce or eliminate activity in one of the two nuclease domains result in RNA-guided nucleases with nickase activity, but it should be noted that the type of nickase activity varies depending on which domain is inactivated. As one example, inactivation of a RuvC domain of a Cas9 will result in a nickase that cleaves the complementary or top strand as shown below (where C denotes the site of cleavage):

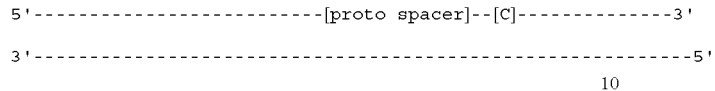

On the other hand, inactivation of a Cas9 HNH domain results in a nickase that cleaves the bottom or non-complementary strand:

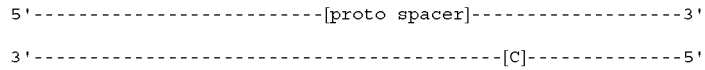

In some embodiments, the PAM sequences recognized by Cas9 nickases are facing inward, directly adjacent to the spacer sequence (the "PAM-in" orientation). In other embodiments, the two PAM sequences recognized by the two Cas9 nickases are facing outward, or positioned at the outer boundaries of the full-length target site (the "PAM-out" orientation).

In some embodiments, the cleavage events described herein are generated by two single-strand breaks, or nicks, effected by a Cas9 molecule having nickase activity, e.g., cleavage activity associated with an HNH-like domain or cleavage activity associated with an N-terminal RuvC-like domain. Such embodiments usually require two gRNAs, one for placement of each single-strand break. In an embodiment, the Cas9 molecule having nickase activity cleaves the strand to which the gRNA hybridizes, but not the strand that is complementary to the strand to which the gRNA hybridizes. In an embodiment, the Cas9 molecule having nickase activity does not cleave the strand to which the gRNA hybridizes, but rather cleaves the strand that is complementary to the strand to which the gRNA hybridizes.

In certain embodiments, the nickase has HNH activity, e.g., a Cas9 molecule having the RuvC activity inactivated, e.g., a Cas9 molecule having a mutation at D10, e.g., the D10A mutation. D10A inactivates RuvC; therefore, the Cas9 nickase has (only) HNH activity and will cut on the strand to which the gRNA hybridizes (e.g., the complementary strand, which does not have the NGG PAM on it). In other embodiments, a Cas9 molecule having an H840, e.g., an H840A, mutation can be used as a nickase. H840A inactivates HNH; therefore, the Cas9 nickase has (only) RuvC activity and cuts on the non-complementary strand (e.g., the strand that has the NGG PAM and whose sequence is identical to the gRNA). In other embodiments, a Cas9 molecule having an N863 mutation, e.g., the N863A mutation, mutation can be used as a nickase. N863A inactivates HNH therefore the Cas9 nickase has (only) RuvC activity and cuts on the non-complementary strand (the strand that has the NGG PAM and whose sequence is identical to the gRNA).

In certain embodiments, in which a nickase and two gRNAs are used to position two single strand nicks, one nick is on the + strand and one nick is on the – strand of the target nucleic acid. In some embodiments, the PAMs can be outwardly facing. In other embodiments, the PAMs can be inwardly facing. The gRNAs can be selected such that the gRNAs are separated by, from about 0-50, 0-100, or 0-200 nucleotides. In one embodiment, there is no overlap between the target sequences that are complementary to the targeting domains of the two gRNAs.

In certain embodiments, a single strand break is accompanied by an additional single strand break, positioned by a second gRNA molecule, as discussed below. For example, the targeting domains can be configured such that a cleavage event, e.g., the two single strand breaks, are positioned within 1, 2, 3, 4, 5, 10, 15, 20, 25, 30, 35, 40, 45, 50, 60, 70, 80, 90, 100, 150, or 200 nucleotides of a target position. In an embodiment, the first and second gRNA molecules are configured such that, when guiding a Cas9 nickase, a single strand break will be accompanied by an additional single strand break, positioned by a second gRNA, sufficiently close to one another to result in alteration of the desired region. In an embodiment, the first and second gRNA molecules are configured such that a single strand break positioned by said second gRNA is within 10, 20, 30, 40, or 50 nucleotides of the break positioned by said first gRNA molecule, e.g., when the Cas9 is a nickase. In an embodiment, the two gRNA molecules are configured to position cuts at the same position, or within a few nucleotides of one another, on different strands, e.g., essentially mimicking a double strand break.

Placement of a First Break and a Second Break Relative to Each Other

In certain embodiments, a double strand break can be accompanied by an additional double strand break, positioned by a second gRNA molecule, as is discussed below.

In certain embodiments, a double strand break can be accompanied by two additional single strand breaks, positioned by a second gRNA molecule and a third gRNA molecule.

In certain embodiments, a first and second single strand breaks can be accompanied by two additional single strand breaks positioned by a third gRNA molecule and a fourth gRNA molecule.

When two or more gRNAs are used to position two or more cleavage events, e.g., double strand or single strand breaks, in a target nucleic acid, it is contemplated that the two or more cleavage events may be made by the same or different Cas9 proteins. For example, when two gRNAs are used to position two double stranded breaks, a single Cas9 nuclease may be used to create both double stranded breaks. When two or more gRNAs are used to position two or more single stranded breaks (nicks), a single Cas9 nickase may be used to create the two or more nicks. When two or more gRNAs are used to position single stranded breaks (nicks) at more than one cleavage site, the same nickase, or a different nickase, may be used to generate breaks at each cleavage site, in some embodiments. When two or more gRNAs are used to position at least one double stranded break and at least one single stranded break, two Cas9 proteins may be used, e.g., one Cas9 nuclease and one Cas9 nickase. In some embodiments, when two or more Cas9 proteins are used, the two or more Cas9 proteins may be delivered sequentially to control specificity of a double stranded versus a single stranded break at the desired position in the target nucleic acid. Other embodiments described herein contemplate the simultaneous or sequential delivery of multiple nucleases, in a manner optimal for the specified application.

In some embodiments, the targeting domain of the first gRNA molecule and the targeting domain of the second gRNA molecules are complementary to opposite strands of the target nucleic acid molecule. In some embodiments, the gRNA molecule and the second gRNA molecule are configured such that the PAMs are oriented outward.

In certain embodiments, two gRNA are selected to direct Cas9-mediated cleavage at two positions that are a preselected distance from each other. In certain embodiments, the two points of cleavage are on opposite strands of the target nucleic acid. In some embodiments, the two cleavage points form a blunt ended break, and in other embodiments, they are offset so that the DNA ends comprise one or two overhangs (e.g., one or more 5' overhangs and/or one or more 3' overhangs). In some embodiments, each cleavage event is a nick. In certain embodiments, the nicks are close enough together that they form a break that is recognized by the double stranded break machinery (as opposed to being recognized by, e.g., the SSBr machinery). In certain embodiments, the nicks are far enough apart that they create an overhang that is a substrate for HDR, i.e., the placement of the breaks mimics a DNA substrate that has experienced some resection. For instance, in some embodiments the nicks are spaced to create an overhang that is a substrate for processive resection. In some embodiments, the two breaks are spaced within 25-65 nucleotides of each other. The two breaks may be, e.g., about 25, 30, 35, 40, 45, 50, 55, 60, or 65 nucleotides of each other. The two breaks may be, e.g., at least about 25, 30, 35, 40, 45, 50, 55, 60, or 65 nucleotides of each other. The two breaks may be, e.g., at most about 30, 35, 40, 45, 50, 55, 60, or 65 nucleotides of each other. In certain embodiments, the two breaks are about 25-30, 30-35, 35-40, 40-45, 45-50, 50-55, 55-60, or 60-65 nucleotides of each other.

In some embodiments, the break that mimics a resected break comprises a 3' overhang (e.g., generated by a DSB and a nick, where the nick leaves a 3' overhang), a 5' overhang (e.g., generated by a DSB and a nick, where the nick leaves a 5' overhang), a 3' and a 5' overhang (e.g., generated by three cuts), two 3' overhangs (e.g., generated by two nicks that are offset from each other), or two 5' overhangs (e.g., generated by two nicks that are offset from each other).

In certain embodiments in which two gRNAs (independently, unimolecular (or chimeric) or modular gRNA) complexing with Cas9 nickases induce two single strand breaks for the purpose of inducing HDR-mediated alteration, the closer nick is between 0-200 bp (e.g., 0 to 175, 0 to 150, 0 to 125, 0 to 100, 0 to 75, 0 to 50, 0 to 25, 25 to 200, 25 to 175, 25 to 150, 25 to 125, 25 to 100, 25 to 75, 25 to 50, 50 to 200, 50 to 175, 50 to 150, 50 to 125, 50 to 100, 50 to 75, 75 to 200, 75 to 175, 75 to 150, 75 to 125, or 75 to 100 bp) away from the target position and the two nicks will ideally be within 25-65 bp of each other (e.g., 25 to 50, 25 to 45, 25 to 40, 25 to 35, 25 to 30, 30 to 55, 30 to 50, 30 to 45, 30 to 40, 30 to 35, 35 to 55, 35 to 50, 35 to 45, 35 to 40, 40 to 55, 40 to 50, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, 20, 10, or 5 bp away from each other). In certain embodiments, the cleavage site is between 0-100 bp (e.g., 0 to 75, 0 to 50, 0 to 25, 25 to 100, 25 to 75, 25 to 50, 50 to 100, 50 to 75, or 75 to 100 bp) away from the target position.

In some embodiments, two gRNAs, e.g., independently, unimolecular (or chimeric) or modular gRNA, are configured to position a double-strand break on both sides of a target position. In other embodiments, three gRNAs, e.g., independently, unimolecular (or chimeric) or modular gRNA, are configured to position a double strand break (i.e., one gRNA complexes with a Cas9 nuclease) and two single strand breaks or paired single stranded breaks (i.e., two gRNAs complex with Cas9 nickases) on either side of the target position. In other embodiments, four gRNAs, e.g., independently, unimolecular (or chimeric) or modular gRNA, are configured to generate two pairs of single stranded breaks (i.e., two pairs of two gRNAs complex with Cas9 nickases) on either side of the target position. The double strand break(s) or the closer of the two single strand nicks in a pair will ideally be within 0-500 bp of the target position (e.g., no more than 450, 400, 350, 300, 250, 200, 150, 100, 50 or 25 bp from the target position). When nickases are used, the two nicks in a pair are, in certain embodiments, within 25-65 bp of each other (e.g., between 25 to 55, 25 to 50, 25 to 45, 25 to 40, 25 to 35, 25 to 30, 50 to 55, 45 to 55, 40 to 55, 35 to 55, 30 to 55, 30 to 50, 35 to 50, 40 to 50, 45 to 50, 35 to 45, 40 to 45 bp, 45 to 50 bp, 50 to 55 bp, 55 to 60 bp, or 60 to 65 bp) and no more than 100 bp away from each other (e.g., no more than 90, 80, 70, 60, 50, 40, 30, or 20 or 10 bp).

When two gRNAs are used to target Cas9 molecules to breaks, different combinations of Cas9 molecules are envisioned. In some embodiments, a first gRNA is used to target a first Cas9 molecule to a first target position, and a second gRNA is used to target a second Cas9 molecule to a second target position. In some embodiments, the first Cas9 molecule creates a nick on the first strand of the target nucleic acid, and the second Cas9 molecule creates a nick on the opposite strand, resulting in a double stranded break (e.g., a blunt ended cut or a cut with overhangs).

Different combinations of nickases can be chosen to target one single stranded break to one strand and a second single stranded break to the opposite strand. When choosing a combination, one can take into account that there are nickases having one active RuvC-like domain, and nickases having one active HNH domain. In certain embodiments, a RuvC-like domain cleaves the non-complementary strand of the target nucleic acid molecule. In certain embodiments, an HNH-like domain cleaves a single stranded complementary domain, e.g., a complementary strand of a double stranded nucleic acid molecule. Generally, if both Cas9 molecules have the same active domain (e.g., both have an active RuvC domain or both have an active HNH domain), one will choose two gRNAs that bind to opposite strands of the target. In more detail, in some embodiments a first gRNA is complementary with a first strand of the target nucleic acid and binds a nickase having an active RuvC-like domain and causes that nickase to cleave the strand that is non-complementary to that first gRNA, i.e., a second strand of the target nucleic acid; and a second gRNA is complementary with a second strand of the target nucleic acid and binds a nickase having an active RuvC-like domain and causes that nickase to cleave the strand that is non-complementary to that second gRNA, i.e., the first strand of the target nucleic acid. Conversely, in some embodiments, a first gRNA is complementary with a first strand of the target nucleic acid and binds a nickase having an active HNH domain and causes that nickase to cleave the strand that is complementary to that first gRNA, i.e., a first strand of the target nucleic acid; and a second gRNA is complementary with a second strand of the target nucleic acid and binds a nickase having an active HNH domain and causes that nickase to cleave the strand that is complementary to that second gRNA, i.e., the second strand of the target nucleic acid. In another arrangement, if one Cas9 molecule has an active RuvC-like domain and the other Cas9 molecule has an active HNH domain, the gRNAs for both Cas9 molecules can be complementary to the same strand of the target nucleic acid, so that the Cas9 molecule with the active RuvC-like domain will cleave the non-complementary strand and the Cas9 molecule with the HNH domain will cleave the complementary strand, resulting in a double stranded break.

Modifications of PAM specificity relative to naturally occurring Cas9 reference molecules has been described by Kleinstiver et al. for both *S. pyogenes* (Kleinstiver et al., Nature. 2015 Jul. 23; 523(7561):481-5 (Kleinstiver I) and *S. aureus* (Kleinstiver et al., Nat Biotechnol. 2015 December; 33(12): 1293-1298 (Klienstiver II)). Kleinstiver et al. have also described modifications that improve the targeting fidelity of Cas9 (Nature, 2016 Jan. 28; 529, 490-495 (Kleinstiver III)). Each of these references is incorporated by reference herein.

RNA-guided nucleases have been split into two or more parts, as described by Zetsche et al. (Nat Biotechnol. 2015 February; 33(2):139-42 (Zetsche II), incorporated by reference), and by Fine et al. (Sci Rep. 2015 Jul. 1; 5:10777 (Fine), incorporated by reference).

RNA-guided nucleases can be, in certain embodiments, size-optimized or truncated, for instance via one or more deletions that reduce the size of the nuclease while still retaining gRNA association, target and PAM recognition, and cleavage activities. In certain embodiments, RNA guided nucleases are bound, covalently or non-covalently, to another polypeptide, nucleotide, or other structure, optionally by means of a linker. Exemplary bound nucleases and linkers are described by Guilinger et al., Nature Biotechnology 32, 577-582 (2014), which is incorporated by reference for all purposes herein.

RNA-guided nucleases also optionally include a tag, such as, but not limited to, a nuclear localization signal to facilitate movement of RNA-guided nuclease protein into the nucleus. In certain embodiments, the RNA-guided nuclease can incorporate C- and/or N-terminal nuclear localization signals. Nuclear localization sequences are known in the art and are described in Maeder and elsewhere.

The foregoing list of modifications is intended to be exemplary in nature, and the skilled artisan will appreciate, in view of the instant disclosure, that other modifications may be possible or desirable in certain applications. For brevity, therefore, exemplary systems, methods and compositions of the present disclosure are presented with reference to particular RNA-guided nucleases, but it should be understood that the RNA-guided nucleases used may be modified in ways that do not alter their operating principles. Such modifications are within the scope of the present disclosure.

Nucleic Acids Encoding RNA-Guided Nucleases

Nucleic acids encoding RNA-guided nucleases, e.g., Cas9, Cpf1 or functional fragments thereof, are provided herein. Exemplary nucleic acids encoding RNA-guided nucleases have been described previously (see, e.g., Cong 2013; Wang 2013; Mali 2013; Jinek 2012).

In some cases, a nucleic acid encoding an RNA-guided nuclease can be a synthetic nucleic acid sequence. For example, the synthetic nucleic acid molecule can be chemically modified. In certain embodiments, an mRNA encoding an RNA-guided nuclease will have one or more (e.g., all) of the following properties: it can be capped; polyadenylated; and substituted with 5-methylcytidine and/or pseudouridine.

Synthetic nucleic acid sequences can also be codon optimized, e.g., at least one non-common codon or less-common codon has been replaced by a common codon. For example, the synthetic nucleic acid can direct the synthesis of an optimized messenger mRNA, e.g., optimized for expression in a mammalian expression system, e.g., described herein. Examples of codon optimized Cas9 coding sequences are presented in Cotta-Ramusino.

In addition, or alternatively, a nucleic acid encoding an RNA-guided nuclease may comprise a nuclear localization sequence (NLS). Nuclear localization sequences are known in the art.

Functional Analysis of Candidate Molecules

Candidate RNA-guided nucleases, gRNAs, and complexes thereof, can be evaluated by standard methods known in the art. See, e.g. Cotta-Ramusino. The stability of RNP complexes may be evaluated by differential scanning fluorimetry, as described below.

Differential Scanning Fluorimetry (DSF)

The thermostability of ribonucleoprotein (RNP) complexes comprising gRNAs and RNA-guided nucleases can be measured via DSF. The DSF technique measures the thermostability of a protein, which can increase under favorable conditions such as the addition of a binding RNA molecule, e.g., a gRNA.

A DSF assay can be performed according to any suitable protocol, and can be employed in any suitable setting, including without limitation (a) testing different conditions (e.g. different stoichiometric ratios of gRNA: RNA-guided nuclease protein, different buffer solutions, etc.) to identify optimal conditions for RNP formation; and (b) testing modifications (e.g. chemical modifications, alterations of sequence, etc.) of an RNA-guided nuclease and/or a gRNA to identify those modifications that improve RNP formation or stability. One readout of a DSF assay is a shift in melting temperature of the RNP complex; a relatively high shift suggests that the RNP complex is more stable (and may thus have greater activity or more favorable kinetics of formation, kinetics of degradation, or another functional characteristic) relative to a reference RNP complex characterized by a lower shift. When the DSF assay is deployed as a screening tool, a threshold melting temperature shift may be specified, so that the output is one or more RNPs having a melting temperature shift at or above the threshold. For instance, the threshold can be 5-10° C. (e.g. 5°, 6°, 7°, 8°, 9°, 10°) or more, and the output may be one or more RNPs characterized by a melting temperature shift greater than or equal to the threshold.

Two non-limiting examples of DSF assay conditions are set forth below:

To determine the best solution to form RNP complexes, a fixed concentration (e.g. 2 µM) of Cas9 in water+10x SYPRO Orange® (Life Technologies cat #S-6650) is dispensed into a 384 well plate. An equimolar amount of gRNA diluted in solutions with varied pH and salt is then added. After incubating at room temperature for 10' and brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

The second assay consists of mixing various concentrations of gRNA with fixed concentration (e.g. 2 µM) Cas9 in optimal buffer from assay 1 above and incubating (e.g. at RT for 10') in a 384 well plate. An equal volume of optimal buffer+10x SYPRO Orange® (Life Technologies cat #S-6650) is added and the plate sealed with Microseal® B adhesive (MSB-1001). Following brief centrifugation to remove any bubbles, a Bio-Rad CFX384™ Real-Time System C1000 Touch™ Thermal Cycler with the Bio-Rad CFX Manager software is used to run a gradient from 20° C. to 90° C. with a 1° C. increase in temperature every 10 seconds.

Genome Editing Strategies

The genome editing systems described above are used, in various embodiments of the present disclosure, to generate edits in (i.e. to alter) targeted regions of DNA within or obtained from a cell. Various strategies are described herein to generate particular edits, and these strategies are generally described in terms of the desired repair outcome, the number and positioning of individual edits (e.g. SSBs or DSBs), and the target sites of such edits.

Genome editing strategies that involve the formation of SSBs or DSBs are characterized by repair outcomes including: (a) deletion of all or part of a targeted region; (b) insertion into or replacement of all or part of a targeted region; or (c) interruption of all or part of a targeted region. This grouping is not intended to be limiting, or to be binding to any particular theory or model, and is offered solely for economy of presentation. Skilled artisans will appreciate that the listed outcomes are not mutually exclusive and that some repairs may result in other outcomes. The description of a particular editing strategy or method should not be understood to require a particular repair outcome unless otherwise specified.

Replacement of a targeted region generally involves the replacement of all or part of the existing sequence within the targeted region with a homologous sequence, for instance through gene correction or gene conversion, two repair outcomes that are mediated by HDR pathways. HDR is promoted by the use of a donor template, which can be single-stranded or double stranded, as described in greater detail below. Single or double stranded templates can be exogenous, in which case they will promote gene correction, or they can be endogenous (e.g. a homologous sequence within the cellular genome), to promote gene conversion. Exogenous templates can have asymmetric overhangs (i.e. the portion of the template that is complementary to the site of the DSB may be offset in a 3' or 5' direction, rather than being centered within the donor template), for instance as described by Richardson et al. (Nature Biotechnology 34, 339-344 (2016), (Richardson), incorporated by reference). In instances where the template is single stranded, it can correspond to either the complementary (top) or non-complementary (bottom) strand of the targeted region.

Gene conversion and gene correction are facilitated, in some cases, by the formation of one or more nicks in or around the targeted region, as described in Ran and Cotta-Ramusino. In some cases, a dual-nickase strategy is used to form two offset SSBs that, in turn, form a single DSB having an overhang (e.g. a 5' overhang).

Interruption and/or deletion of all or part of a targeted sequence can be achieved by a variety of repair outcomes. As one example, a sequence can be deleted by simultaneously generating two or more DSBs that flank a targeted region, which is then excised when the DSBs are repaired, as is described in Maeder for the LCA10 mutation. As another example, a sequence can be interrupted by a deletion generated by formation of a double strand break with single-stranded overhangs, followed by exonucleolytic processing of the overhangs prior to repair.

One specific subset of target sequence interruptions is mediated by the formation of an indel within the targeted sequence, where the repair outcome is typically mediated by NHEJ pathways (including Alt-NHEJ). NHEJ is referred to as an "error prone" repair pathway because of its association with indel mutations. In some cases, however, a DSB is repaired by NHEJ without alteration of the sequence around it (a so-called "perfect" or "scarless" repair); this generally requires the two ends of the DSB to be perfectly ligated. Indels, meanwhile, are thought to arise from enzymatic processing of free DNA ends before they are ligated that adds and/or removes nucleotides from either or both strands of either or both free ends.

Because the enzymatic processing of free DSB ends may be stochastic in nature, indel mutations tend to be variable, occurring along a distribution, and can be influenced by a variety of factors, including the specific target site, the cell type used, the genome editing strategy used, etc. Even so, it is possible to draw limited generalizations about indel formation: deletions formed by repair of a single DSB are most commonly in the 1-50 bp range, but can reach greater than 100-200 bp. Insertions formed by repair of a single DSB tend to be shorter and often include short duplications of the sequence immediately surrounding the break site. However, it is possible to obtain large insertions, and in these cases, the inserted sequence has often been traced to other regions of the genome or to plasmid DNA present in the cells.

Indel mutations—and genome editing systems configured to produce indels—are useful for interrupting target sequences, for example, when the generation of a specific final sequence is not required and/or where a frameshift mutation would be tolerated. They can also be useful in settings where particular sequences are preferred, insofar as the certain sequences desired tend to occur preferentially from the repair of an SSB or DSB at a given site. Indel mutations are also a useful tool for evaluating or screening the activity of particular genome editing systems and their components. In these and other settings, indels can be characterized by (a) their relative and absolute frequencies in the genomes of cells contacted with genome editing systems and (b) the distribution of numerical differences relative to the unedited sequence, e.g. ±1, ±2, ±3, etc. As one example, in a lead-finding setting, multiple gRNAs can be screened to identify those gRNAs that most efficiently drive cutting at a target site based on an indel readout under controlled conditions. Guides that produce indels at or above a threshold frequency, or that produce a particular distribution of indels, can be selected for further study and development. Indel frequency and distribution can also be useful as a readout for evaluating different genome editing system implementations or formulations and delivery methods, for instance by keeping the gRNA constant and varying certain other reaction conditions or delivery methods.

Multiplex Strategies

While exemplary strategies discussed above have focused on repair outcomes mediated by single DSBs, genome editing systems according to this disclosure may also be employed to generate two or more DSBs, either in the same locus or in different loci. Strategies for editing that involve the formation of DSBs, or SSBs, are described in, for instance, Cotta-Ramusino.

Donor Template Design

Donor template design is described in detail in the literature, for instance in Cotta-Ramusino. DNA oligomer donor templates (oligodeoxynucleotides or ODNs), which can be single stranded (ssODNs) or double-stranded (dsODNs), can be used to facilitate HDR-based repair of DSBs, and are particularly useful for introducing alterations into a target DNA sequence, inserting a new sequence into the target sequence, or replacing the target sequence altogether.

Whether single-stranded or double stranded, donor templates generally include regions that are homologous to regions of DNA within or near (e.g. flanking or adjoining) a target sequence to be cleaved. These homologous regions are referred to here as "homology arms," and are illustrated schematically below:

[5' homology arm]-[replacement sequence]-[3' homology arm].

The homology arms can have any suitable length (including 0 nucleotides if only one homology arm is used), and 3' and 5' homology arms can have the same length, or can differ in length. The selection of appropriate homology arm lengths can be influenced by a variety of factors, such as the desire to avoid homologies or microhomologies with certain sequences such as Alu repeats or other very common elements. For example, a 5' homology arm can be shortened to avoid a sequence repeat element. In other embodiments, a 3' homology arm can be shortened to avoid a sequence repeat element. In some embodiments, both the 5' and the 3' homology arms can be shortened to avoid including certain sequence repeat elements. In addition, some homology arm designs can improve the efficiency of editing or increase the frequency of a desired repair outcome. For example, Richardson et al. Nature Biotechnology 34, 339-344 (2016) (Richardson), which is incorporated by reference, found that the relative asymmetry of 3' and 5' homology arms of single stranded donor templates influenced repair rates and/or outcomes.

Replacement sequences in donor templates have been described elsewhere, including in Cotta-Ramusino et al. A replacement sequence can be any suitable length (including zero nucleotides, where the desired repair outcome is a deletion), and typically includes one, two, three or more sequence modifications relative to the naturally-occurring sequence within a cell in which editing is desired. One common sequence modification involves the alteration of the naturally-occurring sequence to repair a mutation that is related to a disease or condition of which treatment is desired. Another common sequence modification involves the alteration of one or more sequences that are complementary to, or code for, the PAM sequence of the RNA-guided nuclease or the targeting domain of the gRNA(s) being used to generate an SSB or DSB, to reduce or eliminate repeated cleavage of the target site after the replacement sequence has been incorporated into the target site.

Where a linear ssODN is used, it can be configured to (i) anneal to the nicked strand of the target nucleic acid, (ii) anneal to the intact strand of the target nucleic acid, (iii) anneal to the plus strand of the target nucleic acid, and/or (iv) anneal to the minus strand of the target nucleic acid. An ssODN may have any suitable length, e.g., about, at least, or no more than 150-200 nucleotides (e.g., 150, 160, 170, 180, 190, or 200 nucleotides).

It should be noted that a template nucleic acid can also be a nucleic acid vector, such as a viral genome or circular double stranded DNA, e.g., a plasmid. Nucleic acid vectors comprising donor templates can include other coding or non-coding elements. For example, a template nucleic acid can be delivered as part of a viral genome (e.g. in an AAV or lentiviral genome) that includes certain genomic backbone elements (e.g. inverted terminal repeats, in the case of an AAV genome) and optionally includes additional sequences coding for a gRNA and/or an RNA-guided nuclease. In certain embodiments, the donor template can be adjacent to, or flanked by, target sites recognized by one or more gRNAs, to facilitate the formation of free DSBs on one or both ends of the donor template that can participate in repair of corresponding SSBs or DSBs formed in cellular DNA using the same gRNAs. Exemplary nucleic acid vectors suitable for use as donor templates are described in Cotta-Ramusino.

Whatever format is used, a template nucleic acid can be designed to avoid undesirable sequences. In certain embodiments, one or both homology arms can be shortened to avoid overlap with certain sequence repeat elements, e.g., Alu repeats, LINE elements, etc.

Target Cells

Genome editing systems according to this disclosure can be used to alter or manipulate or modify a cell or population of cells, e.g., to edit or modify a target nucleic acid in the cell or population of cells. The manipulating can occur, in various embodiments, in vivo or ex vivo.

A variety of cell types can be altered or manipulated or modified according to the embodiments of this disclosure, and in some cases, such as in vivo applications, a plurality of cell types can be altered or modified or manipulated, for example by delivering genome editing systems according to this disclosure to a plurality of cell types. In other cases, however, it may be desirable to limit manipulation or modification to a particular cell type or types. For instance, it can be desirable in some instances to edit a cell, or a population of cells, with limited differentiation potential or a terminally differentiated cell, such as a photoreceptor cell in the case of Maeder (see above), in which modification of a genotype is expected to result in a change in cell phenotype. In other cases, however, it may be desirable to edit a less differentiated, multipotent or pluripotent, stem or progenitor cell, or population of cells. By way of example, the cell may be an embryonic stem cell, induced pluripotent stem cell (iPSC), hematopoietic stem/progenitor cell (HSPC), or other stem or progenitor cell type that differentiates into a cell type of relevance to a given application or indication, or a population of cells thereof.

In certain embodiments, the cell, or population of cells, being manipulated is a eukaryotic cell, or population of cells. For example, but not by way of limitation, the cell is a vertebrate, mammalian, rodent, goat, pig, bird, chicken, turkey, cow, horse, sheep, fish, primate, or human cell, or population of cells. In certain embodiments, the cell being manipulated is a somatic cell, a germ cell, or a prenatal cell, or population of cells. In certain embodiments, the cell being manipulated is a zygotic cell, a blastocyst cell, an embryonic cell, a stem cell, a mitotically competent cell, or a meiotically competent cell, or population of cells. In certain embodiments, the cell, or population of cells, being manipulated is not part of a human embryo. In certain embodiments, the cell being manipulated is a T cell, a $CD8^+$ T cell, a $CD8^+$ naïve T cell, a $CD4^+$ central memory T cell, a $CD8^+$ central memory T cell, a $CD4^+$ effector memory T cell, a $CD4^+$ effector memory T cell, a $CD4^+$ T cell, a $CD4^+$ stem cell memory T cell, a $CD8^+$ stem cell memory T cell, a $CD4^+$ helper T cell, a regulatory T cell, a cytotoxic T cell, a natural killer T cell, a CD4+ naïve T cell, a TH17 $CD4^+$ T cell, a TH1 $CD4^+$ T cell, a TH2 $CD4^+$ T cell, a TH9 $CD4^+$ T cell, a $CD4^+$ $Foxp3^+$ T cell, a $CD4^+$ $CD25^+$ $CD127^-$ T cell, a $CD4^+$ $CD25^+$ $CD127^-$ $Foxp3^+$ T cell, or population of cells. In certain embodiments, the cell(s) being manipulated is a long term hematopoietic stem cell, a short term hematopoietic stem cell, a multipotent progenitor cell, a lineage restricted progenitor cell, a lymphoid progenitor cell, a myeloid progenitor cell, a common myeloid progenitor cell, an erythroid progenitor cell, a megakaryocyte erythroid progenitor cell, a retinal cell, a photoreceptor cell, a rod cell, a cone cell, a retinal pigmented epithelium cell, a trabecular meshwork cell, a cochlear hair cell, an outer hair cell, an inner hair cell, a pulmonary epithelial cell, a bronchial epithelial cell, an alveolar epithelial cell, a pulmonary epithelial progenitor cell, a striated muscle cell, a cardiac muscle cell, a muscle satellite cell, a neuron, a neuronal stem cell, a mesenchymal stem cell, an induced pluripotent stem (iPS) cell, an embryonic stem cell, a monocyte-derived macrophage or dendritic cell, a megakaryocyte, a neutrophil, an eosinophil, a basophil, a mast cell, a reticulocyte, a B cell, e.g., a progenitor B cell, a Pre B cell, a Pro B cell, a memory B cell, a plasma B cell, a gastrointestinal epithelial cell, a biliary epithelial cell, a pancreatic ductal epithelial cell, an intestinal stem cell, a hepatocyte, a liver stellate cell, a Kupffer cell, an osteoblast, an osteoclast, an adipocyte, a preadipocyte, a pancreatic islet cell (e.g., a beta cell, an alpha cell, a delta cell), a pancreatic exocrine cell, a Schwann cell, or an oligodendrocyte. In certain embodiments, the manipulated cell is a plant cell, e.g., a monocot or a dicot cell, or population of cells thereof.

In certain embodiments, the target cell is a circulating blood cell, e.g., a reticulocyte, megakaryocyte erythroid progenitor (MEP) cell, myeloid progenitor cell (CMP/GMP), lymphoid progenitor (LP) cell, hematopoietic stem/progenitor cell (HSC), or endothelial cell (EC). In certain embodiments, the target cell is a bone marrow cell (e.g., a reticulocyte, an erythroid cell (e.g., erythroblast), an MEP cell, myeloid progenitor cell (CMP/GMP), LP cell, erythroid progenitor (EP) cell, HSC, multipotent progenitor (MPP) cell, endothelial cell (EC), hemogenic endothelial (HE) cell, or mesenchymal stem cell). In certain embodiments, the target cell is a myeloid progenitor cell (e.g., a common myeloid progenitor (CMP) cell or granulocyte macrophage progenitor (GMP) cell). In certain embodiments, the target cell is a lymphoid progenitor cell, e.g., a common lymphoid progenitor (CLP) cell. In certain embodiments, the target cell is an erythroid progenitor cell (e.g., an MEP cell). In certain embodiments, the target cell is a hematopoietic stem/progenitor cell (e.g., a long term HSC (LT-HSC), short term HSC (ST-HSC), MPP cell, or lineage restricted progenitor (LRP) cell). In certain embodiments, the target cell is a $CD34^+$ cell, $CD34^+$ $CD90^+$ cell, $CD34^+$ $CD38^-$ cell, $CD34^+$ $CD90^+$ $CD49f^+$ $CD38^-$ $CD45RA^-$ cell, $CD105^+$ cell, $CD31^+$, or $CD133^+$ cell, or a $CD34^+$ $CD90^+$ $CD133^+$ cell. In certain embodiments, the target cell is an umbilical cord blood $CD34^+$ HSPC, umbilical cord venous endothelial cell, umbilical cord arterial endothelial cell, amniotic fluid $CD34^+$ cell, amniotic fluid endothelial cell, placental endothelial cell, or placental hematopoietic $CD34^+$ cell. In certain embodiments, the target cell is a mobilized peripheral blood hematopoietic $CD34^+$ cell (after the patient is treated with a mobilization agent, e.g., G-CSF or Plerixafor). In certain embodiments, the target cell is a peripheral blood endothelial cell, or population of cells.

As a corollary, the cell(s) being modified or manipulated is, variously, a dividing cell or a non-dividing cell, depending on the cell type(s) being targeted and/or the desired editing outcome.

When cells are manipulated or modified ex vivo, the cells can be used (e.g., administered to a subject) immediately, or they can be maintained or stored for later use. Those of skill in the art will appreciate that cells can be maintained in culture or stored (e.g., frozen in liquid nitrogen) using any suitable method known in the art.

The technology described herein can be used to edit numerous types of genomes, including plant genomes. The CRISPR/Cas system has been used for plant genome editing, as has been described in, e.g., Belhaj et al., PLANT METHODS 9:39, 2013. Plant cells can carry out HDR, so a Cas9-induced nick or DSB can be repaired by HDR. Plant cells also have NHEJ machinery, and in some embodiments, NHEJ is inhibited, resulting in stimulation of HDR. Accordingly, in certain embodiments, the cell, or the population of cells, is a plant cell, e.g., a monocot plant cell, or a dicot plant cell, or a population of plant cell. In certain embodiments, the plant is a crop, e.g., a food crop. In certain embodiments, the plant is rice (e.g., *Orzya sativa*), maize (e.g., *Zea mays*), wheat (e.g., *Triticum aestivum*), soy (e.g., *Glycine max*), potato (e.g., *Solanum tuberosum*), a species of *Nicotiana*, a species of *Arabidopsis* e.g., *Arabidopsis thaliana*, cassava, sweet potato, sorghum, yam, plantain, or a citrus plant. In some embodiments, the plant is a pesticide-resistant plant, e.g., a plant that expresses one or more genes that confer resistance to a pesticide. In some embodiments, the plant is herbicide-resistant plant, e.g., a plant that expresses one or more genes that confer resistance to a herbicide. The herbicide may be, e.g., Roundup® (also known as glyphosate or N-(phosphonomethyl)glycine). In some embodiments, the plant produces a pesticide, e.g., Bt.

In some embodiments, the components used in the methods described herein (e.g., a Cas9 molecule and a gRNA) are introduced into the plant cell, or population of cells, via protoplast transformation or agroinfiltration.

In some embodiments, after genome editing using the methods described herein, seeds are screened and a desired sub-population of seeds are selected. The sub-population may be, e.g., cells having a nucleic acid that was successfully altered, or cells having a desired phenotype such as minimal undesired alterations to DNA, or a phenotype that indicates the nucleic acid was successfully altered.

In one embodiment, the disclosure provides methods of using genome editing systems for altering a target nucleic acid in a cell, or population of cells, which is isolated from a subject. In some embodiments, the cell is isolated from a subject suffering from a disease or disorder. In one embodiment, the disease or disorder is an eye disease or a liver disease. In another embodiment, the disease or disorder is Duchenne muscular dystrophy. In another embodiment, the disease or disorder is a blood disease, an immune disease, a neurological disease, a cancer, an infectious disease, a genetic disease, a disorder caused by aberrant mtDNA, a metabolic disease, a disorder caused by aberrant cell cycle, a disorder caused by aberrant angiogenesis, a disorder cause by aberrant DNA damage repair, or a pain disorder.

In one embodiment, the method of altering a target nucleic acid in a cell or population of cells is performed in vitro. In another embodiment, the method of altering a target nucleic acid in a cell or population of cells is performed ex vivo. In another embodiment, the method of altering a target nucleic acid in a cell or population of cells is performed in vivo.

In one embodiment, the cell is an immune cell, e.g., a T cell or an NK cell.

As used herein, the term "a cell" may refer to a single cell or to a population of cells. In one embodiment, a cell is a single cell. In another embodiment, a cell is a population of cells.

Quantitative Measurement of On-Target Gene Editing

It should be noted that the genome editing systems of the present disclosure allow for the detection and quantitative measurement of on-target gene editing outcomes, including targeted integration. The compositions and methods described herein can rely on the use of donor templates comprising a 5' homology arm, a cargo, a one or more priming sites, a 3' homology arm, and optionally stuffer sequence. For example, International Patent Publication No. WO2019/014564 by Ramusino et al. (Ramusino), which is incorporated by reference herein in its entirety, describes compositions and methods which allow for the quantitative analysis of on-target gene editing outcomes, including targeted integration events, by embedding one or more primer binding sites (i.e., priming sites) into a donor template that are substantially identical to a priming site present at the targeted genomic DNA locus (i.e., the target nucleic acid). The priming sites are embedded into the donor template such that, when homologous recombination of the donor template with a target nucleic acid occurs, successful targeted integration of the donor template integrates the priming sites from the donor template into the target nucleic acid such that at least one amplicon can be generated in order to quantitatively determine the on-target editing outcomes.

In some embodiments, the target nucleic acid comprises a first priming site (P1) and a second priming site (P2), and the donor template comprises a cargo sequence, a first priming site (P1'), and a second priming site (P2'), wherein P2' is located 5' from the cargo sequence, wherein P1' is located 3' from the cargo sequence (i.e., A1--P2'--N--P1'--A2), wherein P1' is substantially identical to P1, and wherein P2' is substantially identical to P2. After accurate homology-driven targeted integration, three amplicons are produced using a single PCR reaction with two oligonucleotide primers. The first amplicon, Amplicon X, is generated from the primer binding sites originally present in the genomic DNA (P1 and P2), and may be sequenced to analyze on-target editing events that do not result in targeted integration (e.g., insertions, deletions, gene conversion). The remaining two amplicons are mapped to the 5' and 3' junctions after homology-driven targeted integration. The second amplicon, Amplicon Y, results from the amplification of the nucleic acid sequence between P1 and P2' following a targeted integration event at the target nucleic acid, thereby amplifying the 5' junction. The third amplicon, Amplicon Z, results from the amplification of the nucleic acid sequence between P1' and P2 following a targeted integration event at the target nucleic acid, thereby amplifying the 3' junction. Sequencing of these amplicons provides a quantitative assessment of targeted integration at the target nucleic acid, in addition to information about the fidelity of the targeted integration. To avoid any biases inherent to amplicon size, stuffer sequence may optionally be included in the donor template to keep all three expected amplicons the same length.

Implementation of Genome Editing Systems: Delivery, Formulations, and Routes of Administration As discussed above, the genome editing systems of this disclosure can be implemented in any suitable manner, meaning that the components of such systems, including without limitation the RNA-guided nuclease, gRNA, and optional donor template nucleic acid, can be delivered, formulated, or administered in any suitable form or combination of forms that results in the transduction, expression or introduction of a genome editing system and/or causes a desired repair outcome in a cell, tissue or subject. Tables 3 and 4 set forth several, non-limiting examples of genome editing system implementations. Those of skill in the art will appreciate, however, that these listings are not comprehensive, and that other implementations are possible. With reference to Table 3 in particular, the table lists several exemplary implementations of a genome editing system comprising a single gRNA and an optional donor template. However, genome editing systems according to this disclosure can incorporate multiple gRNAs, multiple RNA-guided nucleases, and other components such as proteins, and a variety of implementations will be evident to the skilled artisan based on the principles illustrated in the table. In the table, [N/A] indicates that the genome editing system does not include the indicated component.

TABLE 3

Genome Editing System Components

| RNA-guided Nuclease | gRNA | Donor Template | Comments |
| --- | --- | --- | --- |
| Protein | RNA | [N/A] | An RNA-guided nuclease protein complexed with a gRNA molecule (an RNP complex) |
| Protein | RNA | DNA | An RNP complex as described above plus a single-stranded or double stranded donor template. |
| Protein | DNA | [N/A] | An RNA-guided nuclease protein plus gRNA transcribed from DNA. |
| Protein | DNA | DNA | An RNA-guided nuclease protein plus gRNA-encoding DNA and a separate DNA donor template. |
| Protein | DNA | | An RNA-guided nuclease protein and a single DNA encoding both a gRNA and a donor template. |
| | DNA | | A DNA or DNA vector encoding an RNA-guided nuclease, a gRNA and a donor template. |
| DNA | DNA | [N/A] | Two separate DNAs, or two separate DNA vectors, encoding the RNA-guided nuclease and the gRNA, respectively. |
| DNA | DNA | DNA | Three separate DNAs, or three separate DNA vectors, encoding the RNA-guided nuclease, the gRNA and the donor template, respectively. |
| DNA | | [N/A] | A DNA or DNA vector encoding an RNA-guided nuclease and a gRNA |
| DNA | | DNA | A first DNA or DNA vector encoding an RNA-guided nuclease and a gRNA, and a second DNA or DNA vector encoding a donor template. |
| DNA | | DNA | A first DNA or DNA vector encoding an RNA-guided nuclease and second DNA or DNA vector encoding a gRNA, and a donor template. |
| | DNA DNA | | A first DNA or DNA vector encoding an RNA-guided nuclease and a donor template, and a second DNA or DNA vector encoding a gRNA |
| | DNA RNA | | A DNA or DNA vector encoding an RNA-guided nuclease and a donor template, and a gRNA |
| RNA | | [N/A] | An RNA or RNA vector encoding an RNA-guided nuclease and comprising a gRNA |
| RNA | | DNA | An RNA or RNA vector encoding an RNA-guided nuclease and comprising a gRNA, and a DNA or DNA vector encoding a donor template. |

Table 4 summarizes various delivery methods for the components of genome editing systems, as described herein. Again, the listing is intended to be exemplary rather than limiting.

TABLE 4

| Delivery Vector/Mode | | Delivery into Non-Dividing Cells | Duration of Expression | Genome Integration | Type of Molecule Delivered |
|---|---|---|---|---|---|
| Physical (e.g., electroporation, particle gun, Calcium Phosphate transfection, cell compression or squeezing) | | YES | Transient | NO | Nucleic Acids and Proteins |
| Viral | Retrovirus | NO | Stable | YES | RNA |
| | Lentivirus | YES | Stable | YES/NO with modifications | RNA |
| | Adenovirus | YES | Transient | NO | DNA |
| | Adeno-Associated Virus (AAV) | YES | Stable | NO | DNA |
| | Vaccinia Virus | YES | Very Transient | NO | DNA |
| | Herpes Simplex Virus | YES | Stable | NO | DNA |
| Non-Viral | Cationic Liposomes | YES | Transient | Depends on what is delivered | Nucleic Acids and Proteins |
| | Polymeric Nanoparticles | YES | Transient | Depends on what is delivered | Nucleic Acids and Proteins |
| Biological Non-Viral Delivery Vehicles | Attenuated Bacteria | YES | Transient | NO | Nucleic Acids |
| | Engineered Bacteriophages | YES | Transient | NO | Nucleic Acids |
| | Mammalian Virus-like Particles | YES | Transient | NO | Nucleic Acids |
| | Biological liposomes: Erythrocyte Ghosts and Exosomes | YES | Transient | NO | Nucleic Acids |

Nucleic Acid-Based Delivery of Genome Editing Systems

Nucleic acids encoding the various elements of a genome editing system according to the present disclosure can be administered to subjects or delivered into cells by art-known methods or as described herein. For example, RNA-guided nuclease-encoding and/or gRNA-encoding DNA, as well as donor template nucleic acids can be delivered by, e.g., vectors (e.g., viral or non-viral vectors), non-vector based methods (e.g., using naked DNA or DNA complexes), or a combination thereof.

Nucleic acids encoding genome editing systems or components thereof can be delivered directly to cells as naked DNA or RNA, for instance by means of transfection or electroporation, or can be conjugated to molecules (e.g., N-acetylgalactosamine) promoting uptake by the target cells (e.g., erythrocytes, HSCs). Nucleic acid vectors, such as the vectors summarized in Table 4, can also be used.

Nucleic acid vectors can comprise one or more sequences encoding genome editing system components, such as an RNA-guided nuclease, a gRNA and/or a donor template. A vector can also comprise a sequence encoding a signal peptide (e.g., for nuclear localization, nucleolar localization, or mitochondrial localization), associated with (e.g., inserted into or fused to) a sequence coding for a protein. As one example, a nucleic acid vectors can include a Cas9 coding sequence that includes one or more nuclear localization sequences (e.g., a nuclear localization sequence from SV40).

The nucleic acid vector can also include any suitable number of regulatory/control elements, e.g., promoters, enhancers, introns, polyadenylation signals, Kozak consensus sequences, or internal ribosome entry sites (IRES). These elements are well known in the art, and are described in Cotta-Ramusino.

Nucleic acid vectors according to this disclosure include recombinant viral vectors. Exemplary viral vectors are set forth in Table 4, and additional suitable viral vectors and their use and production are described in Cotta-Ramusino. Other viral vectors known in the art can also be used. In addition, viral particles can be used to deliver genome editing system components in nucleic acid and/or peptide form. For example, "empty" viral particles can be assembled to contain any suitable cargo. Viral vectors and viral particles can also be engineered to incorporate targeting ligands to alter target tissue specificity.

In addition to viral vectors, non-viral vectors can be used to deliver nucleic acids encoding genome editing systems according to the present disclosure. One important category of non-viral nucleic acid vectors are nanoparticles, which can be organic or inorganic. Nanoparticles are well known in the art, and are summarized in Cotta-Ramusino. Any suitable nanoparticle design can be used to deliver genome editing system components or nucleic acids encoding such components. For instance, organic (e.g. lipid and/or polymer) nanoparticles can be suitable for use as delivery vehicles in certain embodiments of this disclosure. Exemplary lipids for use in nanoparticle formulations, and/or gene transfer are shown in Table 5, and Table 6 lists exemplary polymers for use in gene transfer and/or nanoparticle formulations.

TABLE 5

Lipids Used for Gene Transfer

| Lipid | Abbreviation | Feature |
|---|---|---|
| 1,2-Dioleoyl-sn-glycero-3-phosphatidylcholine | DOPC | Helper |
| 1,2-Dioleoyl-sn-glycero-3-phosphatidylethanolamine | DOPE | Helper |
| Cholesterol | | Helper |
| N-[1-(2,3-Dioleyloxy)propyl]N,N,N-trimethylammonium chloride | DOTMA | Cationic |
| 1,2-Dioleoyloxy-3-trimethylammonium-propane | DOTAP | Cationic |
| Dioctadecylamidoglycylspermine | DOGS | Cationic |
| N-(3-Aminopropyl)-N,N-dimethyl-2,3-bis(dodecyloxy)-1-propanaminium bromide | GAP-DLRIE | Cationic |
| Cetyltrimethylammonium bromide | CTAB | Cationic |
| 6-Lauroxyhexyl ornithinate | LHON | Cationic |
| 1-(2,3-Dioleoyloxypropyl)-2,4,6-trimethylpyridinium | 2Oc | Cationic |
| 2,3-Dioleyloxy-N-[2(sperminecarboxamido-ethyl]-N,N-dimethyl-1-propanaminium trifluoroacetate | DOSPA | Cationic |
| 1,2-Dioleyl-3-trimethylammonium-propane | DOPA | Cationic |
| N-(2-Hydroxyethyl)-N,N-dimethyl-2,3-bis(tetradecyloxy)-1-propanaminium bromide | MDRIE | Cationic |
| Dimyristooxypropyl dimethyl hydroxyethyl ammonium bromide | DMRI | Cationic |
| 3β-[N-(N',N'-Dimethylaminoethane)-carbamoyl]cholesterol | DC-Chol | Cationic |
| Bis-guanidium-tren-cholesterol | BGTC | Cationic |
| 1,3-Diodeoxy-2-(6-carboxy-spermyl)-propylamide | DOSPER | Cationic |
| Dimethyloctadecylammonium bromide | DDAB | Cationic |
| Dioctadecylamidoglicylspermidin | DSL | Cationic |
| rac-[(2,3-Dioctadecyloxypropyl)(2-hydroxyethyl)]-dimethylammonium chloride | CLIP-1 | Cationic |
| rac-[2(2,3-Dihexadecyloxypropyl-oxymethyloxy)ethyl]trimethylammonium bromide | CLIP-6 | Cationic |
| Ethyldimyristoylphosphatidylcholine | EDMPC | Cationic |
| 1,2-Distearyloxy-N,N-dimethyl-3-aminopropane | DSDMA | Cationic |
| 1,2-Dimyristoyl-trimethylammonium propane | DMTAP | Cationic |
| O,O'-Dimyristyl-N-lysyl aspartate | DMKE | Cationic |
| 1,2-Distearoyl-sn-glycero-3-ethylphosphocholine | DSEPC | Cationic |
| N-Palmitoyl D-erythro-sphingosyl carbamoyl-spermine | CCS | Cationic |
| N-t-Butyl-N0-tetradecyl-3-tetradecylaminopropionamidine | diC14-amidine | Cationic |
| Octadecenolyoxy[ethyl-2-heptadecenyl-3 hydroxyethyl] imidazolinium chloride | DOTIM | Cationic |
| N1-Cholesteryloxycarbonyl-3,7-diazanonane-1,9-diamine | CDAN | Cationic |
| 2-(3-[Bis(3-amino-propyl)-amino]propylamino)-N-ditetradecylcarbamoylme-ethyl-acetamide | RPR209120 | Cationic |
| 1,2-dilinoleyloxy-3-dimethylaminopropane | DLinDMA | Cationic |
| 2,2-dilinoleyl-4-dimethylaminoethyl-[1,3]-dioxolane | DLin-KC2-DMA | Cationic |
| dilinoleyl-methyl-4-dimethylaminobutyrate | DLin-MC3-DMA | Cationic |

TABLE 6

Polymers Used for Gene Transfer

| Polymer | Abbreviation |
|---|---|
| Poly(ethylene)glycol | PEG |
| Polyethylenimine | PEI |
| Dithiobis(succinimidylpropionate) | DSP |
| Dimethyl-3,3'-dithiobispropionimidate | DTBP |
| Poly(ethylene imine) biscarbamate | PEIC |
| Poly(L-lysine) | PLL |
| Histidine modified PLL | |
| Poly(N-vinylpyrrolidone) | PVP |
| Poly(propylenimine) | PPI |
| Poly(amidoamine) | PAMAM |
| Poly(amido ethylenimine) | SS-PAEI |
| Triethylenetetramine | TETA |
| Poly(β-aminoester) | |
| Poly(4-hydroxy-L-proline ester) | PHP |
| Poly(allylamine) | |
| Poly(α-[4-aminobutyl]-L-glycolic acid) | PAGA |
| Poly(D,L-lactic-co-glycolic acid) | PLGA |
| Poly(N-ethyl-4-vinylpyridinium bromide) | |
| Poly(phosphazene)s | PPZ |
| Poly(phosphoester)s | PPE |
| Poly(phosphoramidate)s | PPA |
| Poly(N-2-hydroxypropylmethacrylamide) | pHPMA |
| Poly (2-(dimethylamino)ethyl methacrylate) | pDMAEMA |

TABLE 6-continued

Polymers Used for Gene Transfer

| Polymer | Abbreviation |
|---|---|
| Poly(2-aminoethyl propylene phosphate) | PPE-EA |
| Chitosan | |
| Galactosylated chitosan | |
| N-Dodacylated chitosan | |
| Histone | |
| Collagen | |
| Dextran-spermine | D-SPM |

Non-viral vectors optionally include targeting modifications to improve uptake and/or selectively target certain cell types. These targeting modifications can include e.g., cell specific antigens, monoclonal antibodies, single chain antibodies, aptamers, polymers, sugars (e.g., N-acetylgalactosamine (GalNAc)), and cell penetrating peptides. Such vectors also optionally use fusogenic and endosome-destabilizing peptides/polymers, undergo acid-triggered conformational changes (e.g., to accelerate endosomal escape of the cargo), and/or incorporate a stimuli-cleavable polymer, e.g., for release in a cellular compartment. For example, disulfide-based cationic polymers that are cleaved in the reducing cellular environment can be used.

In certain embodiments, one or more nucleic acid molecules (e.g., DNA molecules) other than the components of a genome editing system, e.g., the RNA-guided nuclease component and/or the gRNA component described herein, are delivered. In certain embodiments, the nucleic acid molecule is delivered at the same time as one or more of the components of the Genome editing system. In certain embodiments, the nucleic acid molecule is delivered before or after (e.g., less than about 30 minutes, 1 hour, 2 hours, 3 hours, 6 hours, 9 hours, 12 hours, 1 day, 2 days, 3 days, 1 week, 2 weeks, or 4 weeks) one or more of the components of the Genome editing system are delivered. In certain embodiments, the nucleic acid molecule is delivered by a different means than one or more of the components of the genome editing system, e.g., the RNA-guided nuclease component and/or the gRNA component, are delivered. The nucleic acid molecule can be delivered by any of the delivery methods described herein. For example, the nucleic acid molecule can be delivered by a viral vector, e.g., an integration-deficient lentivirus, and the RNA-guided nuclease molecule component and/or the gRNA component can be delivered by electroporation, e.g., such that the toxicity caused by nucleic acids (e.g., DNAs) can be reduced. In certain embodiments, the nucleic acid molecule encodes a therapeutic protein, e.g., a protein described herein. In certain embodiments, the nucleic acid molecule encodes an RNA molecule, e.g., an RNA molecule described herein.

Delivery of RNPs and/or RNA Encoding Genome Editing System Components

RNPs (complexes of gRNAs and RNA-guided nucleases) and/or RNAs encoding RNA-guided nucleases and/or gRNAs, can be delivered into cells or administered to subjects by art-known methods, some of which are described in Cotta-Ramusino. In vitro, RNA-guided nuclease-encoding and/or gRNA-encoding RNA can be delivered, e.g., by microinjection, electroporation, transient cell compression or squeezing (see, e.g., Lee 2012). Lipid-mediated transfection, peptide-mediated delivery, GalNAc- or other conjugate-mediated delivery, and combinations thereof, can also be used for delivery in vitro and in vivo.

In vitro, delivery via electroporation comprises mixing the cells with the RNA encoding RNA-guided nucleases and/or gRNAs, with or without donor template nucleic acid molecules, in a cartridge, chamber or cuvette and applying one or more electrical impulses of defined duration and amplitude. Systems and protocols for electroporation are known in the art, and any suitable electroporation tool and/or protocol can be used in connection with the various embodiments of this disclosure.

In addition, efficient delivery of RNPs, RNA-guided nucleases, and/or gRNAs can be achieved using cationic lipid transfection reagents. As described by Zuris et al., Nat. Biotech. (2015), 33(1):73-80, gRNA molecules provide the highly anionic character needed for effective delivery of a RNP complex to cells in vitro or in vivo using cationic lipid reagents, such as Lipofectamine 2000 or RNAiMAX. In some embodiments, the RNPs, RNA-guided nucleases, and/or gRNAs can contain an anionic modification to further enhance delivery by cationic lipid reagents. For example, the RNPs, RNA-guided nucleases, and/or gRNAs described herein can be modified by fusion to a supernegatively charged protein, e.g., a supernegatively charged green fluorescent protein (GFP).

Route of Administration

Genome editing systems, or cells altered or manipulated using such systems, can be administered to subjects by any suitable mode or route, whether local or systemic. Systemic modes of administration include oral and parenteral routes. Parenteral routes include, by way of example, intravenous, intramarrow, intrarterial, intramuscular, intradermal, subcutaneous, intranasal, and intraperitoneal routes. Components administered systemically can be modified or formulated to target, e.g., HSCs, hematopoietic stem/progenitor cells, or erythroid progenitors or precursor cells.

Local modes of administration include, by way of example, intramarrow injection into the trabecular bone or intrafemoral injection into the marrow space, and infusion into the portal vein. In certain embodiments, significantly smaller amounts of the components (compared with systemic approaches) can exert an effect when administered locally (for example, directly into the bone marrow) compared to when administered systemically (for example, intravenously). Local modes of administration can reduce or eliminate the incidence of potentially toxic side effects that may occur when therapeutically effective amounts of a component are administered systemically.

Administration can be provided as a periodic bolus (for example, intravenously) or as continuous infusion from an internal reservoir or from an external reservoir (for example, from an intravenous bag or implantable pump). Components can be administered locally, for example, by continuous release from a sustained release drug delivery device.

In addition, components can be formulated to permit release over a prolonged period of time. A release system can include a matrix of a biodegradable material or a material which releases the incorporated components by diffusion. The components can be homogeneously or heterogeneously distributed within the release system. A variety of release systems can be useful, however, the choice of the appropriate system will depend upon rate of release required by a particular application. Both non-degradable and degradable release systems can be used. Suitable release systems include polymers and polymeric matrices, non-polymeric matrices, or inorganic and organic excipients and diluents such as, but not limited to, calcium carbonate and sugar (for example, trehalose). Release systems may be natural or synthetic. However, synthetic release systems are preferred because generally they are more reliable, more reproducible and produce more defined release profiles. The release system material can be selected so that components having different molecular weights are released by diffusion through or degradation of the material.

Representative synthetic, biodegradable polymers include, for example: polyamides such as poly(amino acids) and poly(peptides); polyesters such as poly(lactic acid), poly(glycolic acid), poly(lactic-co-glycolic acid), and poly (caprolactone); poly(anhydrides); polyorthoesters; polycarbonates; and chemical derivatives thereof (substitutions, additions of chemical groups, for example, alkyl, alkylene, hydroxylations, oxidations, and other modifications routinely made by those skilled in the art), copolymers and mixtures thereof. Representative synthetic, non-degradable polymers include, for example: polyethers such as poly (ethylene oxide), poly(ethylene glycol), and poly(tetramethylene oxide); vinyl polymers-polyacrylates and polymethacrylates such as methyl, ethyl, other alkyl, hydroxyethyl methacrylate, acrylic and methacrylic acids, and others such as poly(vinyl alcohol), poly(vinyl pyrolidone), and poly (vinyl acetate); poly(urethanes); cellulose and its derivatives such as alkyl, hydroxyalkyl, ethers, esters, nitrocellulose, and various cellulose acetates; polysiloxanes; and any chemical derivatives thereof (substitutions, additions of chemical groups, for example, alkyl, alkylene, hydroxylations, oxidations, and other modifications routinely made by those skilled in the art), copolymers and mixtures thereof.

Poly(lactide-co-glycolide) microsphere can also be used. Typically the microspheres are composed of a polymer of lactic acid and glycolic acid, which are structured to form hollow spheres. The spheres can be approximately 15-30 microns in diameter and can be loaded with components described herein.

Multi-Modal or Differential Delivery of Components

Skilled artisans will appreciate, in view of the instant disclosure, that different components of genome editing systems disclosed herein can be delivered together or separately and simultaneously or nonsimultaneously. Separate and/or asynchronous delivery of genome editing system components can be particularly desirable to provide temporal or spatial control over the function of genome editing systems and to limit certain effects caused by their activity.

Different or differential modes as used herein refer to modes of delivery that confer different pharmacodynamic or pharmacokinetic properties on the subject component molecule, e.g., a RNA-guided nuclease molecule, gRNA, template nucleic acid, or payload. For example, the modes of delivery can result in different tissue distribution, different half-life, or different temporal distribution, e.g., in a selected compartment, tissue, or organ.

Some modes of delivery, e.g., delivery by a nucleic acid vector that persists in a cell, or in progeny of a cell, e.g., by autonomous replication or insertion into cellular nucleic acid, result in more persistent expression of and presence of a component. Examples include viral, e.g., AAV or lentivirus, delivery.

By way of example, the components of a genome editing system, e.g., a RNA-guided nuclease and a gRNA, can be delivered by modes that differ in terms of resulting half-life or persistent of the delivered component the body, or in a particular compartment, tissue or organ. In certain embodiments, a gRNA can be delivered by such modes. The RNA-guided nuclease molecule component can be delivered by a mode which results in less persistence or less exposure to the body or a particular compartment or tissue or organ.

More generally, in certain embodiments, a first mode of delivery is used to deliver a first component and a second mode of delivery is used to deliver a second component. The first mode of delivery confers a first pharmacodynamic or pharmacokinetic property. The first pharmacodynamic property can be, e.g., distribution, persistence, or exposure, of the component, or of a nucleic acid that encodes the component, in the body, a compartment, tissue or organ. The second mode of delivery confers a second pharmacodynamic or pharmacokinetic property. The second pharmacodynamic property can be, e.g., distribution, persistence, or exposure, of the component, or of a nucleic acid that encodes the component, in the body, a compartment, tissue or organ.

In certain embodiments, the first pharmacodynamic or pharmacokinetic property, e.g., distribution, persistence or exposure, is more limited than the second pharmacodynamic or pharmacokinetic property.

In certain embodiments, the first mode of delivery is selected to optimize, e.g., minimize, a pharmacodynamic or pharmacokinetic property, e.g., distribution, persistence or expo sure.

In certain embodiments, the second mode of delivery is selected to optimize, e.g., maximize, a pharmacodynamic or pharmacokinetic property, e.g., distribution, persistence or expo sure.

In certain embodiments, the first mode of delivery comprises the use of a relatively persistent element, e.g., a nucleic acid, e.g., a plasmid or viral vector, e.g., an AAV or lentivirus. As such vectors are relatively persistent product transcribed from them would be relatively persistent.

In certain embodiments, the second mode of delivery comprises a relatively transient element, e.g., an RNA or protein.

In certain embodiments, the first component comprises gRNA, and the delivery mode is relatively persistent, e.g., the gRNA is transcribed from a plasmid or viral vector, e.g., an AAV or lentivirus. Transcription of these genes would be of little physiological consequence because the genes do not encode for a protein product, and the gRNAs are incapable of acting in isolation. The second component, a RNA-guided nuclease molecule, is delivered in a transient manner, for example as mRNA or as protein, ensuring that the full RNA-guided nuclease molecule/gRNA complex is only present and active for a short period of time.

Furthermore, the components can be delivered in different molecular form or with different delivery vectors that complement one another to enhance safety and tissue specificity.

Use of differential delivery modes can enhance performance, safety, and/or efficacy, e.g., the likelihood of an eventual off-target modification can be reduced. Delivery of immunogenic components, e.g., Cas9 molecules, by less persistent modes can reduce immunogenicity, as peptides from the bacterially-derived Cas enzyme are displayed on the surface of the cell by MHC molecules. A two-part delivery system can alleviate these drawbacks.

Differential delivery modes can be used to deliver components to different, but overlapping target regions. The formation active complex is minimized outside the overlap of the target regions. Thus, in certain embodiments, a first component, e.g., a gRNA is delivered by a first delivery mode that results in a first spatial, e.g., tissue, distribution. A second component, e.g., a RNA-guided nuclease molecule is delivered by a second delivery mode that results in a second spatial, e.g., tissue, distribution. In certain embodiments, the first mode comprises a first element selected from a liposome, nanoparticle, e.g., polymeric nanoparticle, and a nucleic acid, e.g., viral vector. The second mode comprises a second element selected from the group. In certain embodiments, the first mode of delivery comprises a first targeting element, e.g., a cell specific receptor or an antibody, and the second mode of delivery does not include that element. In certain embodiments, the second mode of delivery comprises a second targeting element, e.g., a second cell specific receptor or second antibody.

When the RNA-guided nuclease molecule is delivered in a virus delivery vector, a liposome, or polymeric nanoparticle, there is the potential for delivery to and therapeutic activity in multiple tissues, when it may be desirable to only target a single tissue. A two-part delivery system can resolve this challenge and enhance tissue specificity. If the gRNA and the RNA-guided nuclease molecule are packaged in separated delivery vehicles with distinct but overlapping tissue tropism, the fully functional complex is only be formed in the tissue that is targeted by both vectors.

EXAMPLES

The following Examples are merely illustrative and are not intended to limit the scope or content of the invention in any way.

Protospacer sequences used in the following examples are set forth in SEQ ID NOs: 1-8. Oligonucleotide donor template sequences are set forth in SEQ ID NOs: 9-23.

Nucleic acids positioned between the donor template homology arms are underlined. Exemplary gRNAs are set forth as SEQ ID NOs: 24-25.

Figure 4:
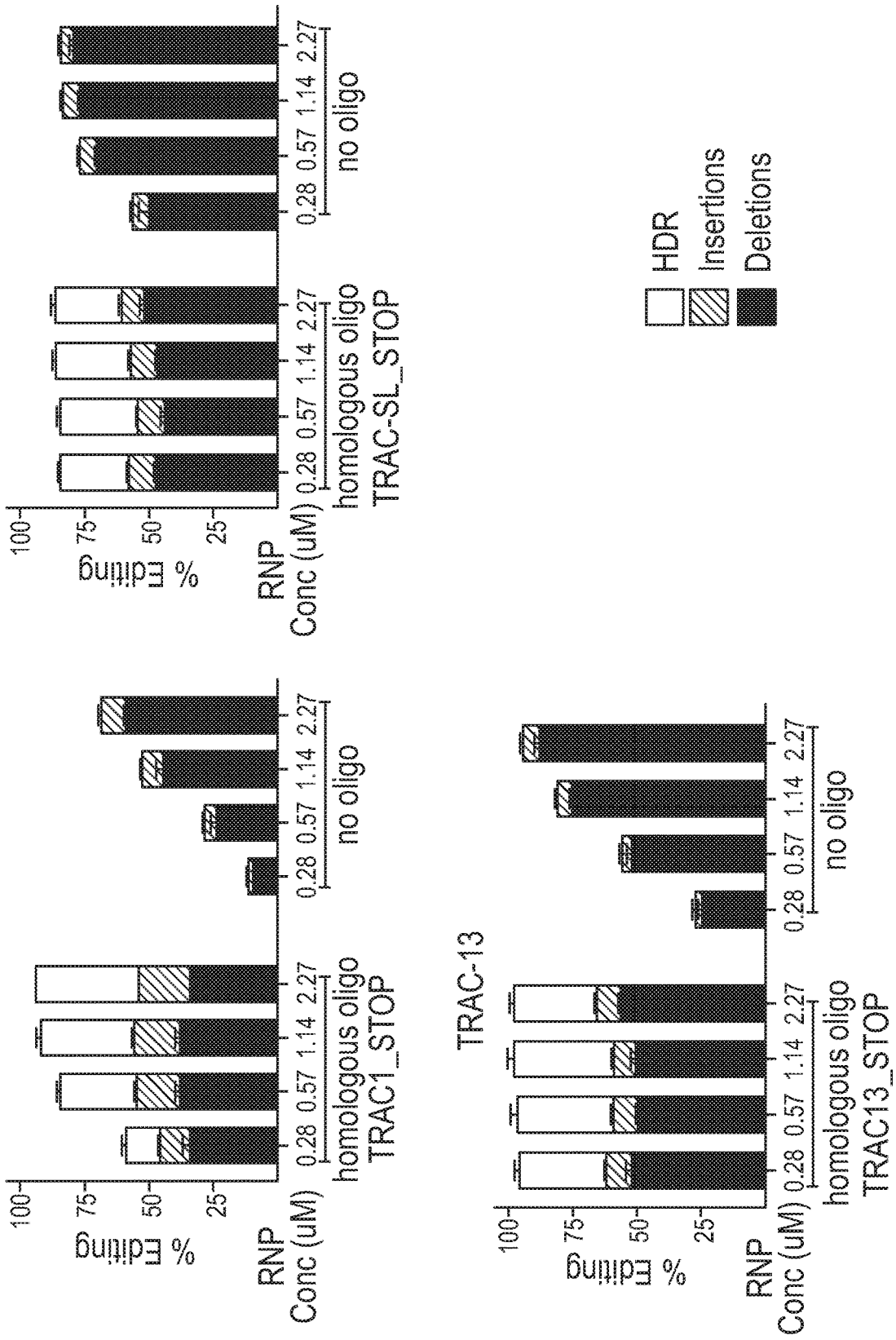
FIG. 4 depicts the percentage of gene editing events that occur in cells exposed to an oligonucleotide donor template containing a stop codon, at varying concentrations of RNP complex. Three distinct loci (TRAC-1, TRAC-13, and TRAC-SL) were targeted using oligonucleotide donor templates containing a stop codon.

Example 1: Generating Functional Knockouts Using a ssODN Containing a Stop Codon Three ssODNs were generated, each of which is capable of homologous recombination with one of the following three target loci: TRAC-1, TRAC-13, or TRAC-SL. Each ssODN contains a stop codon positioned between two homology arms having substantial identity to the sequence flanking the target cleavage site. This ssODN configuration is referred to herein as a STOP-ssODN. The STOP-ssODN specific for a given target locus was provided to primary human T cells with varying molar concentrations of a Cas9/gRNA RNP complex specific for the target locus. Editing efficiency was compared to primary human T cells provided with the Cas9/gRNA RNP complex in the absence of the STOP-ssODN. Editing and repair outcomes were determined by Illumina sequencing, the results of which are depicted in FIG. 4. A significantly higher percentage of alleles were edited in the presence of the STOP-ssODN than in the no-oligo controls, particularly at reduced RNP concentrations, independent of the locus targeted.

Figure 5A:
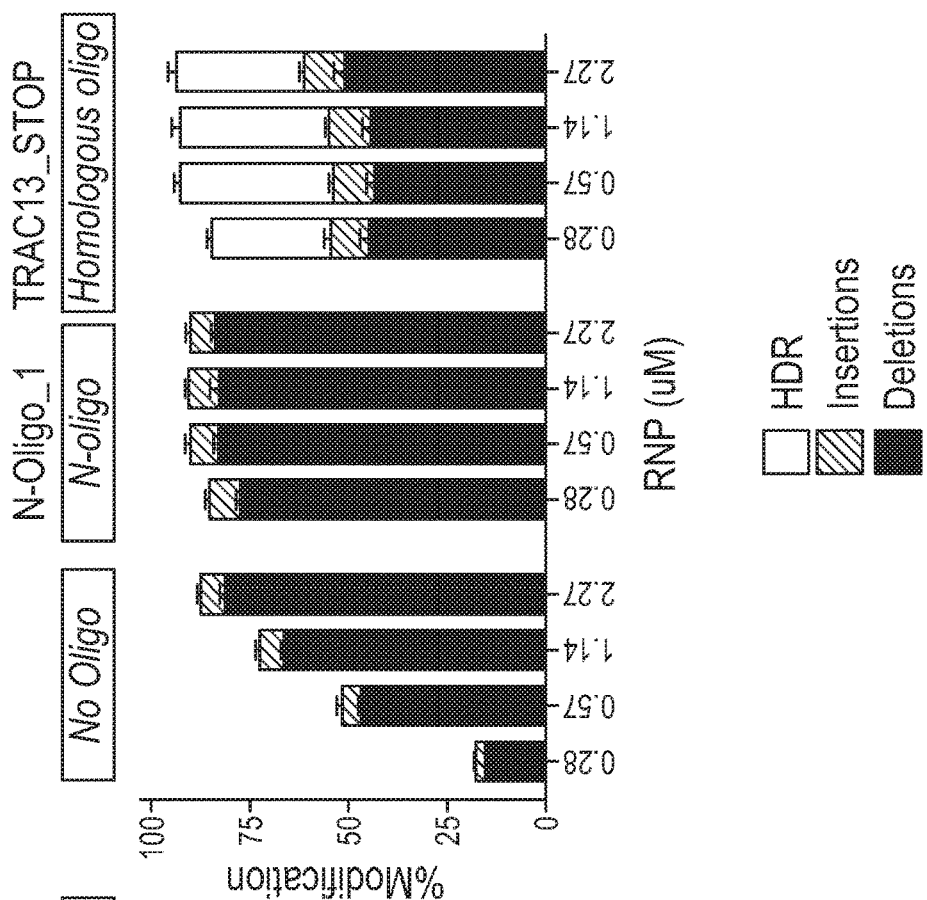
FIG. 5A and FIG. 5B depict the gene editing outcome in cells exposed to (i) no oligonucleotide donor template ("No Oligo"), (ii) a non-specific oligo containing a stop codon ("N-Oligo"), and (iii) an oligonucleotide donor template containing a stop codon and homology arms specific for the target nucleic acid ("homologous oligo").
Figure 5B:
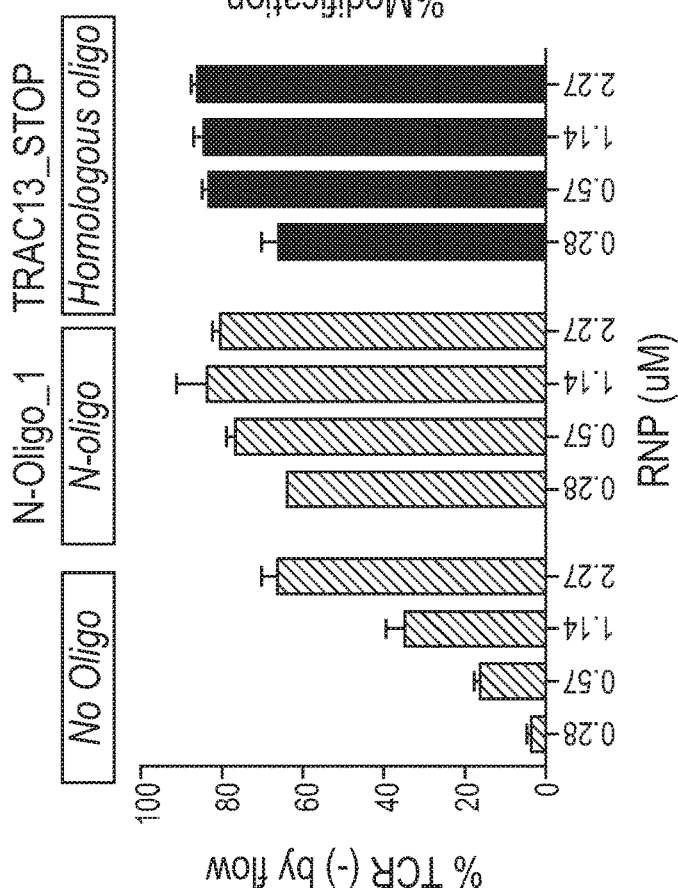

To confirm that the STOP-ssODN is integrated into the target locus, primary human T cells were treated with varying concentrations of a Cas9/gRNA RNP complex targeting TRAC-13, and either (i) a STOP-ssODN containing a stop codon positioned between two homology arms having substantial identity to the sequence flanking the TRAC-13 cleavage site (homologous oligo), or (ii) a non-specific single-stranded oligo with no substantial identity to the TRAC-13 locus (N-oligo). A control group of cells was treated only with the RNP complex (no oligo). Results are presented in FIG. 5. The homologous oligo and the N-oligo were used at concentrations of 2.27 µM (50 pmol). Similar results were obtained when the homologous oligo and the N-oligo were used at concentrations of 0.56 µM (12.5 pmol) (not shown). Both the homologous oligo and the N-oligo increase the proportion of modified TRAC13 alleles at reduced concentrations of RNP complex. Efficient editing was observed in the presence of the homologous oligo or the N-oligo at the lowest RNP concentration tested (0.28 µM). Flow cytometry was used to confirm that the modifications resulted in functional knockouts at the TRAC locus, using an anti-TCR antibody as a marker (FIG. 5A). Illumina-sequencing was used to determine the nature of the modification at the TRAC-13 locus (FIG. 5B). The control (no oligo) and the N-oligo treated cells contained insertions and deletions introduced through the NHEJ-mediated DNA repair pathway. The presence of the N-oligo increased the overall rate of NHEJ relative to the no oligo control, particularly at reduced concentrations of RNP complex. Insertion of the non-specific N-oligo at the cleavage site was not observed. 40-50% of alleles treated with the homologous oligo contained a precise disruption at the TRAC-13 locus mediated by HDR through the STOP-ssODN, at all concentrations of RNP complex tested. Accordingly, the homologous oligo serves as a template for HDR.

Figure 6:
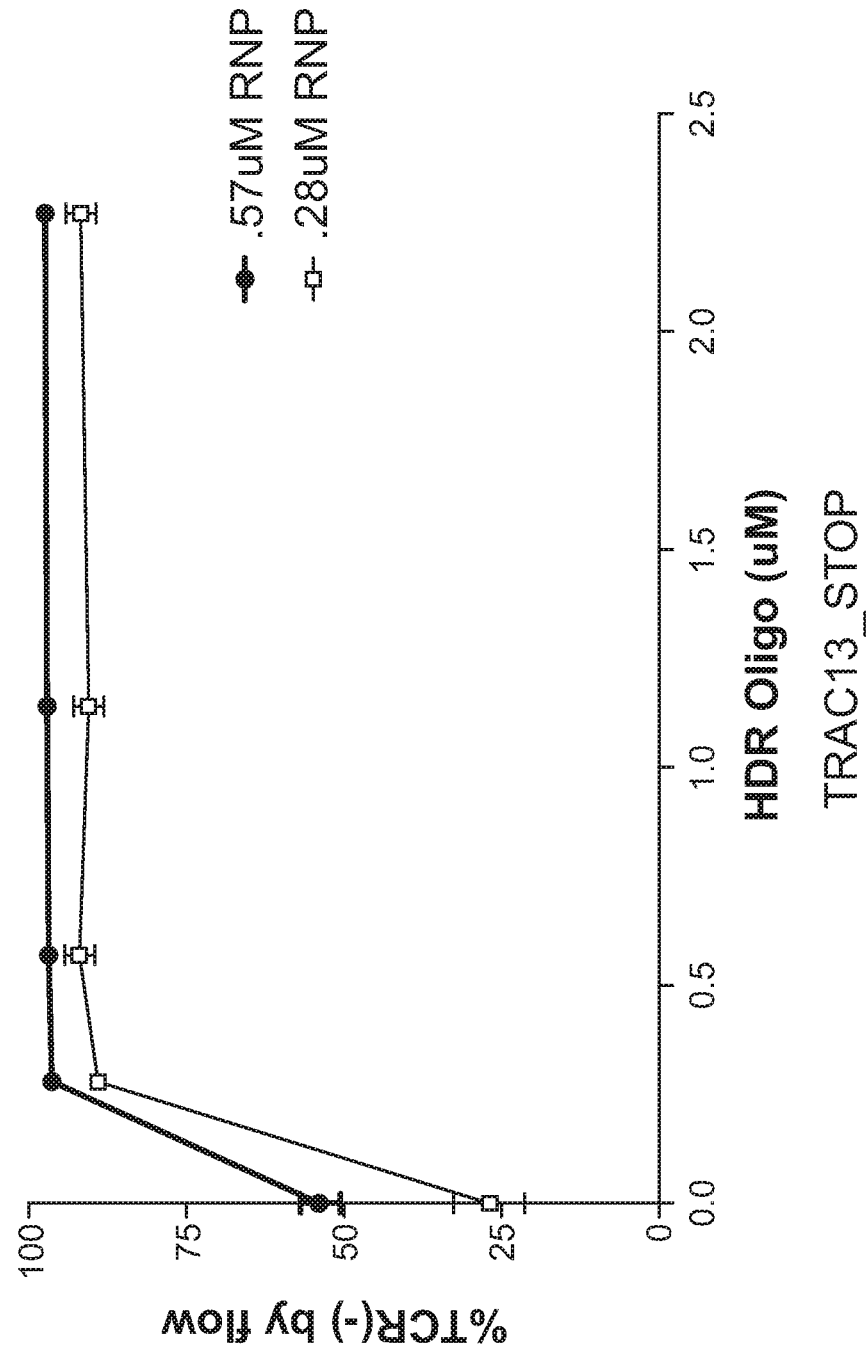
FIG. 6 depicts the percentage of cells containing a functional knockout (TCR(−)) following gene editing in the presence of varying concentrations of a homologous oligonucleotide donor template containing a stop codon.

The ability of the STOP-ssODN to induce efficient editing at reduced concentrations of RNP complex persists at low concentrations of the STOP-ssODN. Primary human T cells were treated with two concentrations of RNP complex containing Cas9 and gRNA targeting the TRAC-13 locus. The cells were simultaneously treated with various concentrations of a STOP-ssODN specific for TRAC-13. Functional knockout of the TRAC locus was assessed by flow cytometry, using an anti-TCR antibody as a marker (FIG. 6). Functional knockouts were generated in a large proportion of cells using a low concentration (0.57 µM or 0.28 µM) of RNP complex, at concentrations of the STOP-ssODN reduced to 0.5 µM or less.

Example 2: Multiplex Editing Using a STOP-ssODN

Figure 7A:
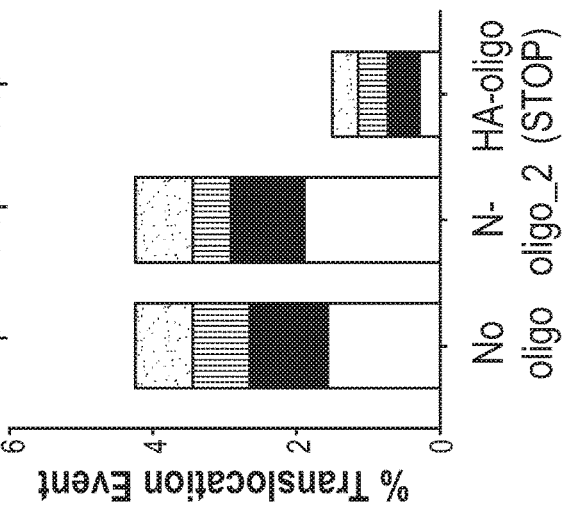
FIG. 7A-FIG. 7C depict the percentage of cells containing a modification or a translocation event following simultaneous editing of two target loci in the presence of (i) a homologous oligonucleotide donor template containing a stop codon (HA-oligo (STOP)), (ii) a non-specific oligonucleotide donor template containing a stop codon (N-oligo), or (iii) in the absence of an oligonucleotide donor template (No oligo).
Figure 7B:
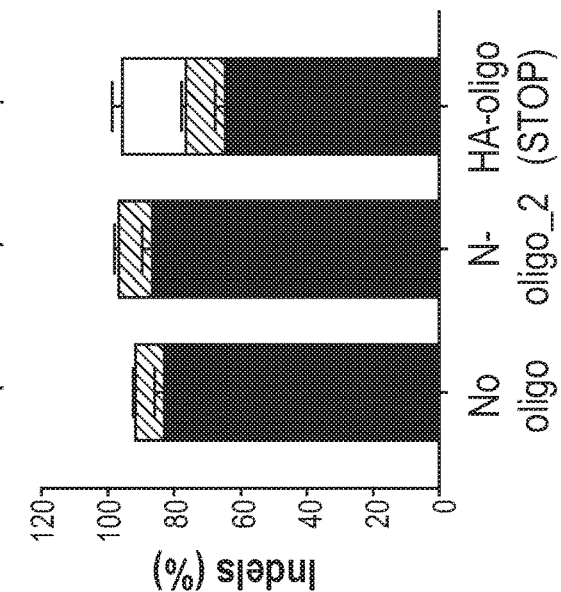
Figure 7C:
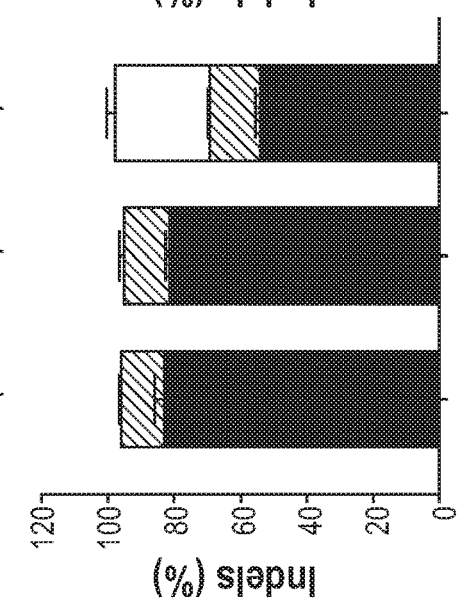

Two STOP-ssODNs were designed to induce targeted incorporation of the stop codon at two distinct target loci (B2M and TRAC). Primary human T cells were treated simultaneously with two Cas9/gRNA RNP complexes using the TRAC5 gRNA and the B2M12 gRNA to direct the Cas9 nucleases to the TRAC and B2M loci, and with either a STOP-ssODN specific for each locus, a non-specific N-oligo, or no oligo, exploiting the observation described above that the presence of either oligo allows for a 10-fold reduction in RNP concentration to achieve similar levels of gene disruption, as compared with the no oligo control. A first subset of cells (HA-oligo (STOP)) was treated with two STOP-ssODNs, one specific for B2M (B2M12-STOP), and one specific for TRAC (TRAC5 STOP). The cells were also treated with 0.3 µM of a first RNP complex containing Cas9 and a gRNA targeting B2M12, and 0.3 µM of a second RNP complex containing Cas9 and a gRNA targeting TRAC5. A second subset of cells (N-oligo) received a non-specific N-oligo (N-oligo 2), 0.5 µM of the first RNP complex, and 0.5 µM of the second RNP complex. A third subset of cells did not receive either oligo (no oligo control), and was treated with 2.2 µM of the first RNP complex, and 2.2 µM of the second RNP complex. After four days, cells were harvested. Genomic DNA was analyzed by Illumina sequencing for editing and HDR efficiency, and by ddPCR to assess translocation formation (FIG. 7). Both the N-oligo and the STOP-ssODNs allow for a reduction in RNP concentration of at least 10-fold, while maintaining editing efficiency. The translocation rate is not significantly altered in cells receiving the N-oligo relative to the control, indicating that the N-oligo leads to increased NHEJ-mediated DNA repair even at lower RNP concentration. In contrast, cells receiving the STOP-ssODNs exhibited a 3-fold reduction in translocation formation relative to the control. This reduction was accompanied by a reduction in NHEJ and an increase in HDR. Accordingly, the STOP-ssODN maintained editing and HDR levels at a reduced concentration of RNP while reducing translocation frequency, relative to control cells.

Example 3: Multiplex Editing Using Sequential Nuclease Administration

Figure 8B:
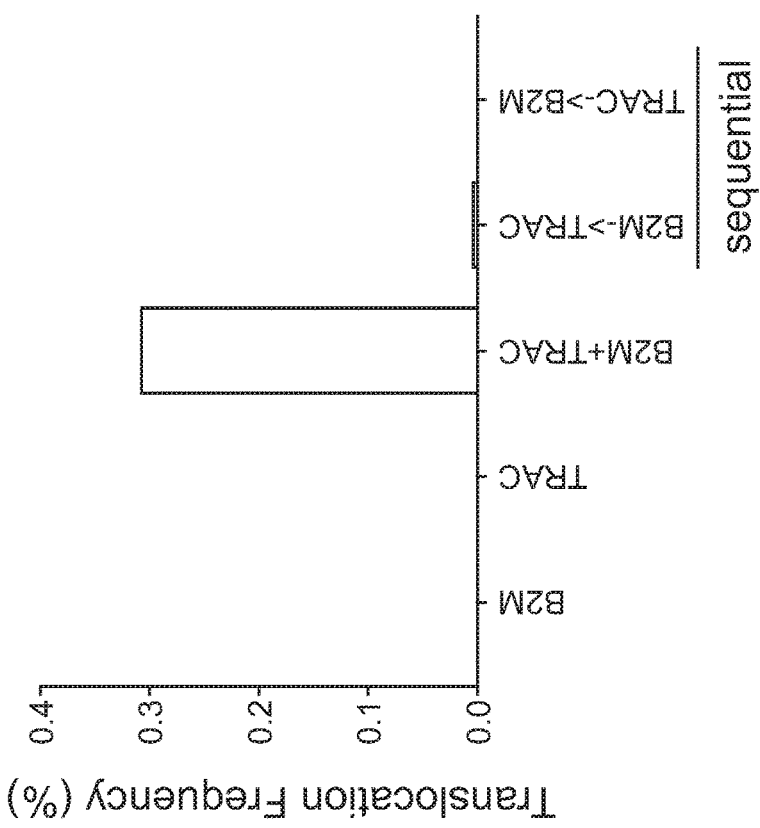
FIG. 8A and FIG. 8B depict the percentage of cells undergoing a translocation event during sequential and simultaneous editing of two target loci.
Figure 8A:
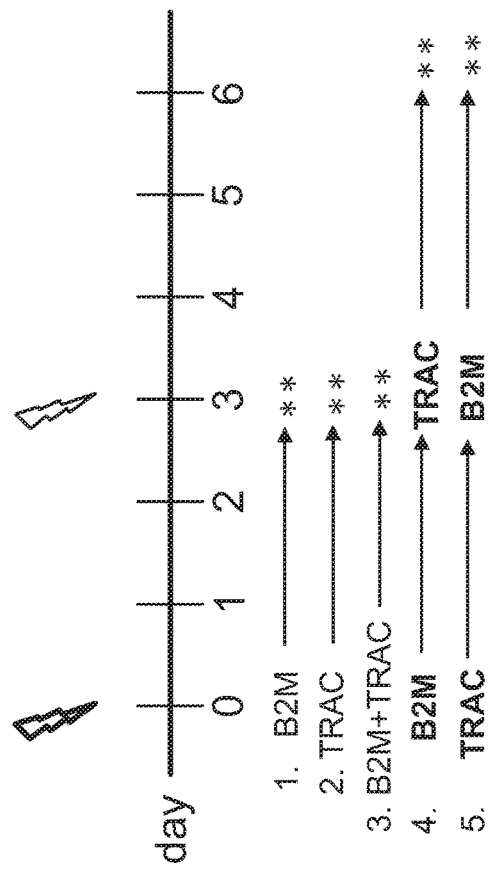

RNP complexes were prepared containing Cas9 and either a gRNA targeting B2M (B2M12) or a gRNA targeting TRAC (TRAC5). RNP complexes were introduced into primary human T cells by nucleofection, as shown in FIG. 8A. A first subset of cells was nucleofected with B2M12 RNP on day 0, and cells were harvested on day 3. A second subset of cells was nucleofected with TRAC5 RNP on day 0, and cells were harvested on day 3. A third subset of cells was simultaneously nucleofected with B2M12 RNP and TRAC5 RNP on day 0, and cells were harvested on day 3. A fourth subset of cells was nucleofected with B2M12 RNP on day 0, and nucleofected with TRAC5 RNP on day 3. Cells were harvested on day 6. A fifth subset of cells was nucleofected with TRAC5 RNP on day 0, and nucleofected with B2M12 RNP on day 3. Cells were harvested on day 6. Translocation frequency was measured in the harvested cells using ddPCR (FIG. 8B). Cells treated simultaneously with both RNP complexes had a significantly increased rate of translocation formation, relative to cells receiving a either RNP complex alone, indicating that the presence of simultaneous cleavage events increases the translocation frequency in edited cells. In contrast, the translocation frequency was significantly reduced in cells treated sequentially with both RNP complexes, indicating that translocation formation can be reduced or prevented by modulating the timing of multiple cleavage events to minimize their co-occurrence.

Example 4: Multiplex Editing Using Different Nucleases

Figure 9A:
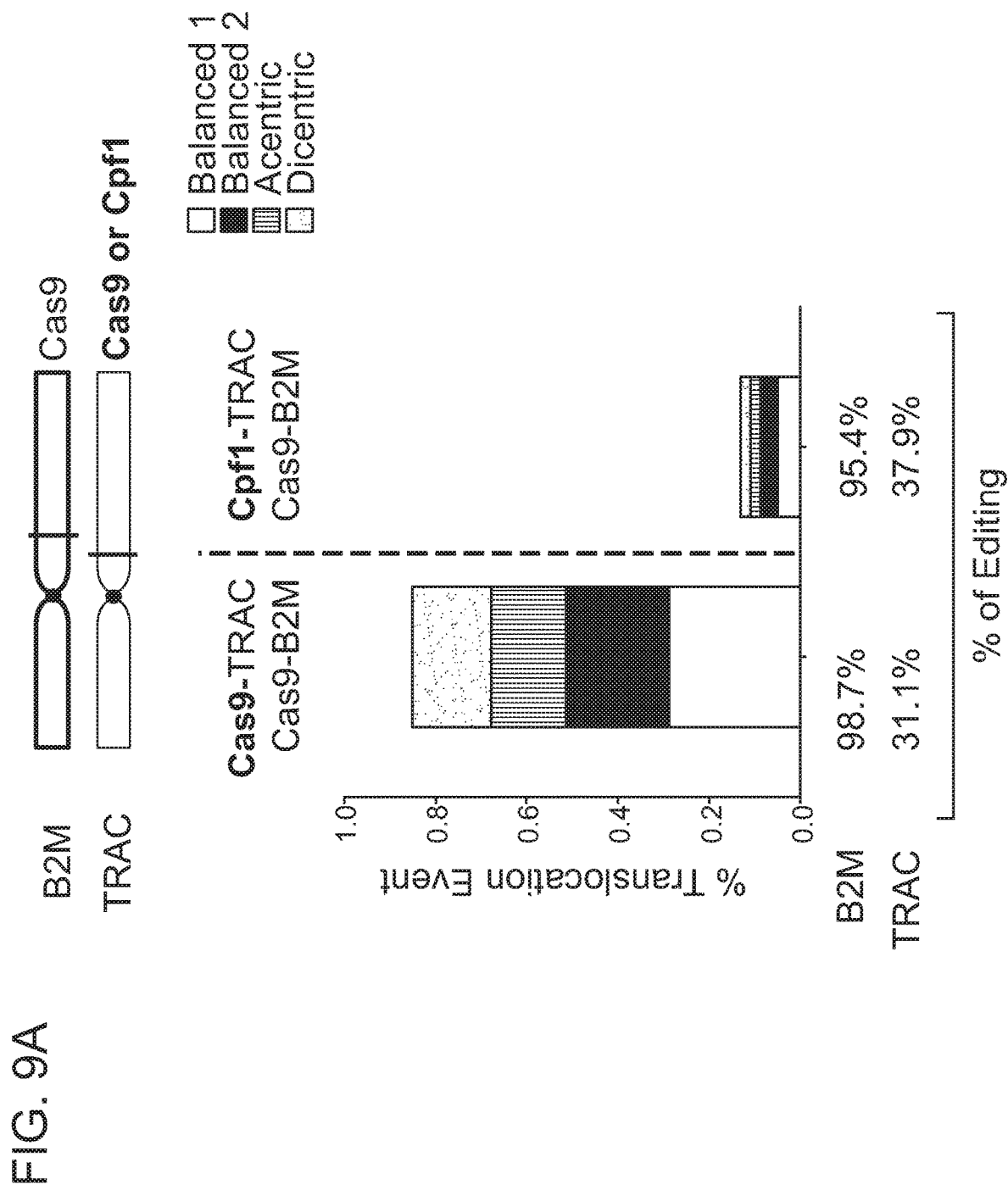

Primary human T cells were simultaneously nucleofected with two RNP complexes each targeting distinct genetic loci. In one subset of cells, the first RNP complex contained Cas9 and a gRNA targeting TRAC (TRAC5), and the second RNP complex contained Cas9 and a gRNA targeting B2M (B2M12). In a second subset of cells, the first RNP complex contained Cpf1 and a gRNA targeting TRAC (GWED546), and the second RNP complex contained Cas9 and a gRNA targeting B2M (B2M12). Editing was assessed using Illumina sequencing, and translocation frequency was measured using ddPCR (in samples that had comparable editing efficiencies). The results are shown in FIG. 9A. Cells simultaneously exposed to RNPs containing different nucleases (Cas9 and Cpf1) had a significantly lower translocation frequency, compared to cells simultaneously exposed to RNPs containing the same nuclease (Cas9 and Cas9).

In a second experiment, in one subset of cells, the first RNP complex contained Cas9 and a gRNA targeting TRAC (TRAC5), and the second RNP complex contained Cas9 and a gRNA targeting B2M (B2M16). In a second subset of cells, the first RNP complex contained Cpf1 and a gRNA targeting TRAC (GWED546), and the second RNP complex contained Cpf1 and a gRNA targeting B2M (B2M-Cpf-12). Editing was assessed using Illumina sequencing, and translocation frequency was measured using ddPCR (in samples that had comparable editing efficiencies). The results are shown in FIG. 9B. Cells simultaneously exposed to Cpf1/Cpf1 RNPs had a significantly lower translocation frequency, compared to cells simultaneously exposed to RNPs containing Cas9.

In another experiment, primary human T cells were simultaneously nucleofected with a first RNP complex containing *S. pyogenes* Cas9 and a gRNA targeting TRAC (TRAC5), and a second RNP complex containing *S. pyogenes* Cas9 and a gRNA targeting B2M Exon 1 (B2M12 sp) at the indicated molar concentrations. In parallel, a second group of primary human T cells were simultaneously nucleofected with a first RNP complex containing *Acidaminococcus* sp. Cpf1 (AsCpf1) and a gRNA targeting TRAC (GWED564 (as)), and a second RNP complex containing *S. pyogenes* Cas9 and gRNA targeting B2M Exon 1 (B2M12 sp) at the indicated molar concentrations. Editing was assessed using Illumina sequencing, and translocation frequency was measured four days after nucleofection using ddPCR. The results are shown in FIG. 9C. These results show that a combination of simultaneous *S. pyogenes* Cas9 and *Acidaminococcus* sp. Cpf1 for multiplexing leads to lower translocation formation than two simultaneous *S. pyogenes* Cas9 editing events.

Figure 9D:
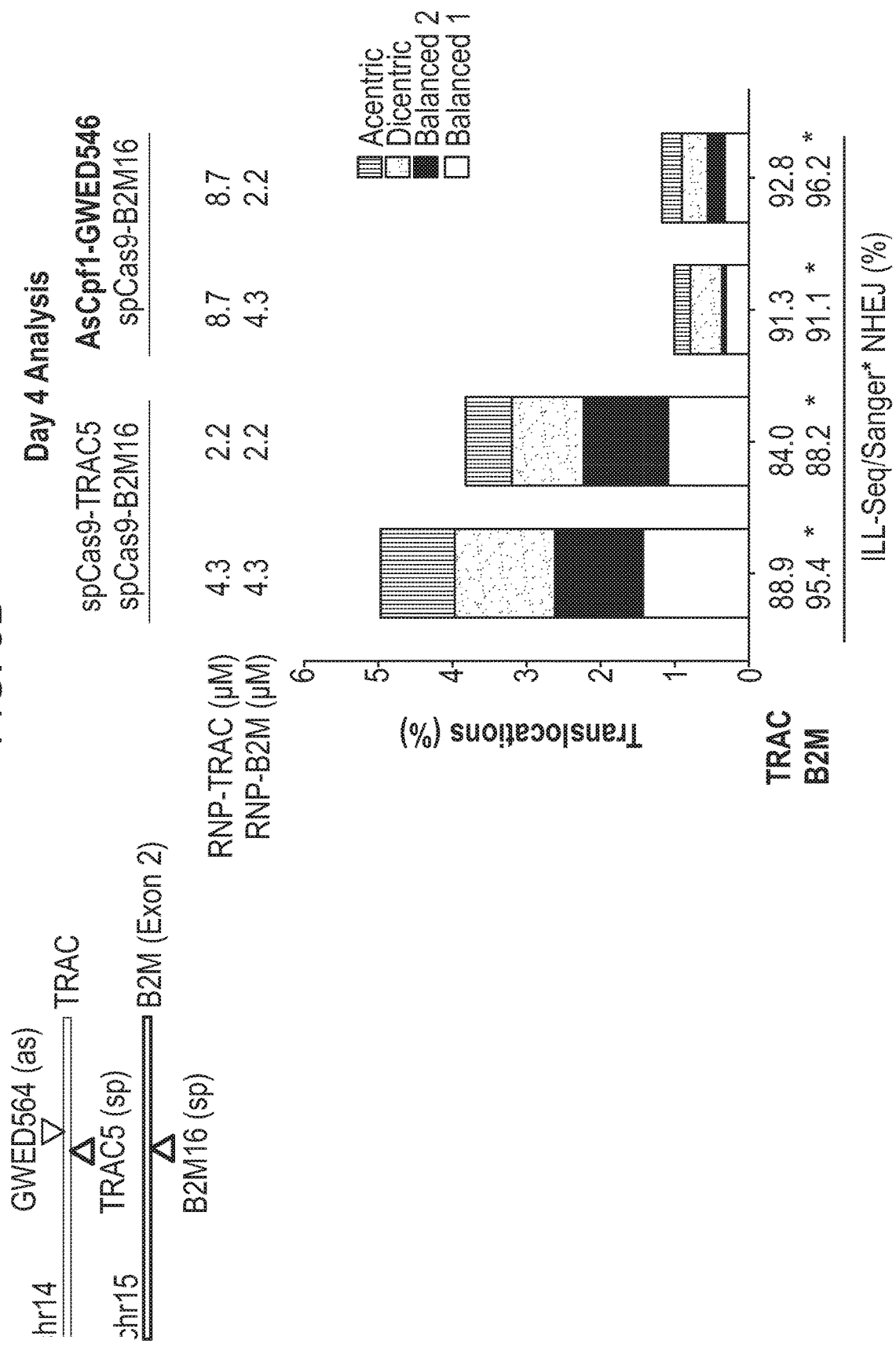

Primary human T cells were then nucleofected with RNP complexes targeting TRAC and B2M as shown in FIG. 9D. A first group of cells were simultaneously nucleofected with a first RNP complex containing *S. pyogenes* Cas9 and gRNA targeting TRAC (TRAC5), and a second RNP complex containing *S. pyogenes* Cas9 and gRNA targeting B2M Exon 2 (B2M16 sp) at the indicated molar concentrations. A second group of cells were simultaneously nucleofected with a first RNP complex containing AsCpf1 and gRNA targeting TRAC (GWED564 (as)), and a second RNP complex containing *S. pyogenes* Cas9 and gRNA targeting B2M Exon 2 (B2M16 sp) at the indicated molar concentrations. Editing was assessed using Illumina sequencing or Sanger sequencing (*), and translocation frequency was measured 4 days after nucleofection using ddPCR. The results are shown in FIG. 9D. These results show that a combination of simultaneous *S. pyogenes* Cas9 and *Acidaminococcus* sp. Cpf1 for multiplexing leads to lower translocation formation than two simultaneous *S. pyogenes* Cas9 editing events.

Figure 9E:
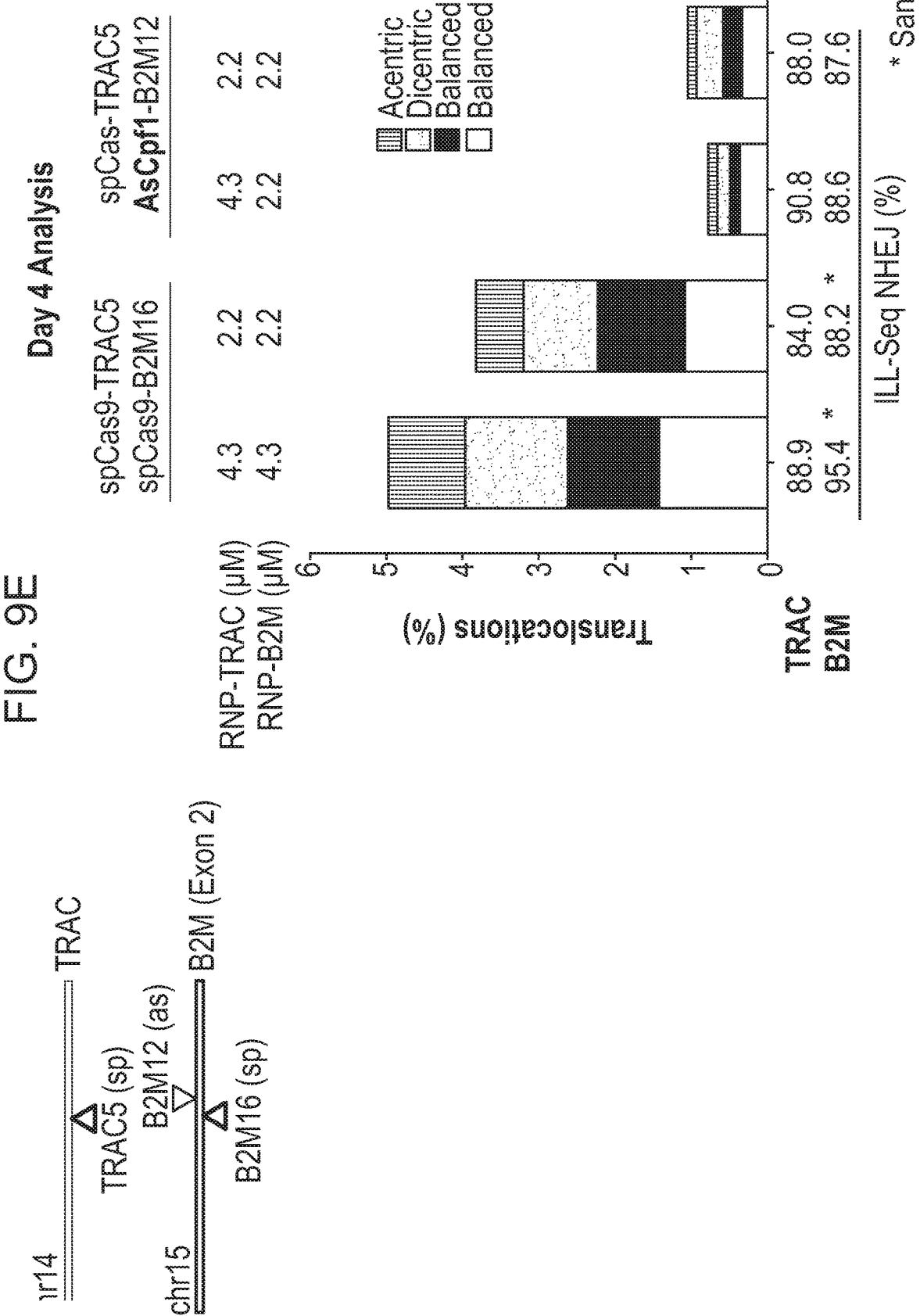

In another experiment, primary human T cells were nucleofected with RNP complexes targeting TRAC and B2M Exon 2 as shown in FIG. 9E. A first group of cells were simultaneously nucleofected with a first RNP complex containing *S. pyogenes* Cas9 and gRNA targeting TRAC (TRAC5), and a second RNP complex containing *S. pyogenes* Cas9 and gRNA targeting B2M Exon 2 (B2M16 sp). A second group of cells were simultaneously nucleofected with a first RNP complex containing *S. pyogenes* Cas9 and gRNA targeting TRAC (TRAC5), and a second RNP complex containing AsCpf1 and gRNA targeting B2M Exon 2 (B2M12 as). Editing was assessed using Illumina sequencing or Sanger sequencing (*), and translocation frequency was measured 4 days after nucleofection using ddPCR. The results are shown in FIG. 9E. These results show that a combination of simultaneous *S. pyogenes* Cas9 and *Acidaminococcus* sp. Cpf1 for multiplexing leads to lower translocation formation than two simultaneous *S. pyogenes* Cas9 editing events.

Figure 9F:
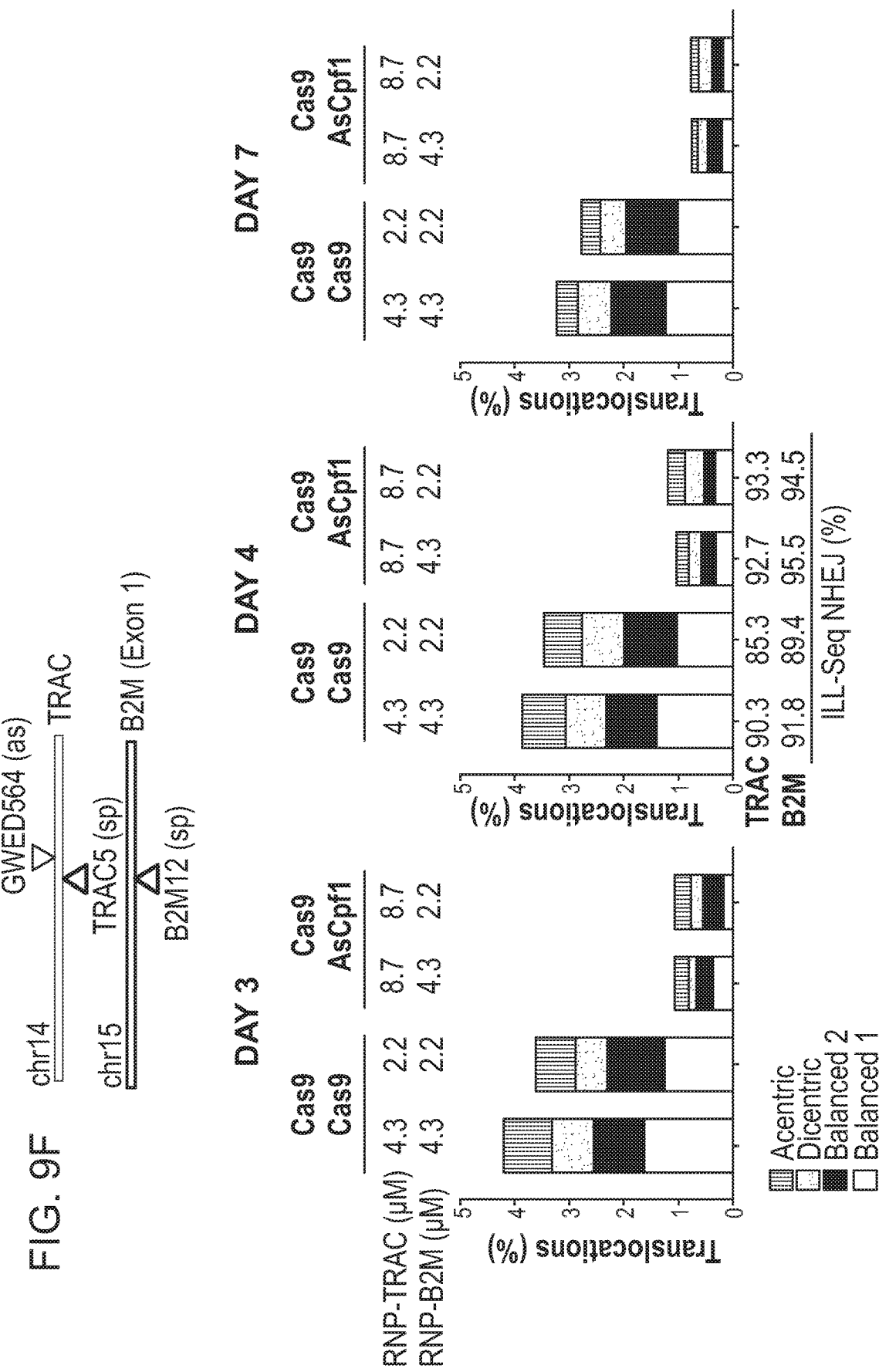

To assess the translocation frequency at different time points, primary human T cells were nucleofected with RNP complexes targeting TRAC and B2M Exon 1 as shown in FIG. 9F. A first group of cells were simultaneously nucleofected with a first RNP complex containing *S. pyogenes* Cas9 and gRNA targeting TRAC (TRAC5), and a second RNP complex containing *S. pyogenes* Cas9 and gRNA targeting B2M Exon 1 (B2M12 sp). A second group of cells were simultaneously nucleofected with a first RNP complex containing AsCpf1 and gRNA targeting TRAC (GWED564 (as)), and a second RNP complex containing *S. pyogenes* Cas9 and gRNA targeting B2M Exon 1 (B2M12 sp). Editing was assessed using Illumina sequencing, and translocation frequency was measured at 3 days, 4 days, and 7 days after nucleofection using ddPCR. The results are shown in FIG. 9F. These results show that independent of the time the assay is performed following nucleofection, a combination of simultaneous *S. pyogenes* Cas9 and *Acidaminococcus* sp. Cpf1 for multiplexing leads to lower translocation formation that two simultaneous *S. pyogenes* Cas9 editing events.

Figure 9G:
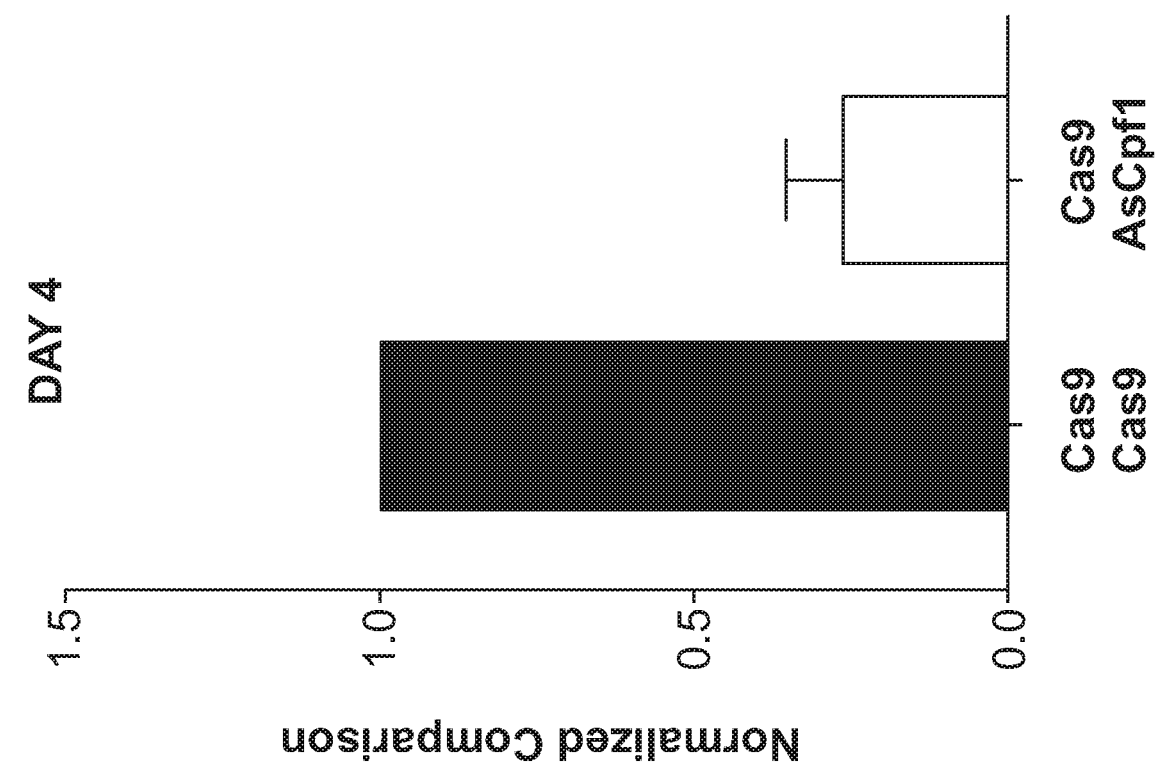

A normalized comparison of fifteen independent measurements across thirteen independent experiments indicates that there is a significant reduction in the translocation rate when simultaneously editing two genetic loci if different nucleases (Cas9 and Cpf1) are used for editing at each locus (see FIG. 9G). The reduction in translocation rate is independent of the locus to be edited, independent of the Cpf1 gRNA, and independent of the assay used to detect translocation frequency. The results presented herein were independently validated using UDiTaS™.

To assess the translocation frequency when simultaneously editing two genes using Cas9 at both sites, Cpf1 at both sites, or Cas9 at one site and Cpf1 at the other site, primary human T cells were nucleofected with RNP complexes targeting TRAC and B2M Exon 2 as shown in FIG. 9H. A first group of cells were simultaneously nucleofected with a first RNP complex containing *S. pyogenes* Cas9 and gRNA targeting TRAC (TRAC5), and a second RNP complex containing *S. pyogenes* Cas9 and gRNA targeting B2M Exon 2 (B2M16 sp). A second group of cells were simultaneously nucleofected with a first RNP complex containing AsCpf1 and gRNA targeting TRAC (GWED564 (as)), and a second RNP complex containing *S. pyogenes* Cas9 and gRNA targeting B2M Exon 2 (B2M16 sp). A third group of cells were simultaneously nucleofected with a first RNP complex containing AsCpf1 and gRNA targeting TRAC (GWED564 (as)), and a second RNP complex containing AsCpf1 and gRNA targeting B2M Exon 2 (B2M12 as). Editing was assessed using Illumina sequencing or Sanger sequencing, and translocation frequency was measured 4 days after nucleofection using ddPCR. The results are shown in FIG. 9H. These results show that a reduction in translocation frequency can be achieved by simultaneously administering two *Acidaminococcus* sp. Cpf1 RNP complexes compared to two simultaneous *S. pyogenes* Cas9 editing events.

Example 5: Multiplex Editing Using Different Nuclease Concentrations

To explore the relationship between cutting activity (measured indirectly as the number of indels following RNP exposure) and translocation formation, cells were simultaneously treated by nucleofection with two RNP complexes at varying concentrations. The first RNP complex contained Cas9 (wild-type) and a gRNA targeting TRAC (TRAC5 gRNA). The second RNP complex contained Cas9 (wild-type) and a gRNA targeting B2M (B2M12 gRNA). In one experiment, the concentration of the TRAC RNP complex was kept constant, and the concentration of the B2M RNP complex was titrated down, as shown in FIG. 10A. In another experiment, the concentration of the B2M RNP complex was kept constant, and the concentration of TRAC RNP complex was titrated down, as shown in FIG. 10B. After 4 days, cells were harvested, gRNA was extracted, and the translocation frequency was measured using ddPCR. As shown in FIG. 10, reducing the dose of a single Cas9 cut can significantly reduce the rate of translocation formation.

Example 6: Multiplex Editing Using a RNP Complex and a Cas9 Expression Construct Primary human T cells are simultaneously nucleofected with (i) a RNP complex containing Cas9 and gRNA targeting TRAC, (ii) a mRNA encoding Cas9, and (iii) a gRNA targeting B2M. The RNP complex will initiate editing of the TRAC nucleic acid immediately following nucleofection. Following translation of Cas9 from the mRNA, Cas9 and the gRNA targeting B2M will associate in an RNP complex that will initiate editing of the B2M nucleic acid. The translocation frequency in edited cells is reduced, relative to cells in which RNP complexes targeting TRAC and B2M are delivered simultaneously.

Figure 11A:
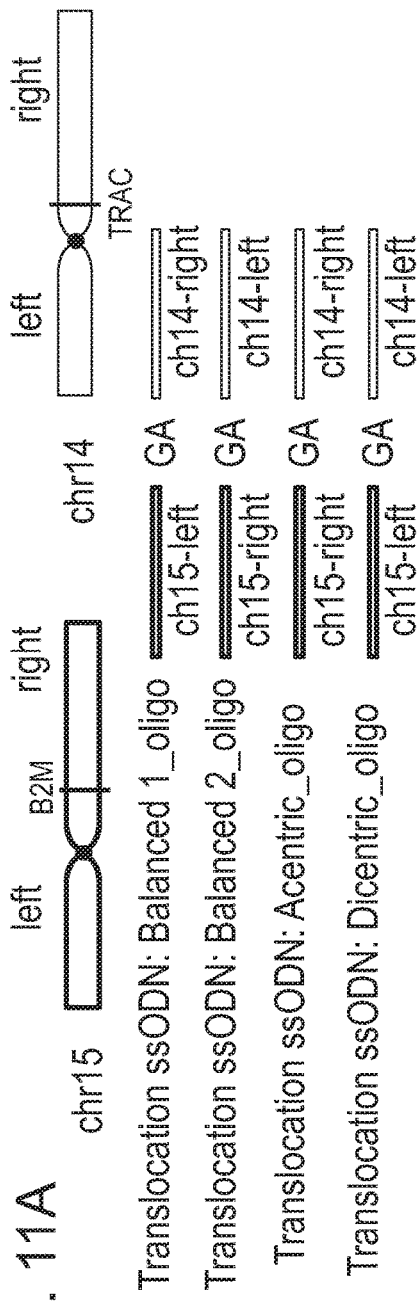
FIG. 11A and FIG. 11B depict a strategy for increasing the rate of translocation formation using an oligonucleotide donor template.
Figure 11B:
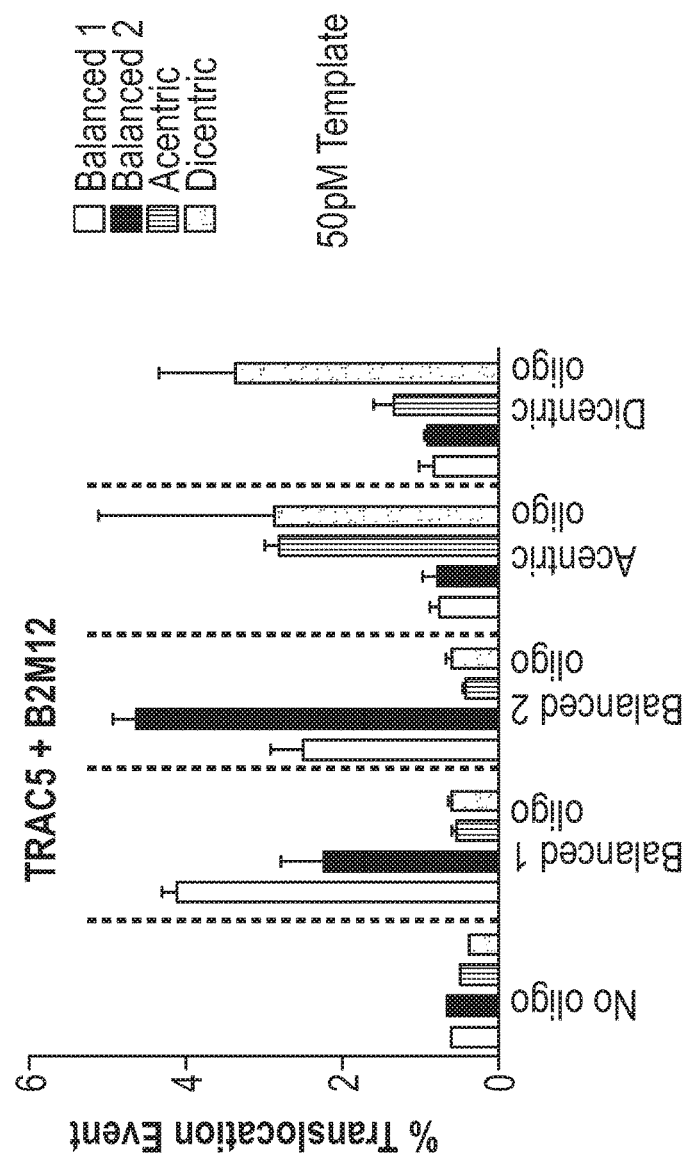

Example 7: Increasing Translocation Frequency Using an Oligonucleotide Donor Template To enhance the formation of a specific chromosomal rearrangement, a ssODN was designed having a 5' homology arm that contains 70 nucleotides identical to a sequence on chromosome 15 adjacent to the cut site of a RNP complex containing Cas9 and B2M gRNA, and a 3' homology arm that contains 70 nucleotides identical to a sequence on chromosome 14 adjacent to the cut site of a RNP complex containing Cas9 and TRAC gRNA. Oligos that promote the formation of desired translocation events were designed by selecting sequences centromeric (left) or acentromeric (right) of the cut site on each chromosome, as depicted in FIG. 11A. In this way, oligos promoting a balanced 1 translocation, a balanced 2 translocation, an acentric translocation, and a dicentric translocation were generated. Additional nucleotides (GA) were inserted between the homology arms to facilitate detection of oligo-induced translocation events. Two simultaneous DSBs were introduced in primary human T cells by nucleofection with Cas9/B2M (B2M12 gRNA) and Cas9/TRAC (TRAC5 gRNA) RNP complexes at a concentration of 0.6 µM, along with one of the translocation promoting oligos depicted in FIG. 11A. Specifically, cells were treated with either the plus or minus strand of the balanced 1 oligo, the balanced 2 oligo, the acentric oligo, or the dicentric oligo. The average translocation rates induced by the plus and minus strand of each translocation promoting oligo are shown in FIG. 11B. Translocation promoting oligos enhanced the specific translocation event induced by the provided ssODN. The translocation promoting oligos also enhanced partnered translocation events, as shown in FIG. 11B (e.g., the Balanced 1 oligo enhanced the formation of Balanced 1 and Balanced 2 translocation products, the Balanced 2 oligo enhanced the formation of Balanced 2 and Balanced 1 translocation products, the Acentric oligo enhanced the formation of Acentric and Dicentric translocation products, and the Dicentric oligo enhanced the formation of Dicentric and Acentric translocation products).

Example 8: Induction of Large Intrachromosomal Deletions

Figure 12:
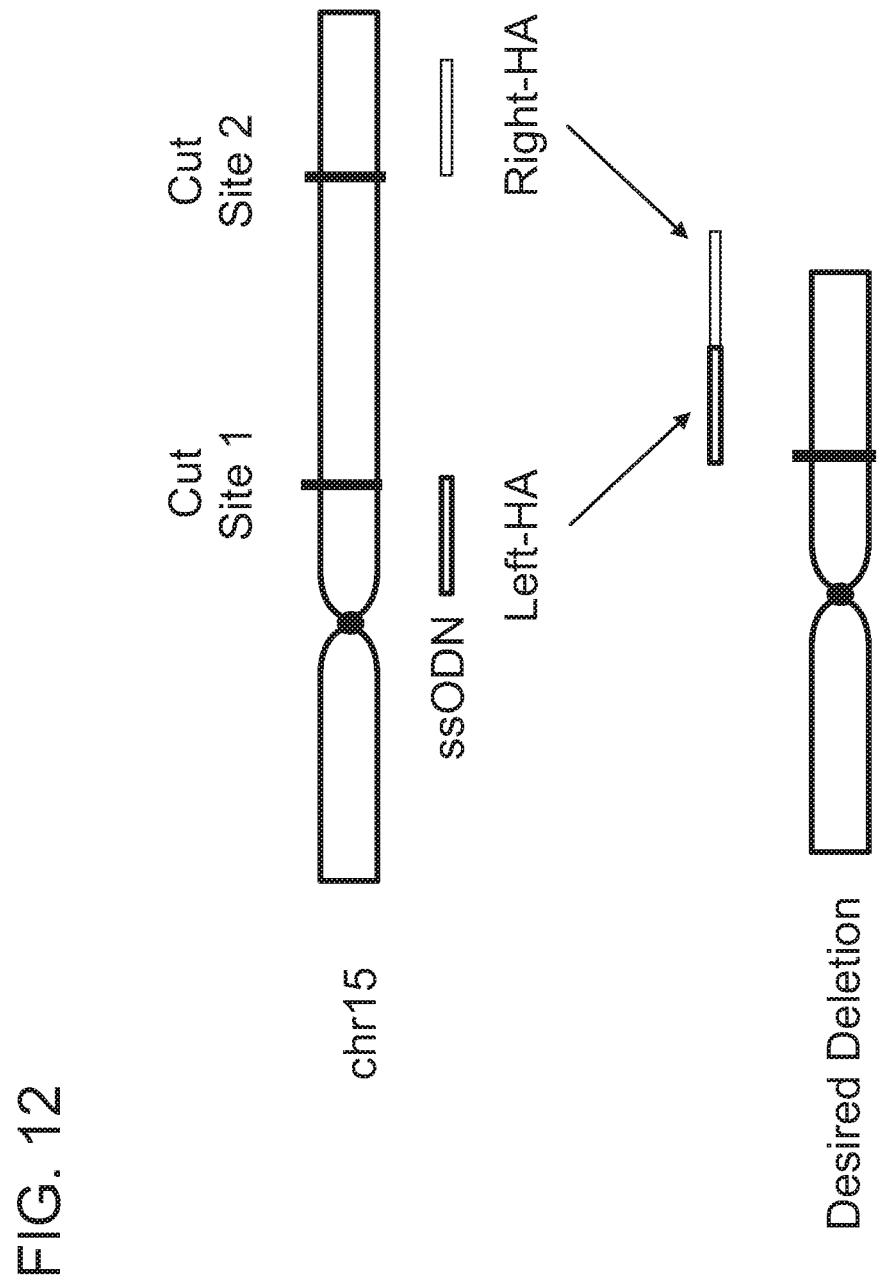
FIG. 12 depicts a strategy for generating a large intrachromosomal deletion using a ssODN. The ssODN contains homology arms flanking the region of the chromosome to be deleted. In this example, the ssODN contains a first homology arm substantially identical to the region to the left of Cut Site 1 in Chromosome 15, and a second homology arm substantially identical to the region to the right of Cut Site 2 in Chromosome 15. Treatment with the ssODN promotes the formation of alleles containing the desired deletion, in which the region between Cut Site 1 and Cut Site 2 is removed.

To enhance the formation of a desired chromosomal deletion, a ssODN can be designed with homology arms identical to the portions of the chromosome flanking the deletion site. Cells are treated with two RNP complexes that target two different genes on the same chromosome. To enhance the desired deletion, cells are simultaneously nucleofected with a ssODN containing a first homology arm substantially identical to the left portion of cut site 1 and a second homology arm substantially identical to the right portion of cut site 2, as shown in FIG. 12. The ssODN enhances the frequency of alleles harboring the desired deletion.

Figure 13B:
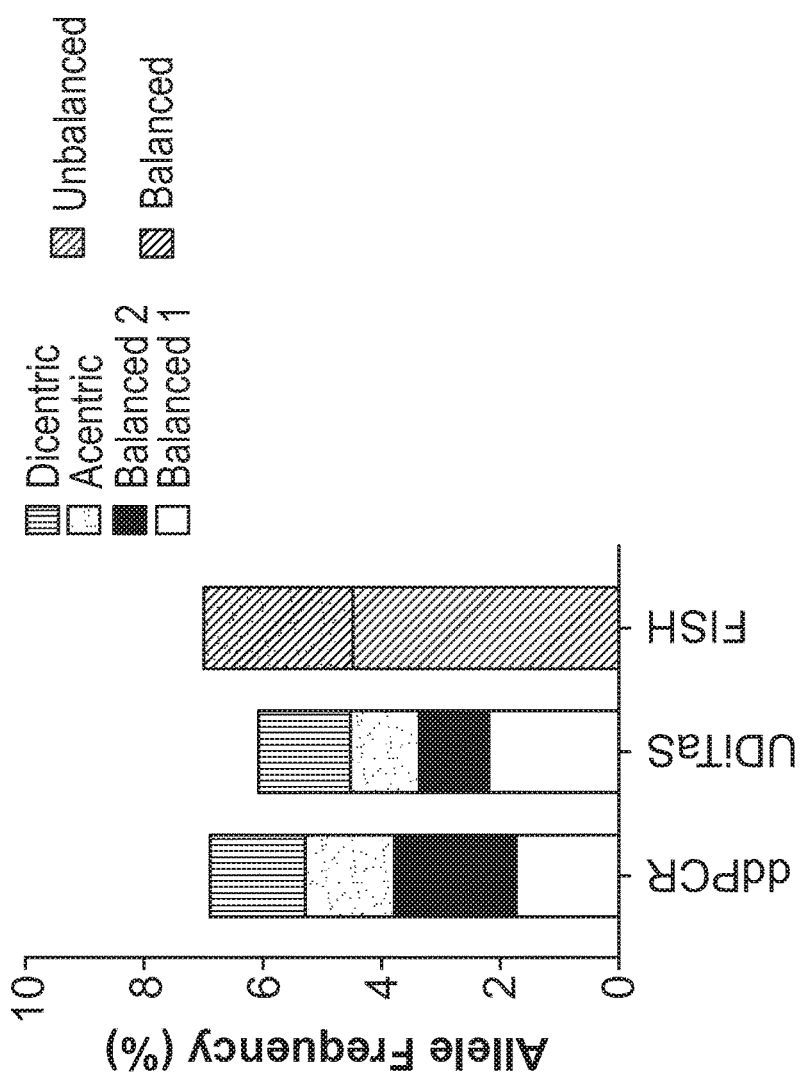
FIG. 13A and FIG. 13B depict translocation rates with different complementary detection methods. Primary human T cells were simultaneously contacted with 2 µM RNP complex of Cas9 and a gRNA targeting TRAC (TRAC5) and 2 µM RNP complex of Cas9 and a gRNA targeting B2M (B2M12).
Figure 13A:
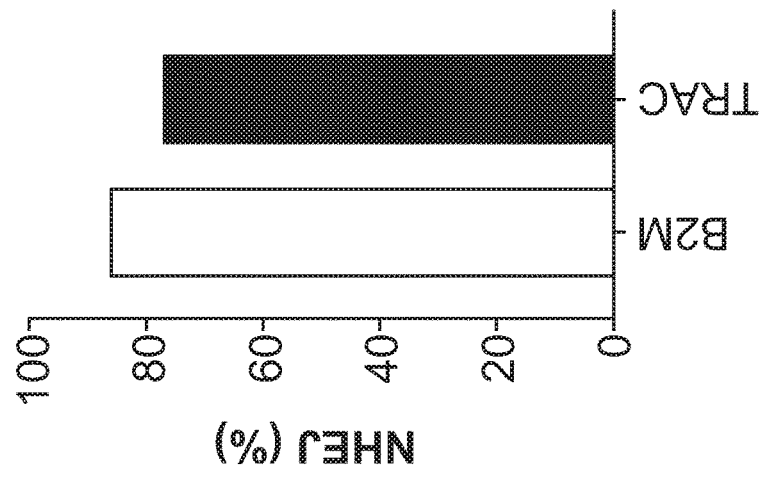

Example 9: Comprehensive Assessment of Translocation Rates with Different Complementary Detection Methods RNP complexes were prepared containing Cas9 and either a gRNA targeting B2M (B2M12) or a gRNA targeting TRAC (TRAC5). RNP complexes (2 µM each) were introduced into primary human T cells by nucleofection and harvested for assessment of NHEJ efficiency at the TRAC and B2M loci as well as for translocation formation between the TRAC and B2M loci by ddPCR, UDiTaS analysis or FISH analysis three days post nucleofection. NHEJ efficiency at TRAC was 77.3% while NHEJ efficiency at B2M was 86.3%. As shown FIG. 13, translocations measurements were comparable between all three different methods and were 6.9% by ddPCR, 6.1% by UDiTaS, and 7.0% by FISH.

Example 10: Translocations are Dependent on NHEJ Activity

Figure 14:
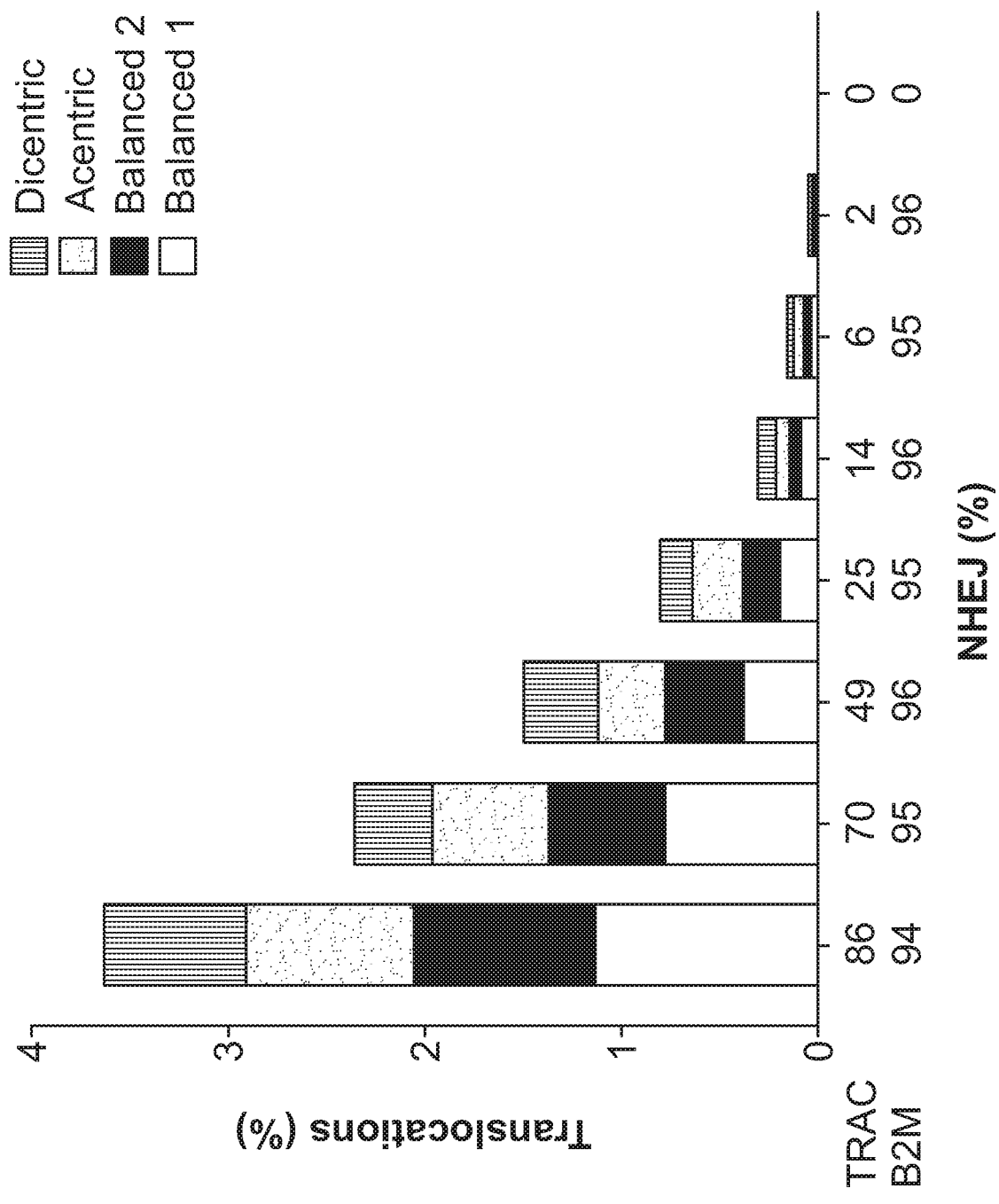
FIG. 14 depicts the percentage of cells undergoing a translocation event in primary human T cells that were simultaneously contacted with a RNP complex of Cas9 and a gRNA targeting TRAC (TRAC5) and a RNP complex of Cas9 and a gRNA targeting B2M (B2M12). The dose of B2M RNP was held constant at 2.504, while the TRAC5 RNP was serially diluted 2-fold with a starting concentration of 2.504. On day three post nucleofection, the primary human T cells were assessed for NHEJ efficiency at the TRAC and B2M loci by Illumina sequencing, and translocation rates were measured by ddPCR three days post nucleofection with the two RNPs.

RNP complexes were prepared containing Cas9 and either a gRNA targeting B2M (B2M12) or a gRNA targeting TRAC (TRAC5). The starting concentration of both RNP complexes was 2.5 μM. The TRAC5 RNP complex was introduced into primary human T cells at different concentrations: while the B2M RNP complex was kept constant at 2.504, the TRAC5 RNP complex was serially diluted 2-fold starting out at 2.504. On day three post nucleofection, T cells were assessed for NHEJ efficiency at the TRAC and B2M loci by Illumina sequencing, and translocation rates were measured by ddPCR. As shown in FIG. 14, translocation rates were dependent in NHEJ activity: decreased editing at the TRAC locus due to decreased RNP concentration leads to lower rates of translocations compared to translocations at the maximum RNP concentration.

Example 11: Measuring Translocations Between an On- and Off-Target Site

The TRAC5 gRNA has several known off targets that were determined by the standard guide-sequencing method. Two off-targets were chosen for analysis: high off target on chromosome 1 (Start: 151384697, End: 151384720) and the low off-target on chr 15 (Start: 88628537, End: 8862855). ddPCR assays were designed to measure translocations between the TRAC5 on-target site and either the high-off target site or the low off target sites. To determine translocation rates between on and off target sites, cells were treated with 2.504 RNP directed to TRAC5 or were left untreated as a control. Cells were harvested three days post nucleofection and assessed for NHEJ activity by Illumina sequencing at the on target TRAC5 sites and both the high and low off-target cells, as well as for translocations between the on-target TRAC5 site and either the high or low off target cells. Analyses were performed on TRAC5 treated cells as well as untreated cells as a control. As shown in FIG. 15, translocations could be detected at the expected rates (based on the standard curve from FIG. 14) at the high-off target site for which also NHEJ was detected to be 6.1%. However, the low off-target site had NHEJ at background levels (0.2%) and consequently no translocations above background between the low off-target site and TRAC5 could be detected.

Example 12: Reducing Translocation Formation with Different Nuclease Combinations In another experiment, primary human T cells were simultaneously nucleofected with a first RNP complex containing *S. pyogenes* Cas9 and a gRNA targeting TRAC (TRAC5), and a second RNP complex containing *S. pyogenes* Cas9 and a gRNA targeting B2M Exon 1 (B2M12 sp) at 2.2 μM each. In parallel, a second group of primary human T cells were simultaneously nucleofected with a first RNP complex containing *Acidaminococcus* sp. Cpf1 RR variant (AsCpf1-RR) and a gRNA targeting TRAC (TRAC140 as-RR) and a second RNP complex containing *S. pyogenes* Cas9 and a gRNA targeting B2M Exon 1 (B2M12 sp) at 8.7 μM and 2.2 μM respectively. A third group of primary human T cells were simultaneously nucleofected with a first RNP complex containing *Acidaminococcus* sp. Cpf1 RR variant (AsCpf1-RR) and a gRNA targeting TRAC (TRAC140 as-RR) and a second RNP complex containing *Acidaminococcus* Cpf1 and a gRNA targeting B2M Exon 2 (B2M-Cpf1-12 as) at 8.7 μM and 2.2 μM respectively. Editing was assessed using Illumina sequencing, and translocation frequency was measured three days after nucleofection using ddPCR. As shown in FIG. 16A, a combination of simultaneous *Acidaminococcus* sp. Cpf1 and *Acidaminococcus* sp. Cpf1-RR variant for multiplexing led to lower translocation formation than two simultaneous *S. pyogenes* Cas9 editing events or combined editing events of simultaneous *S. pyogenes* Cas9 and *Acidaminococcus* sp. Cpf1-RR variant.

Figure 16B:
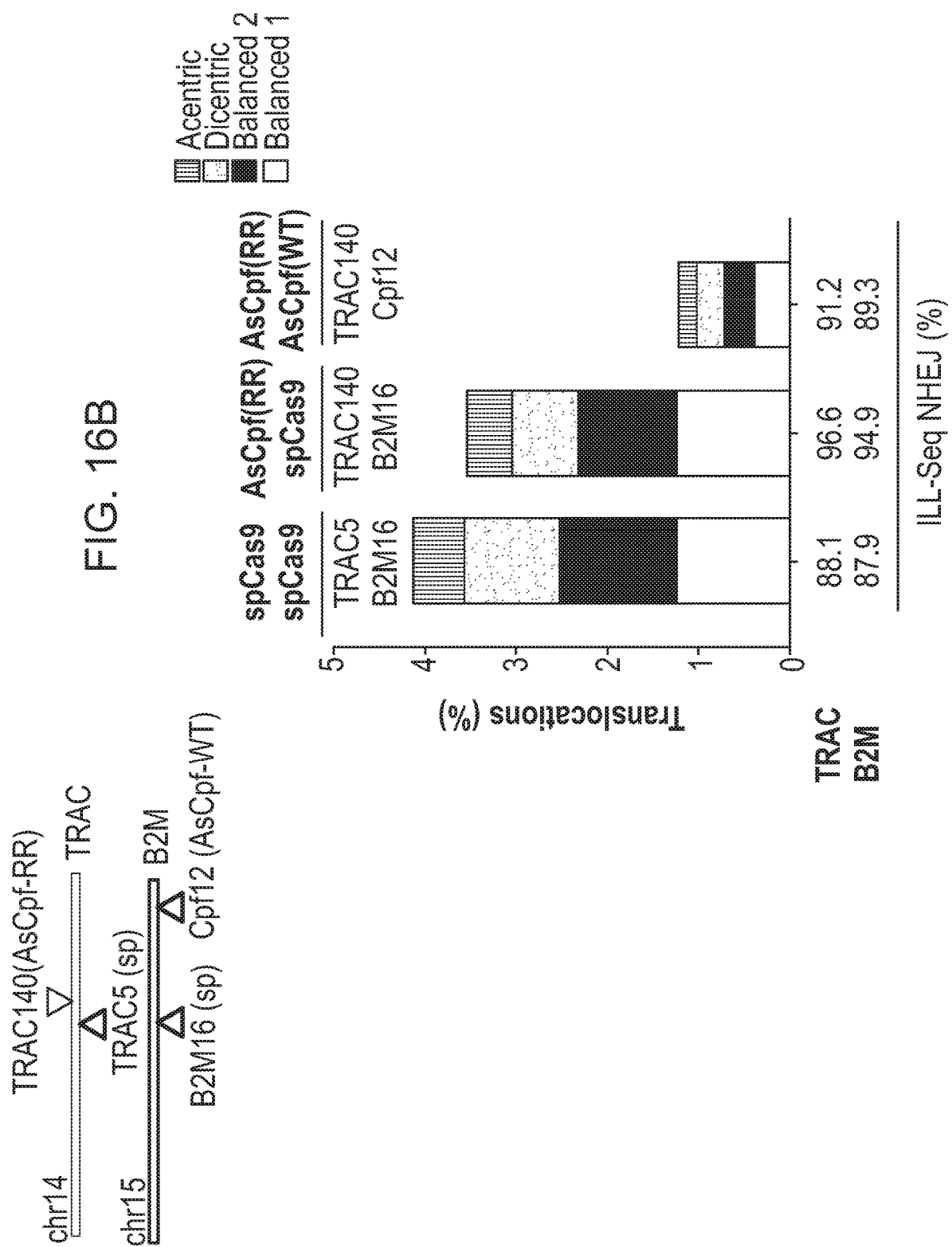

In another experiment, primary human T cells were simultaneously nucleofected with a first RNP complex containing *S. pyogenes* Cas9 and a gRNA targeting TRAC (TRAC5), and a second RNP complex containing *S. pyogenes* Cas9 and a gRNA targeting B2M Exon 2 (B2M16 sp) at 4.3 μM each. In parallel, a second group of primary human T cells were simultaneously nucleofected with a first RNP complex containing *Acidaminococcus* sp. Cpf1 RR variant (AsCpf1-RR) and a gRNA targeting TRAC (TRAC140 as-RR) and a second RNP complex containing *S. pyogenes* Cas9 and a gRNA targeting B2M Exon 2 (B2M16 sp) at 8.7 μM and 4.3 μM respectively. A third group of primary human T cells were simultaneously nucleofected with a first RNP complex containing *Acidaminococcus* sp. Cpf1 RR variant (AsCpf1-RR) and a gRNA targeting TRAC (TRAC140 as-RR) and a second RNP complex containing *Acidaminococcus* Cpf1 and a gRNA targeting B2M Exon 2 (B2M-Cpf1-12 as) at 8.7 μM and 2.2 μM respectively. Editing was assessed using Illumina sequencing, and translocation frequency was measured three days after nucleofection using ddPCR. As shown in FIG. 16B, a combination of simultaneous *Acidaminococcus* sp. Cpf1 and *Acidaminococcus* sp. Cpf1-RR variant for multiplexing led to lower translocation formation than two simultaneous *S. pyogenes* Cas9 editing events or combined editing events of simultaneous *S. pyogenes* Cas9 and *Acidaminococcus* sp. Cpf1-RR variant.

In another experiment, primary human T cells were simultaneously nucleofected with a first RNP complex containing *Acidaminococcus* sp. Cpf1 RR variant (AsCpf1-RR) and a gRNA targeting B2M Exon 2 (B2M29 as-RR) and a second RNP complex containing *S. pyogenes* Cas9 and a gRNA targeting TRAC (TRAC5 sp) at 4.3 μM and 8.7 μM respectively. A third group of primary human T cells were simultaneously nucleofected with a first RNP complex containing *Acidaminococcus* sp. Cpf1 RR variant (AsCpf1-RR) and a gRNA targeting B2M Exon 2 (B2M29 as-RR) and a second RNP complex containing *Acidaminococcus* Cpf1 and a gRNA targeting TRAC (GWED546) at 8.7 μM each. Editing was assessed using Illumina sequencing, and translocation frequency was measured three days after nucleofection using ddPCR. As shown in FIG. 16C, a combination of simultaneous *Acidaminococcus* sp. Cpf1 and *Acidaminococcus* sp. Cpf1-RR variant for multiplexing led to lower translocation formation than two simultaneous *S.*

Figure 17A:
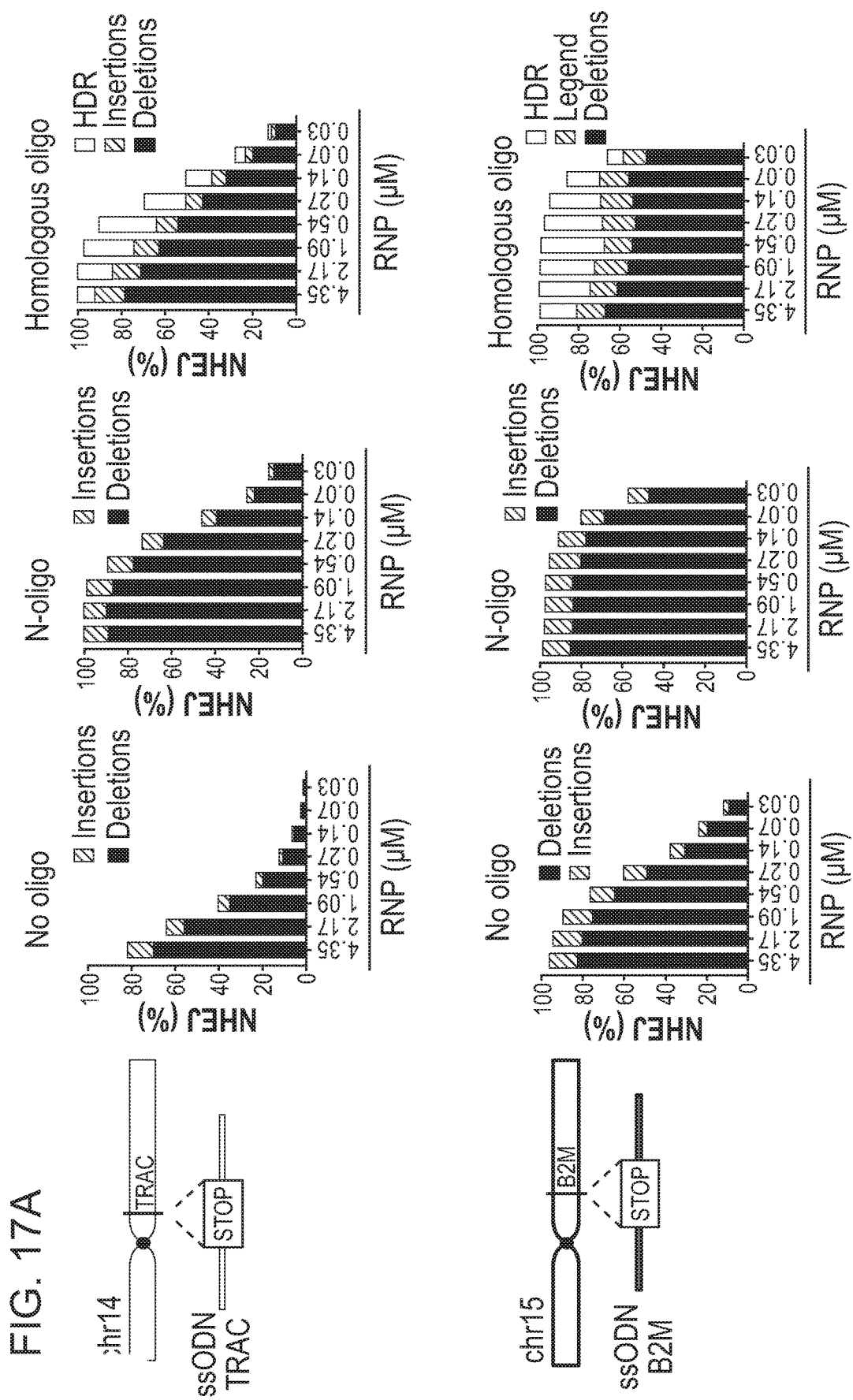
FIG. 17A depicts that a significantly higher percentage of alleles were edited in the presence of the STOP-ssODN and N-oligo than in the no-oligo controls, particularly at reduced RNP concentrations, independent of the locus targeted. Human primary T cells were nucleofected with RNP complexes targeting the TRAC locus (top) or the B2M locus (bottom) at the indicated molar concentration in the absence of an ssODN (No oligo), the presence of a non-homologous oligo (N-oligo) or a locus specific homologous ssOND (STOP-ssODN). NHEJ efficiency was measured by Illumina sequencing four days post nucleofection.

Example 13: Generating Functional Knockouts Using a ssODN Containing a Stop Codon and Modulating Translocation Formation with Homologous ssODNs Two homologous STOP ssODNs were generated to target the B2M or the TRAC locus at B2M12 and TRAC5. Each ssODN contains a stop codon positioned between two homology arms having substantial identity to the sequence flanking the target cleavage site. This ssODN configuration is referred to herein as a STOP-ssODN. One additional oligo not bearing homology to either TRAC or B2M was generated (N-oligo). Each ssODN contains a stop codon positioned between two homology arms having substantial identity to the sequence flanking the target cleavage site. The STOP-ssODN specific for a given target locus or the N-oligo was provided to primary human T cells with varying molar concentrations of a Cas9/gRNA RNP complex specific for the target locus. Editing efficiency was compared to primary human T cells provided with the Cas9/gRNA RNP complex in the absence of the STOP-ssODN. Editing and repair outcomes were determined by Illumina sequencing, the results of which are depicted in FIG. 17A. A significantly higher percentage of alleles were edited in the presence of the STOP-ssODN and N-oligo than in the no-oligo controls, particularly at reduced RNP concentrations, independent of the locus targeted.

Figure 17B:
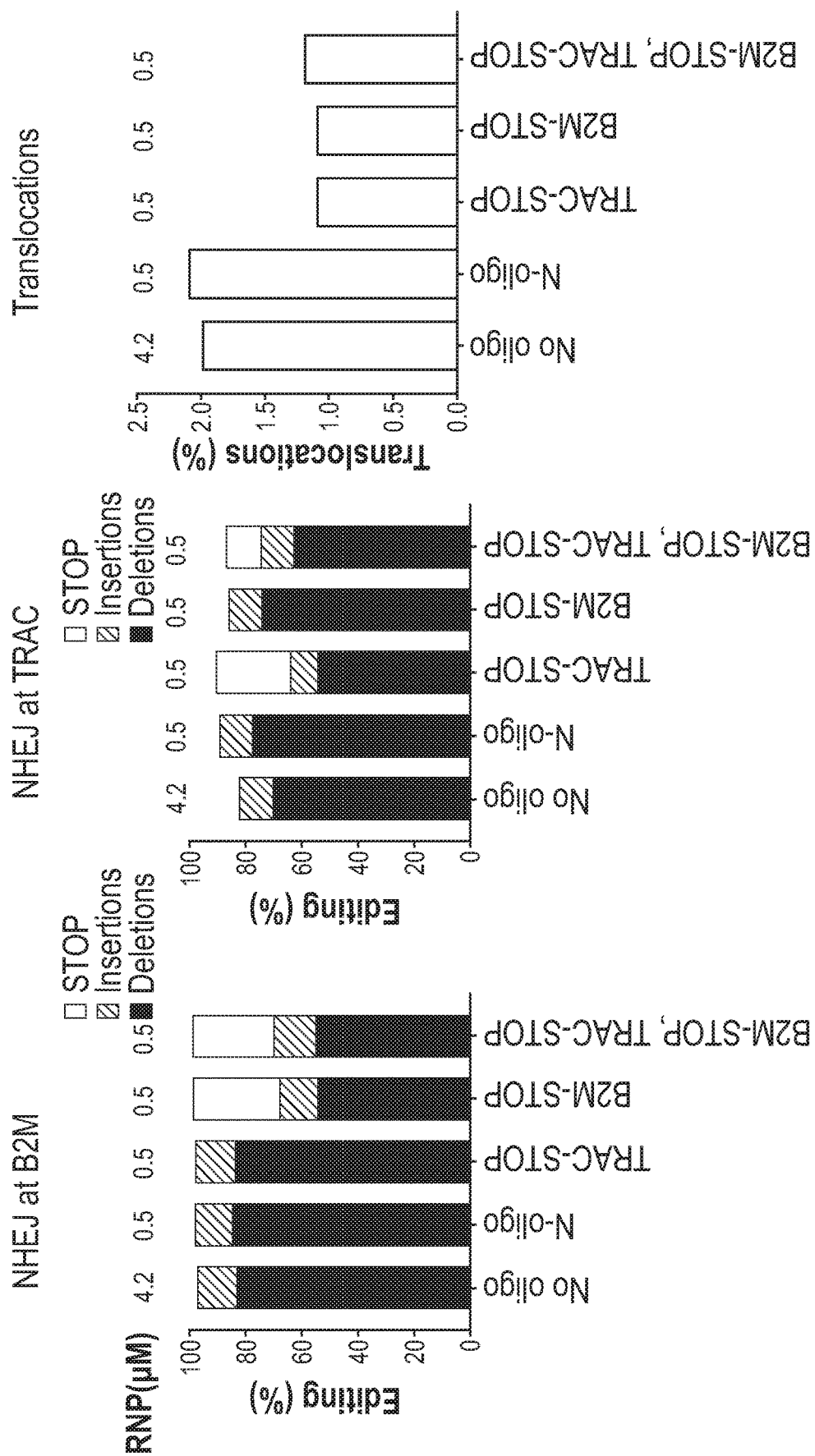
FIG. 17B depicts that both the N-oligo and the STOP-ssODNs alone or in combination allow for a reduction in RNP concentration of at least 5-fold, while maintaining editing efficiency. The translocation rate is not significantly altered in cells receiving the N-oligo relative to the control, indicating that the N-oligo leads to increased NHEJ-mediated DNA repair even at lower RNP concentration. In contrast, cells receiving the STOP-ssODNs exhibited a 2-fold reduction in translocation formation relative to the control. This reduction was accompanied by a reduction in NHEJ and an increase in HDR. Accordingly, the STOP-ssODN maintained editing and HDR levels at a reduced concentration of RNP while reducing translocation frequency, relative to control cells. Human primary T cells were nucleofected with RNP complexes targeting the TRAC and B2M loci at the indicated molar concentration in the absence of an ssODN (No oligo), the presence of a non-homologous oligo (N-oligo), a TRAC locus specific homologous ssOND (TRAC-STOP), a B2M locus specific homologous ssOND (B2M-STOP), or two homologous ssODN directed to TRAC and B2M (B2M-STOP, TRAC-STOP). NHEJ efficiency was measured by Illumina sequencing four days post nucleofection and translocation rates were determined by ddPCR for the indicated conditions four days after nucleofection.

Two STOP-ssODNs were designed to induce targeted incorporation of the stop codon at two distinct target loci (B2M and TRAC). Primary human T cells were treated simultaneously with two Cas9/gRNA RNP complexes using the TRAC5 gRNA and the B2M12 gRNA to direct the Cas9 nucleases to the TRAC and B2M loci, and with either a STOP-ssODN specific for each locus, a non-specific N-oligo, or no oligo, exploiting the observation described above that the presence of either oligo allows for a reduction in RNP concentration to achieve similar levels of gene disruption, as compared with the no oligo control. A first subset of cells was treated with 4.2 µM of RNP complex containing Cas9 and a gRNA targeting B2M12, and 4.2 µM of a second RNP complex containing Cas9 and a gRNA targeting TRAC5. A second subset of cells was treated with 0.5 µM of RNP complex containing Cas9 and a gRNA targeting B2M12, and 0.5 µM of a second RNP complex containing Cas9 and a gRNA targeting TRAC5 and a non-homologous N-oligo. A third subset of cells was treated with 0.5 µM of RNP complex containing Cas9 and a gRNA targeting B2M12, and 0.5 µM of a second RNP complex containing Cas9 and a gRNA targeting TRAC5 and homologous STOP-ssODN targeting the TRAC locus (TRAC-STOP). A fourth subset of cells was treated with 0.5 µM of RNP complex containing Cas9 and a gRNA targeting B2M12, and 0.5 µM of a second RNP complex containing Cas9 and a gRNA targeting TRAC5 and homologous STOP-ssODN targeting the B2M locus (B2M-STOP). A fifth subset of cells was treated with 0.5 µM of RNP complex containing Cas9 and a gRNA targeting B2M12, and 0.5 µM of a second RNP complex containing Cas9 and a gRNA targeting TRAC5 and homologous STOP-ssODN targeting the B2M locus (B2M-STOP) and another homologous ssODN targeting the TRAC locus (TRAC-STOP). After four days, cells were harvested. Genomic DNA was analyzed by Illumina sequencing for editing and HDR efficiency, and by ddPCR to assess translocation formation. As shown in FIG. 17B, Both the N-oligo and the STOP-ssODNs alone or in combination allow for a reduction in RNP concentration of at least 5-fold, while maintaining editing efficiency. The translocation rate is not significantly altered in cells receiving the N-oligo relative to the control, indicating that the N-oligo leads to increased NHEJ-mediated DNA repair even at lower RNP concentration. In contrast, cells receiving the STOP-ssODNs exhibited a 2-fold reduction in translocation formation relative to the control. This reduction was accompanied by a reduction in NHEJ and an increase in HDR. Accordingly, the STOP-ssODN maintained editing and HDR levels at a reduced concentration of RNP while reducing translocation frequency, relative to control cells.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments described herein. Such equivalents are intended to be encompassed by the following claims.

INFORMAL SEQUENCE LISTING

| SEQ ID NO: | Nuclease | Name | Protospacer Sequence (5' to 3') |
|---|---|---|---|
| 1 | spCas9 | TRAC1 | TCTCTCAGCTGGTACACGGC |
| 2 | spCas9 | TRAC13 | CTTCAAGAGCAACAGTGCTG |
| 3 | spCas9 | TRAC-SL | CAGGGTTCTGGATATCTGT |
| 4 | spCas9 | TRAC5 | GGCCACGGAGCGAGACATCT |
| 5 | spCas9 | B2M12 | GCTGGTACACGGCAGGGTCA |
| 6 | spCas9 | B2M16 | CAGTAAGTCAACTTCAATGT |
| 7 | AsCpf1 | GWED546 | GAGTCTCTCAGCTGGTACACGGC |

| | INFORMAL SEQUENCE LISTING | |
|---|---|---|
| 8 | AsCpf1 | B2M-Cpf1-12    AGTGGGGGTGATTTCAGTGT |

| SEQ ID NO: | Name | Sequence (5' to 3')<br>*Phosphorothioate Bond |
|---|---|---|
| 9 | TRAC5_STOP | A*TCAAAATCGGTGAATAGGCAGACAGACTTGTCACTGGATTTAGAGTCTC<br>TCAGCTGGTACACGGCAGGGCTAATTATTCATCAGGGTTCTGGATATCTGT<br>GGGACAAGAGGATCAGGGTTAGGACATGATCTCATTTCCCTCTTTGCCC*C |
| 10 | B2M12_STOP | T*CACGCTGGATAGCCTCCAGGCCAGAAAGAGAGAGTAGCGCGAGCACAGC<br>TAAGGCCACGGAGCGAGACACTAATTATTCATCTCGGCCCGAATGCTGTCA<br>GCTTCAGGAATGCCCGCCAGCGCGACGCCTCCACTTATATTAAACGCGT*G |
| 11 | TRACI_STOP | A*GAGGGAAATGAGATCATGTCCTAACCCTGATCCTCTTGTCCCACAGATA<br>TCCAGAACCCTGACCCTGCCAAAGCTTCTTGTGTACCAGCTGAGAGACTCT<br>AAATCCAGTGACAAGTCTGTCTGCCTATTCACCGATTTTGATTCTCAA*A |
| 12 | TRAC13_STOP | A*TTCTGATGTGTATATCACAGACAAAACTGTGCTAGACATGAGGTCTATG<br>GACTTCAAGAGCAACAGTGAAAGCTTCTTCTGTGGCCTGGAGCAACAAATC<br>TGACTTTGCATGTGCAAACGCCTTCAACAACAGCATTATTCCAGAAGA*C |
| 13 | TRAC-SL_Stop | G*GACTCCAGCCTGGGTTGGGGCAAAGAGGGAAATGAGATCATGTCCTAAC<br>CCTGATCCTCTTGTCCCACAAAAGCTTCTTGATATCCAGAACCCTGACCCT<br>GCCGTGTACCAGCTGAGAGACTCTAAATCCAGTGACAAGTCTGTCTGC*C |
| 14 | N-Oligo_1 | C*CTGTTAGAAAAATCTCATGACATTAATTCTAGGTCCAGATCCTAAGAGA<br>GGACACTCAAGTATCCCTGAAAGAAGCTTTTAAAGTGCAATCATCCAGATG<br>CTTTCTAGCCACAGTTCCTGCATCCAGAATTTTAGGAACAGCCAGAAA*A |
| 15 | N-Oligo_2 | T*TACATATTGTGCGGTCGAATTCAGGGAGCCGATAATGCGGTTACAATAA<br>TTCCTATACTTAAATATACAAAGATTTAAAATTTCAAAAAATGGTTACCAG<br>CATCGTTAGTGCGTATACATCAAGAGGCACGTGCCCCGGAGAC*A |
| 16 | Dicentric oligo (Plus strand) | C*ACGCGTTTAATATAAGTGGAGGCGTCGCGCTGGCGGGCATTCCTGAAGC<br>TGACAGCATTCGGGCCGAGATGATTCAGGGTTCTGGATATCTGTGGGACAAG<br>AGGATCAGGGTTAGGACATGATCTCATTTCCCTCTTTGCCC*C |
| 17 | Dicentric oligo (Minus strand) | G*GGGCAAAGAGGGAAATGAGATCATGTCCTAACCCTGATCCTCTTGTCCC<br>ACAGATATCCAGAACCCTGATCATCTCGGCCCGAATGCTGTCAGCTTCAGG<br>AATGCCCGCCAGCGCGACGCCTCCACTTATATTAAACGCGT*G |
| 18 | Balanced1 oligo (Plus strand) | C*ACGCGTTTAATATAAGTGGAGGCGTCGCGCTGGCGGGCATTCCTGAAGC<br>TGACAGCATTCGGGCCGAGATGACCCTGCCGTGTACCAGCTGAGAGACTCT<br>AAATCCAGTGACAAGTCTGTCTGCCTATTCACCGATTTTGA*T |
| 19 | Balanced1 oligo (Minus strand) | A*TCAAAATCGGTGAATAGGCAGACAGACTTGTCACTGGATTTAGAGTCTC<br>TCAGCTGGTACACGGCAGGGTCATCTCGGCCCGAATGCTGTCAGCTTCAGG<br>AATGCCCGCCAGCGCGACGCCTCCACTTATATTAAACGCGT*G |
| 20 | Balanced2 oligo (Plus strand) | G*GGCAAAGAGGGAAATGAGATCATGTCCTAACCCTGATCCTCTTGTCCC<br>ACAGATATCCAGAACCCTGATGATGTCTCGCTCCGTGGCCTTAGCTGTGCT<br>CGCGCTACTCTCTCTTTCTGGCCTGGAGGCTATCCAGCGTG*A |
| 21 | Balanced2 oligo (Minus strand) | T*CACGCTGGATAGCCTCCAGGCCAGAAAGAGAGAGTAGCGCGAGCACAGC<br>TAAGGCCACGGAGCGAGACATCATCAGGGTTCTGGATATCTGTGGGACAAG<br>AGGATCAGGGTTAGGACATGATCTCATTTCCCTCTTTGCCC*C |
| 22 | Acentric oligo (Plus strand) | A*TCAAAATCGGTGAATAGGCAGACAGACTTGTCACTGGATTTAGAGTCTC<br>TCAGCTGGTACACGGCAGGGTGZTGTCTCGCTCCGTGGCCTTAGCTGTGCT<br>CGCGCTACTCTCTCTTTCTGGCCTGGAGGCTATCCAGCGTG*A |
| 23 | Acentric oligo (Minus strand) | T*CACGCTGGATAGCCTCCAGGCCAGAAAGAGAGAGTAGCGCGAGCACAGC<br>TAAGGCCACGGAGCGAGACATCACCCTGCCGTGTACCAGCTGAGAGACTCT<br>AAATCCAGTGACAAGTCTGTCTGCCTATTCACCGATTTTGA*T |
| 24 | B2M29 | GTGGGGGTGAATTCAGTGTA |
| 25 | TRAC140 | GTGACAAGTCTGTCTGCCTA |

The invention claimed is:

1. A method of altering a cell at two target nucleic acids in the cell, the method comprising the step of delivering to the cell two ribonucleoprotein (RNP) complexes, wherein a first RNP complex comprises a SpCas9 RNA-guided nuclease, and wherein a second RNP complex comprises an Acidaminococcus sp. Cpf1 nuclease, thereby altering the cell at the two target nucleic acids.

2. A method of reducing the risk of translocations in a cell when the cell is altered at two target nucleic acids, the method comprising delivering to the cell two RNP complexes, wherein a first RNP complex comprises a SpCas9 RNA-guided nuclease, and wherein a second RNP complex comprises an Acidaminococcus sp. Cpf1 nuclease, thereby reducing the risk of translocations in the cell.

3. The method of claim 2, wherein the translocation may occur between an on-target site and an off-target site.

4. The method of claim 1, wherein the two RNP complexes are delivered to the cell sequentially in any order, or simultaneously.

5. A method of altering a cell at a first target nucleic acid and a second target nucleic acid, comprising the steps of:
   forming at least one single- or double-stranded break at a first cleavage site in the first target nucleic acid by delivering to the cell a ribonucleoprotein (RNP) complex comprising a first RNA-guided nuclease and a first guide RNA (gRNA) capable of directing the first RNA-guided nuclease to the first target nucleic acid, wherein the first cleavage site is repaired by at least one DNA repair pathway to produce an altered first target nucleic acid; and
   forming at least one single- or double-stranded break at a second cleavage site in the second target nucleic acid by delivering to the cell a second RNA-guided nuclease expressed in the cell from an exogenous nucleic acid encoding the second RNA-guided nuclease, wherein the second cleavage site is repaired by at least one DNA repair pathway to produce an altered second target nucleic acid,
   wherein the first RNA-guided nuclease is SpCas9 nuclease and the second RNA-guided nuclease is an *Acidaminococcus* sp. Cpf1 nuclease, and wherein the first and the second RNA complexes may be delivered simultaneously or sequentially in any order.

6. A method of altering a cell at a first target nucleic acid and a second target nucleic acid, comprising the steps of:
   forming at least one single- or double-stranded break at a first cleavage site in the first target nucleic acid by delivering to the cell a first ribonucleoprotein (RNP) complex comprising a first RNA-guided nuclease and a first guide RNA (gRNA) capable of directing the first RNA-guided nuclease to the first cleavage site in the first target nucleic acid, wherein the first RNA-guided nuclease is an SpCas9 nuclease, and wherein the first cleavage site is repaired by at least one DNA repair pathway to produce an altered first target nucleic acid; and
   after a period of time sufficient for repair of the first cleavage site, forming at least one single- or double-stranded break at a second cleavage site by delivering to the cell a second ribonucleoprotein (RNP) complex comprising a second RNA-guided nuclease and a second guide RNA (gRNA) capable of directing the second RNA-guided nuclease to the second cleavage site in the second target nucleic acid, wherein the second RNA-guided nuclease is an *Acidaminococcus* sp. Cpf1 nuclease, and wherein the second cleavage site is repaired by at least one DNA repair pathway to produce an altered second target nucleic acid, thereby altering the cell.

7. The method of claim 6, wherein the first RNP complex and the second RNP complex are delivered in different amounts.

8. The method of claim 7, wherein the concentration of the second RNP complex is at least 2-fold, 3-fold, 4-fold, 5-fold, 10-fold, 20-fold, 30-fold or 50-fold lower than the amount of the first RNP complex.

9. The method of claim 6, wherein the time sufficient for repair of the first cleavage site is at least 12 hours, at least 24 hours, at least 36 hours, at least 48 hours, at least 72 hours, at least 96 hours, or at least 120 hours.

10. The method of claim 5, wherein the cell is a T cell, an NK cell, an embryonic stem cell, an induced pluripotent stem cell (iPSC), a CD34+ cell, or a hematopoietic stem/progenitor cell (HSPC).

11. The method of claim 10, wherein the cell is a T cell, and the first target nucleic acid is selected from the group consisting of TRAC, TRBC, CIITA, and B2M.

12. The method of claim 11, wherein the second target nucleic acid is different from the first target nucleic acid.

13. The method of claim 12, wherein the second target nucleic acid is selected from the group consisting of TRAC, TRBC, CIITA, and B2M.

14. The method of claim 1, wherein the method is performed ex vivo.

15. The method of claim 1, wherein the method is performed in vivo.

16. The method of claim 1, wherein the cell is a T cell, an NK cell, an embryonic stem cell, an induced pluripotent stem cell (iPSC), a CD34+ cell, or a hematopoietic stem/progenitor cell (HSPC).

17. The method of claim 1, further comprising contacting the cell with an exogenous oligonucleotide.

18. The method of claim 17, wherein the exogenous oligonucleotide is an exogenous oligonucleotide donor template.

\* \* \* \* \*